(12) United States Patent
Ulm, III

(10) Patent No.: US 11,399,854 B2
(45) Date of Patent: *Aug. 2, 2022

(54) CLOT RETRIEVAL SYSTEM

(71) Applicant: LEGACY VENTURES LLC, Nashville, TN (US)

(72) Inventor: Arthur John Ulm, III, Nashville, TN (US)

(73) Assignee: Legacy Ventures LLC, Nashville, TN (US)

( * ) Notice: Subject to any disclaimer, the term of this patent is extended or adjusted under 35 U.S.C. 154(b) by 379 days.

This patent is subject to a terminal disclaimer.

(21) Appl. No.: 16/479,985

(22) PCT Filed: Jan. 25, 2018

(86) PCT No.: PCT/US2018/015406
§ 371 (c)(1),
(2) Date: Jul. 23, 2019

(87) PCT Pub. No.: WO2018/140702
PCT Pub. Date: Aug. 2, 2018

(65) Prior Publication Data
US 2019/0365396 A1    Dec. 5, 2019

Related U.S. Application Data

(63) Continuation-in-part of application No. 15/710,648, filed on Sep. 20, 2017, now Pat. No. 9,955,987, and (Continued)

(51) Int. Cl.
*A61B 17/221* (2006.01)
*A61B 17/00* (2006.01)
(Continued)

(52) U.S. Cl.
CPC .. *A61B 17/221* (2013.01); *A61B 2017/00477* (2013.01); *A61B 2017/2212* (2013.01); (Continued)

(58) Field of Classification Search
CPC ........ A61B 17/221; A61B 2017/00477; A61B 2017/22034; A61B 2017/22084; (Continued)

(56) References Cited

FOREIGN PATENT DOCUMENTS

| WO | 2012120490 A2 | 9/2012 |
| WO | 2015103547 A1 | 7/2015 |

OTHER PUBLICATIONS

European Search Report for EP3573536 (dated Sep. 17, 2020).

*Primary Examiner* — Thomas McEvoy
(74) *Attorney, Agent, or Firm* — Shane Cortesi

(57) ABSTRACT

Catheter-delivered endovascular medical devices are described. The devices may include a pull wire attached to a distal body. The distal body may be formed of a distal body outer body comprising a basket comprised of a plurality of cells defined by a plurality of basket strips and a distal body inner body located in the interior of the distal body outer body and comprising a plurality of distal braided mesh openings formed by a plurality of woven linear strands. The distal braided mesh openings may be smaller than the cells when the device is in the relaxed state. Methods of using and making the devices are also described.

36 Claims, 67 Drawing Sheets

Related U.S. Application Data a continuation-in-part of application No. 15/629,703, filed on Jun. 21, 2017, now Pat. No. 9,808,271, and a continuation-in-part of application No. 15/611,762, filed on Jun. 1, 2017, now Pat. No. 10,492,809, and a continuation-in-part of application No. 15/610,209, filed on May 31, 2017, now Pat. No. 9,814,478, and a continuation-in-part of application No. 15/449,901, filed on Mar. 3, 2017, now Pat. No. 9,826,998, and a continuation-in-part of application No. 15/417,505, filed on Jan. 27, 2017, now Pat. No. 9,801,644.

(51) Int. Cl.
*A61B 17/22* (2006.01)
*A61F 2/01* (2006.01)

(52) U.S. Cl.
CPC ............... *A61B 2017/22034* (2013.01); *A61B 2017/22084* (2013.01); *A61F 2002/016* (2013.01); *A61F 2230/0067* (2013.01); *A61F 2230/0093* (2013.01)

(58) Field of Classification Search
CPC ....... A61B 2017/2212; A61F 2002/016; A61F 2230/0067; A61F 2230/0093
See application file for complete search history.

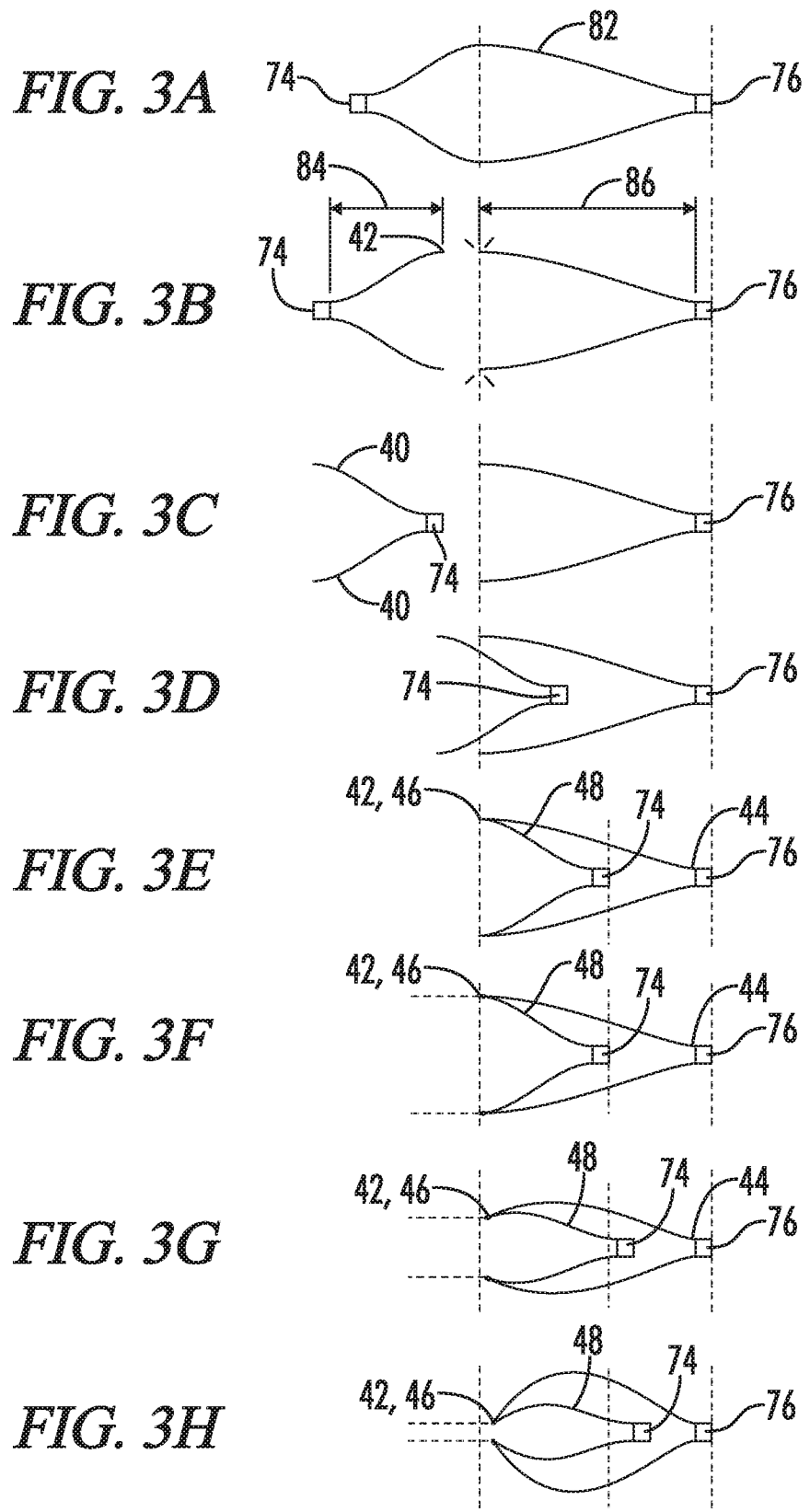

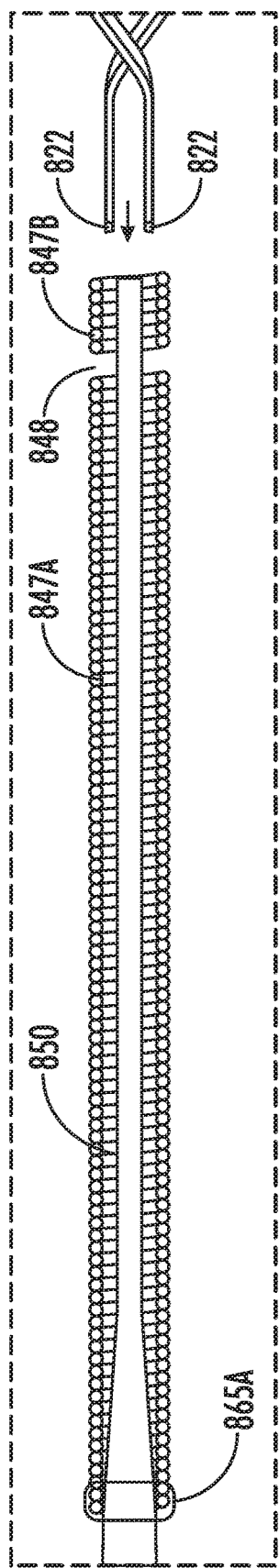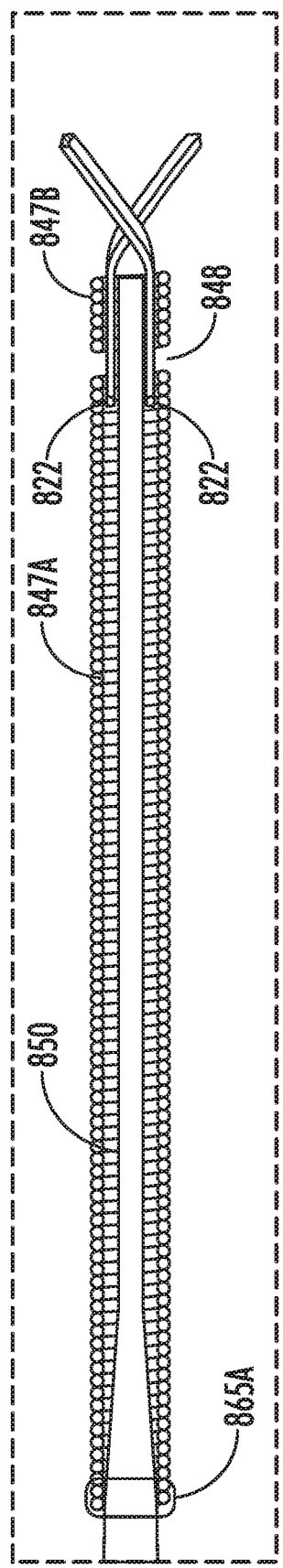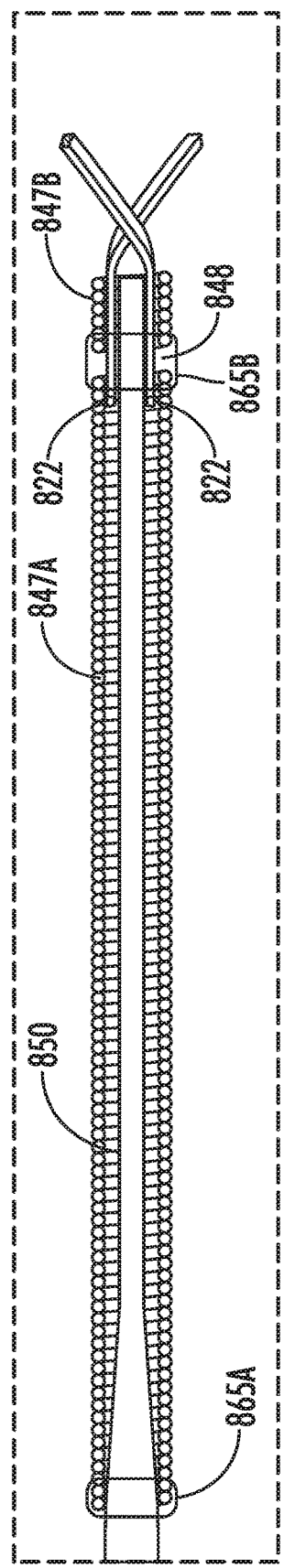

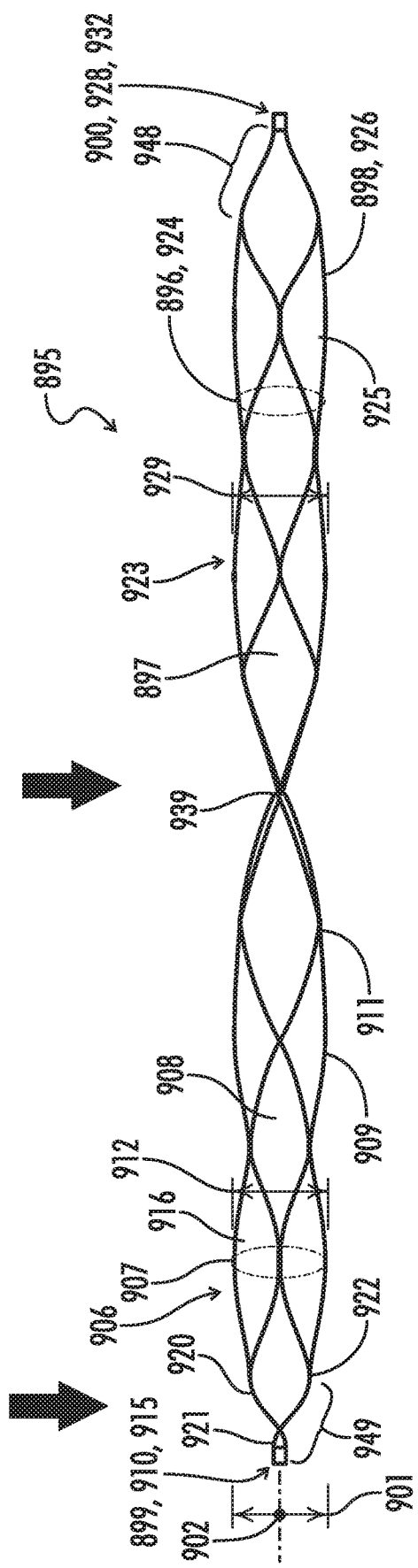
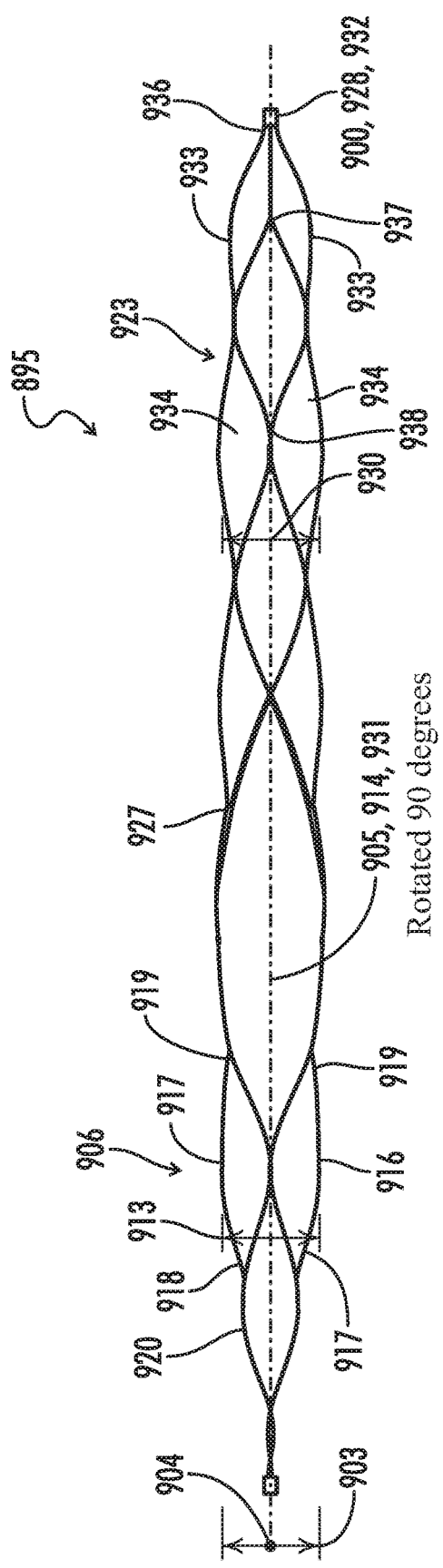
FIG. 50
FIG. 51

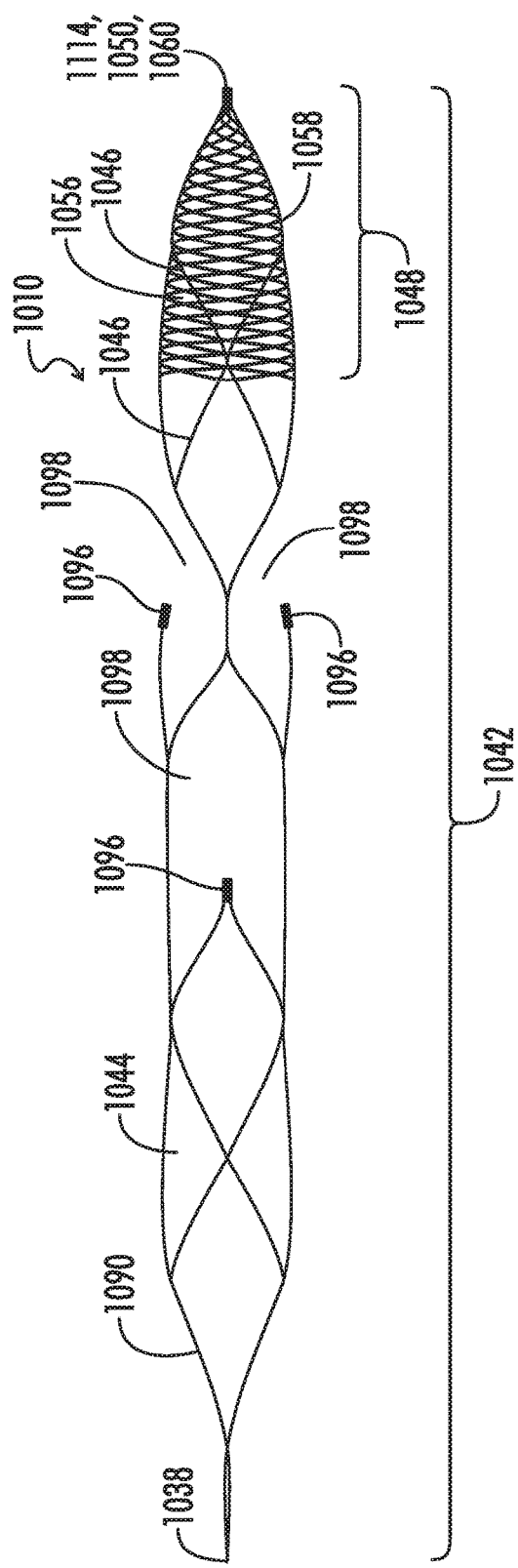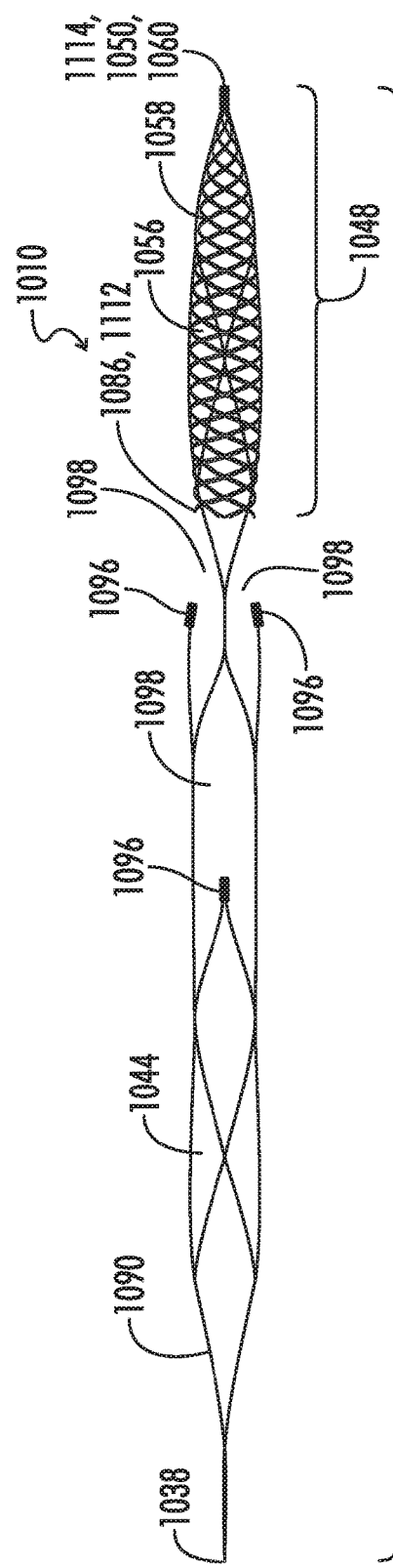
FIG. 63
FIG. 64

CLOT RETRIEVAL SYSTEM

TECHNICAL FIELD

The present invention relates to a deployable system for removing a blood clot or other object from a lumen of an animal as well as to methods of manufacturing catheter-delivered medical devices from a tube of a memory metal.

BACKGROUND ART

Acute ischemic strokes develop when a blood clot (thrombus) blocks an artery supplying blood to the brain. Needless to say, when a blood clot creates such a blockage, time in removing the clot is critical.

The removal of intracranial obstructions is limited by several factors, such as the distance of the intracranial obstruction from the femoral access site, the tortuosity (twists and turns in the artery as it enters the base of the skull) of the cervical and proximal intracranial vasculature, the small size of the vessels and the extremely thin walls of intracranial vessels, which lack a significant muscular layer. These limitations require a device to be small and flexible enough to navigate through tortuous vessels within a guide catheter and microcatheter, expand after delivery at the site of occlusion and be retrievable into the microcatheter and yet be strong enough to dislodge strongly adherent thrombus from the vessel wall. In addition, the device should distally entrap or encase the thrombus to prevent embolization to other vessels and to completely remove the occlusion. The device should be retrievable without the need for proximal occlusion of the vessel, which carries risk of further ischemia and risk of vessel injury. The device should be simple to use and be capable of multi-use within the same patient treatment. The device should not be abrasive and should not have sharp corners exposed to the endothelial layer of the vessel wall.

Currently available intravascular thrombus and foreign body removal devices lack several of these features. Currently available devices include the MERCI™ RETRIEVER clot retriever device marketed by Concentric Medical, Inc. (Mountainview, Calif.), the PENUMBRA™ system marketed by Penumbra Inc. (Alameda, Calif.) to retrieve clots, and the newer stent retrieval devices TREVO™ (Stryker, Kalamazoo, Mich.) and SOLITAIRE™ (eV3 Endovascular Inc., Plymouth, Mass., which is a subsidiary of Covidien). All the devices are ineffectual at removing organized hard thrombus that embolize to the brain from the heart and from atherosclerotic proximal vessels. These "hard" thrombi constitute the majority of strokes which are refractory to medical treatment and are therefore referred for removal by mechanical means through an endovascular approach. The MERCI retrieval system is comprised of coiled spring-like metal and associated suture material. The method of use is deployment distal to the thrombus and by withdrawing the device through the thrombus, the thrombus becomes entangled in the coil and mesh and then is retrieved. The MERCI system requires occlusion of the proximal vessel with a balloon catheter and simultaneous aspiration of blood while the thrombus is being removed. Most of the time, the device fails to dislodge the thrombus from the wall of the vessel and often, even when successfully dislodging the thrombus, the thrombus embolizes into another or the same vessel due to the open ended nature of the device.

The next attempt at a thrombus removal system was the PENUMBRA. The PENUMBRA is a suction catheter with a separator that macerates the thrombus which is then removed by suction. The device is ineffective at removing hard, organized thrombus which has embolized from the heart, cholesterol plaque from proximal feeding arteries and other foreign bodies.

The SOLITAIRE and TREVO systems are self-expanding non-detachable stents. The devices are delivered across the thrombus which is then supposed to become entwined in the mesh of the stent and which is then removed in a manner similar to the MERCI system. Again, these devices are ineffectual at treating hard thrombus. In fact, the thrombus is often compressed against the vessel wall by the stent which temporarily opens the vessel by outwardly pressing the clot against the vessel wall. Upon retrieval of the devices, the clot remains or is broken up into several pieces which embolize to vessels further along the vessel.

Thus, there is a need for new, easy-to-use, easy-to-manufacture, safe surgical devices for removing obstructions, such as blood clots, from internal lumens of humans and other animals in a timely manner.

In addition, it may be desirable to make memory-metal based mechanical thrombectomy devices, also referred to in the art as stent retrievers, from a single tube of the memory-metal (e.g., nitinol), and in the process, laser cut and shape set the middle portion to form the capture portion (e.g., the basket) and leave the proximal and distal ends at least partially intact. To provide design flexibility to the designer of the basket (so that he/she may include complicated structure in the middle portion), it is desirable that the single tube have a relatively large diameter. However, it is also desirable to allow the devices to fit into a small catheter (called a microcatheter), which creates issues if the proximal and distal ends remain on the device. Thus, there is a need for processes of making devices that have the advantages of being cut from a larger diameter tube but are also able to fit inside a small catheter.

DISCLOSURE OF THE INVENTION

The present disclosure provides several systems for removing obstructions and other objects within a blood vessel or other lumen of an animal. The system may be deployed in the lumen from a distal end of a catheter and, in some embodiments, includes a pull wire having a proximal end and a distal end; a distal body attached to the pull wire, the distal body comprising an interior, an exterior, a proximal end, a distal end, a plurality of proximal memory metal strips located at the proximal end, a proximal hub/junction located in the distal body interior, and a distal hub/junction located distal relative to the proximal hub/junction. The distal body has a relaxed state wherein the distal body has a first height and width and a collapsed state wherein the distal body has a second height and width, the second height less than said first height, the second width less than the first width. The system further includes a catheter having an interior, a proximal end leading to the interior and a distal end leading to the interior, the catheter comprised of a biocompatible material and configured to envelope the distal body when the distal body is in the collapsed state. Each of the proximal memory metal strips has a proximal end and a distal end and preferably, in the relaxed state, each of the proximal ends of the proximal memory metal strips is located proximal relative to the proximal hub/junction. Preferably, in the relaxed state, the proximal ends of the proximal memory metal strips are configured to move towards each other and towards the pull wire when an operator moves the proximal hub/junction distally and closer to the stationary distal hub/junction (i.e., when the operator decreases the distance between the hubs/junctions). Preferably, in the relaxed state, the proximal ends of the proximal memory metal strips are configured to move away from each other and away from the pull wire by moving the proximal hub/junction proximally away from the stationary distal hub/junction (i.e., when the operator increases the distance between the hubs/junctions).

Optionally, the system further includes a plurality of memory metal connector strips, the plurality of memory metal connector strips each having a proximal end attached to a proximal memory metal strip and a distal end attached to the proximal hub/junction. Optionally, the connector strips are integral with the proximal hub/junction (i.e., optionally, the connector strips and the proximal hub/junction are formed from the same piece of memory metal). Optionally, the proximal hub/junction is a tube having an aperture and the pull wire passes through the aperture. Optionally, in the relaxed state, the proximal hub/junction is slideable along the pull wire (i.e., at least a segment of the pull wire). Optionally, in the relaxed state, the proximal memory metal strips are distributed substantially evenly about a perimeter of the distal body. Optionally, the distal hub/junction is a tube having an aperture. Optionally, the distal hub/junction is attached to the pull wire such that the distal hub/junction is not slideable along the pull wire. Optionally, the distal body further comprises a lead wire extending distally from the distal hub/junction. Optionally, the distal body comprises a basket comprised of a plurality of memory metal strips distal relative to the proximal memory metal strips. Optionally, the distal hub/junction, the proximal hub/junction, and the distal basket are comprised of a nitinol having the same material composition. Optionally, the distal body further comprises an x-ray marker. Optionally, the proximal memory metal strips form a claw, the claw having a closeable proximal end formed by the proximal ends of the proximal memory metal strips. Optionally, between 2 and 4 proximal memory metal strips form the claw. Optionally, the distal body, in the relaxed state, has a tapered shape in which the distal body height and width decrease from the proximal end to the distal end. Optionally, the distal body, in the relaxed state, has a bullet shape. Optionally, the proximal hub/junction and the distal hub/junction are generally cylindrical in shape and each has an outer diameter and an inner diameter that forms the apertures of the proximal and distal hub/junctions, the outer diameters of the proximal and distal hub/junctions are substantially the same size, and the inner diameters of the proximal and distal hubs/junctions are substantially the same size. Optionally, the outer diameters of the proximal and distal hubs/junctions are from about 0.011 inches to about 0.054 inches, and the inner diameters of the proximal and distal hubs are from about 0.008 inches to about 0.051 inches. Optionally, the pull wire is generally cylindrical and the diameter of the pull wire is between about 0.008 inches and about 0.051 inches. Optionally, the proximal memory metal strips have a length of between about 10 and about 60 millimeters. Optionally, the first height and first width of the distal body are between about 2 millimeters (mm) and about 6 millimeters. Optionally, the proximal memory metal strips are configured to a separate a clot from a blood vessel wall.

The present invention also provides a method of removing an object from an interior lumen of an animal, the lumen having an interior wall forming the lumen. In some embodiments, the method includes:

a) providing a system comprising: i) a pull wire having a proximal end and a distal end; ii) a distal body attached to the pull wire, the distal body comprising a proximal end, a distal end, and a claw, the claw comprised of a plurality of memory metal strips, the distal body having a relaxed state wherein the distal body has a first height and width and a collapsed state wherein the distal body has a second height and width, the second height less than said first height, the second width less than said first width; and iii) a catheter having an interior, a proximal end leading to the interior and a distal end leading to the interior, the catheter comprised of a biocompatible material and configured to envelope the distal body when said distal body is in said collapsed state;

b) positioning the system in the lumen;

c) deploying the distal body from the distal end of the catheter;

d) allowing the height and width of said distal body to increase; and e) moving the memory metal strips towards each other and the pull wire so as to capture the obstruction. Optionally, the claw and the memory metal strips are located at the proximal end of said distal body and the distal body is deployed distal to said object. Optionally, the proximal memory metal strips have a proximal end forming the proximal end of the claw and a distal end, and the method includes moving the proximal ends of the memory metal strips towards each other and the pull wire so as to capture the obstruction. Optionally, the distal body further comprises a proximal hub/junction located in the distal body interior, and a distal hub/junction located distal relative to the proximal hub/junction, each of the memory metal strips has a proximal end and a distal end, each of the proximal ends of the memory metal strips is located proximal relative to the proximal hub/junction, and the proximal ends of the memory metal strips are configured to move towards each other and towards the pull wire by moving the proximal hub/junction distally and closer to the distal hub/junction, and the proximal ends of the memory metal strips are configured to move away from each other and away from the pull wire by moving the proximal hub/junction proximally and away from the distal hub/junction, and the method further comprises moving the proximal hub/junction distally and closer to the distal hub/junction so as to capture the obstruction in the claw. Optionally, the interior lumen is an intracranial artery and the obstruction is a blood clot. Optionally, the method further comprises using the clot to move the proximal hub/junction toward the distal hub/junction and exert tension on the proximal memory metal strips. Optionally, the method further comprises using a tube to move the proximal hub/junction toward the distal hub/junction and exert tension on the proximal memory metal strips.

The present invention also provides a method of manufacturing a system for removing objects within an interior lumen of an animal. In some embodiments, the method includes:

a) providing a single tube comprised of a memory metal, the single tube having an exterior, a hollow interior, a wall separating the exterior from the hollow interior, a proximal portion comprising an aperture leading to the hollow interior, a distal portion comprising an aperture leading to the hollow interior, and a middle portion between the proximal portion and the distal portion;

b) cutting the wall of the middle portion with a laser;

c) removing the pieces of the middle portion cut by the laser to form a proximal tube, a middle portion comprising a plurality of memory metal strips attached to the proximal tube and a distal tube;

d) altering the shape of the middle portion;

e) allowing the middle portion to expand relative to the distal tube and the proximal tube;

f) cutting the memory metal strips to form a first segment comprising the proximal tube and a proximal segment of the memory metal strips, and a second segment comprising the distal tube and a distal segment of the memory metal strips; and g) joining the proximal segments to the distal segments such that the distal segments form the proximal end of a distal body, such that the proximal tube is located inside an interior of said distal body, and such that the proximal tube is located distal relative to the proximal end.

Optionally, the method further includes placing a pull wire through the proximal tube such that the proximal tube is slideable along at least a segment of the pull wire. Optionally, the method further includes attaching the pull wire to the distal tube. Optionally, the step of joining the proximal segments to the distal segments comprises welding or soldering the proximal segments to the distal segments. Optionally, after the step of joining the proximal segments to the distal segments, the proximal end forms a claw comprised of between 2 and 4 memory metal strips, the claw memory metal strips configured to move towards each by moving said proximal tube distally and closer to the distal tube, and the claw memory metal strips configured to move away from each other by moving the proximal tube proximally and away from said distal tube. Optionally, the method further includes not altering the shape of the proximal and distal portions while altering the shape of the middle portion. Optionally, the method further includes cooling the proximal portion, the middle portion, and the distal portion after step D) and, after cooling, the proximal and distal portions have substantially the same size as the proximal and distal portions had prior to step A). Optionally, the method of allowing said middle portion to expand comprises heating the middle portion. Optionally, the method of altering the shape of the middle portion comprises using a mandrel. Optionally, the mandrel is tapered. Optionally, the proximal portion and the distal portion are not cut by the laser. Optionally, prior to cutting the memory metal tube, the memory metal tube has an outer diameter that is from about 0.011 inches to about 0.054 inches and an inner diameter that is from about 0.008 inches to about 0.051 inches.

In an alternate embodiment, the present disclosure provides a system for removing objects from an interior lumen of an animal that includes:
a pull wire having a proximal end and a distal end;
a distal body attached to the pull wire, the distal body comprising an interior, a proximal end, a distal end, a distal body length extending from the proximal end to the distal end, a proximal hub/junction (preferably in the form of a tube) forming the proximal end of the distal body, a basket comprised of a plurality of cells formed by a plurality of basket strips, a plurality of proximal strips, and, optionally a distal hub/junction (preferably in the form of a tube) forming a distal end of the basket, the basket comprising a basket interior, each proximal strip having a proximal end attached to the proximal hub/junction, and a distal end attached to a cell, the distal body having a relaxed state wherein the distal body has a first height and a first width, and a collapsed state wherein the distal body has a second height and a second width, the second height less than the first height, the second width less than the first width; and
a catheter having an interior, a proximal end leading to the interior and a distal end leading to the interior, the catheter comprised of a biocompatible material and configured to envelope the distal body when the distal body is in the collapsed state,
wherein, in the relaxed state, the basket comprises a first pair of distal crowns not attached to another cell of the basket and pointing generally in the distal direction, the first pair of distal crowns located approximately the same distance from the proximal hub/junction and approximately 180 degrees relative to each other (e.g., between about 150 degrees and about 180 degrees relative to each other), and further wherein the basket further comprises a second pair of distal crowns not attached to another cell of the basket and pointing generally in the distal direction, the second pair of distal crowns located distally relative to, and approximately 90 degrees relative to, the first pair of distal crowns (e.g., each distal crown of the second pair of distal crowns is located approximately 60 degrees to 90 degrees relative to a distal crown of the first pair of distal crowns), the distal crowns in the second pair of distal crowns located approximately the same distance from the proximal hub/junction and further wherein each of the distal crowns in the first and second pair of distal crowns comprises an x-ray marker, the x-ray maker more visible under x-ray as compared to the basket strips when the distal body is located in a cranial blood vessel inside the body of a human and the x-ray is taken from outside the human's body. When it is said that the first pair of distal crowns are located approximately the same distance from the proximal hub/junction, it will be understood that if one of the first pair of distal crowns is located X distance from the proximal hub/junction, the other of the first pair of distal crowns is located X distance plus or minus (+/−) 3 mm from the proximal hub/junction, more preferably X distance plus or minus (+/−) 0.5 mm from the proximal hub/junction. Similarly, when it is said that the second pair of distal crowns are located approximately the same distance from the proximal hub/junction, it will be understood that if one of the second pair of distal crowns is located Y distance from the proximal hub/junction, the other of the first pair of distal crowns is located Y distance plus or minus (+/−) 3 mm from the proximal hub/junction, more preferably Y distance plus or minus (+/−) 0.5 mm from the proximal hub/junction. Optionally, instead of a distal hub/junction, the basket includes an open distal end.

Optionally, the x-ray markers are comprised of a material different than the material forming the basket strips. Optionally, in the relaxed state, the basket interior is substantially hollow. Optionally, in the relaxed state, the distal body does not have another x-ray marker that is located approximately the same distance from the proximal hub/junction as the first pair of x-ray markers and the distal body does not have another x-ray marker that is located approximately the same distance from the proximal hub/junction as the second pair of x-ray markers. In other words, the first and second pair of x-ray markers are the only markers their respective distances from the proximal hub/junction. Optionally, each distal crown in the first and second pair of distal crowns forms part of an enlarged cell and further wherein the surface area of each enlarged cell in the relaxed state is greater than the surface area of each of the other individual cells of the basket and further wherein the enlarged cells are configured to allow a thrombus to pass therethrough and into the basket interior. Optionally, in the relaxed state, the distal body does not have another free distal-pointing crown that is located approximately the same distance from the proximal hub/junction as the first pair of distal crowns and the distal body does not have another free distal-pointing crown that is located approximately the same distance from the proximal hub/junction as the second pair of distal crowns. Optionally, the basket strips are comprised of a memory metal. Optionally, each of the distal crowns in the first pair and second pair of distal crowns curve radially inward toward the basket interior in the relaxed state, wherein the distal crowns of the first pair of distal crowns are configured to contact each other when an exterior, external compressive force (such as a thrombus) is exerted on a distal crown of the first pair of distal crowns when the distal body is in the relaxed state, and further wherein the distal crowns of the second pair of distal crowns are configured to contact each other when an exterior, external compressive force (such as a thrombus) is exerted on a distal crown of the second pair of distal crowns when the distal body is in the relaxed state. Optionally, the proximal hub/junction is located approximately in the center of the first height and first width in the relaxed state. For example, preferably the proximal hub/junction is located within 0.5 mm of the center of first width and the first height. Optionally, the catheter is comprised of a polymeric material (i.e., one or more polymeric materials such as silicone, PVC, latex rubber or braided nylon). Optionally, the pull wire is comprised of a biocompatible metallic material (e.g., a biocompatible metal or a biocompatible metal alloy). Optionally, the proximal end of a first proximal strip is located at least about 65 degrees (e.g., between about 65 and about 180 degrees) relative to the distal end of the first proximal strip, wherein the proximal end of a second proximal strip is located at least about 65 degrees (e.g., between about 65 and about 180 degrees) relative to the distal end of the second proximal strip, and further wherein the first and second proximal strips intersect adjacent and distal to the proximal hub/junction (e.g., within about 0 and about 4 mm of the proximal hub/junction). Optionally, each distal crown forms part of a cell that further comprises a proximal crown pointing generally in the proximal direction and connected to a memory metal strip (e.g., a proximal strip comprised of a memory metal or a basket strip comprised of a memory metal). In other words, the proximal crowns are not free. Optionally, the basket, the proximal hub/junction and the proximal strips are comprised of a memory metal, wherein the proximal hub/junction comprises a proximal end and a distal end, and further wherein the proximal strips are integral with the distal end of the proximal hub/junction. Optionally, the length of the distal body from the proximal hub/junction to the distal hub/junction (not including any lead wire) is from about 20 mm to about 65 mm. Optionally, the system is used in a method of removing a blood clot from a blood vessel of an animal the method comprising the steps of:

a) providing the system;
b) positioning the system in the lumen;
c) deploying the distal body from the distal end of the catheter;
d) allowing the height and width of the distal body to increase;
e) irradiating the distal body with x-rays;
f) moving the clot into the distal basket interior; and
g) moving the distal body proximally out of the blood vessel.

Optionally, the method further comprises irradiating the distal body with x-rays at at least two different angles. Optionally, at least one x-ray marker attached to the distal crowns is distal to the clot when the distal body is deployed from the distal end of the catheter. Optionally, the method further comprises applying contrast dye proximally and distally to the clot. Optionally, the method further comprises providing a suction catheter having a proximal end and a distal end, and attaching the distal end of the suction catheter to the clot by applying suction to the suction catheter. Optionally, the method further comprises aspirating by hand a pre-determined volume of fluid from the suction catheter using a syringe and then locking the syringe at the pre-determined volume. Optionally, the method further comprises delivering the suction catheter adjacent to the clot by advancing the catheter over the pull wire.

In yet another embodiment, the system includes:

a pull wire having a proximal end and a distal end;
a distal body attached to the pull wire, the distal body comprising an interior, a proximal end, a distal end, a distal body length extending from the proximal end to the distal end, a proximal hub/junction (preferably in the form of a tube) forming the proximal end of the distal body, a basket comprised of a plurality of cells formed by a plurality of basket strips, a plurality of proximal strips, and optionally a distal hub/junction (preferably in the form of a tube) forming a distal end of the basket, the basket comprising a basket interior, each proximal strip having a proximal end attached to the proximal hub/junction, and a distal end attached to a cell, the distal body having a relaxed state wherein the distal body has a first height and a first width, and a collapsed state wherein the distal body has a second height and a second width, the second height less than the first height, the second width less than the first width; and
a catheter having an interior, a proximal end leading to the interior and a distal end leading to the interior, the catheter comprised of a biocompatible material and configured to envelop the distal body when the distal body is in the collapsed state,
wherein, in the relaxed state, the basket comprises a first pair of distal crowns not attached to another cell of the basket and pointing generally in the distal direction, the first pair of distal crowns located approximately the same distance from the proximal hub/junction and approximately 180 degrees relative to each other (e.g., between about 150 degrees and about 180 degrees relative to each other), and further wherein the basket further comprises a second pair of distal crowns not attached to another cell of the basket and pointing generally in the distal direction, the second pair of distal crowns located distally relative to, and approximately 90 degrees relative to, the first pair of distal crowns (e.g., each distal crown of the second pair of distal crowns is located approximately 60 degrees to 90 degrees relative to a distal crown of the first pair of distal crowns), the distal crowns in the second pair of distal crowns located approximately the same distance from the proximal hub/junction, wherein each distal crown of the first and second pair of distal crowns form a cell, each cell further comprising a proximal crown pointing generally in the proximal direction and connected to a memory metal strip, wherein each of the distal crowns in the first pair and second pair of distal crowns curve radially inward toward the basket interior in the relaxed state, wherein the distal crowns of the first pair of distal crowns are configured to contact each other when an exterior, external compressive force (e.g., a thrombus) is exerted on a distal crown of the first pair of distal crowns when the distal body is in the relaxed state, and further wherein the distal crowns of the second pair of distal crowns are configured to contact each other when an exterior, external compressive force (e.g., a thrombus) is exerted on a distal crown of the second pair of distal crowns when the distal body is in the relaxed state. When it is said that a proximal crown pointing generally in the proximal direction and is connected to a memory metal strip, it is meant that the proximal crown is either connected to a basket strip or a proximal strip comprised of a memory metal (e.g., nitinol). When it is said that the first pair of distal crowns are located approximately the same distance from the proximal hub/junction, it will be understood that if one of the first pair of distal crowns is located X distance from the proximal hub/junction, the other of the first pair of distal crowns is located X distance plus or minus (+/−) 3 mm, more preferably plus or minus (+/−) 0.5 mm, from the proximal hub/junction. Similarly, when it is said that the second pair of distal crowns are located approximately the same distance from the proximal hub/junction, it will be understood that if one of the second pair of distal crowns is located Y distance from the proximal hub/junction, the other of the first pair of distal crowns is located Y distance plus or minus (+/−) 3 mm, more preferably plus or minus (+/−) 0.5 mm, from the proximal hub/junction. Optionally, instead of a distal hub/junction, the basket includes an open distal end.

Optionally, the proximal hub/junction is located approximately in the center of the first height and first width in the relaxed state. For example, preferably the proximal hub/junction is located within 0.5 mm of the center of first width and the first height. Optionally, the catheter is comprised of a polymeric material (i.e., one or more polymeric materials such as silicone, PVC, latex rubber or braided nylon). Optionally, the pull wire is comprised of a biocompatible metallic material (e.g., a biocompatible metal or a biocompatible metal alloy). Optionally, in the relaxed state, the basket interior is substantially hollow. Optionally, the proximal end of a first proximal strip is located at least about 65 degrees (e.g., between about 65 and about 180 degrees) relative to the distal end of the first proximal strip, wherein the proximal end of a second proximal strip is located at least about 65 degrees (e.g., between about 65 and about 180 degrees) relative to the distal end of the second proximal strip, and further wherein the first and second proximal strips intersect adjacent and distal to the proximal hub/junction (e.g., within about 0 mm and about 4 mm of the proximal hub/junction). Optionally, each distal crown in the first and second pair of distal crowns forms part of an enlarged cell and further wherein the surface area of each enlarged cell in the relaxed state is at least twice as large as the surface area of each other individual cell of the basket and further wherein the enlarged cells are configured to allow a thrombus to pass therethrough and into the basket interior. Optionally, the pull wire is attached to the proximal hub/junction. Optionally, the basket, the proximal hub/junction and the proximal strips are comprised of a memory metal, wherein the proximal hub/junction comprises a proximal end and a distal end, and further wherein the proximal strips are integral with the distal end of the proximal hub/junction. Optionally, the distal body further comprises a lead wire extending distally from the distal hub/junction, the lead wire having a length of from about 3 mm to about 10 mm. Optionally, the distal hub/junction, the proximal hub/junction, and the basket are comprised of a nitinol having the same material composition and further wherein the proximal and the distal hubs/junctions are tubular and generally cylindrical in shape and each has an outer diameter and an inner diameter, the inner diameter forming apertures of the proximal and distal hubs/junctions and further wherein the outer diameters of the proximal and distal hubs/junctions are substantially the same size and further wherein the inner diameters of the proximal and distal hubs/junctions are substantially the same size. Optionally, the length of the distal body from the proximal hub/junction to the distal hub/junction (not including any lead wire) is from about 20 mm to about 65 mm.

Optionally, the system is used in a method of removing a blood clot from a blood vessel of an animal the method comprising the steps of:
a) providing the system;
b) positioning the system in the lumen;
c) deploying the distal body from the distal end of the catheter;
d) allowing the height and width of the distal body to increase;
e) irradiating the distal body with x-rays;
f) moving the clot into the distal basket interior; and
g) moving the distal body proximally out of the blood vessel.

Optionally, the method further comprises irradiating the distal body with x-rays at at least two different angles.

In still further embodiments, the present disclosure provides a method of manufacturing a medical device comprising:

a) providing a first tube comprised of a memory metal, the first tube having a first tube exterior, a first tube hollow interior, a first tube wall separating the first tube exterior from the first tube hollow interior, a first tube proximal end comprising a first tube proximal aperture leading to the first tube hollow interior, a first tube distal end comprising a first tube distal aperture leading to the first tube hollow interior, a first tube length extending from the first tube proximal end to the first tube distal end, a first tube perimeter generally perpendicular to the first tube length, a first tube outer width generally perpendicular to the first tube length, and a middle portion between the first tube proximal end and the first tube distal end, the middle portion having a middle portion width generally parallel to the first tube outer width;

b) using a cutting instrument to cut portions of the first tube wall and form i) a matrix in the middle portion comprising a plurality of middle portion memory metal strips forming a plurality of cells; ii) a plurality of proximal memory metal strips, each proximal memory metal strip having a proximal memory metal strip proximal end, a proximal memory metal strip distal end connected to a cell of the middle portion and a proximal memory metal strip length extending from the proximal memory metal strip proximal end to the proximal memory metal strip distal end; iii) a plurality of proximal longitudinal perforations, the plurality of longitudinal perforations non-contiguous and located in a proximal segment of each respective proximal memory metal strip and extending generally along the first tube length, a plurality of proximal longitudinal gaps, each proximal longitudinal gap separating adjacent proximal longitudinal perforations and formed from uncut portions of the first tube wall, the plurality of proximal longitudinal gaps and plurality of proximal longitudinal perforations forming first and second longitudinal sides of each proximal segment, wherein a proximal longitudinal tab is located between and connects adjacent proximal segments of adjacent proximal memory metal strips and is formed from uncut portions of the first tube wall;

c) shape setting at least the middle portion to expand the width of the middle portion;

d) after step c), polishing the first tube, wherein said polishing expands the plurality of proximal longitudinal perforations so that the proximal longitudinal gaps become smaller and adjacent proximal longitudinal perforations approach each other;

e) tearing along the plurality of proximal longitudinal perforations to free the proximal segments from the proximal longitudinal tabs and each other;

f) joining the free proximal segments of the proximal memory metal strips to form a medical device comprised of the joined proximal segments of the proximal memory metal strips, and the shape set middle portion, the medical device having a medical device length extending at least from the shape set middle portion to at least the joined proximal segments of the proximal memory metal strips and a medical device width generally perpendicular to the medical device length; and g) inserting the medical device into a catheter comprising a catheter interior having an interior width, an open catheter proximal end leading to the catheter interior, an open catheter distal end leading to the catheter interior, the catheter comprised of a biocompatible material, wherein the medical device comprises a collapsed state wherein the medical device width is less than the catheter interior width and an expanded state wherein the medical device width is greater than the catheter interior width, wherein the catheter is configured to envelope the medical device when the medical device is in the collapsed state, and further wherein the catheter interior width is less than the first tube outer width.

Optionally, the first tube is generally cylindrical in shape and comprises a first tube outer diameter forming said first tube width, wherein said catheter is generally cylindrical in shape and comprises a catheter inner diameter forming said catheter interior width, wherein said step of joining the free proximal segments of the proximal memory metal strips comprises attaching the free proximal segments of the proximal memory metal strips to a second tube, the second tube generally cylindrical in shape and comprising a second tube outer diameter, wherein said second tube outer diameter is less than said first tube outer diameter and less than said catheter inner diameter. Optionally, the second tube comprises a coil system, said coil system comprising a pull wire and at least one coil surrounding the pull wire. Optionally, step f) comprises attaching the proximal segments of the proximal memory metal strips to the coil system between the pull wire and the at least one coil. Optionally, said coil system comprises a proximal coil and a distal coil separated by a longitudinal space and said step f) comprises attaching the proximal segments of the proximal memory metal strips to the proximal and distal coils by a solder at the longitudinal space. Optionally, said pull wire comprises a pull wire proximal end, a pull wire distal end, a pull wire length extending from the pull wire proximal end to the pull wire distal end and a pull wire width generally perpendicular to the pull wire length and further wherein said pull wire width comprises a segment in which the pull wire width tapers along the pull wire length. Optionally, step b) further comprises using the cutting instrument to form iv) a plurality of distal memory metal strips, each distal memory metal strip having a distal memory metal strip distal end, a distal memory metal strip proximal end connected to a cell of the middle portion and a distal memory metal strip length extending from the distal memory metal strip proximal end to the distal memory metal strip distal end; v) a plurality of distal longitudinal perforations, the distal longitudinal perforations non-contiguous and located in a distal segment of each respective distal memory metal strip and extending generally along the first tube length, a plurality of distal longitudinal gaps, each distal longitudinal gap separating adjacent distal longitudinal perforations and formed from uncut portions of the first tube wall, the plurality of distal longitudinal gaps and plurality of distal longitudinal perforations forming first and second longitudinal sides of each distal segment, and a plurality of distal longitudinal tabs connecting adjacent distal segments of adjacent distal memory metal strips and formed from uncut portions of the first tube wall; wherein said polishing expands the plurality of distal longitudinal perforations so that the distal longitudinal gaps become smaller and adjacent distal longitudinal perforations approach each other; wherein step e) further comprises tearing along the plurality of distal longitudinal perforations to free the distal segments from the distal longitudinal tabs and each other; wherein step f) further comprises joining the free distal segments of the distal memory metal strips to form a medical device comprised of the joined proximal segments of the proximal memory metal strips, the joined distal segments of the distal memory metal strips, and the shape set middle portion, the medical device having a medical device length extending at least from the joined distal segments of the distal memory metal strips to at least the joined proximal segments of the proximal memory metal strips and a medical device width generally perpendicular to the medical device length. Optionally, said step of joining the free distal segments of the distal memory metal strips comprises attaching the free distal segments of the distal memory metal strips to a third tube, the third tube generally cylindrical in shape and comprising a third tube outer diameter, wherein said third tube outer diameter is less than said first tube outer diameter and less than said catheter inner diameter. Optionally, step b) further comprises using the cutting instrument to cut portions of the first tube wall and form a plurality of proximal perimeter perforations, the plurality of proximal perimeter perforations located adjacent to the first tube proximal end, spaced about the perimeter of the first tube and a plurality proximal perimeter gaps, each proximal perimeter gap separating adjacent proximal perimeter perforations and formed from uncut portions of the first tube wall, the plurality of proximal perimeter perforations and the proximal perimeter gaps defining a proximal end tab located at the proximal end of the first tube, wherein the proximal end of each proximal memory metal strip is connected to the proximal end tab, wherein the proximal end tab connects the proximal ends of the proximal memory metal strips, wherein said polishing expands the plurality of proximal perimeter perforations so that the proximal perimeter gaps become smaller and adjacent proximal perimeter perforations approach each other and step e) further comprises tearing along the plurality of proximal perimeter perforations to free the proximal ends of the proximal memory metal strips from the proximal end tab and each other. Optionally, the first tube is generally cylindrical in shape and comprises a first tube outer diameter and a first tube circumference and further wherein the proximal perimeter perforations are arranged in a generally straight line about the circumference of the first tube and the distal perimeter perforations are arranged in a generally straight line about the circumference of the first tube. Optionally step b) further comprises using the cutting instrument to cut portions of the first tube wall and form a plurality of distal perimeter perforations, the plurality of distal perimeter perforations located adjacent to the first tube distal end, spaced about the perimeter of the first tube and a plurality of distal perimeter gaps, each distal perimeter gap separating adjacent distal perimeter perforations and formed from uncut portions of the first tube wall, the plurality of distal perimeter perforations and the distal perimeter gaps defining a distal end tab located at the distal end of the first tube, wherein the distal end of each distal memory metal strip is connected to the distal end tab, wherein the distal end tab connects the distal ends of the distal memory metal strips, wherein said polishing expands the plurality of distal perimeter perforations so that the distal perimeter gaps become smaller and adjacent distal perimeter perforations approach each other and step e) further comprises tearing along the plurality of distal perimeter perforations to free the distal ends of the distal memory metal strips from the distal end tab and each other. Optionally, the method further comprises connecting the joined proximal memory metal strips to a pull wire. Optionally, said proximal memory metal strips comprise a width generally perpendicular to the first tube length and further wherein said widths of said proximal memory metal strips taper as the proximal memory metal strips approach the proximal end of the first tube. Optionally, after step d), the plurality of proximal longitudinal perforations become nearly continuous. Optionally, said polishing the first tube comprises electropolishing the first tube. Optionally, said middle portion memory metal strips of said shape set middle portion form a basket comprising a basket interior and a basket length generally parallel to the medical device length. Optionally, in the expanded state, the basket is configured to capture a foreign object in an interior lumen of an animal Optionally, in the expanded state, the medical device width is less than the medical device length. Optionally, said catheter interior width is at least 0.001 inches less than said first tube outer width. Optionally, after step e), the proximal memory metal strips comprise a smooth periphery. Optionally, in step b), each distal end of each proximal memory metal strip is connected to a proximal crown of a cell of the middle portion.

In still further embodiments, the present disclosure provides a method of manufacturing a medical device comprising:

a) providing a first tube comprised of a memory metal, the first tube generally cylindrical in shape having a first tube exterior, a first tube hollow interior, a first tube wall separating the first tube exterior from the first tube hollow interior, a first tube proximal end comprising a first tube proximal aperture leading to the first tube hollow interior, a first tube distal end comprising a first tube distal aperture leading to the first tube hollow interior, a first tube length extending from the first tube proximal end to the first tube distal end, a first tube circumference generally perpendicular to the first tube length, a first tube outer diameter generally perpendicular to the first tube length, and a middle portion between the first tube proximal end and the first tube distal end, the middle portion having a middle portion width generally parallel to the first tube width;

b) using a cutting instrument to cut portions of the first tube wall and form a matrix in the middle portion comprising a plurality of middle portion memory metal strips and a plurality of perforations located adjacent to the proximal and distal ends of the first tube, wherein the plurality of perforations are non-contiguous and each adjacent perforation is separated by a gap formed of uncut portions of the first tube wall;

c) shape setting at least the middle portion to expand the width of the middle portion;

d) after step c), expanding the plurality of perforations so that adjacent perforations approach each other;

e) tearing along the plurality of perforations to remove at least a portion of the proximal end and at least a portion of the distal end of the first tube and form a medical device comprised of a plurality of proximal memory metal strips, a plurality of distal memory metal strips, and the shape set middle portion, the medical device having a length extending from at least the plurality of proximal memory metal strips to at least the plurality of distal memory metal strips and a medical device width perpendicular to the medical device length;

f) joining the proximal memory metal strips by attaching the proximal memory metal strips to a second tube, the second tube generally cylindrical in shape and comprising a second tube outer diameter and joining the distal memory metal strips by attaching the distal memory metal strips to a third tube, the third tube generally cylindrical in shape and comprising a third tube outer diameter; and g) inserting the medical device into a catheter generally cylindrical in shape comprising a catheter interior having an inner diameter, an open catheter proximal end leading to the catheter interior, an open catheter distal end leading to the catheter interior, the catheter comprised of a biocompatible material, wherein the medical device comprises a collapsed state wherein the medical device width is less than the catheter inner diameter and an expanded state wherein the medical device width is greater than the catheter inner diameter, wherein the catheter is configured to envelope the medical device when the medical device is in the collapsed state, wherein the catheter inner diameter is less than the first tube outer diameter, and further wherein said second tube outer diameter and said third tube outer diameter are less than said first tube outer diameter and less than said catheter inner diameter.

In addition, the method may include one or more steps described with the method of manufacturing described above, including without limitation the method of attaching to a coil and a pull wire, the method of forming the longitudinal and perimeter perforations and tabs described above, and the method of forming the basket.

In yet still further embodiments, the present disclosure provides a method of manufacturing a medical device comprising:

a) providing a first tube comprised of a memory metal, the first tube having a first tube exterior, a first tube hollow interior, a first tube wall separating the first tube exterior from the first tube hollow interior, a first tube proximal end comprising a first tube proximal aperture leading to the first tube hollow interior, a first tube distal end comprising a first tube distal aperture leading to the first tube hollow interior, a first tube length extending from the first tube proximal end to the first tube distal end, a first tube perimeter generally perpendicular to the first tube length, a first tube outer width generally perpendicular to the first tube length, and a middle portion between the first tube proximal end and the first tube distal end, the middle portion having a middle portion width generally parallel to the first tube width;

b) using a cutting instrument to cut portions of the first tube wall and form i) a matrix in the middle portion comprising a plurality of middle portion memory metal strips forming a plurality of cells; ii) a plurality of proximal memory metal strips, each proximal memory metal strip having a proximal memory metal strip proximal end, a proximal memory metal strip distal end connected to a cell of the middle portion and a proximal memory metal strip length extending from the proximal memory metal strip proximal end to the proximal memory metal strip distal end; iii) a plurality of proximal longitudinal perforations, the plurality of longitudinal perforations non-contiguous and located in a proximal segment of each respective proximal memory metal strip and extending generally along the first tube length, a plurality of proximal longitudinal gaps, each proximal longitudinal gap separating adjacent proximal longitudinal perforations and formed from uncut portions of the first tube wall, the plurality of proximal longitudinal gaps and plurality of proximal longitudinal perforations forming first and second longitudinal sides of each proximal segment, wherein a proximal longitudinal tab is located between and connects adjacent proximal segments of proximal memory metal strips and is formed from uncut portions of the first tube wall;

c) shape setting at least the middle portion to expand the width of the middle portion;

d) after step c), polishing the first tube, wherein said polishing expands the plurality of proximal longitudinal perforations so that the proximal longitudinal gaps become smaller and adjacent proximal longitudinal perforations approach each other;

e) tearing along the plurality of proximal longitudinal perforations to free the proximal segments from the proximal longitudinal tabs and each other;

f) joining the free proximal segments of the proximal memory metal strips by attaching the proximal memory metal strips to a second tube having a second tube outer width to form a medical device comprised of the joined proximal segments of the proximal memory metal strips, and the shape set middle portion, the medical device having a medical device length extending at least from the shape set middle portion to at least the joined proximal segments of the proximal memory metal strips and a medical device width generally perpendicular to the medical device length; and g) inserting the medical device into a catheter comprising a catheter interior having an interior width, an open catheter proximal end leading to the catheter interior, an open catheter distal end leading to the catheter interior, the catheter comprised of a biocompatible material, wherein the medical device comprises a collapsed state wherein the medical device width is less than the catheter interior width and an expanded state wherein the medical device width is greater than the catheter interior width, wherein the catheter is configured to envelope the medical device when the medical device is in the collapsed state, and further wherein the second tube outer width is less than the first tube outer width.

In addition, the method may include one or more steps described with the method of manufacturing described above, including without limitation the method of attaching to a coil and a pull wire, the method of forming the perimeter perforations and tabs described above, and the shape set middle portion may be a basket.

In still further embodiments, the present disclosure provides a catheter-delivered endovascular device comprising:
a) a pull wire having a proximal end, a distal end and a pull wire longitudinal axis extending from the proximal end to the distal end;
b) a deployable dual basket system attached to the pull wire and comprising a system circumference separating a system interior from a system exterior, a system proximal end, a system distal end, a system height having a system height center, a system width perpendicular to the system height and having a system width center, a system longitudinal axis from the system proximal end to the system distal end and extending through the system height center and system width center, the deployable dual basket system comprising:
i) a proximal basket attached to the pull wire, the proximal basket comprising a proximal basket circumference separating a proximal basket interior from a proximal basket exterior, a proximal end forming the system proximal end, a distal end, a proximal basket height generally parallel to the system height, a proximal basket width generally parallel to the system width and perpendicular to the proximal basket height, a proximal basket longitudinal axis extending from the proximal basket proximal end to the proximal basket distal end and generally parallel to the system longitudinal axis and generally perpendicular to the proximal basket height and proximal basket width, a proximal junction located at the proximal end of the proximal basket, a plurality of proximal cells distal to the proximal junction and defined by a plurality of proximal basket memory metal strips, each proximal cell comprising a proximal crown located at the proximal end of the proximal cell and pointing generally in the proximal direction and a distal crown located at the distal end of the proximal cell and pointing generally in the distal direction, a plurality of proximal tether memory metal strips located between the proximal junction and the proximal cells and connecting the proximal cells to the proximal junction, each proximal tether memory metal strip having a proximal end attached to the proximal junction, a distal end attached to a proximal crown of a proximal cell, the proximal basket having a relaxed state wherein the proximal basket has a first height and a first width and a collapsed state wherein the proximal basket has a second height and a second width, the second height less than the first height and the second width less than the first width; and ii) a distal basket distal to the proximal basket and comprising a distal basket circumference separating a distal basket interior from a distal basket exterior, a proximal end, a distal end forming the system distal end, a distal basket height generally parallel to the system height, a distal basket width generally parallel to the system width and generally perpendicular to the distal basket height, a distal basket longitudinal axis extending from the distal basket proximal end to the distal basket distal end and generally parallel to the system longitudinal axis, a distal junction located at the distal end of the distal basket, a plurality of distal cells proximal to the distal junction and defined by a plurality of distal basket memory metal strips, each distal cell comprising a proximal crown located at the proximal end of the distal cell and pointing generally in the proximal direction and a distal crown located at the distal end of the distal cell and pointing generally in the distal direction, the distal basket having a relaxed state wherein the distal basket has a first height and a first width and a collapsed state wherein the distal basket has a second height and a second width, the second height less than the first height; and iii) a plurality of basket connector tether memory metal strips located between the proximal basket and the distal basket and connecting the proximal basket to the distal basket and located between the proximal basket and the distal basket, each basket connector tether memory metal strip having a proximal end attached to a distal crown of a cell located at the distal end of the proximal basket and a distal end attached to a proximal crown of a cell located at the proximal end of the distal basket; and c) a catheter having an interior, a proximal end leading to the interior and a distal end leading to the interior, the catheter comprised of a biocompatible material and configured to envelope the deployable dual basket system when the proximal basket and distal basket are in the collapsed state, wherein, in the relaxed state and the collapsed state, the basket connector tether memory metal strips rotate a degree of rotation about the system circumference relative to the proximal basket longitudinal axis, the distal basket longitudinal axis and the system longitudinal axis.

Optionally, in the relaxed state and the collapsed state, a distal crown of the proximal basket attached to the proximal end of a basket connector tether memory metal strip is offset about the system circumference relative to the proximal crown of the distal basket attached to the distal end of the same basket connector tether memory metal strip. Optionally, each basket connector tether memory metal strip rotates a greater degree of rotation in the collapsed state as compared to the degree of rotation of the same basket tether connector memory metal strip in the relaxed state. Optionally, at least some of the distal basket memory metal strips are located at the distal end of the distal basket, wherein each of the distal basket memory metal strips located at the distal end of the distal basket have a distal end, wherein each of the distal ends of the distal basket memory metal strips located at the distal end of the distal basket converge at the distal junction and further wherein the distal basket, in the relaxed state, comprises a tapered region in which the distal basket height and width decrease as the distal basket memory metal strips located at the distal end of the distal basket approach the distal junction. Optionally, the proximal basket, in the relaxed state, comprises a tapered region in which the proximal basket height and width decrease as the proximal tether memory metal strips approach the proximal junction. Optionally, in the relaxed state, except for the tapered regions and the basket connector tether memory metal strips, the deployable dual basket system has a generally tubular shape. Optionally, in the relaxed state, the radial force of the deployable dual basket system from the proximal ends of the basket connector tether memory metal strips to the distal ends of the basket connector tether memory metal strips is less than the radial force of the proximal basket, as measured from the proximal crowns of the cells of the proximal basket attached to the plurality of proximal memory metal strips to the distal crowns of the cells of the proximal basket attached to the plurality of basket connector tether memory metal strips.

Optionally, the system has two basket connector tether memory metal strips. Optionally, in the relaxed state, the basket connector tether memory metal strips each rotate at least about fifteen degrees in the same direction relative to the proximal basket longitudinal axis and the distal basket longitudinal axis. Optionally, in the collapsed state, the distal end of a first basket connector tether memory metal strip is located between about 90 degrees and about 270 degrees relative to the proximal end of the first basket connector tether memory metal strip, and further wherein in the collapsed state, the distal end of a second basket connector tether memory metal strip is located between about 90 degrees and about 270 degrees relative to the proximal end of the second connector tether memory metal strip. Optionally, in the relaxed state, the height of the proximal basket is greater than the height of the distal basket and further wherein the width of the proximal basket is greater than the width of the distal basket. Optionally, in the relaxed state, the radial force of the distal basket, as measured from the proximal crowns of the cells of the distal basket attached to the plurality of basket connector tether memory metal strips to the distal-most crown of the distal cells of the distal basket, is less than the radial force of the proximal basket, as measured from the proximal crowns of the cells of the proximal basket attached to the plurality of proximal memory metal strips to the distal crowns of the cells of the proximal basket attached to the plurality of basket connector tether memory metal strips. Optionally, in the relaxed state, the radial force of the proximal basket is substantially uniform from the proximal crowns of the cells of the proximal basket attached to the plurality of proximal memory metal strips to the distal crowns of the cells of the proximal basket attached to the plurality of basket connector tether memory metal strips. Optionally, in the relaxed state, the radial force of the distal basket is substantially uniform from the proximal crowns of the cells of the distal basket attached to the plurality of basket connector tether memory metal strips to the distal-most crown of the distal cells of the distal basket. Optionally, the proximal basket interior and the distal basket interior are generally hollow and the proximal basket cells are spaced about the circumference of the proximal basket and further wherein the distal basket cells are spaced about the circumference of the distal basket. Optionally, the basket connector tether memory metal strips do not traverse the system interior. Optionally, each of the distal crowns of the proximal basket connected to the basket connector tether memory metal strips are approximately the same distance from the proximal junction and further wherein each of the proximal crowns of the distal basket connected to the basket connector tether memory metal strips are approximately same distance from the distal junction. Optionally, each of the proximal crowns of the proximal basket and distal basket are connected to a memory metal strip extending proximally from the proximal crowns and each of the distal crowns of the proximal basket and distal basket are connected to a memory metal strip extending distally from the distal crowns. Optionally, the basket connector tether memory metal strips and the proximal tether memory metal strips form flex points of the deployable dual basket system. Optionally, in the collapsed state, the distal end of a first proximal tether memory metal strip is located between about 90 degrees and about 270 degrees relative to the proximal end of the first proximal tether memory metal strip, and further wherein in the collapsed state, the distal end of a second proximal tether memory metal strip is located between about 90 degrees and about 270 degrees relative to the proximal end of the second proximal tether memory metal strip. Optionally, the first and second proximal memory metal strips intersect adjacent and distal to the proximal junction. Optionally, the basket connector tether memory metal strips form the sole attachment of the proximal basket to the distal basket.

The present disclosure also provides a method of treating vasospasm using the catheter-delivered endovascular device to open a blood vessel. For example, the method may involve treating a human having a subarrachnoid hemorrhage induced vasospasm in a constricted blood vessel having a proximal region having a constricted height and a constricted width and a distal region having a constricted height and a constricted width, the method comprising the steps of:

a) providing the catheter-delivered endovascular device, wherein the distal basket and the proximal basket are in the collapsed state and located in the catheter interior;
b) positioning the deployable dual basket system in the blood vessel so that the distal end of the catheter is distal to the distal region of the blood vessel;
c) deploying the proximal basket and the distal basket from the distal end of the catheter into the distal region of the blood vessel;
d) allowing the height and width of the distal basket and the proximal basket to increase and cause the height and width of the distal region of the blood vessel to increase;
e) moving the deployable dual basket system proximally in the relaxed state within the blood vessel and into the proximal region to cause the height and width of the proximal region of the blood vessel to increase; and
f) withdrawing the deployable dual basket system from the blood vessel and out of the human.

Optionally, the blood vessel is lined with endothelium and the method comprises performing steps a)-f) without damaging the endothelium.

In still further embodiments, the present disclosure provides a catheter-delivered endovascular device comprising:
a) a pull wire having a proximal end, a distal end and a pull wire longitudinal axis extending from the proximal end to the distal end;
b) a deployable dual basket system attached to the pull wire and comprising a system circumference separating a system interior from a system exterior, a system proximal end, a system distal end, a system height having a system height center, a system width perpendicular to the system height and having a system width center, a system longitudinal axis from the system proximal end to the system distal end and extending through the system height center and system width center, the deployable dual basket system comprising:

i) a proximal basket attached to the pull wire, the proximal basket comprising a proximal basket circumference separating a proximal basket interior from a proximal basket exterior, a proximal end forming the system proximal end, a distal end, a proximal basket height generally parallel to the system height, a proximal basket width generally parallel to the system width and perpendicular to the proximal basket height, a proximal basket longitudinal axis extending from the proximal basket proximal end to the distal end and generally parallel to the system longitudinal axis and generally perpendicular to the proximal basket height and proximal basket width, a proximal junction located at the proximal end of the proximal basket, a plurality of proximal cells distal to the proximal junction and defined by a plurality of proximal basket memory metal strips, each proximal cell comprising a proximal crown located at the proximal end of the proximal cell and pointing generally in the proximal direction and a distal crown located at the distal end of the proximal cell and pointing generally in the distal direction, a plurality of proximal tether memory metal strips located between the proximal junction and the proximal cells and connecting the proximal cells to the proximal junction, each proximal tether memory metal strip having a proximal end attached to the proximal junction, a distal end attached to a proximal crown of a proximal cell, the proximal basket having a relaxed state wherein the proximal basket has a first height and a collapsed state wherein the proximal basket has a second height, the second height less than the first height and the second width less than the first width; and ii) a distal basket distal to the proximal basket and comprising a distal basket circumference separating a distal basket interior from a distal basket exterior, a proximal end, a distal end forming the system distal end, a distal basket height generally parallel to the system height, a distal basket width generally parallel to the system width and generally perpendicular to the distal basket height, a distal basket longitudinal axis extending from the distal basket proximal end to the distal end and generally parallel to the system longitudinal axis, a distal junction located at the distal end of the distal basket, a plurality of distal cells proximal to the distal junction and defined by a plurality of distal basket memory metal strips, each distal cell comprising a proximal crown located at the proximal end of the distal cell and pointing generally in the proximal direction and a distal crown located at the distal end of the distal cell and pointing generally in the distal direction, the distal basket having a relaxed state wherein the distal basket has a first height and a first width and a collapsed state wherein the distal basket has a second height and a second width, the second height less than the first height; and iii) a plurality of basket connector tether memory metal strips located between the proximal basket and the distal basket and connecting the proximal basket to the distal basket and located between the proximal basket and the distal basket, each basket connector tether memory metal strip having a proximal end attached to a distal crown of a cell located at the distal end of the proximal basket and a distal end attached to a proximal crown of a cell located at the proximal end of the distal basket; and c) a catheter having an interior, a proximal end leading to the interior and a distal end leading to the interior, the catheter comprised of a biocompatible material and configured to envelope the deployable dual basket system when the proximal basket and distal basket are in the collapsed state, Optionally, in the relaxed state, each basket connector tether memory metal strip rotates a degree of rotation about the system circumference relative to the proximal basket longitudinal axis, the distal basket longitudinal axis and the system longitudinal axis. Optionally, in the relaxed state, a distal crown of the proximal basket attached to the proximal end of a basket connector tether memory metal strip is offset about the system circumference relative to the proximal crown of the distal basket attached to the distal end of the same basket connector tether memory metal strip.

The present disclosure also provide a method of manufacturing a medical device comprising a proximal basket and a distal basket, the method comprising:

a) providing a first tube comprised of a memory metal, the first tube having a first tube exterior, a first tube hollow interior, a first tube wall separating the first tube exterior from the first tube hollow interior, a first tube proximal end comprising a first tube proximal aperture leading to the first tube hollow interior, a first tube distal end comprising a first tube distal aperture leading to the first tube hollow interior, a first tube length extending from the first tube proximal end to the first tube distal end, a first tube longitudinal axis generally parallel to the first tube length, a first tube perimeter generally perpendicular to the first tube length, a first tube outer width generally perpendicular to the first tube length, a proximal middle portion between the first tube proximal end and the first tube distal end, the proximal middle portion having a proximal middle portion width generally parallel to the first tube outer width, and a distal middle portion between the proximal middle portion and the distal middle portion;

b) using a cutting instrument to cut portions of the first tube wall and form a proximal matrix in the proximal middle portion comprising a plurality of proximal middle portion memory metal strips forming a plurality of proximal matrix cells, each proximal matrix cell having a proximal crown pointing generally in the proximal direction and a distal crown pointing generally in the distal direction and a proximal matrix cell length extending from the proximal crown to the distal crown and generally parallel to the first tube longitudinal axis; ii) a plurality of proximal tether memory metal strips, each proximal tether memory metal strip having a proximal tether memory metal strip proximal end, a proximal tether memory metal strip distal end connected to a proximal crown of a proximal matrix cell and a proximal tether memory metal strip length extending from the proximal tether memory metal strip proximal end to the proximal tether memory metal strip distal end, the proximal tether memory metal strips formed by moving the cutting instrument at an angle of between about 90 degrees and 270 degrees relative to the first tube longitudinal axis; iii) a distal matrix in the proximal middle portion comprising a plurality of distal middle portion memory metal strips forming a plurality of distal matrix cells, each distal matrix cell having a proximal crown pointing generally in the proximal direction and a distal crown pointing generally in the distal direction and a distal matrix cell length extending from the proximal crown to the distal crown and generally parallel to the first tube longitudinal axis; iv) a plurality of basket connector tether memory metal strips, each basket connector tether memory metal strip having a basket connector tether memory metal strip proximal end connected to a distal crown of a proximal matrix cell, a basket connector tether memory metal strip distal end connected to a proximal crown of a distal matrix cell and a basket connector tether memory metal strip length extending from the basket connector tether memory metal strip proximal end to the basket connector tether memory metal strip distal end, the basket connector tether memory metal strips formed by rotating the first tube about the first tube longitudinal axis relative to the cutting instrument so that the proximal end of a basket connector tether memory metal strip is located between about 90 degrees and about 270 degrees relative to the distal end of the same basket connector tether memory metal strip; and v) a plurality of proximal longitudinal perforations, the plurality of longitudinal perforations non-contiguous and located in a proximal segment of each respective proximal memory metal strip and extending generally along the first tube length, a plurality of proximal longitudinal gaps, each proximal longitudinal gap separating adjacent proximal longitudinal perforations and formed from uncut portions of the first tube wall, the plurality of proximal longitudinal gaps and plurality of proximal longitudinal perforations forming first and second longitudinal sides of each proximal segment, wherein a proximal longitudinal tab is located between and connects adjacent proximal segments of adjacent proximal memory metal strips and is formed from uncut portions of the first tube wall;

c) shape setting at least the proximal middle portion and the distal middle portion to expand the width of the proximal middle portion and the distal middle portion and form a proximal basket comprised of the proximal matrix cells and a distal basket comprised of the distal matrix cells, the proximal basket and the distal basket connected by the basket connector tether memory metal strips;

d) after step c), polishing the first tube, wherein said polishing expands the plurality of proximal longitudinal perforations so that the proximal longitudinal gaps become smaller and adjacent proximal longitudinal perforations approach each other;

e) tearing along the plurality of proximal longitudinal perforations to free the proximal segments from the proximal longitudinal tabs and each other;

f) joining the free proximal segments of the proximal tether memory metal strips to form a medical device comprised of the joined proximal segments of the proximal tether memory metal strips, the proximal basket, the basket connector tether memory metal strips and the distal basket, the medical device having a medical device length extending at least from the distal basket to at least the joined proximal segments of the proximal tether memory metal strips and a medical device width generally perpendicular to the medical device length; and g) inserting the medical device into a catheter comprising a catheter interior having an interior width, an open catheter proximal end leading to the catheter interior, an open catheter distal end leading to the catheter interior, the catheter comprised of a biocompatible material, wherein the medical device comprises a collapsed state wherein the medical device width is less than the catheter interior width and a relaxed state wherein the medical device width is greater than the catheter interior width, wherein the catheter is configured to envelope the medical device when the medical device is in the collapsed state, and further wherein the catheter interior width is less than the first tube outer width.

The present disclosure also provides a system for removing objects from an interior lumen of an animal, the system comprising: a pull wire having a proximal end and a distal end; a distal body attached to the pull wire, the distal body comprising a distal body perimeter separating a distal body interior from a distal body exterior, a proximal end having a proximal end center, a distal end having distal end center, a distal body length extending from the proximal end to the distal end, a longitudinal axis extending through the proximal end center and the distal end center and parallel to the distal body length, a proximal junction forming the proximal end of the distal body, a basket comprising a proximal portion comprised of a plurality of proximal cells spaced about the distal body perimeter and formed by a plurality of basket memory metal strips and a distal portion located adjacent to a distal end of the basket and connected to the proximal portion at at least one connection point, the proximal portion comprising a proximal portion interior, the distal portion comprised of a plurality of distal braided mesh openings formed by a plurality of woven linear strands, the distal portion having a perimeter, each woven linear strand rotating about the distal portion perimeter relative to the distal body longitudinal axis a plurality of times in a helical fashion, the distal basket comprising a basket interior, the distal body having a relaxed state wherein the distal body has a first height and a first width, and a collapsed state wherein the distal body has a second height and a second width, the second height less than the first height, the second width less than the first width; and a catheter having an interior, a proximal end leading to the interior and a distal end leading to the interior, the catheter comprised of a biocompatible material and configured to envelope the distal body when the distal body is in the collapsed state.

Optionally, in the relaxed state, the median surface area of the proximal cells is larger than the median surface area of the distal braided mesh openings. Optionally, in the relaxed state, the median radial force of the distal portion is substantially less than the median radial force of the proximal portion. Optionally, the radial force of the proximal portion through its connection to the distal portion at the at least one connection point is configured to cause the distal portion to move to the relaxed state when the proximal portion moves from the collapsed state to the relaxed state. Optionally, the proximal portion and the distal portion each have a length generally parallel to the distal body length, the proximal portion and distal portion lengths configured to elongate upon moving from the relaxed state to the collapsed state. Optionally, upon moving from the relaxed state to the collapsed state, the length of the distal portion is configured to elongate a greater percentage as compared to the elongation of the proximal portion. Optionally, the woven linear strands rotate about the distal portion perimeter relative to the distal body longitudinal axis a fewer number of times per unit of distance in the collapsed state as compared to the relaxed state.

Optionally, in the relaxed state, the distal portion comprises at least a segment distal to the proximal portion. Optionally, the distal portion is located in the proximal portion interior. Optionally, the distal basket further comprises a distal junction comprising a proximal end, the proximal end of the distal junction forming the distal end of the basket, wherein the basket strips and the distal woven strands are attached to the distal junction and the at least one connection point is the distal junction. Optionally, the distal junction is a tube. Optionally, the proximal portion, but not the distal portion, is configured to alter the shape of a curved intracranial artery. Optionally, in the relaxed state, the distal portion is more flexible than the proximal portion. Optionally, distal portion in the relaxed state comprises a tapered region in which the distal body height and width decrease as the woven linear strands approach the distal end of the distal basket. Optionally, in the relaxed state, the basket interior is substantially hollow. Optionally, the proximal portion comprises a distal end comprising between two and four basket memory metal strip distal ends and further wherein each woven linear strand comprises a proximal end attached to a basket memory metal strip distal end. Optionally, the distal portion comprises at least two woven linear strands attached to each basket memory metal strip distal end. Optionally, in the relaxed state, the proximal portion comprises an interior surface facing the distal body interior and the distal portion comprises an outer surface facing and connected to the proximal portion interior surface, and further wherein at least a segment of the distal portion is interior to the proximal portion in the relaxed state. Optionally, each woven linear strand comprises a free proximal end and further wherein all free proximal ends of the woven linear strands are located in the proximal portion interior in the relaxed state. Optionally, the distal portion is configured to elongate proximally and distally relative to the proximal portion and the at least one connection point upon moving from the relaxed state to the collapsed state. Optionally, the distal portion is attached to the proximal portion by at least two connection points, and further wherein said at least two connection points are located a different distance from the proximal junction in the relaxed state, and further wherein said at least two connection points are located a different distance from the proximal junction in the collapsed state. Optionally, in the relaxed state, the distal portion impedes blood flow to a greater extent than the proximal portion when the proximal portion and the distal portion are placed in a blood vessel. Optionally the distal portion is configured to reduce blood flow by at least 25% when the distal portion is placed in a blood vessel. Optionally, the distal body further comprises a plurality of proximal strips, each proximal strip having a distal end attached to a proximal cell and a proximal end, the proximal ends of the proximal strips converging at the proximal junction. Optionally, in the relaxed state, the proximal portion comprises a first pair of distal crowns not attached to another cell of the basket and pointing generally in the distal direction, the distal crowns in the first pair of distal crowns located approximately the same distance from the proximal junction and between 150 degrees and 180 degrees relative to each other, and further wherein the basket further comprises a second pair of distal crowns not attached to another cell of the basket and pointing generally in the distal direction, the second pair of distal crowns located distally relative to the first pair of distal crowns, each of the distal crowns in the second pair of distal crowns located between 60 degrees and 90 degrees relative to a distal crown in the first pair of distal crowns, the distal crowns in the second pair of distal crowns located approximately the same distance from the proximal junction, each of the distal crowns forming a portion of a proximal cell, wherein each distal crown in the first and second pair of distal crowns forms part of a different enlarged proximal cell, each enlarged proximal cell having a center,
wherein the centers of the enlarged proximal cells of the first pair of distal crowns are approximately 180 degrees relative to each other (i.e., 150 degrees to 180 degrees relative to each other) and approximately 90 degrees relative to the centers of the enlarged cells of the second pair of distal crowns (i.e., between 60 degrees and 90 degrees relative to the centers of the enlarged cells of the second pair of distal crowns),
wherein the surface area of the enlarged proximal cells in the relaxed state is greater than the surface area of the other cells of the basket,
wherein the enlarged proximal cells are configured to allow a thrombus to pass therethrough and into the basket interior.

Optionally, the distal portion is radiopaque. Optionally, the system is used in a method of removing a blood clot from a blood vessel of an animal, the method comprising the steps of: a) providing the system; b) positioning the system in the blood vessel; c) deploying the distal body from the distal end of the catheter; d) allowing the height and width of the distal body to increase; e) moving the blood clot into the basket interior; and f) moving the distal body proximally out of the blood vessel. Optionally, the method further includes applying contrast dye proximally and distally to the blood clot.

In still further embodiments, the present disclosure provides a system for removing objects from an interior lumen of an animal, the system comprising: a pull wire having a proximal end and a distal end; a distal body comprising a distal body proximal end comprising a distal body proximal junction attached to the pull wire, a distal body distal end comprising a distal body distal junction, a distal body length extending from the distal body proximal end to the distal body distal end, a distal body longitudinal axis extending from the distal body proximal junction to the distal body distal junction, and a distal body height and width perpendicular to the distal body length. The distal body may include a distal body outer body (also referred to herein as the proximal portion of the distal body) extending from the distal body proximal end to the distal body distal end, the distal body outer body comprising the distal body proximal junction and the distal body distal junction, the distal body outer body comprising a distal body outer body perimeter separating a distal body outer body interior from a distal body outer body exterior, the distal body outer body comprising a basket comprised of a plurality of cells spaced about the distal body outer body perimeter and formed by a plurality of basket memory metal strips, wherein at least some of the basket memory metal strips are located at a distal end of the basket, wherein each of the basket strips located at the distal end of the basket have a distal end, and wherein each of the distal ends of the basket strips located at the distal end of the basket converge at, and are attached to, the distal junction. The distal body may also include a distal body inner body (also referred to herein as the distal portion of the distal body) comprised of a plurality of braided mesh openings formed by a plurality of woven linear strands, the distal body inner body having a distal body inner body perimeter, each woven linear strand rotating about the distal body inner body perimeter relative to the distal body longitudinal axis a plurality of times in a helical fashion, the distal body inner body comprising a distal body inner body proximal end and a distal body inner body distal end. Optionally, in the relaxed state, the proximal ends of at least some of the woven linear strands are adjacent to the interior surface of at least some of the basket memory metal strips.

Optionally, the distal body has a relaxed state wherein the distal body has a first height and a first width, and a collapsed state wherein the distal body has a second height and a second width, the second height less than the first height, the second width less than the first width. Optionally, the system further comprises a catheter having an interior, a proximal end leading to the interior and a distal end leading to the interior, the catheter comprised of a biocompatible material and configured to envelope the distal body when the distal body is in the collapsed state. Optionally, at least some (preferably all) of the woven linear strand comprises a free proximal end and a distal end attached to the distal junction. Optionally, in the relaxed state, the median surface area of the cells is larger than the median surface area of the braided mesh openings. Optionally, the distal body inner body and the distal body outer body each have a length generally parallel to the distal body length, the distal body inner body and distal body outer body lengths configured to elongate upon moving from the relaxed state to the collapsed state. Optionally, upon moving from the relaxed state to the collapsed state, the length of the distal body inner body is configured to elongate a greater percentage than the length of the distal body outer body. Optionally, upon moving from the relaxed state to the collapsed state, the distal body inner body is configured to elongate proximally within the distal body outer body interior toward the distal body proximal junction. Optionally, in the relaxed state, the distal body inner body proximal end is located a first distance distal from the distal body proximal junction. Optionally, in the collapsed state, the distal body inner body proximal end is located a second distance distal from the proximal junction, the second distance less than the first distance. Optionally, in the collapsed state and in the relaxed state, the distal body inner body is located in the distal body outer body interior. Optionally, the woven linear strands rotate about the distal body inner body perimeter relative to the distal body longitudinal axis a fewer number of times per unit of length in the collapsed state as compared to the relaxed state. Optionally, the basket memory metal strips are located on the distal body outer body perimeter and comprise an interior surface facing the distal body outer body interior and an exterior surface opposite the interior surface, and further wherein in the relaxed state, at least a portion of the woven linear strands are adjacent to and preferably contact the interior surface of at least a portion of the basket memory metal strips. Optionally, the proximal ends of the woven linear strands are free floating within the distal body outer body interior.

Optionally, the distal junction is the sole connection point of the distal body inner body to the distal body outer body. Optionally, the distal junction is a tube. Optionally, in the relaxed state, the distal body outer body, but not the distal body inner body, is configured to alter the shape of a curved intracranial artery. Optionally, in the relaxed state, the distal body inner body is more flexible than the distal body outer body and wherein, in the relaxed state, the median radial force of the distal body inner body is substantially less than the median radial force of the distal body outer body. Optionally, wherein the distal body inner body comprises a distal body inner body height and a distal body inner body width, wherein the distal body inner body in the relaxed state comprises a distal body inner body distal tapered region in which the distal body inner body height and the distal body inner body width decrease as the strand distal ends approach the distal junction, wherein the distal body outer body comprises a distal body outer body height and a distal body outer body width, and further wherein the distal body outer body comprises a tapered region in which the distal body inner body height and the distal body inner body width decrease as the distal ends of the basket memory metal strips located at the distal end of the basket approach the distal junction. Optionally, in the relaxed state, the distal body inner body impedes blood flow to a greater extent than the distal body outer body when the distal body outer body and the distal body inner body are placed in a blood vessel. Optionally, the distal body inner body is configured to reduce blood flow by at least 25% when the distal body inner body is placed in a blood vessel. Optionally, in the relaxed state, the distal body outer body comprises a first pair of distal crowns not attached to another cell of the basket and pointing generally in the distal direction, the distal crowns in the first pair of distal crowns located approximately the same distance from the proximal junction and between 150 degrees and 180 degrees relative to each other. Optionally, the basket further comprises a second pair of distal crowns not attached to another cell of the basket and pointing generally in the distal direction, the second pair of distal crowns located distally relative to the first pair of distal crowns, each of the distal crowns in the second pair of distal crowns located between 60 degrees and 90 degrees relative to a distal crown in the first pair of distal crowns. Optionally, distal crowns in the second pair of distal crowns are located approximately the same distance from the proximal junction, each of the distal crowns forming a portion of a cell. Optionally, each distal crown in the first and second pair of distal crowns forms part of a different enlarged cell. Optionally, each enlarged cell has a center, wherein the centers of the enlarged cells of the first pair of distal crowns are between 150 degrees and 180 degrees relative to each other and between 60 degrees and 90 degrees relative to the centers of the enlarged cells of the second pair of distal crowns. Optionally, the surface area of the enlarged cells in the relaxed state is greater than the surface area of the other cells of the basket. Optionally, the enlarged cells are configured to allow a thrombus to pass therethrough and into the basket interior. Optionally, in the relaxed state, the distal body inner body is located distally relative to the first and second pair of distal crowns. Optionally, the distal body inner body is radiopaque. Optionally, in the relaxed state, the distal body inner body length is no more than about 33% of the distal body outer body length.

The present disclosure also provides a method of removing a blood clot from a blood vessel of an animal, the method comprising the steps of: a) providing the system; b) positioning the system in the blood vessel; c) deploying the distal body from the distal end of the catheter; d) allowing the height and width of the distal body to increase; e) moving the blood clot into an interior of the distal body outer body; and f) moving the distal body proximally out of the blood vessel.

Optionally, the distal body outer body further comprises a plurality of proximal strips, each proximal strip having a distal end attached to a proximal crown of a cell and a proximal end, the proximal ends of the proximal strips converging at the distal body proximal junction.

In still further embodiments, the present disclosure also provides a system for removing objects from an interior lumen of an animal, the system comprising: a pull wire having a proximal end and a distal end; a distal body comprising a distal body proximal end comprising a distal body proximal junction attached to the pull wire, a distal body distal end comprising a distal body distal junction, a distal body length extending from the distal body proximal end to the distal body distal end, a distal body longitudinal axis extending from the distal body proximal junction to the distal body distal junction, and a distal body height and width perpendicular to the distal body length. The distal body may include a distal body outer body extending from the distal body proximal end to the distal body distal end, the distal body outer body comprising the distal body proximal junction and the distal body distal junction, the distal body outer body comprising a distal body outer body perimeter separating a distal body outer body interior from a distal body outer body exterior, the distal body outer body comprising a basket comprised of a plurality of cells spaced about the distal body outer body perimeter and formed by a plurality of basket memory metal strips. Optionally, at least some of the basket memory metal strips are located at a distal end of the basket, wherein each of the basket strips located at the distal end of the basket have a distal end, and wherein each of the distal ends of the basket strips located at the distal end of the basket converge at, and are attached to, the distal junction. Optionally, the system further includes a distal body inner body comprised of a plurality of braided mesh openings formed by a plurality of woven linear strands, the distal body inner body having a distal body inner body perimeter, each woven linear strand rotating about the distal body inner body perimeter relative to the distal body longitudinal axis a plurality of times in a helical fashion, the distal body inner body comprising a distal body inner body proximal end and a distal body inner body distal end. Optionally, the distal body has a relaxed state wherein the distal body has a first height and a first width, and a collapsed state wherein the distal body has a second height and a second width, the second height less than the first height, the second width less than the first width. Optionally, the system further comprises a catheter having an interior, a proximal end leading to the interior and a distal end leading to the interior, the catheter comprised of a biocompatible material and configured to envelope the distal body when the distal body is in the collapsed state. Optionally, the woven linear strands comprise a proximal end and a distal end, and at least some (preferably all) of the distal ends of the woven linear strands are attached to the distal junction. Optionally, in the relaxed state, the median surface area of the cells is larger than the median surface area of the braided mesh openings. Optionally, the distal body inner body and the distal body outer body each have a length generally parallel to the distal body length, the distal body inner body and distal body outer body lengths configured to elongate upon moving from the relaxed state to the collapsed state. Optionally, upon moving from the relaxed state to the collapsed state, the length of the distal body inner body is configured to elongate a greater percentage than the length of the distal body outer body. Optionally, upon moving from the relaxed state to the collapsed state, the distal body inner body is configured to elongate proximally within the distal body outer body interior toward the distal body proximal junction. Optionally, in the relaxed state, the distal body inner body proximal end is located a first distance distal from the distal body proximal junction. Optionally, in the collapsed state, the distal body inner body proximal end is located a second distance distal from the proximal junction, the second distance less than the first distance. Optionally, in the collapsed state and in the relaxed state, the distal body inner body is located in the distal body outer body interior. Optionally, the woven linear strands rotate about the distal body inner body perimeter relative to the distal body longitudinal axis a fewer number of times per unit of length in the collapsed state as compared to the relaxed state. Optionally, the proximal ends of at least some (preferably all) of the woven linear strands converge at and are attached to a distal body inner body proximal junction. Optionally, the distal body inner body proximal junction forms the proximal end of the distal body inner body and is free floating within the distal body outer body interior.

Optionally, the basket memory metal strips are located on the distal body outer body perimeter and comprise an interior surface facing the distal body outer body interior and an exterior surface opposite the interior surface, and further wherein in the relaxed state, at least a portion of the woven linear strands contact the interior surface of at least a portion of the basket memory metal strips. Optionally, the distal body inner body proximal junction is located approximately in the center of the distal body height and the distal body width in the relaxed state. Optionally, the distal body inner body in the relaxed state comprises a distal body inner body proximal tapered region in which the distal body inner body height and the distal body inner body width decrease as the proximal ends of the woven linear strands approach the distal body inner body proximal junction. Optionally, the distal junction is the sole connection point of the distal body inner body to the distal body outer body. Optionally, the distal body outer body further comprises a plurality of proximal strips, each proximal strip having a distal end attached to a proximal crown of a cell and a proximal end, the proximal ends of the proximal strips converging at the distal body proximal junction. Optionally, the proximal ends of each of the woven linear strands converge at and are attached to the distal body inner body proximal junction and further wherein the distal ends of each of the woven linear strands converge at and are attached to the distal body distal junction. Optionally, in the relaxed state, the distal body inner body is more flexible than the distal body outer body and wherein, in the relaxed state, the median radial force of the distal body inner body is substantially less than the median radial force of the distal body outer body. Optionally, the distal body inner body comprises a distal body inner body height and a distal body inner body width, wherein the distal body inner body in the relaxed state comprises a distal body inner body distal tapered region in which the distal body inner body height and the distal body inner body width decrease as the strand distal ends approach the distal junction, wherein the distal body outer body comprises a distal body outer body height and a distal body outer body width, and further wherein the distal body outer body comprises a tapered region in which the distal body inner body height and the distal body inner body width decrease as the distal ends of the basket memory metal strips located at the distal end of the basket approach the distal junction. Optionally, in the relaxed state, the distal body inner body impedes blood flow to a greater extent than the distal body outer body when the distal body outer body and the distal body inner body are placed in a blood vessel. Optionally, the distal body inner body is configured to reduce blood flow by at least 25% when the distal body inner body is placed in a blood vessel. Optionally, in the relaxed state, the distal body outer body comprises a first pair of distal crowns not attached to another cell of the basket and pointing generally in the distal direction, the distal crowns in the first pair of distal crowns located approximately the same distance from the proximal junction and between 150 degrees and 180 degrees relative to each other. Optionally, the basket further comprises a second pair of distal crowns not attached to another cell of the basket and pointing generally in the distal direction. Optionally, the second pair of distal crowns are located distally relative to the first pair of distal crowns. Optionally, each of the distal crowns in the second pair of distal crowns is located between 60 degrees and 90 degrees relative to a distal crown in the first pair of distal crowns. Optionally, the distal crowns in the second pair of distal crowns located approximately the same distance from the proximal junction, each of the distal crowns forming a portion of a cell. Optionally, each distal crown in the first and second pair of distal crowns forms part of a different enlarged cell, each enlarged cell having a center. Optionally, the centers of the enlarged cells of the first pair of distal crowns are between 150 degrees and 180 degrees relative to each other and between 60 degrees and 90 degrees relative to the centers of the enlarged cells of the second pair of distal crowns. Optionally, the surface area of the enlarged cells in the relaxed state is greater than the surface area of the other cells of the basket. Optionally, the enlarged cells are configured to allow a thrombus to pass therethrough and into the basket interior. Optionally, in the relaxed state, the distal body inner body is located distally relative to the first and second pair of distal crowns. Optionally, the distal body inner body is radiopaque. Optionally, in the relaxed state, the distal body inner body length is no more than about 33% of the distal body outer body length.

In still further embodiments, the present disclosure provides a method of removing a blood clot from a blood vessel of an animal, the method comprising the steps of: a) providing the system; b) positioning the system in the blood vessel; c) deploying the distal body from the distal end of the catheter; d) allowing the height and width of the distal body to increase; e) moving the blood clot into an interior of the distal body outer body; and f) moving the distal body proximally out of the blood vessel.

In still further embodiments, the present disclosure provides a system for removing objects from an interior lumen of an animal, the system comprising: a pull wire having a proximal end and a distal end; a distal body comprising a distal body proximal end comprising a distal body proximal junction (which may be attached to the pull wire), a distal body distal end comprising a distal body distal junction, a distal body length extending from the distal body proximal end to the distal body distal end, a distal body longitudinal axis extending from the distal body proximal junction to the distal body distal junction, and a distal body height and width perpendicular to the distal body length. The distal body may comprise a distal body outer body extending from the distal body proximal end to the distal body distal end, the distal body outer body comprising the distal body proximal junction and the distal body distal junction. The distal body outer body may comprise a distal body outer body perimeter separating a distal body outer body interior from a distal body outer body exterior. The distal body outer body may comprise a basket comprised of a plurality of cells spaced about the distal body outer body perimeter and formed by a plurality of basket memory metal strips. At least some of the basket memory metal strips may be located at a distal end of the basket. Each of the basket strips located at the distal end of the basket may have a distal end, and each of the distal ends of the basket strips located at the distal end of the basket may converge at, and be attached to, the distal junction. The distal body may also include a distal body inner body comprised of a plurality of braided mesh openings formed by a plurality of woven linear strands. The distal body inner body may have a distal body inner body perimeter. Each woven linear strand may rotate about the distal body inner body perimeter relative to the distal body longitudinal axis a plurality of times in a helical fashion. The distal body inner body may comprise a distal body inner body proximal end and a distal body inner body distal end. Optionally, the distal body has a relaxed state wherein the distal body has a first height and a first width, and a collapsed state wherein the distal body has a second height and a second width, the second height less than the first height, the second width less than the first width. Optionally, the system further comprises a catheter having an interior, a proximal end leading to the interior and a distal end leading to the interior, the catheter comprised of a biocompatible material and configured to envelope the distal body when the distal body is in the collapsed state. Optionally, the woven linear strands comprise a proximal end and a distal end, and at least some of the distal ends of the woven linear strands are attached to the distal junction. Optionally, in the relaxed state, the median surface area of the cells is larger than the median surface area of the braided mesh openings. Optionally, the distal body inner body and the distal body outer body each have a length generally parallel to the distal body length, and optionally, the distal body inner body and distal body outer body lengths are configured to elongate upon moving from the relaxed state to the collapsed state. Optionally, upon moving from the relaxed state to the collapsed state, the length of the distal body inner body is configured to elongate a greater percentage than the length of the distal body outer body. Optionally, upon moving from the relaxed state to the collapsed state, the distal body inner body is configured to elongate proximally within the distal body outer body interior toward the distal body proximal junction. Optionally, in the relaxed state, the distal body inner body proximal end is located a first distance distal from the distal body proximal junction. Optionally, in the collapsed state, the distal body inner body proximal end is located a second distance distal from the distal body proximal junction, the second distance less than the first distance. Optionally, in the collapsed state and in the relaxed state, the distal body inner body is located in the distal body outer body interior. Optionally, the woven linear strands rotate about the distal body inner body perimeter relative to the distal body longitudinal axis a fewer number of times per unit of length in the collapsed state as compared to the relaxed state. Optionally, the proximal ends of at least some of the woven linear strands converge at and are attached to a distal body inner body proximal junction. Optionally, the distal body inner body proximal junction forms the proximal end of the distal body inner body.

Optionally, the system further comprises a tether connecting the distal body proximal junction to the distal body inner body proximal junction. Optionally, the tether is a segment of the pull wire. Optionally, the tether is comprised of a conductive material. Optionally, the tether is comprised of a synthetic polymer. Optionally, the tether comprises a proximal end attached to the distal body proximal junction and a distal end attached to the distal body inner body proximal junction. (The attachment can be soldering, welding, crimping, etc.). Optionally, the tether is located approximately in the center of the distal body height and the distal body width of the distal body when the distal body is in the relaxed state and the tether is generally parallel to the distal body longitudinal axis when the distal body is in the relaxed state. Optionally, the basket memory metal strips are located on the distal body outer body perimeter and comprise an interior surface facing the distal body outer body interior and an exterior surface opposite the interior surface, and further wherein in the relaxed state, at least some of the woven linear strands contact the interior surface of at least some of the basket memory metal strips. Optionally, the distal body inner body proximal junction is located approximately in the center of the distal body height and the distal body width in the relaxed state. Optionally, the distal body inner body comprises a distal body inner body height and a distal body inner body width and wherein the distal body inner body in the relaxed state comprises a distal body inner body proximal tapered region in which the distal body inner body height and the distal body inner body width decrease as the proximal ends of the woven linear strands approach the distal body inner body proximal junction. Optionally, the distal junction is the sole connection point of the distal body inner body to the distal body outer body. Optionally, the distal body outer body further comprises a plurality of proximal strips, each proximal strip having a distal end attached to a proximal crown of a cell and a proximal end, the proximal ends of the proximal strips converging at the distal body proximal junction. Optionally, the proximal ends of each of the woven linear strands converge at and are attached to the distal body inner body proximal junction and further wherein the distal ends of each of the woven linear strands converge at and are attached to the distal body distal junction. Optionally, in the relaxed state, the distal body inner body is more flexible than the distal body outer body and wherein, in the relaxed state, the median radial force of the distal body inner body is substantially less than the median radial force of the distal body outer body. Optionally, the distal body inner body comprises a distal body inner body height and a distal body inner body width, wherein the distal body inner body in the relaxed state comprises a distal body inner body distal tapered region in which the distal body inner body height and the distal body inner body width decrease as the strand distal ends approach the distal junction, wherein the distal body outer body comprises a distal body outer body height and a distal body outer body width, and further wherein the distal body outer body comprises a tapered region in which the distal body inner body height and the distal body inner body width decrease as the distal ends of the basket memory metal strips located at the distal end of the basket approach the distal junction. Optionally, in the relaxed state, the distal body inner body impedes blood flow to a greater extent than the distal body outer body when the distal body outer body and the distal body inner body are placed in a blood vessel. Optionally, the distal body inner body is configured to reduce blood flow by at least 25% when the distal body inner body is placed in a blood vessel. Optionally, in the relaxed state, the distal body outer body comprises a first pair of distal crowns not attached to another cell of the basket and pointing generally in the distal direction, the distal crowns in the first pair of distal crowns located approximately the same distance from the proximal junction and located between 150 degrees and 180 degrees relative to each other, and further wherein the basket further comprises a second pair of distal crowns not attached to another cell of the basket and pointing generally in the distal direction, the second pair of distal crowns located distally relative to the first pair of distal crowns, each of the distal crowns in the second pair of distal crowns located between 60 degrees and 90 degrees relative to a distal crown in the first pair of distal crowns, the distal crowns in the second pair of distal crowns located approximately the same distance from the distal body proximal junction, each of the distal crowns forming a portion of a cell, wherein each distal crown in the first and second pair of distal crowns forms part of a different enlarged cell, each enlarged cell having a center, wherein the centers of the enlarged cells of the first pair of distal crowns are between 150 degrees and 180 degrees relative to each other and between 60 degrees and 90 degrees relative to the centers of the enlarged cells of the second pair of distal crowns, wherein the surface area of the enlarged cells in the relaxed state is greater than the surface area of the other cells of the basket, and wherein the enlarged cells are configured to allow a thrombus to pass therethrough and into the basket interior.

Optionally, in the relaxed state, the distal body inner body is located distally relative to the first and second pair of distal crowns. Optionally, the distal body inner body is radiopaque. Optionally, in the relaxed state, the distal body inner body length is no more than about 33% of the distal body outer body length.

In still further embodiments, the present disclosure provides a method of removing a blood clot from a blood vessel of an animal, the method comprising the steps of: a) providing the system; b) positioning the system in the blood vessel; c) deploying the distal body from the distal end of the catheter; d) allowing the height and width of the distal body to increase; e) moving the blood clot into the interior of the distal body outer body; and f) moving the distal body proximally out of the blood vessel.

Optionally the system further comprises a tether connecting the distal body proximal junction to the distal body inner body proximal junction. Optionally, the method further comprises propagating an electrical charge from the pull wire, through the tether, and to the distal body inner body.

In still further embodiments, the present disclosure provides a system for removing objects from an interior lumen of an animal, the system comprising: a pull wire having a proximal end and a distal end; a distal body attached to the pull wire and comprising a distal body proximal end comprising a distal body proximal junction, a distal body distal end comprising a distal body distal junction, a distal body length extending from the distal body proximal end to the distal body distal end, a distal body longitudinal axis extending from the distal body proximal junction to the distal body distal junction, and a distal body height and width perpendicular to the distal body length. The distal body may comprise a distal body outer body extending from the distal body proximal end to the distal body distal end, the distal body outer body comprising the distal body proximal junction and the distal body distal junction, the distal body outer body comprising a distal body outer body perimeter separating a distal body outer body interior from a distal body outer body exterior, the distal body outer body comprising a basket comprised of a plurality of cells spaced about the distal body outer body perimeter and formed by a plurality of basket memory metal strips. Optionally, at least some of the basket memory metal strips are located at a distal end of the basket. Optionally, each of the basket memory metal strips located at the distal end of the basket have a distal end. Optionally, each of the distal ends of the basket memory metal strips located at the distal end of the basket converge at, and are attached to, the distal body distal junction. The distal body may also include a distal body inner body comprised of a plurality of braided mesh openings formed by a plurality of woven linear strands, the distal body inner body having a distal body inner body perimeter, each woven linear strand rotating about the distal body inner body perimeter relative to the distal body longitudinal axis a plurality of times in a helical fashion, the distal body inner body comprising a distal body inner body proximal end and a distal body inner body distal end.

Optionally, the distal body has a relaxed state wherein the distal body has a first height and a first width, and a collapsed state wherein the distal body has a second height and a second width, the second height less than the first height, the second width less than the first width. Optionally, the system further comprises a catheter having an interior, a proximal end leading to the interior and a distal end leading to the interior, the catheter comprised of a biocompatible material and configured to envelope the distal body when the distal body is in the collapsed state. Optionally, the woven linear strands comprise a proximal end and a distal end, and at least some of the distal ends of the woven linear strands are attached to the distal junction. Optionally, in the relaxed state, the median surface area of the cells is larger than the median surface area of the braided mesh openings. Optionally, the distal body inner body and the distal body outer body each have a length generally parallel to the distal body length, the distal body inner body and distal body outer body lengths configured to elongate upon moving from the relaxed state to the collapsed state. Optionally, upon moving from the relaxed state to the collapsed state, the length of the distal body inner body is configured to elongate a greater percentage than the length of the distal body outer body. Optionally, upon moving from the relaxed state to the collapsed state, the distal body inner body is configured to elongate proximally within the distal body outer body interior toward the distal body proximal junction. Optionally, in the relaxed state, the distal body inner body proximal end is located a first distance distal from the distal body proximal junction. Optionally, in the collapsed state, the distal body inner body proximal end is located a second distance distal from the distal body proximal junction, the second distance less than the first distance. Optionally, in the collapsed state and in the relaxed state, the distal body inner body is located in the distal body outer body interior. Optionally, the woven linear strands rotate about the distal body inner body perimeter relative to the distal body longitudinal axis a fewer number of times per unit of length in the collapsed state as compared to the relaxed state. Optionally, the distal body inner body comprises an active agent when the distal body inner body is in the catheter interior.

Optionally, the active agent is selected from the group consisting of a reolytic agent, a neuroprotective agent and combinations thereof. Optionally, the active agent is located in the distal body inner body interior. Optionally, the active agent is too large to pass through the braided mesh openings when the distal body inner body is located in the catheter interior. Optionally, the woven linear strands are coated with the active agent. Optionally, the basket memory metal strips are not coated with the active agent. Optionally, the proximal ends of at least some of the woven linear strands converge at and are attached to a distal body inner body proximal junction, the distal body inner proximal junction located distal relative to the distal body proximal junction. Optionally, the distal body inner body proximal junction forms the proximal end of the distal body inner body. Optionally, the system further comprises a tether connecting the distal body proximal junction to the distal body inner body proximal junction. Optionally, the tether is a segment of the pull wire. Optionally, the tether is comprised of a conductive material. Optionally, the tether is comprised of a synthetic polymer. Optionally, the tether comprises a proximal end attached to the distal body proximal junction and a distal end attached to the distal body inner body proximal junction. Optionally, the tether is located approximately in the center of the distal body height and the distal body width of the distal body when the distal body is in the relaxed state and the tether is generally parallel to the distal body longitudinal axis when the distal body is in the relaxed state. Optionally, the distal body outer body further comprises a plurality of proximal strips, each proximal strip having a distal end attached to a proximal crown of a cell and a proximal end, the proximal ends of the proximal strips converging at the distal body proximal junction. Optionally, the proximal ends of each of the woven linear strands converge at and are attached to the distal body inner body proximal junction and further wherein the distal ends of each of the woven linear strands converge at and are attached to the distal body distal junction. Optionally, the basket memory metal strips are located on the distal body outer body perimeter and comprise an interior surface facing the distal body outer body interior and an exterior surface opposite the interior surface, and further wherein in the relaxed state, at least some of the woven linear strands contact the interior surface of at least some of the basket memory metal strips. Optionally, the distal junction is the sole connection point of the distal body inner body to the distal body outer body. Optionally, in the relaxed state, the distal body inner body is more flexible than the distal body outer body and wherein, in the relaxed state, the median radial force of the distal body inner body is substantially less than the median radial force of the distal body outer body. Optionally, the distal body inner body comprises a distal body inner body height and a distal body inner body width, wherein the distal body inner body in the relaxed state comprises a distal body inner body distal tapered region in which the distal body inner body height and the distal body inner body width decrease as the strand distal ends approach the distal junction, wherein the distal body outer body comprises a distal body outer body height and a distal body outer body width, and further wherein the distal body outer body comprises a tapered region in which the distal body inner body height and the distal body inner body width decrease as the distal ends of the basket memory metal strips located at the distal end of the basket approach the distal junction. Optionally, in the relaxed state, the distal body inner body impedes blood flow to a greater extent than the distal body outer body when the distal body outer body and the distal body inner body are placed in a blood vessel. Optionally, the distal body inner body is configured to reduce blood flow by at least 25% when the distal body inner body is placed in a blood vessel. Optionally, in the relaxed state, the distal body outer body comprises a first pair of distal crowns not attached to another cell of the basket and pointing generally in the distal direction, the distal crowns in the first pair of distal crowns located approximately the same distance from the proximal junction and located between 150 degrees and 180 degrees relative to each other, and further wherein the basket further comprises a second pair of distal crowns not attached to another cell of the basket and pointing generally in the distal direction, the second pair of distal crowns located distally relative to the first pair of distal crowns, each of the distal crowns in the second pair of distal crowns located between 60 degrees and 90 degrees relative to a distal crown in the first pair of distal crowns, the distal crowns in the second pair of distal crowns located approximately the same distance from the proximal junction, each of the distal crowns forming a portion of a cell, wherein each distal crown in the first and second pair of distal crowns forms part of a different enlarged cell, each enlarged cell having a center, wherein the centers of the enlarged cells of the first pair of distal crowns are between 150 degrees and 180 degrees relative to each other and between 60 degrees and 90 degrees relative to the centers of the enlarged cells of the second pair of distal crowns, wherein the surface area of the enlarged cells in the relaxed state is greater than the surface area of the other cells of the basket, wherein the enlarged cells are configured to allow a thrombus to pass therethrough and into the basket interior.

Optionally, in the relaxed state, the distal body inner body is located distally relative to the first and second pair of distal crowns. Optionally, the distal body inner body is radiopaque. Optionally, in the relaxed state, the distal body inner body length is no more than about 33% of the distal body outer body length.

The present disclosure provides a method of removing a blood clot from a blood vessel of an animal, the method comprising the steps of: a) providing the system; b) positioning the system in the blood vessel; c) deploying the distal body from the distal end of the catheter; d) allowing the height and width of the distal body to increase; e) moving the blood clot into the interior of the distal body outer body; f) before, after or simultaneous with step e) delivering the active agent from the distal body inner body into the blood vessel; and g) moving the distal body proximally out of the blood vessel.

Optionally, the proximal ends of at least some of the woven linear strands converge at and are attached to a distal body inner body proximal junction, the distal body inner proximal junction located distal relative to the distal body proximal junction, and further wherein the system further comprises a tether connecting the distal body proximal junction to the distal body inner body proximal junction. Optionally, the method further comprises propagating an electrical charge from the pull wire, through the tether, and to the distal body inner body to deliver the active agent from the distal body inner body into the blood vessel.

The present disclosure also provides a system for removing objects from an interior lumen of an animal, the system comprising: a pull wire having a proximal end and a distal end; a distal body attached to the pull wire and comprising a distal body proximal end comprising a distal body proximal junction, a distal body distal end comprising a distal body distal junction, a distal body length extending from the distal body proximal end to the distal body distal end, a distal body longitudinal axis extending from the distal body proximal junction to the distal body distal junction, and a distal body height and width perpendicular to the distal body length. The distal body may comprise a distal body outer body extending from the distal body proximal end to the distal body distal end, the distal body outer body comprising the distal body proximal junction and the distal body distal junction, the distal body outer body comprising a distal body outer body perimeter separating a distal body outer body interior from a distal body outer body exterior, the distal body outer body comprising a basket comprised of a plurality of cells spaced about the distal body outer body perimeter and formed by a plurality of basket memory metal strips. Optionally, at least some of the basket memory metal strips are located at a distal end of the basket. Optionally, each of the basket memory metal strips located at the distal end of the basket have a distal end. Optionally, each of the distal ends of the basket memory strips located at the distal end of the basket converge at, and are attached to, the distal body distal junction. Optionally, the distal body may also include a distal body inner body comprised of a plurality of braided mesh openings formed by a plurality of woven linear strands, the distal body inner body having a distal body inner body perimeter, each woven linear strand rotating about the distal body inner body perimeter relative to the distal body longitudinal axis a plurality of times in a helical fashion, the distal body inner body comprising a distal body inner body proximal end and a distal body inner body distal end.

Optionally, the distal body has a relaxed state wherein the distal body has a first height and a first width, and a collapsed state wherein the distal body has a second height and a second width, the second height less than the first height, the second width less than the first width. Optionally, the system further comprises a catheter having an interior, a proximal end leading to the interior and a distal end leading to the interior, the catheter comprised of a biocompatible material and configured to envelope the distal body when the distal body is in the collapsed state. Optionally, the woven linear strands comprise a proximal end and a distal end, and at least some of the distal ends of the woven linear strands are attached to the distal junction. Optionally, in the relaxed state, the median surface area of the cells is larger than the median surface area of the braided mesh openings. Optionally, the distal body inner body and the distal body outer body each have a length generally parallel to the distal body length, the distal body inner body and distal body outer body lengths configured to elongate upon moving from the relaxed state to the collapsed state. Optionally, upon moving from the relaxed state to the collapsed state, the length of the distal body inner body is configured to elongate a greater percentage than the length of the distal body outer body. Optionally, upon moving from the relaxed state to the collapsed state, the distal body inner body is configured to elongate proximally within the distal body outer body interior toward the distal body proximal junction. Optionally, in the relaxed state, the distal body inner body proximal end is located a first distance distal from the distal body proximal junction. Optionally, in the collapsed state, the distal body inner body proximal end is located a second distance distal from the distal body proximal junction, the second distance less than the first distance. Optionally, in the collapsed state and in the relaxed state, the distal body inner body is located in the distal body outer body interior. Optionally, the woven linear strands rotate about the distal body inner body perimeter relative to the distal body longitudinal axis a fewer number of times per unit of length in the collapsed state as compared to the relaxed state. Optionally, the pull wire is in the form of an active agent delivery catheter having an open proximal end and an open distal end, the active agent delivery catheter configured to deliver an active agent to the distal body.

Optionally, the active agent delivery catheter distal end is located distal relative to the distal body proximal junction. Optionally, the active agent delivery catheter comprises a wall, wherein the distal body outer body further comprises a plurality of proximal strips, each proximal strip having a distal end attached to a proximal crown of a cell and a proximal end and a proximal end attached to the wall of the active agent delivery catheter.

The present disclosure also provides a method of removing a blood clot from a blood vessel of an animal, the method comprising the steps of: a) providing a system comprising a distal body outer body having one or more features described above, a distal body inner body located in the distal body outer body interior and having one or more features described above, a pull wire, a catheter and an active agent delivery catheter; b) positioning the system in the blood vessel; c) deploying the distal body outer body and distal body inner body from the distal end of the catheter; d) allowing the height and width of the distal body to increase; e) moving the blood clot into the interior of the distal body outer body; f) before, after or simultaneous with step e), delivering an active agent from the active agent delivery catheter to the into the blood vessel; and g) moving the distal body outer body and distal body inner body proximally out of the blood vessel.

In still further embodiments, the present disclosure provides a system for removing objects from an interior lumen of an animal. The system may include a pull wire having a proximal end and a distal end. Optionally, the system may also include a distal body attached to the pull wire and comprising a distal body proximal end comprising a distal body proximal junction, a distal body distal end comprising a distal body distal junction, a distal body length extending from the distal body proximal end to the distal body distal end, a distal body longitudinal axis extending from the distal body proximal junction to the distal body distal junction, and a distal body height and width perpendicular to the distal body length. Optionally, the distal body further comprises a distal body outer body that may extend from the distal body proximal end to the distal body distal end, the distal body outer body may comprise the distal body proximal junction and the distal body distal junction, the distal body outer body may comprise a distal body outer body perimeter separating a distal body outer body interior from a distal body outer body exterior, the distal body outer body may comprise a basket comprised of a plurality of cells spaced about the distal body outer body perimeter and formed by a plurality of basket memory metal strips. Optionally, at least some of the basket memory metal strips are located at a distal end of the basket, wherein each of the basket memory metal strips located at the distal end of the basket have a distal end, and wherein each of the distal ends of the basket memory metal strips located at the distal end of the basket converge at, and are attached to, the distal body distal junction. Optionally, the distal body further comprises a distal body inner body that may be comprised of a plurality of braided mesh openings formed by a plurality of woven linear strands, the distal body inner body may have a distal body inner body perimeter, each woven linear strand rotating about the distal body inner body perimeter relative to the distal body longitudinal axis a plurality of times in a helical fashion, the distal body inner body may comprise a distal body inner body proximal end and a distal body inner body distal end. Optionally, the distal body has a relaxed state wherein the distal body has a first height and a first width, and a collapsed state wherein the distal body has a second height and a second width, the second height less than the first height, the second width less than the first width. Optionally, the system further comprises a catheter having an interior, a proximal end leading to the interior and a distal end leading to the interior, the catheter comprised of a biocompatible material and configured to envelope the distal body when the distal body is in the collapsed state. Optionally, the woven linear strands comprise a proximal end and a distal end, and at least some of the distal ends of the woven linear strands are attached to the distal body distal junction. Optionally, in the relaxed state, the median surface area of the cells is larger than the median surface area of the braided mesh openings. Optionally, the distal body inner body and the distal body outer body each have a length generally parallel to the distal body length, the distal body inner body and distal body outer body lengths configured to elongate upon moving from the relaxed state to the collapsed state. Optionally, upon moving from the relaxed state to the collapsed state, the length of the distal body inner body is configured to elongate a greater percentage than the length of the distal body outer body. Optionally, upon moving from the relaxed state to the collapsed state, the distal body inner body is configured to elongate proximally within the distal body outer body interior toward the distal body proximal junction. Optionally, in the relaxed state, the distal body inner body proximal end is located a first distance distal from the distal body proximal junction. Optionally, in the collapsed state, the distal body inner body proximal end is located a second distance distal from the distal body proximal junction, the second distance less than the first distance. Optionally, in the collapsed state and in the relaxed state, the distal body inner body is located in the distal body outer body interior. Optionally, the woven linear strands rotate about the distal body inner body perimeter relative to the distal body longitudinal axis a fewer number of times per unit of length in the collapsed state as compared to the relaxed state. Optionally, the proximal ends of at least some of the woven linear strands converge at and are attached to a distal body inner body proximal junction. Optionally, the distal body inner body proximal junction forms the proximal end of the distal body inner body. Optionally, the system further comprises a tether connecting the distal body proximal junction to the distal body inner body proximal junction, the tether comprising a segment in the form of a helical coil, the helical coil having a coil length generally parallel to the distal body length, the helical coil having an expanded state in which the helical coil has a first length and a relaxed state in which the helical coil has a second length, the first length greater than the second length.

Optionally, the helical coil is adjacent to the distal body inner body proximal junction. Optionally, the helical coil is configured to move to the expanded state when tension is exerted on the tether. Optionally, the tether is a segment of the pull wire. Optionally, the tether is comprised of a conductive material. Optionally, the tether is comprised of a synthetic polymer. Optionally, the tether comprises a proximal end attached to the distal body proximal junction and a distal end attached to the distal body inner body proximal junction. Optionally, the tether is located approximately in the center of the distal body height and the distal body width when the distal body is in the relaxed state and the tether is generally parallel to the distal body longitudinal axis when the distal body is in the relaxed state. Optionally, the basket memory metal strips are located on the distal body outer body perimeter and comprise an interior surface facing the distal body outer body interior and an exterior surface opposite the interior surface, and further wherein in the relaxed state, at least some of the woven linear strands contact the interior surface of at least some of the basket memory metal strips. Optionally, the distal body inner body proximal junction is located approximately in the center of the distal body height and the distal body width in the relaxed state. Optionally, the distal body inner body comprises a distal body inner body height and a distal body inner body width and wherein the distal body inner body in the relaxed state comprises a distal body inner body proximal tapered region in which the distal body inner body height and the distal body inner body width decrease as the proximal ends of the woven linear strands approach the distal body inner body proximal junction. Optionally, in the relaxed state, the basket does not have any free crowns that point generally in the proximal direction. Optionally, the distal body outer body further comprises a plurality of proximal strips, each proximal strip having a distal end attached to a proximal crown of a cell and a proximal end, the proximal ends of the proximal strips converging at the distal body proximal junction. Optionally, the proximal ends of each of the woven linear strands converge at and are attached to the distal body inner body proximal junction and further wherein the distal ends of each of the woven linear strands converge at and are attached to the distal body distal junction. Optionally, in the relaxed state, the distal body inner body is more flexible than the distal body outer body and wherein, in the relaxed state, the median radial force of the distal body inner body is substantially less than the median radial force of the distal body outer body. Optionally, the distal body inner body comprises a distal body inner body height and a distal body inner body width, wherein the distal body inner body in the relaxed state comprises a distal body inner body distal tapered region in which the distal body inner body height and the distal body inner body width decrease as the woven linear strand distal ends approach the distal body distal junction, wherein the distal body outer body comprises a distal body outer body height and a distal body outer body width, and further wherein the distal body outer body comprises a tapered region in which the distal body outer body height and the distal body outer body width decrease as the distal ends of the basket memory metal strips located at the distal end of the basket approach the distal body distal junction. Optionally, in the relaxed state, the distal body inner body impedes blood flow to a greater extent than the distal body outer body when the distal body outer body and the distal body inner body are placed in a blood vessel. Optionally, wherein, prior to removal of an obstruction, the distal body inner body is configured to automatically reduce blood flow when the distal body inner body is placed in a blood vessel. Optionally, in the relaxed state, the distal body outer body comprises a first pair of distal crowns not attached to another cell of the basket and pointing generally in the distal direction, the distal crowns in the first pair of distal crowns located approximately the same distance from the distal body proximal junction and located between 150 degrees and 180 degrees relative to each other, and further wherein the basket further comprises a second pair of distal crowns not attached to another cell of the basket and pointing generally in the distal direction, the second pair of distal crowns located distally relative to the first pair of distal crowns, each of the distal crowns in the second pair of distal crowns located between 60 degrees and 90 degrees relative to a distal crown in the first pair of distal crowns, the distal crowns in the second pair of distal crowns located approximately the same distance from the distal body proximal junction, each of the distal crowns forming a portion of a cell, wherein each distal crown in the first and second pair of distal crowns forms part of a different enlarged cell, each enlarged cell having a center,
wherein the centers of the enlarged cells of the first pair of distal crowns are between 150 degrees and 180 degrees relative to each other and between 60 degrees and 90 degrees relative to the centers of the enlarged cells of the second pair of distal crowns,
wherein the enlarged cells are configured to allow a thrombus to pass therethrough and into the basket interior. Optionally, in the relaxed state, the distal body inner body proximal junction is located distally relative to the first and second pair of distal crowns. Optionally, the distal body inner body is radiopaque. Optionally, in the relaxed state, the distal body inner body length is no more than about 33% of the distal body outer body length. Optionally, the system further comprises a lead wire extending distally from the distal body distal junction. Optionally, the distal body inner body proximal end is substantially closed. Optionally, the system is used in
a method of removing a blood clot from a blood vessel of an animal, the method comprising the steps of: a) providing the system; b) positioning the system in the blood vessel; c) deploying the distal body from the distal end of the catheter; d) allowing the height and width of the distal body to increase; e) moving the blood clot into the interior of the distal body outer body; and f)
moving the distal body proximally out of the blood vessel. Optionally, the method further comprises propagating an electrical charge from the pull wire, through the tether, and to the distal body inner body.

BRIEF DESCRIPTION OF THE DRAWINGS

in FIG. 2A, the tube is shown as though it were flat for purposes of illustrating the cut pattern only.

in FIG. 2C, the tube is rotated as compared to FIG. 2B.

FIGS. 3A-3H illustrate a method of manufacturing a distal body of one embodiment of the present invention using the laser cut memory metal tube of FIGS. 1 and 2; in FIGS. 3A-3H, the basket portion of the distal body is not shown for simplicity of illustration.

in FIGS. 4A-4D, the basket portion of the distal body is not shown for simplicity of illustration.

in FIG. 8, the basket portion of the distal body is not shown for simplicity of illustration.

in FIG. 9, the basket portion of the distal body is not shown for simplicity of illustration.

in FIG. 10, the basket portion of the distal body is not shown for simplicity of illustration.

in FIG. 26, the user has locked the syringe lever at the desired volume.

in FIG. 27, the suction catheter has partially sucked the distal body and clot into the suction catheter.

in FIG. 28, the suction catheter has completely sucked the distal body and clot into the suction catheter.

in FIG. 34, the tube is shown as though it were flat for purposes of illustrating the cut pattern only.

in FIG. 35, the tube is shown as though it were flat for purposes of illustrating the cut pattern only.

in FIG. 36, the tube is shown as though it were flat for purposes of illustrating the cut pattern only.

in FIG. 37, the tube is shown as though it were flat for purposes of illustrating the cut pattern only.

in FIG. 38, the tube is shown as though it were flat for purposes of illustrating the cut pattern only.

in FIG. 39, the tube is shown as though it were flat for purposes of illustrating the cut pattern only.

FIG. 43E, FIG. 43F and FIG. 43G illustrate stepwise, side elevation views of the proximal ends of the proximal memory metal strips of FIG. 42 being soldered to the coil system of FIG. 43D; as shown in FIG. 43F and FIG. 43G, the proximal memory strips are placed between the core and the coil.

in FIG. 47, the middle portion is in the form of a basket with offset enlarged areas/drop zones adjacent to crowns pointing generally in the distal direction; FIG. 47 also includes proximal memory metal strips having a free proximal end and a distal end connected to a proximal cell of the basket and distal memory metal strips having a free distal end and a proximal end connected to a distal cell of the basket.

in FIG. 49, only longitudinal perforations are present, and as with FIG. 46, the line is merely drawn in to show how each proximal memory metal strips tapers adjacent to the proximal end of the respective proximal memory metal strips (and the line is not present in the device).

FIG. 50 illustrates a side elevation view of a deployable dual basket system of another embodiment of the present invention.

FIG. 51 illustrates another side elevation view of the deployable dual basket system of FIG. 50; as compared to FIG. 50, the deployable dual basket system has been rotated 90 degrees.

in FIG. 52, the tube is shown as though it were flat for purposes of illustrating the cut pattern only.

in FIG. 53A, the tube is shown as though it were flat for purposes of illustrating the cut pattern only.

in FIG. 53B, the tube is shown as though it were flat for purposes of illustrating the cut pattern only.

in FIG. 57 the basket is in the relaxed state.

in FIG. 59 the basket is in the partially collapsed state.

in FIG. 61, the basket is in the relaxed state and a segment of the distal portion is located in the proximal portion interior.

in FIG. 62, the basket is in the partially collapsed state.

FIG. 63 illustrates a side elevation view of a deployable basket system of another embodiment of the present invention; in FIG. 63, the basket is in the relaxed state.

FIG. 64 illustrates a side elevation view of the deployable basket system of FIG. 63; in FIG. 64, the basket is in the partially collapsed state.

in FIG. 65, the deployable basket system is at an initial step of deployment from the catheter.

BEST MODE FOR CARRYING OUT THE INVENTION

Figure 1A:
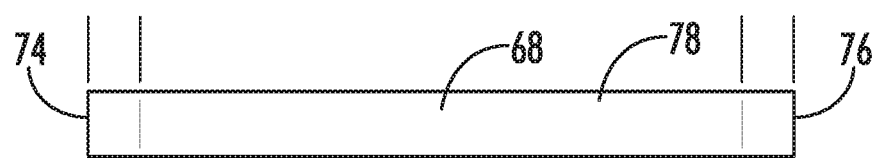
FIG. 1A illustrates a side, elevation view of a memory metal tube prior to being cut by a laser.
Figure 1B:
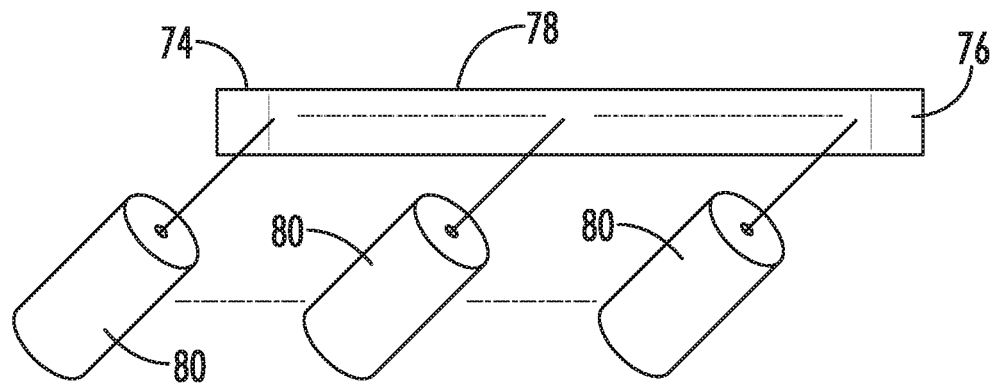
FIG. 1B illustrates a side, elevation view of the memory metal tube of FIG. 1A being cut by a laser.

With reference to FIGS. 1-10, the present disclosure provides a deployable system, generally designated by the numeral 10, for removing an obstruction such as a blood clot 12 or other object from a blood vessel 14 or other interior lumen of an animal. In addition to a blood clot 12, the obstruction may be, for example, extruded coils during aneurysm treatment, intravascular embolic material such as onyx or other obstructions requiring mechanical intravascular removal from small distal vessels. In the drawings, not all reference numbers are included in each drawing for the sake of clarity.

Referring further to FIGS. 1-10, the deployable system 10 includes a pull wire 16 that has a proximal end (not shown) and a distal end 20. Optionally, the diameter of the pull wire is between about 0.008 inches and about 0.051 inches. Preferably, the pull wire 16 is comprised of a biocompatible metallic material.

The system 10 further includes a distal body 22, which is attached to the pull wire 16. The distal body 22 has a proximal end 24, a distal end 26, an interior 28, and an exterior 30. The distal body 22 has a collapsed state, wherein the distal body 22 has a first height and width and is configured to fit into a catheter 50 (see FIG. 10A), and a relaxed state wherein the distal body 22 has a different height 32 and width and is configured to expand to about the height and width of a human blood vessel 14 when the distal body 22 is deployed from the catheter 50 (see FIGS. 10B-G). The distal body 22 further includes a proximal hub/junction 74 and a distal hub/junction 76 that is located distal relative to the proximal hub/junction 74. In some embodiments, the distal body 22 includes a plurality of strips 40 comprised of a memory metal (e.g., a memory metal alloy such as nitinol) that form the proximal end 24 of the distal body 22. Optionally, the proximal memory metal strips 40 each have a distal end 44 and a proximal end 42 that forms an openable and closeable claw 46. Optionally, the proximal memory metal strips 40 are attached to the proximal hub/junction 74 through connector memory metal strips 48. In such embodiments, the proximal hub/junction 74 may be slideable along at least a segment of the pull wire 16, in contrast to the distal hub/junction 76, which is optionally fixed to the pull wire 16 and not slideable along the pull wire 16. Moving the proximal hub/junction 74 distally and closer to the distal hub/junction 76 (i.e., shortening the distance 88 between the proximal hub/junction 74 and distal hub/junction 76 by moving the proximal hub/junction 74 distally while keeping the distal hub/junction 76 stationary) exerts tension on the connector memory metal strips 48 and, in turn, the proximal memory metal strips 40. This tension, in turn, causes the proximal ends 42 of the proximal memory metal strips 40 to move radially toward each other and the pull wire 16. As the proximal ends 42 of the proximal memory metal strips 40 move radially toward each other and the pull wire 16, the claw 46 (formed by the proximal memory metal strips 40) is brought from the open position to at least a partially closed position, which in turn, separates the obstruction 12 from the wall of the human lumen 14 and captures the obstruction 12. See FIG. 3H, FIG. 8, FIG. 9F, and FIGS. 10F and 10G. Conversely, preferably, movement of the proximal hub/junction 74 proximally and away from the distal hub/junction 76 (i.e., increasing the distance 88 between the hubs/junctions 74 and 76) releases the tension in the proximal memory metal strips 40, which in turn, causes the proximal ends 42 of the proximal memory metal strips 40 to move away from each other and the pull wire 16, opening the claw 46. The claw 46 and proximal hub/junction 74 form several functions. First, as described, closing of the claw 46 captures the obstruction 12. Second, closing the claw 46 retracts the claw 46 from the wall of the lumen 14 so that the claw 46 does not scrape against (and damage) the lumen wall while capturing the obstruction 12. Third, closing the claw 46 reduces the height and width of the distal body 22, which allows the distal body 22 to be re-sheathed in the catheter 50, which may be desired, for example, if the operator seeks to re-deploy the distal body 22 in another location in the body (which may be the case if the operator originally deploys the distal body 22 in the wrong location in the lumen 14). For purposes of the present invention, "closing the claw" embraces both partially closing the claw 46 (where the proximal ends 42 of the proximal memory metal strips 40 do not contact the pull wire 16) and fully closing the claw 46 (where the proximal ends 42 contact the pull wire 16).

The claw 46 may be comprised of any number of proximal memory metal strips 40. Preferably, however, between 2 and 4 proximal memory metal strips 40 comprise the claw 46 (it being understood that the connector strips 48, if present, merely serve to tether the claw 46 to the proximal hub/junction 74). Preferably, the proximal memory metal strips 40 have a length of between about 10 and about 60 millimeters. The proximal memory metal strips 40 can be thought of as arms of the claw 46.

In some embodiments, the connector strips 48 are integral with the proximal hub/junction 74 (i.e., formed from the same piece of memory metal). In other embodiments, the proximal hub/junction 74 may be welded or soldered to the connector strips 48. Optionally, in the relaxed state, the proximal memory metal strips 42 are distributed substantially evenly about a perimeter of the distal body 22.

Optionally, the distal body 22 includes a lead wire 52 extending distally from the distal body 22. Optionally, the lead wire 52 extends distally from the distal hub/junction 76. If present, the lead wire 52 may be used to facilitate movement of the system 10 in the lumen 14.

Figure 2A:
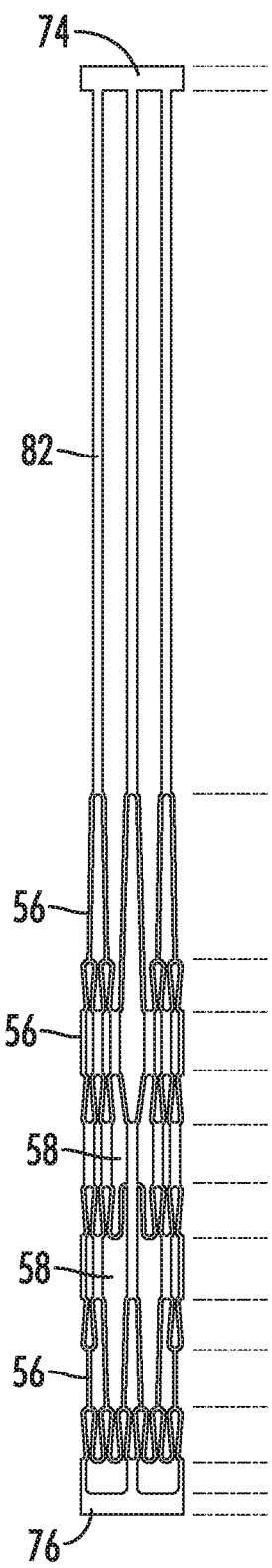
FIG. 2A illustrates a side, elevation view of the memory metal tube of FIG. 1B after being cut by a laser.
Figure 2B:
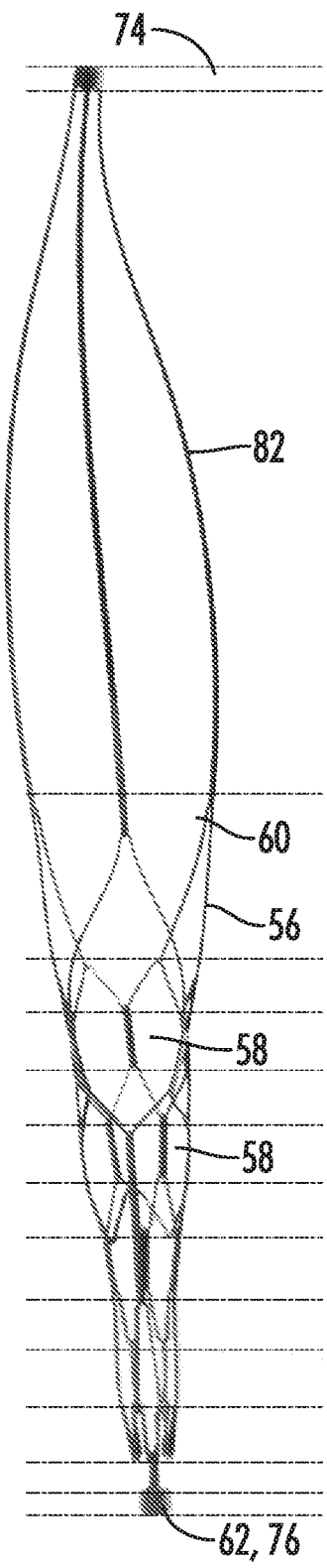
FIG. 2B illustrates a side, perspective view of the memory metal tube of FIG. 1B after being cut by a laser.
Figure 2C:
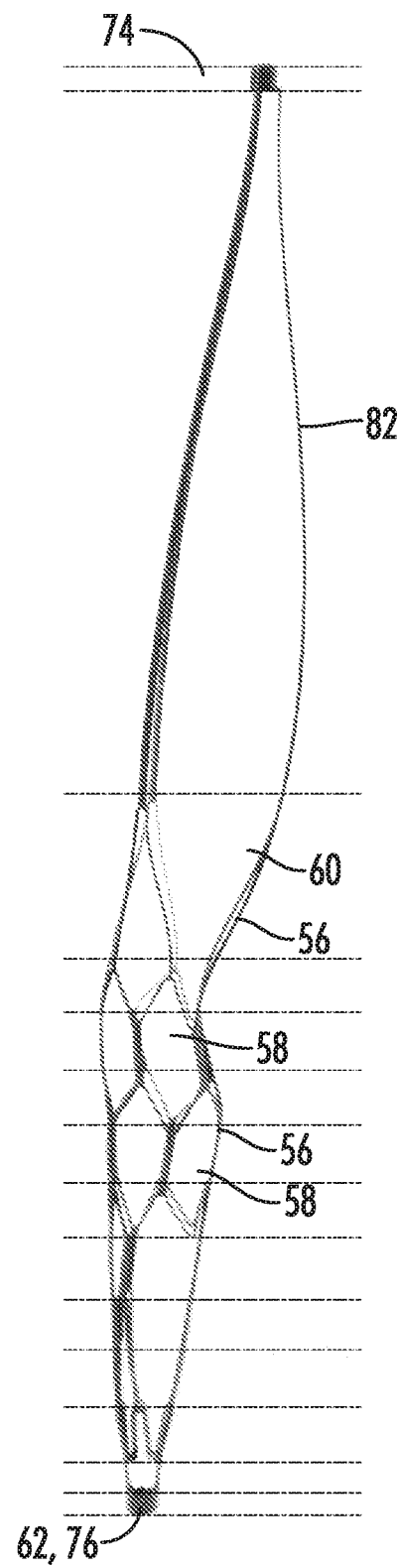
FIG. 2C illustrates another side, perspective view of the memory metal tube of FIG. 1B after being cut by a laser.
Figure 4A:
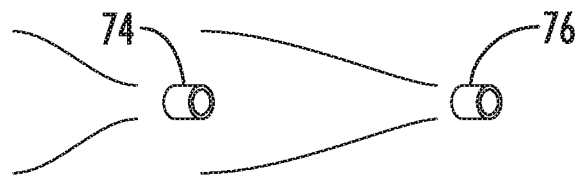
FIGS. 4A-4D illustrate the welding steps of the method of manufacturing shown in FIG. 3.
Figure 4B:
Figure 4C:
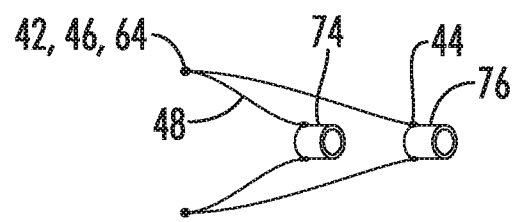
Figure 4D:
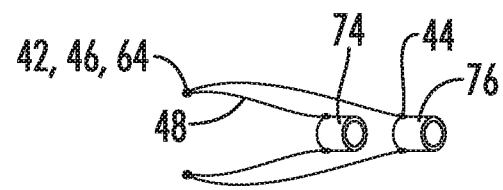
Figure 5:
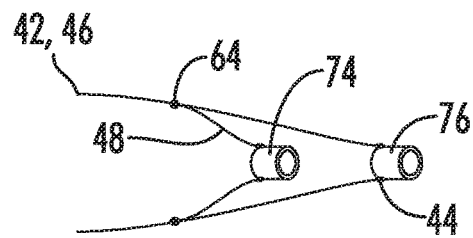
FIGS. 5 and 6 illustrate different locations that connector strips may be welded to the proximal memory metal strips.
Figure 6:
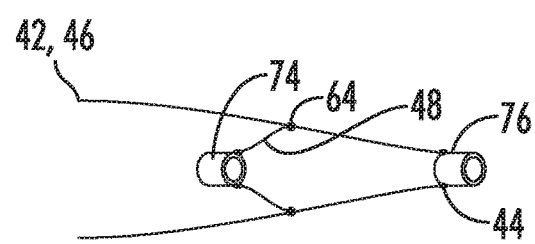
Figure 7:
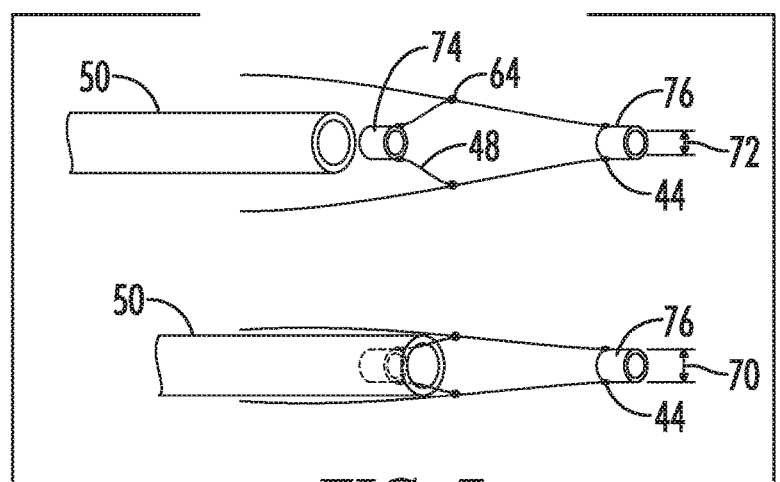
FIG. 7 illustrates a side, elevation view of a catheter and the distal body of FIG. 6.
Figure 8:
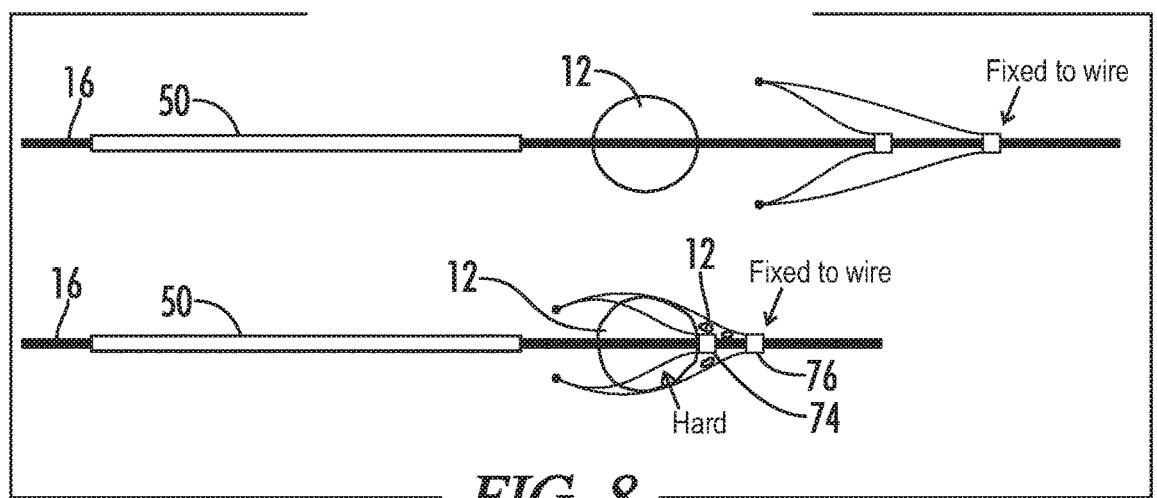
FIG. 8 illustrates a side, elevation view of a deployable system of one embodiment of the present invention being used to capture a blood clot.
Figure 9:
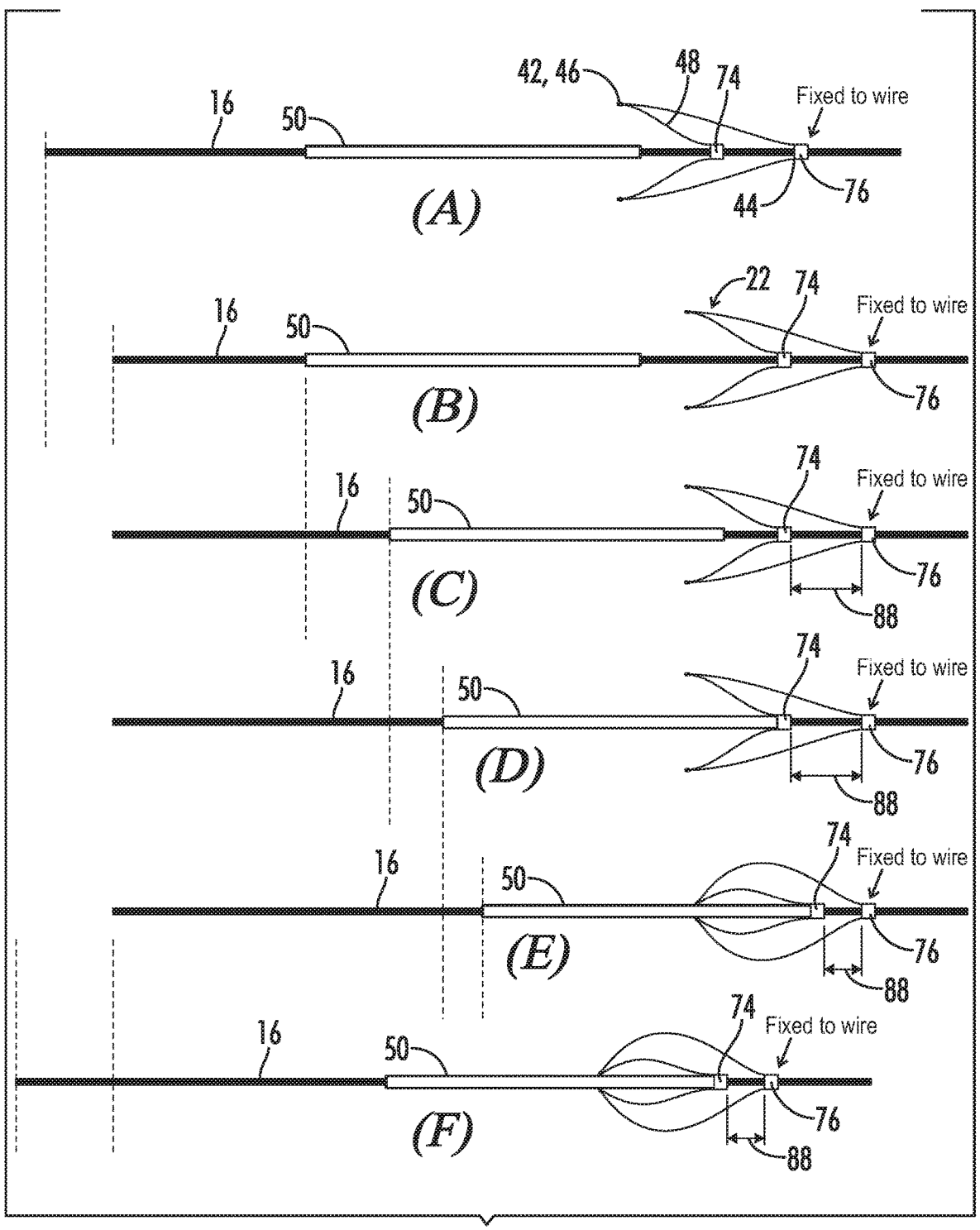
FIG. 9 illustrates a side, elevation view of a claw of one embodiment of the present invention being closed by a claw actuator tube.
Figure 10:
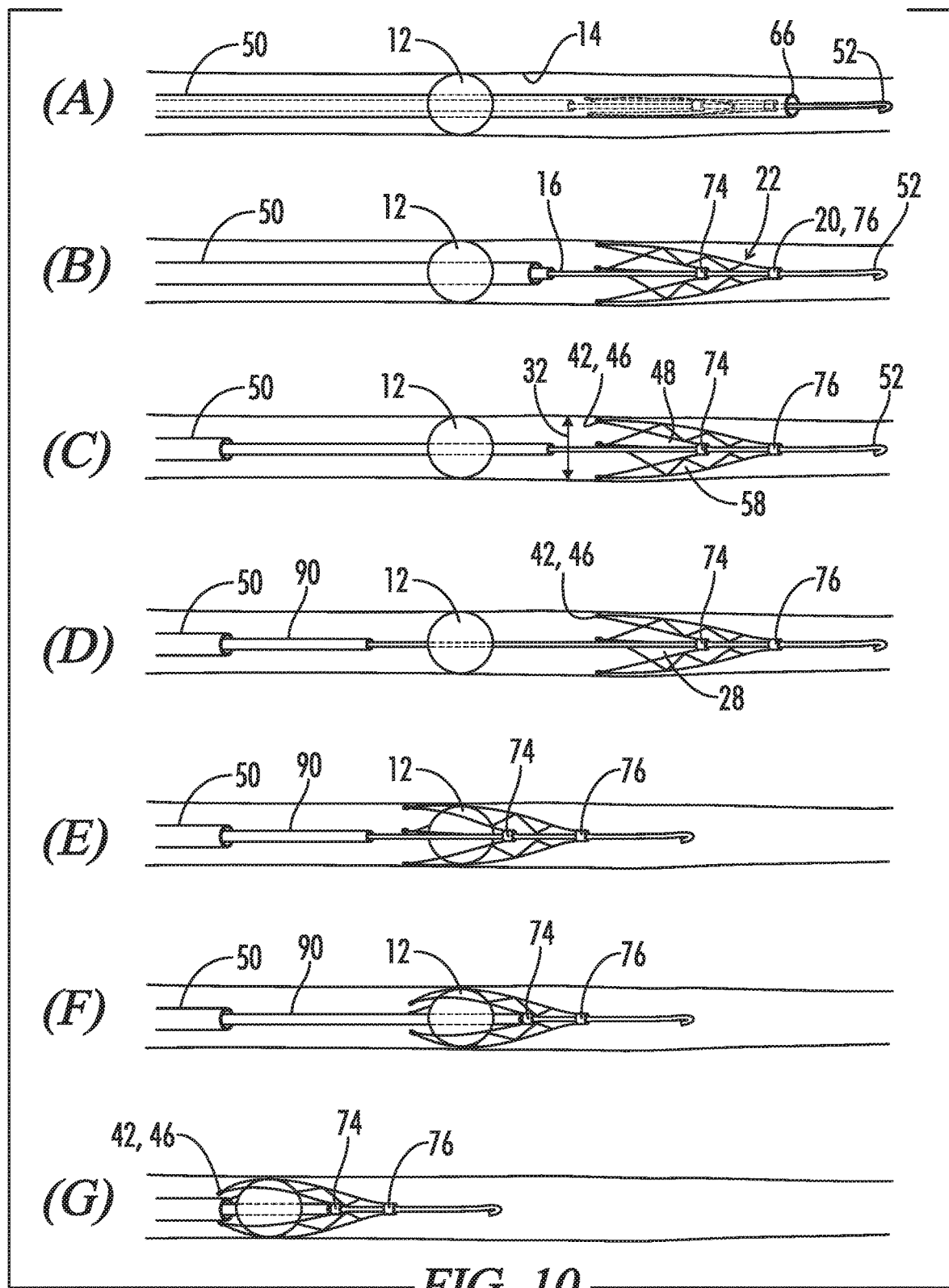
FIG. 10 illustrates a side, elevation view of a deployable system of one embodiment of the present invention being used to capture a blood clot.

Optionally, the distal body 22 includes a basket 54 distal to the proximal memory metal strips 40, the basket 54 comprised of a plurality of memory metal strips 56 distal relative to the proximal memory metal strips 40. The distal memory metal strips 56 may, for example, form a basket 54 with a plurality of mesh openings 58. Optionally, the size of the mesh openings 58 in the basket 54 when the distal body 22 is in its relaxed state is less (preferably significantly less) than the diameter of an average-sized ischemic blood clot 12 so that the blood clot 12 does not escape from the distal basket 54 after being captured by the distal body 22. Optionally, the basket 54 has an open proximal end 60 and a substantially closed distal end 62, which is formed by distal tube 76. Optionally, the distal and proximal hubs/junctions 74 and 76 and the distal basket 54 are comprised of a nitinol having the same material composition. Optionally, the size of the mesh openings 58 decreases from the proximal end 60 of the basket 54 to the distal end 62. The distal basket 54 is best seen in FIG. 2 and can be comprised of a different number of cell patterns. The distal basket 54 is not shown in FIGS. 3-10 for ease of illustrating the other components in the system 10.

Optionally, the proximal hub/junction 74 and the distal hub/junction 76 are cylindrical tubes comprising substantially circular apertures that span the length of the hubs/junctions 74 and 76 and the hubs/junctions 74 and 76 have approximately the same inner diameter 72 and the same outer diameter 70. Preferably, the inner diameter 72 is at least slightly larger than the diameter of the pull wire 16 so that the pull wire 16 can slide through the proximal hub/junction 74. In some embodiments, the outer diameters 70 of the proximal and distal hubs/junctions 74 and 76 may be from about 0.011 inches to about 0.054 inches and the inner diameters 72 of the proximal and distal hubs/junctions 74 and 76 may be from about 0.008 inches to about 0.051 inches.

Optionally, the distal body 22 further comprises an x-ray marker 64 that is more visible under x-ray as compared to the proximal memory metal strips 40 when the distal body 22 is located in a cranial blood vessel inside the body of a human and the x-ray is taken from outside the human's body. If the connector strips 48 are welded or soldered to the proximal memory metal strips 40, the x-ray markers 64 may be, for example, located at the welding or soldering site. In some cases, the increased thickness at the welding or soldering site may in of itself comprise the x-ray marker 64. Preferably, the x-ray marker 64 is comprised of a radiopaque material. Some examples of radiopaque materials can include, but are not limited to, gold, platinum, palladium, tantalum, tungsten alloy, polymer material loaded with radiopaque filler, and the like. Preferably, the proximal memory metal strips 40 are comprised of nitinol and the x-ray marker 64 is comprised of a material having a density greater than the nitinol.

A catheter 50 with an open proximal end (not shown) and an open distal end 66 initially envelopes the system 10. As used herein, the term "catheter" generally refers to any suitable tube through which the system 10 can be deployed. Preferably, the catheter 50 is sterile and comprised of a biocompatible material (i.e., a material that does not irritate the human body during the course of a 45 minute operation that involves using the system 10 to remove a clot 12 from an intracranial blood vessel 14). The catheter 50 can be any suitable shape, including but not limited to generally cylindrical. Preferably, the catheter 50 is a microcatheter. For purposes of the present invention, when it is said that the catheter 50 envelopes the system 10, it will be understood that the catheter 50 envelopes at least one component of the system 10 (preferably, the distal body 22, the lead wire 52, and the pull wire 16). In some embodiments, the catheter 50 is about 2.5 French in diameter. Optionally, the catheter 50 is delivered to the region of the lumen 14 that has the obstruction 12 as follows: a guide wire is delivered to the obstruction region past the obstruction 12; the catheter 50 is delivered over the guide wire; the guide wire is removed; and the system 10 is delivered with its pull wire 16 and lead wire 52 through the catheter 50. Optionally, the pull wire 16 is used to push the system 10 through the catheter 50 as well as to retrieve the distal body 22 after capturing the obstruction 14 as described below. The system 10 may utilize a plurality of catheters 50, such as, for example, a wider catheter that travels to the brain and a very flexible, smaller diameter microcatheter that is delivered from the first catheter and travels through the small arteries of the brain. Preferably, the catheter 50 is comprised of a biocompatible, polymeric material (i.e., one or more polymeric materials such as silicone, PVC, latex rubber or braided nylon).

Optionally, in the relaxed, opened-claw state, the distal body 22 or optionally just the distal basket 54 has a tapered shape (e.g., substantially conical or bullet in shape) so that the distal body 22 or just the distal basket 54 tapers from the distal body 22 or the distal basket's 54 proximal end to the distal end.

The proximal end of the system 10 is shown at the left end of FIGS. 1 and 3-10 and the distal end of the system 10 is shown at the right end of FIGS. 1 and 3-10 because a principal use of the system 10 is to remove a blood clot 12 from a human intracranial artery 14, in which case the system 10 generally will enter the artery 14 at its proximal end by the surgeon entering the patient's body near the groin and pushing the catheter 50 towards the brain. The diameter of human arteries 14 generally decrease from their proximal end to their distal end. However, when used in other types of lumens, the distal body 22 may be located proximally relative to the catheter 50 as the term proximally and distally are used in that lumen.

The surgeon may deploy the distal body 22 by, for example, moving the catheter 50 proximally so as to unsheathe the distal body 22 or by pushing the distal body 22 out of the catheter 50.

Use of the system 10 will now be described to remove a blood clot 12 from an intracranial artery 14 of a human ischemic stroke patient, however, it will be appreciated that the system 10 may be used to remove other objects from other interior lumens.

A catheter 50, which contains the collapsed distal body 22 is positioned in the lumen 14 distal to the clot 12. See FIG. 10A.

The distal body 22 is deployed from the catheter 50 and the height and width of the distal body 22 expand to about the height and width of the blood vessel 14. See FIG. 10B.

The catheter 50 is pulled proximally and a claw-actuator tube 90 is deployed into the blood vessel 14. See FIG. 10C.

The distal body 22 is moved proximally so that the clot 12 is located in the interior 28 of the distal body 22. See FIGS. 10D and 10E.

The claw-actuator tube 90 is moved distally, which pushes the proximal hub/junction 74 distally so that the distance 88 between the proximal hub/junction 74 and the distal hub/junction 76 (which is fixed to the pull wire 16 and kept stationary) decreases. Distal movement of the proximal hub/junction 74 exerts tension on the connector and proximal memory metal strips 40 and 48, which in turn, closes the claw 46. See FIG. 10F. (The claw actuator tube 90 should float on the pull wire 16—i.e., have an aperture extending the tube's length that has a diameter larger than the diameter of the pull wire 16—and the aperture of the claw actuator tube 90 should be smaller than the diameter of the proximal hub/junction 74 so that the claw actuator tube 90 pushes the proximal hub/junction 74).

The system 10 is withdrawn proximally and removed from the body. See FIG. 10G.

To test the efficacy of the system 10, a distal body 22 with a distal basket 54, proximal and distal hubs/junctions 74 and 76, and a claw 46 comprised of three proximal memory metal strips 42 was tested in a flow model that included a tube and a moist cotton ball located in the tube. The cotton ball was used to simulate a blood clot. The system 10 was deployed distal to the cotton ball. The claw 46 was closed by moving the proximal hub/junction 74 distally to capture the cotton ball. The system 10 and cotton ball were withdrawn proximally in the tube.

In some embodiments, the distal body 22 is prepared by a process that includes one or more of the following steps, as illustrated in FIGS. 1-4
a) providing a single tube 68 comprised of a memory metal such as nitinol, the single tube 68 having an exterior, a substantially hollow interior, a wall separating the exterior from the substantially hollow interior, an open proximal end 74, an open distal end 76, a middle portion 78 between the open proximal end 74 and the open distal end 76 (see FIG. 1A);
b) cutting the wall of the middle portion 78 with a laser 80 (see FIG. 1B);
c) removing the pieces of the middle portion 78 cut by the laser 80 to form a proximal tube 74, a distal tube 76 and a middle portion 78 comprising a plurality of memory metal strips 82 attached to the proximal tube 74;
d) altering the shape of the middle portion 78 using a mandrel and allowing the middle portion 78 to expand relative to the distal tube 76 and proximal tube 74 to form the distal basket 54;
e) quenching the middle portion 78 at room temperature;
f) removing the mandrel from the middle portion 78 (see FIGS. 2 and 3A);
g) mechanically or chemically electropolishing the middle portion 78 to remove oxides;
h) cutting the memory metal strips 82 to form a first segment 84 comprising the proximal tube 74 and a proximal segment of the memory metal strips 82 and a second segment 86 comprising the distal tube 76 and a distal segment of the memory metal strips 82 (see FIG. 3B); and
i) joining the proximal segments to the distal segments such that the distal segments form the proximal end 24 of the distal body 22, such that the proximal tube 74 is located inside the interior 28 of the distal body 22, and such the proximal tube 74 is located distal relative to the distal body proximal end 24 (see FIGS. 3C-3E).

In some embodiments, the method further includes placing the pull wire 16 through the proximal tube 74 so that the proximal tube 74 is slideable along at least a segment of the pull wire 16.

In some embodiments, the method further includes attaching the pull wire 16 to the distal tube 76 so that the distal tube 76 is not slideable along the pull wire 16 but instead the distal tube 76 moves with the pull wire 16.

In some embodiments, after step i, the proximal end 24 of the distal body 22 forms a claw 46 comprised of between 2 to 4 proximal memory metal strips 40, the claw proximal memory metal strips 40 configured to move towards each other and the pull wire 16 by moving the proximal tube 74 distally and toward the distal tube 76 (i.e., decreasing the distance 88 between the tubes 74 and 76) and the claw memory metal strips 40 configured to move away from each other and away from the pull wire (i.e., increasing the distance 88 between the tubes 74 and 76) by moving the proximal tube 76 proximally and away from the distal tube 76 (as described previously).

In some embodiments, the middle portion 78 is expanded by heating the mandrel and the middle portion 78 by, for example, placing the mandrel and the middle portion 78 in a fluidized sand bath at about 500° C. for about 3 to about 7 minutes. As the middle portion 78 is heated, the heating causes the crystalline structure of the memory metal tube 68 to realign. Preferably, the mandrel is tapered (e.g., substantially conical or bullet in shape) so that the distal basket 54 formed from the middle portion 78 tapers from the proximal end 60 to the distal end 62. Preferably, the proximal and distal ends of the tube 74 and 76 are not shape set by the mandrel and are not cut by the laser 80 so that the proximal and distal ends 74 and 76 do not change in shape and only slightly expand in size under heating and return to the size of the native tube 68 after the heat is removed. Preferably, the laser cuts are programmed via a computer. To ensure that the laser cuts only one surface of the tube wall at the time (and not the surface directly opposite the desired cutting surface), the laser 80 is preferably focused between the inner and outer diameter of the desired cutting surface and a coolant is passed through the memory metal tube 68 so that the laser 80 cools before reaching the surface directly opposite the desired cutting surface.

The portions of the wall not cut by the laser 80 create the distal basket 53, proximal and distal tubes 74 and 76, and memory metal strips 40, 48 and 56, as described.

Preferably, the memory metal selected for the native tube 68 has a heat of transformation below average human body temperature (37° C.) so that the distal body 22 has sufficient spring and flexibility after deployment from the catheter 50 in the human blood vessel 14.

In some embodiments, the native tube 68 (and hence the distal and proximal tubes 74 and 76) have an outer diameter of less than about 4 French, e.g., a diameter of about 1 to about 4 French. In some embodiments, the diameter of the pull wire 16 is between about 0.008 inches and about 0.051, as noted above, and in such embodiments, the diameter of the pull wire 16 may be approximately equal to the inner diameter 72 of the native nitinol tube 68.

Without being bound by any particular theory, it is believed that manufacturing the distal body 22 from a single memory metal tube 68 provides ease of manufacturing and safety from mechanical failure and provides tensile strength necessary for the system 10 to remove hard thrombus 12 and other obstructions.

The Embodiments of FIGS. 11-29

FIGS. 11-29 illustrate an alternate embodiment 200 that includes one or more of the following additional features, as described below: twisting proximal strips/tethers 252, unattached/free distal-pointing crowns 258 that optionally curve inward and have x-ray markers 244, and enlarged openings/drop zones 262 in the basket 246 immediately distal to the unattached, distal-pointing crowns 258 that allow the obstruction or other object 270 to enter the distal basket interior 222.

Figure 11:
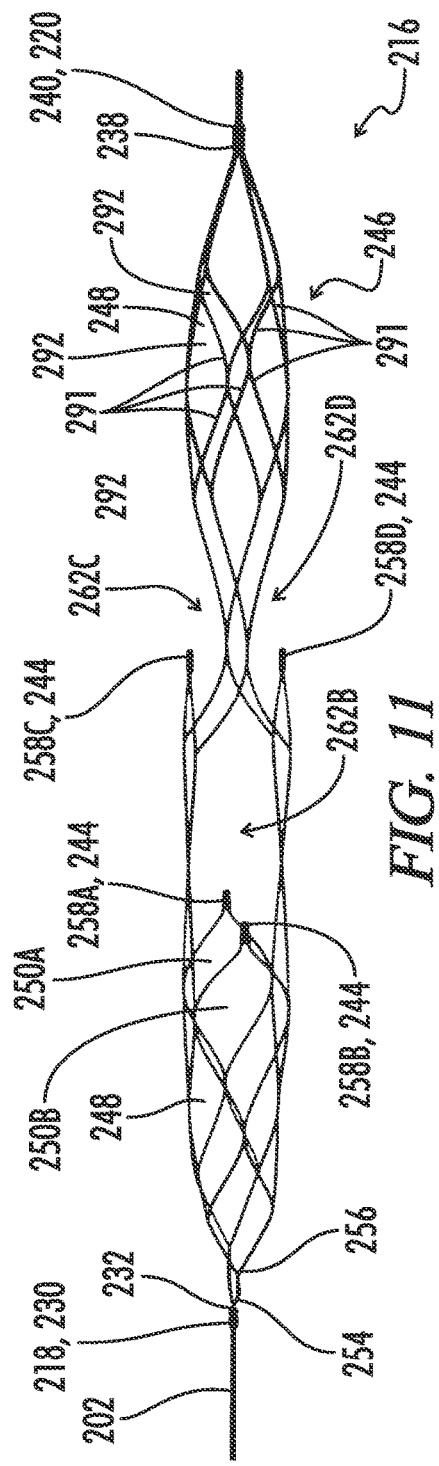
FIG. 11 illustrates a first, perspective view of a distal body of an alternate embodiment of the present invention; the distal body is in what is referred to herein as "Orientation 1".

More specifically, as shown in FIGS. 11-29, the system 200 may include a pull wire 202 having a proximal end 204 and a distal end 206, as described above, a distal body 216 attached to the pull wire 202, the distal body 216 comprising an interior 222, a proximal end 218, a distal end 220, a distal body length 226 extending from the proximal end 218 to the distal end 220, a distal body height 224, a proximal hub/junction 228 (preferably in the form of a tube and which has a proximal end 230 and a distal end 232) forming the proximal end 218 of the distal body 216, a basket 246 comprised of a plurality of cells/openings 248 formed by a plurality of basket strips 291 that preferably are comprised of a memory metal, optionally a distal hub/junction 236 that forms the distal end 220 of the basket 246 (preferably in the form of a tube that has a proximal end 238 and a distal end 240), and a plurality of proximal strips 252 (preferably the proximal strips 252 are comprised of a memory metal), each proximal strip 252 having a proximal end 254 attached to the proximal hub/junction/tube 228, and a distal end 256 attached to a cell 248 (more specifically a proximal-pointing crown of a cell 248 located at the proximal end of the basket 246), the basket comprising a basket interior 292, the distal body 216 having a relaxed state wherein the distal body 216 has a first height and width, a collapsed state wherein the distal body 216 has a second height and width, the second height less than the first height, the second width less than the first width; and a delivery catheter 208 for delivering the distal body 216, as described above, having an interior 210, a proximal end 212 leading to the interior 210 and a distal end 214 leading to the interior 210, the delivery catheter 208 comprised of a biocompatible (preferably polymeric) material and configured to envelope the distal body 216 when the distal body 216 is in the collapsed state. Optionally, the basket interior 292 is substantially hollow—i.e., unlike U.S. Patent Publication No. 2013/0345739, the basket interior 292 does not contain an inner elongate body. Optionally, instead of a distal hub/junction 236, the basket 246 includes an open distal end. Optionally, at least two cells 250 of the basket 246 comprise a proximal crown 260 pointing generally in the proximal direction and a distal crown 258 pointing generally in the distal direction, and the distal crowns 258 of the at least two cells 250 are not attached to another cell 248 of the basket 246. In other words, the distal crowns 258 of at least two cells 250 are free floating and are not attached to any strip except for the strips forming part of the at least two cells 250; such distal crowns 258 are referred to below as unattached, distal-pointing crowns 258. Preferably, the distal tips of the unattached, distal-pointing crowns 258 terminate at an x-ray marker 244. (Cells labeled with the numerals 250, 250A, 250B, 250C, and 250D refer to the at least two cells that include a proximal crown 260 pointing generally in the proximal direction and an unattached, distal-pointing crown 258, cells labeled with the numerals 262, 262A, 262B, 262C, and 262D refer to the enlarged cells/drop zones adjacent to (preferably immediately distal to) an unattached, distal-pointing crown 258, and cells designated with numeral 248 refer to generally the cells of the basket 246). (When it is said that the enlarged cells/drop zones 262 are preferably immediately distal to an unattached, distal-pointing crown 258, it will be understood that at least a portion of an enlarged cell/drop zone 262 is immediately distal to an unattached, distal-pointing crown 258, and that a portion of the enlarged cell/drop zone 262 may be proximal to an unattached, distal-pointing crown 258, as shown in FIGS. 11-12 due to the shape of the enlarged cells/drop zones 262). It will be understood that part number 250 refers generally to one or more of the at least two cells, whereas part numbers 250A, 250B, 250C, and 250D refer to a specific one of the at least two cells. Similarly, it will be understood that part number 262 refers generally to one or more of the enlarged cells/drop zones, whereas part numbers 262A, 262B, 262C, and 262D refer to a specific one of the enlarged cells/drop zones. Similarly, it will be understood that part number 258 refers generally to one or more of the unattached, distal-pointing crowns, whereas part numbers 258A, 258B, 258C, and 258D refer to a specific one of the unattached, distal-pointing crowns.

Figure 12A:
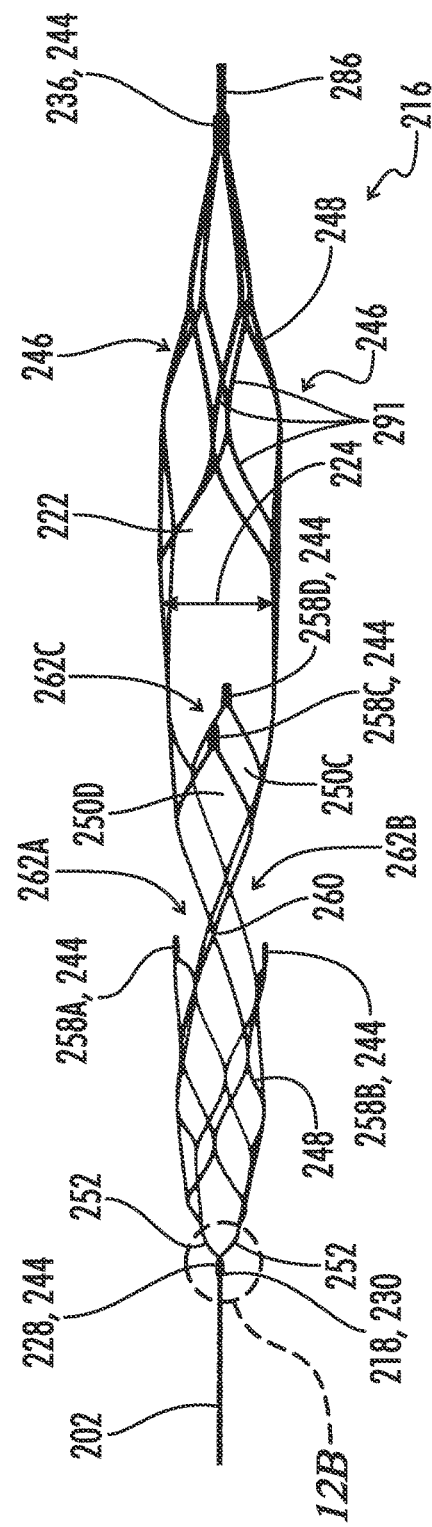
FIG. 12A illustrates a second, perspective view of the distal body of FIG. 11; the distal body is in what is referred to herein as "Orientation 2".
Figure 12B:
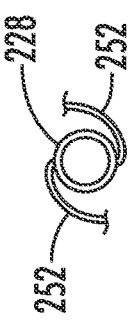
FIG. 12B illustrates a proximal, elevation view of the proximal strips of the distal body of FIG. 11.

Optionally, at least two of the unattached, distal-pointing crowns 258 are located approximately 180 degrees (e.g., about 150 to about 180 degrees) relative to each other and approximately the same distance from the proximal hub/junction/tube 228, as best seen in FIG. 12A. Optionally, the basket 246 comprises a first pair of unattached, distal-pointing crowns 258A and 258B, each of the first pair of unattached, distal-pointing crowns 258A and 258B is located approximately the same distance from the proximal hub/junction/tube 228 and approximately 180 degrees relative to each other, and the basket 246 further comprises a second pair of unattached, distal-pointing crowns 258C and 258D located distally relative to, and approximately 90 degrees (e.g., between about 60 and about 90 degrees) relative to, the first pair of unattached, distal-pointing crowns 258A and 258B. Optionally, the second pair of unattached, distal-pointing crowns 258C and 258D form cells 250C and 250D that are adjacent to, but offset from, the cells 250A and 250B formed by the first pair of unattached, distal-pointing crowns 258A and 258B. (In other words, optionally, the center of cell 250A is about 90 degrees relative to the centers of cells 250C and 250D and optionally the center of cell 250B is also about 90 degrees relative to the centers of cells 250C and 250D). Optionally, at least one of (and preferably all) the unattached, distal-pointing crowns 258A, 258B, 258C or 258D comprise an x-ray marker 244 that is more visible under x-ray as compared to the basket strips 291 when the distal body 216 is located in a cranial blood vessel 266 inside the body of a human and the x-ray is taken from outside the human's body. Preferably, the x-ray marker 244 is a radiopaque material. Some examples of radiopaque materials can include, but are not limited to, gold, platinum, palladium, tantalum, tungsten alloy, polymer material loaded with radiopaque filler, and the like. Preferably, the basket strips 291 are comprised of nitinol and the x-ray marker 244 is comprised of a material having a density greater than the nitinol. In some embodiments, the x-ray markers 244 comprise a heavy metal welded or soldered to the unattached, distal-pointing crowns 258. Optionally, the unattached, distal-pointing crowns 258 curve subtly towards the interior 222 of the distal basket 246, which decreases the likelihood that the unattached, distal-pointing crowns 258 will rub against and damage the vessel wall 268. Optionally, the basket 246 comprises at least two cells proximal to the at least two cells 250 that include the unattached, distal-pointing crowns 258. Optionally, the unattached, distal-pointing distal crowns 258 are located about at least 5 mm (e.g., about 5 to about 30 mm) from the proximal hub/junction/tube 228. Optionally, the unattached, distal-pointing crowns 258 are located at least about 5 mm from the distal hub/junction/tube 236. Optionally, the unattached, distal-pointing crowns 258 of the at least two cells 250 also each form part (namely a portion of the proximal boundary) of an enlarged cell 262 (which is the entry point of hard thrombus 270B into the basket interior 222) and further wherein the surface area of the enlarged cells 262 in the relaxed state is greater than the surface area of the other cells of the basket 246 in the relaxed state. Optionally, the unattached, distal-pointing crowns 258 serve several functions: 1) they form flex points of the basket 246, which makes it easier for the system 200 to navigate the curves of the blood vessels 266 of the brains; 2) through the use of x-ray markers 244 on the unattached, distal-pointing crowns 258, they allow the operator to locate the enlarged cells 262 of the basket 246 that form the point at which hard thrombuses 270B enter the basket 246; and 3) they allow the operator to ratchet or force the object 270 into the basket 246 by moving the unattached, distal-pointing crowns 258 proximally and distally relative to the object 270. (As explained below, the numeral 270 refers to clots/thrombuses and other objects generally, and 270A refers to a soft clot, 270B refers to a hard clot and 270C refers to a deformable, cohesive, adherent clot). Optionally, the proximal end 254 of a proximal strip 252 is located about 65-180 degrees (preferably approximately 180 degrees) relative to the distal end 256 of the same proximal strip 252, as best seen in FIG. 12B. In other words, preferably the proximal end 254 of a first proximal strip 252 is attached to the 12 o'clock position on the proximal tube 228 and the distal end 256 of the first proximal strip 252 (which terminates at a proximal cell 248 of the basket 246) is located at the 6 o'clock position (i.e., 180 degrees from the start position), and the proximal end 254 of a second proximal strip 252 is attached to the 6 o'clock position on the proximal tube 228 and the distal end 254 (which terminates at a cell 248 of the basket 246) of the second proximal strip 252 is located at the 12 o'clock position (i.e., 180 degrees from the start position). This twisting feature serves two functions: 1) it allows the proximal strips 252 to surround the object 270; and 2) it allows the manufacturer to insert a mandrel into the basket 246 during the shape-setting procedure. Optionally, the pull wire 202 is attached to the proximal tube 228 (e.g., by gluing, welding, soldering or the like). Preferably, the pull wire 202 does not extend through the distal basket interior 222. Optionally, the proximal strips 252 are integral with the distal end 232 of the proximal tube 228 and the entire distal body 216 is created from a single tube 264 of a memory metal. Optionally, the proximal crowns 260 of the at least two cells 250 that include the unattached, distal pointing-crowns 258 are each attached to another cell 248 of the basket 246. In other words, preferably the basket 246 does not have any free-floating proximal-pointing crowns, as free-floating proximal-pointing crowns could damage the vessel 266 when the distal body 216 is pulled proximally Optionally, the system 200 further comprises a lead wire 286 extending distally from the distal tube 236, the lead wire 286 having a length of from about 3 mm to about 10 mm. Optionally, the distal hub/junction/tube 236, the proximal hub/junction/tube 228, and the basket 246 are comprised of a nitinol having the same material composition. In other words, as with the prior embodiment of FIGS. 1-10, optionally the entire distal body 216 is manufactured from a single tube of nitinol 264. Optionally, the proximal and distal hubs/junctions/tubes 228 and 236 comprise an x-ray marker 244 that is more visible under x-ray as compared to the basket strips 291 when the distal body 216 is located in a cranial blood vessel 266 inside the body of a human and the x-ray is taken from outside the human's body. Preferably, the x-ray marker 244 is a radiopaque material. Some examples of radiopaque materials can include, but are not limited to, gold, platinum, palladium, tantalum, tungsten alloy, polymer material loaded with radiopaque filler, and the like. Preferably, the basket strips 291 are comprised of nitinol and the x-ray marker 244 is comprised of a material having a density greater than the nitinol. In some embodiments, the proximal and distal hubs/junctions/tube interiors 234 and 242 may comprise tantalum welded or otherwise attached to the interior 234 and 242 of the proximal and distal hubs/junctions/tubes 228 and 236. Optionally, the proximal and the distal tubes 228 and 236 are generally cylindrical in shape and each has an outer diameter and an inner diameter, the inner diameter forming apertures of the proximal and distal tubes 228 and 236 and further wherein the outer diameters of the proximal and distal tubes 228 and 236 are substantially the same size and further wherein the inner diameters of the proximal and distal tubes 228 and 236 are substantially the same size. Optionally, the outer diameters of the proximal and distal tubes 228 and 236 are from about 0.011 inches to about 0.054 inches, and further wherein the inner diameters of the proximal and distal tubes 228 and 236 are from about 0.008 inches to about 0.051 inches. Optionally, the pull wire 202 is generally cylindrical and further wherein the diameter of the pull wire 202 is between about 0.008 inches and about 0.051 inches. Optionally, the distal body 216 has a length of between about 10 and about 60 millimeters. Optionally, the first height 224 and first width 226 of the distal body 216 are between about 2 millimeters and about 6 millimeters.

The present disclosure also provides a method of removing a clot or other object 270 from an interior lumen 266 of an animal, the method comprising the steps of:

a) providing the system 200 of FIGS. 11-29, wherein at least two cells 250 of the basket 246 comprise a proximal crown 260 pointing generally in the proximal direction and a distal crown 258 pointing generally in the distal direction, and the distal crowns 258 of the at least two cells 250 are not attached to another cell 248 of the basket 246 (i.e., free-floating), and further wherein at least one of the unattached, distal-pointing crowns 258 comprises an x-ray marker 244;

b) positioning the system 200 in the lumen 266;

c) deploying the distal body 216 from the distal end 214 of the delivery catheter 208;

d) allowing the height and width 224 and 226 of the distal body 216 to increase;

e) irradiating the x-ray marker 244 with x-ray radiation and f) moving the object 270 into the distal basket interior 222.

Optionally, the object 270 enters the distal basket interior 222 adjacent to (preferably adjacent and immediately distal to) at least one of the unattached, distal-pointing crowns 258—i.e., in the enlarged cells/drop zones 262. In some embodiments, the distal body 216 is deployed so that at least one (e.g., preferably the two proximal 258A and 258B) of the unattached, distal-pointing crowns 258 is distal to the object 270. As explained below, the x-ray markers 244 of the unattached, distal-pointing crowns 258 are used to locate the distal body 216 relative to the clot or other object 270. It will be appreciated that clots 270 can generally be located in blood vessels 266 by injecting a contrast dye, for example, into the blood vessel 266 proximal and distal to the believed area of obstruction and viewing on an x-ray where the fluid stops moving in the blood vessel 266. It will also appreciated that if the object 270 is not a blood clot but is a radio-opaque object, the object 270 may be viewed on an x-ray.

Figure 13:
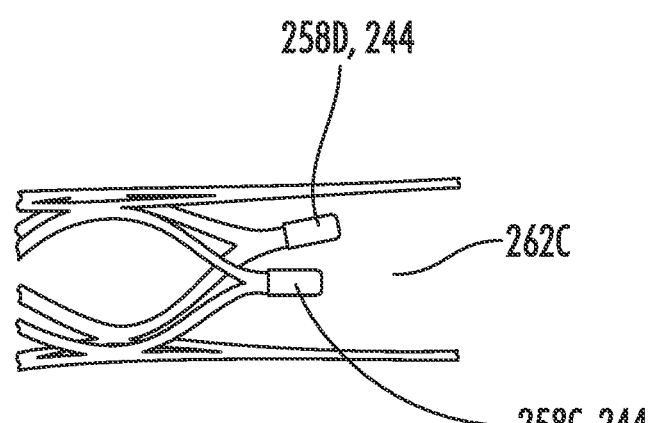
FIG. 13 illustrates a close-up, perspective view of two unattached distal-pointing crowns of the distal body of FIG. 11.
Figure 14A:
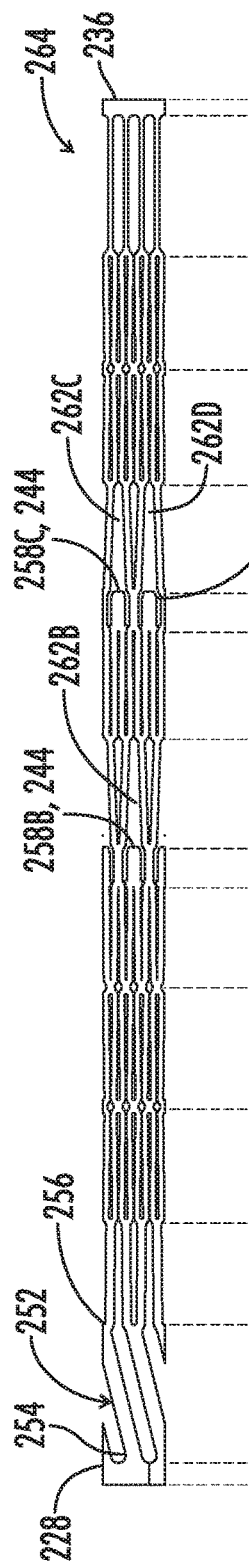
FIG. 14A illustrates a native memory metal tube used to manufacture the distal body of FIG. 11; the native tube has been rolled out flat and the lines in the tube indicate where the tube has been cut by a laser.
Figure 14B:
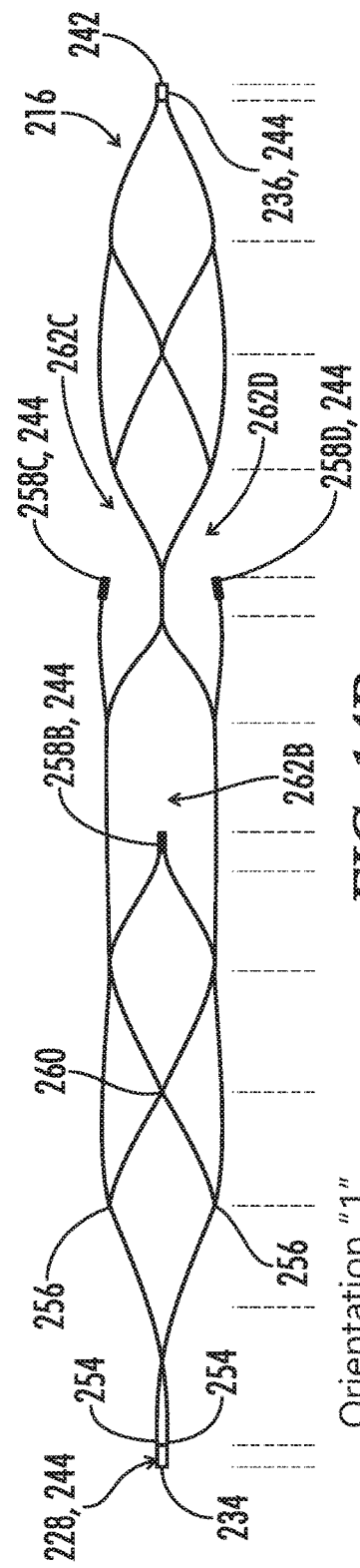
FIG. 14B illustrates a first, perspective view of the distal body manufactured from the native tube of FIG. 14A; the distal body is in Orientation 1.
Figure 14C:
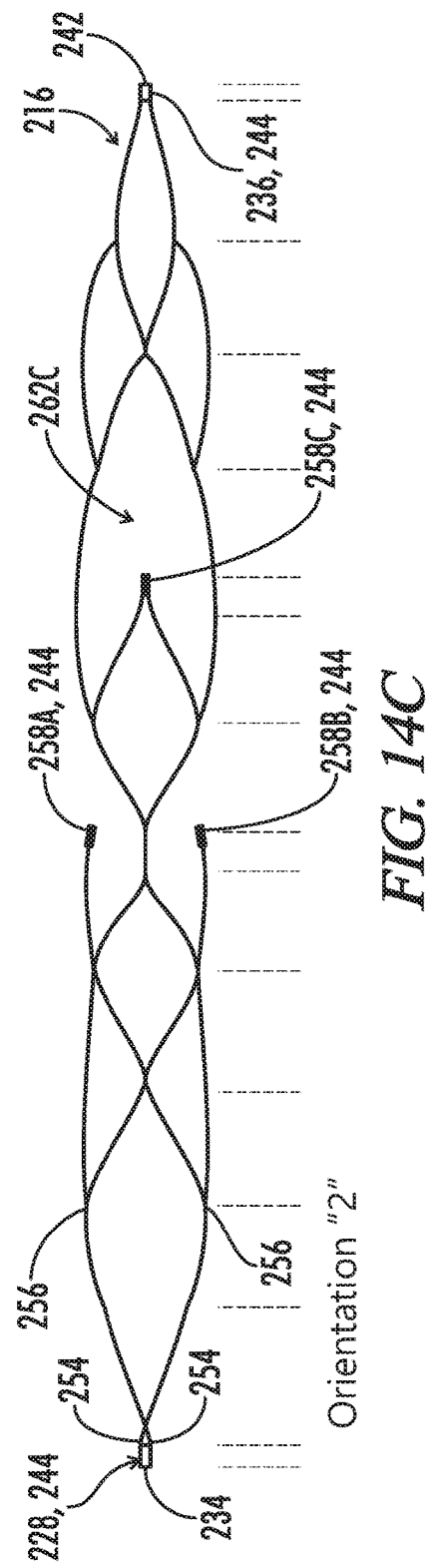
FIG. 14C illustrates a second, perspective view of the distal body manufactured from the native tube of FIG. 14A; the distal body is in Orientation 2.
Figure 30:
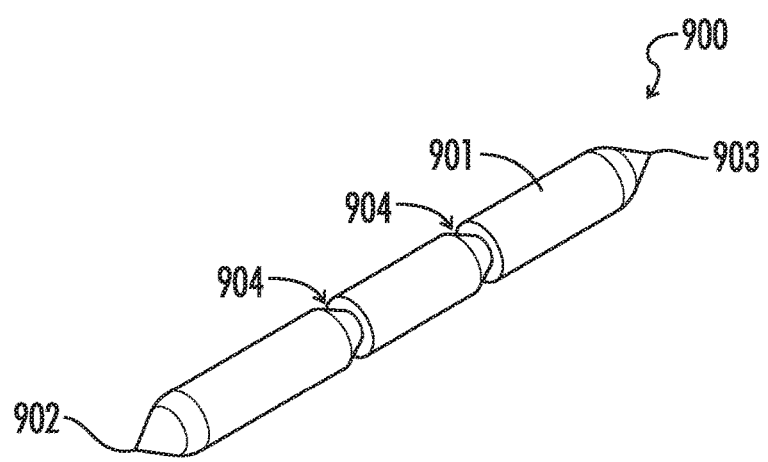
FIG. 30 illustrates a right side perspective view of a mandrel used to prepare unattached distal-pointing crowns that curve radially toward the basket interior.
Figure 31:
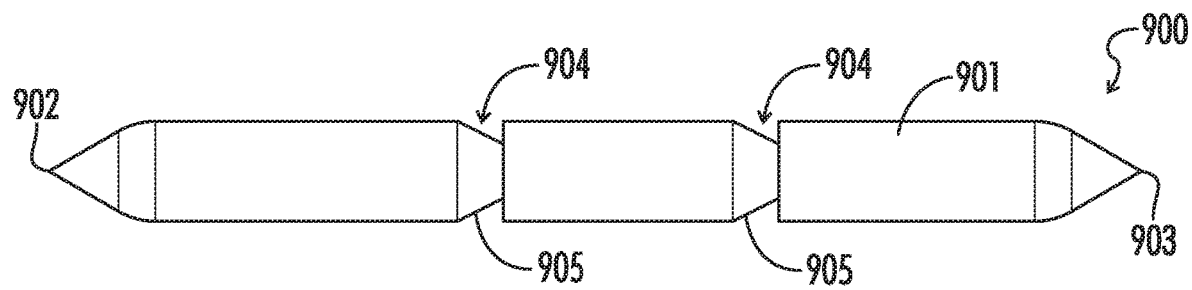
FIG. 31 illustrates a right side elevation view of the mandrel of FIG. 30.

FIGS. 11 and 14B illustrate a first, perspective view of one embodiment of a distal body 216 with twisting proximal strips 252, unattached distal-pointing crowns 258 that subtly curve inward and have x-ray markers 244, and enlarged openings/drop zones 262 in the basket 246 that allow the obstruction or other object 270 to enter. In FIGS. 11 and 14B, the distal body 216 is in Orientation 1. (To prepare a basket 246 with unattached distal-pointing crowns 258 that curve inward toward the basket interior 292, a mandrel 900 such as that illustrated in FIGS. 30 and 31 may be used. The mandrel 900 includes a generally cylindrical body 901 with tapered proximal and distal ends 902 and 903 that slope like the ends of a pencil. The cylindrical body 901 includes two grooves 904 that extend around the circumference of the cylindrical body 901. The grooves 904 include tapered portions 905 that slope towards the distal end 903, which are designed to shape the unattached distal-pointing crowns 258. The grooves 904 are generally in the shape of a truncated cone, as shown in FIGS. 30-31). The two proximal, unattached distal-pointing crowns 258A and 258B are located approximately the same distance from the proximal hub/junction/tube 228 and are oriented approximately 180 degrees relative to each other. The two distal, unattached distal-pointing crowns 258C and 258D are located approximately the same distance from the proximal hub/junction/tube 228 as each other (and distal to the two proximal, unattached distal-pointing crowns 258A and 258B) and are oriented approximately 180 degrees relative to each other and approximately 90 degrees to the proximal, unattached distal-pointing crowns 258A and 258B. The two proximal enlarged openings/drop zones 262A and 262B distal to the proximal, unattached distal pointing crowns 258A and 258B are located approximately the same distance from the proximal hub/junction/tube 228 and the centers of the two proximal enlarged openings/drop zones 262A and 262B are oriented approximately 180 degrees relative to each other. (As noted above, preferably, the proximal, unattached distal-pointing crowns 258A and 258B form part of the proximal boundary of the proximal, enlarged cells/drop zones 262A and 262B, and the distal, unattached distal-pointing crowns 258C and 258C form part of the proximal boundary of the distal, enlarged cells/drop zones 262C and 262D). The two distal, enlarged openings/drop zones 262C and 262D distal to the distal, unattached distal pointing crowns 258C and 258D are located approximately the same distance from the proximal hub/junction/tube 228 and the centers of the distal, enlarged openings/drop zones 262C and 262D are oriented approximately 180 degrees relative to each other and approximately 90 degrees relative to the proximal enlarged openings/drop zones 262A and 262B. FIGS. 12A and 14C illustrate a second view of the distal body 216 of FIG. 11 (Orientation 2). FIG. 13 is a close-up view of two unattached, distal-pointing crowns 262. The lines in FIG. 14 show how a nitinol tube 264 is cut with a laser to create the distal body 216 shown in FIG. 14B and FIG. 14C. It will be appreciated that FIG. 14B is a simplified view of the distal body 216 and orientation shown in FIG. 11 and FIG. 14C is a simplified view of the distal body 216 and orientation shown in FIG. 12A.

As described below, FIGS. 15-19 describe how the distal body 216 is used to retrieve, soft clots 270A, hard clots 270B, and deformable, cohesive adhesive clots 270C in a human intracranial artery 266. (In FIGS. 15-19, the center of the artery 266 is denominated by the dashed line). As explained below, the distal body 216 has four rows of x-ray markers namely, 1) a first row of one x-ray marker, which is located inside the proximal tube denominated by the numeral 228, 244; 2) a second row of two x-ray markers, which are located at the two proximal, unattached distal-pointing crowns (the two markers are oriented 180 degrees relative to each other) denominated by the numerals 258A, 244 and 258B, 244; 3) a third row of two x-ray markers, which are located at the two distal, unattached distal-pointing crowns (these two markers are oriented 180 degrees relative to each other and 90 degrees relative to the two proximal, unattached distal-pointing crowns) denominated by the numerals 258C, 244 and 258D, 244; and 4) a fourth row of one x-ray marker, which is located inside the distal tube denominated by the numeral 236, 244. (It will be appreciated that the first number in the sequence describes the position of the x-ray marker and the second number, 244, represents the fact that the item is an x-ray marker). As explained below, upon deploying the distal body 216 so that the two proximal, unattached distal-pointing crowns 258A, 244 and 258B, 244 are immediately distal to the clot 270, the surgeon interventionalist (i.e., operator of the distal body 216) detects the four rows of x-ray markers using x-ray radiation from a first vantage point and from a second vantage point that is offset from the first vantage point (e.g. 90 degrees). Next, the surgeon moves the distal body 216 proximally relative to the clot 270 and takes additional x-rays from the first and second vantage points. As explained in greater detail below, the surgeon uses the x-ray markers of the proximal and distal, unattached distal-pointing crowns, namely 258A, 244; 258B, 244; 258C, 244; and 258D, 244 (more specifically, the convergence or lack thereof of the proximal and distal, unattached distal-pointing crowns 258A, 244; 258B, 244; 258C, 244; and 258D, 244 as shown on the x-ray) to determine whether the clot 270 is located inside the distal body interior 222 or whether the clot 270 is collapsing the distal body 216.

Figure 15A:
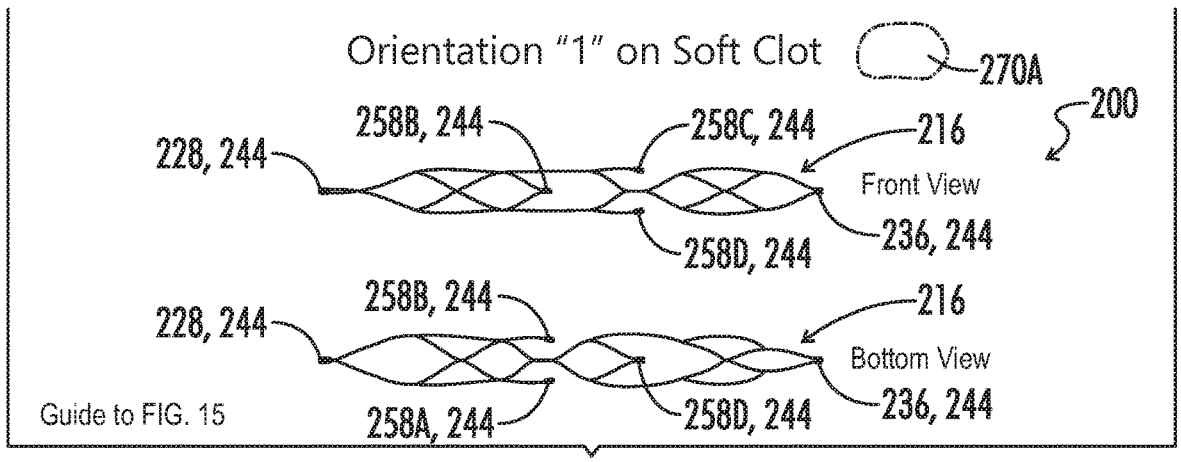
FIGS. 15A-G illustrate stepwise use of the distal body of FIG. 11 in retrieving a soft clot; the distal body is in Orientation 1.
Figure 15B:
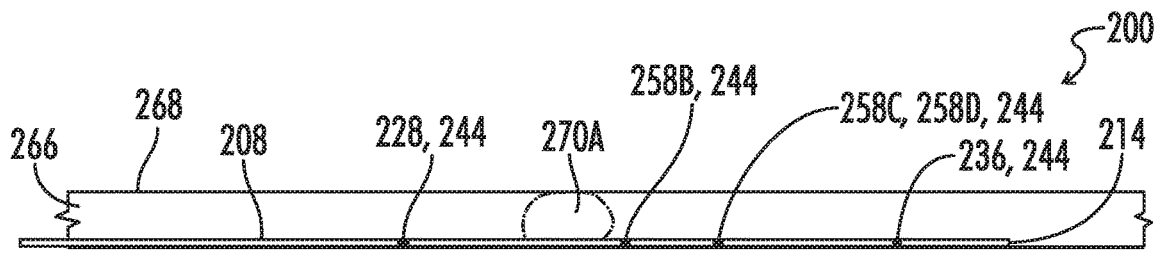
Figure 15C:
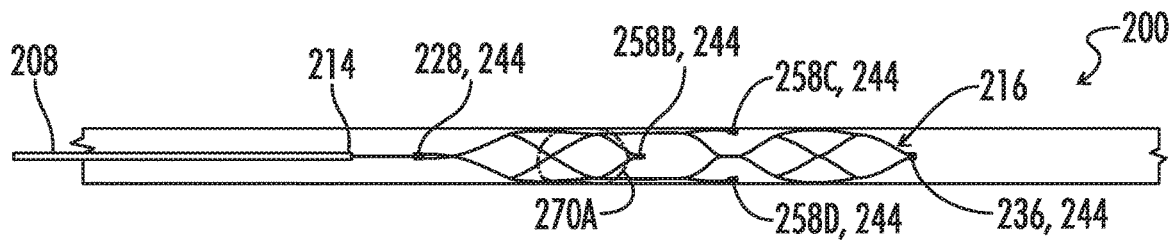
Figure 15D:
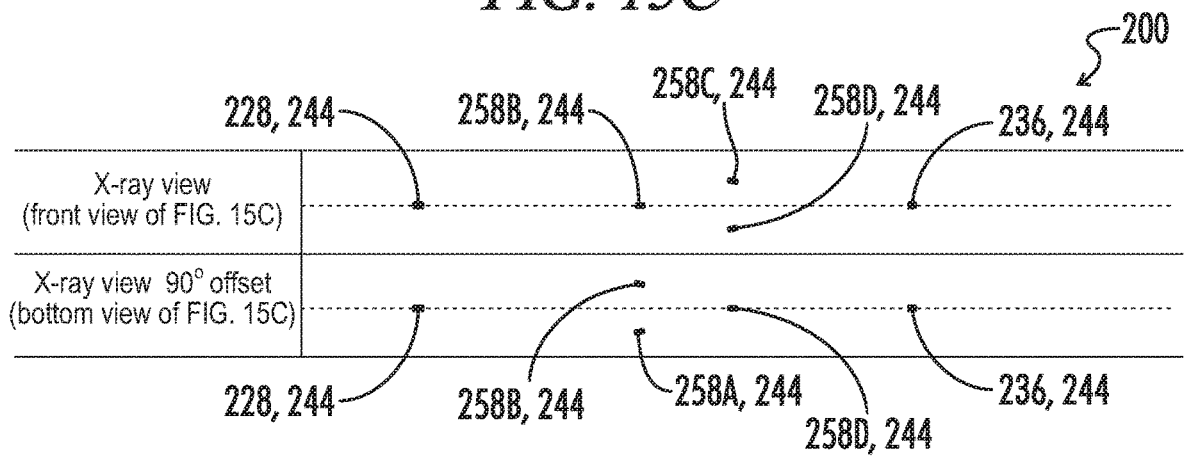
Figure 15E:
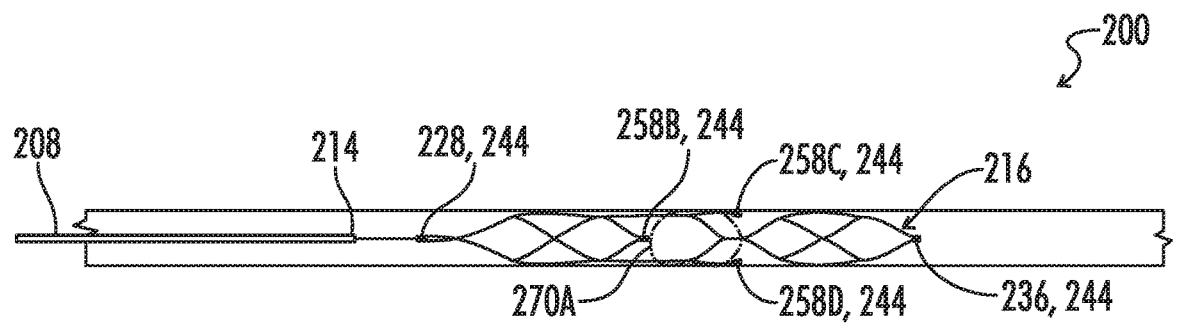
Figure 15F:
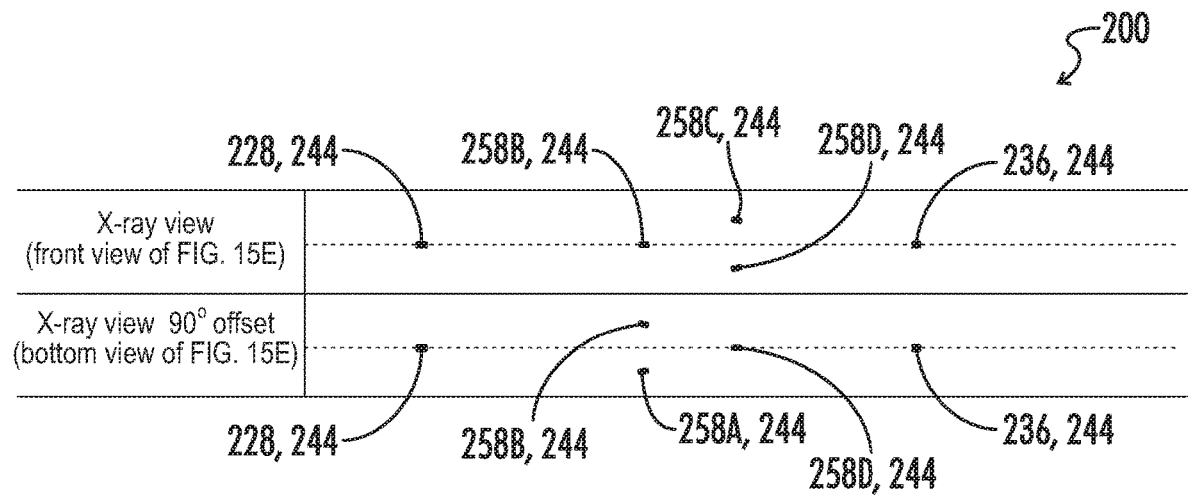
Figure 15G:
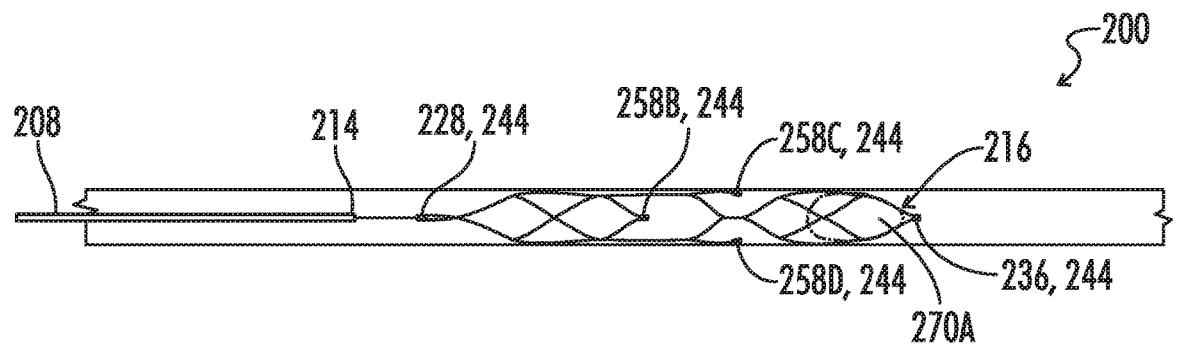

More specifically, FIGS. 15A-G illustrate stepwise use of the distal body 216 in retrieving a soft clot 270A in a human intracranial artery 266. (The distal body 216 in FIGS. 15A-15G is in Orientation 1). First, as always, the surgeon determines the location of the clot 270A in the vessel 266 using, for example, a contrast dye injected proximal and distal to the clot 270A. Next, the delivery catheter 208, which is enveloping the distal body 216, is positioned in the blood vessel 266 so that the two proximal, unattached distal-pointing crowns 258A and 258B are immediately distal to the clot 270A. See FIG. 15B. The distal body 216 is then deployed from the delivery catheter 208 by moving the catheter 208 proximally. The soft clot 270A, which is unable to collapse the distal body 216, then enters the distal body interior 222. See FIG. 15C. However, at this time, the surgeon is unaware that the clot 270A has entered into the distal body interior 222. Thus, without moving the distal body 216, the surgeon irradiates the four rows of x-ray markers at a first vantage point (i.e., from the front of the distal body 216 in the orientation shown in FIGS. 15A-G; i.e., into the page). As shown in FIG. 15D, the first vantage point shows four rows of x-ray markers. The first row is a single point, which represents the x-ray marker located in the proximal tube 228, 244; the proximal tube x-ray marker 228, 244 always appears as a single point. The second row is a single point, which represents the x-ray marker located at the front, proximal, unattached distal-pointing crown 258B, 244; the reason that this second row of markers is a single point is that the rear x-ray marker of the second row 258A, 244 is hidden from view because it is directly behind the front x-ray marker of the second row 258B, 244. The third row has two points, which represents the two x-ray markers located at the distal, unattached distal-pointing crowns 258C, 244 and 258D, 244; the reason that this third row of markers has two points is that neither marker in the third row 258C, 244 and 258D, 244 is hidden from view on the x-ray at this angle—rather, one marker 258C, 244 is located above the other marker 258D, 244—and as shown in FIG. 15C, the distal body 216 is not collapsed at the distal, unattached distal-pointing crowns 258C, 244 and 258D, 244. The fourth row is a single point, which represents the x-ray marker located in the distal tube 236, 244; the distal tube x-ray marker 236, 244 always appears as a single point. Without moving the distal body 216, the surgeon then irradiates the four rows of x-ray markers from a second vantage point 90 degrees offset from the first vantage point (i.e., from the bottom of the distal body 216 in the orientation shown in FIG. 15A). As shown, the first row is, as always, a single point, which represents the x-ray marker located in the proximal tube 228, 244. The second row has two points, which represents the two x-ray markers located at the proximal, unattached distal-pointing crown 258A, 244 and 258B, 244; the reason that this second row of markers shows up as two points is that neither marker 258A, 244 and 258B, 244 in the second row is hidden from view on the x-ray at this offset angle—rather, one marker 258B, 244 is located above the other marker 258A, 244—and the distal body 216 is not collapsed at the proximal, unattached distal-pointing crowns 258A, 244 and 258B, 244. The third row is a single point, which represents the x-ray marker located at the bottom, distal, unattached distal-pointing crown 258D, 244; the reason that this third row of markers is a single point is that the top x-ray marker of the third row 258C, 244 is directly behind the bottom x-ray marker of the third row 258D, 244, and thus, hidden from view. The fourth row is, as always, a single point, which represents the x-ray marker located in the distal tube 236, 244. The surgeon, thus, concludes that neither the x-ray markers at the second row 258A, 244 and 258B, 244 nor the x-ray markers at the third row 258C, 244 and 258D, 244 (i.e., the x-ray markers at both the proximal and distal unattached distal pointing-crowns) have converged. As shown in FIG. 15E, the surgeon then moves the distal body 216 proximally relative to the soft clot 270A so that the distal, unattached distal-pointing crowns 258C, 244 and 258D, 244 are immediately distal to the clot 270A and then the surgeon irradiates the four rows of x-ray markers again from the first vantage point and the second vantage point. As shown in FIG. 15F, the results are the same as FIG. 15D. With the results from FIGS. 15D and 15F, the surgeon concludes that neither x-ray markers at the second row 258A, 244 and 258B, 244 nor the x-ray markers at the third row 258C, 244 and 258D, 244 (i.e., the x-ray markers at both the proximal and distal unattached distal pointing-crowns) converged at either the original position of the distal body 216 (FIGS. 15C and 15D) or the position after moving the distal body 216 proximally (FIGS. 15E and 15F), and, thus, the distal body 216 was expanded in the vessel 266 in both positions. Thus, the surgeon concludes that the clot is a soft clot 270A that has entered into the distal body interior 222 and the surgeon removes the distal body 216 and the soft clot 270A, captured by the distal body 216, by moving the distal body 216 proximally out of the vessel 266, as shown in FIG. 15G.

Figure 16A:
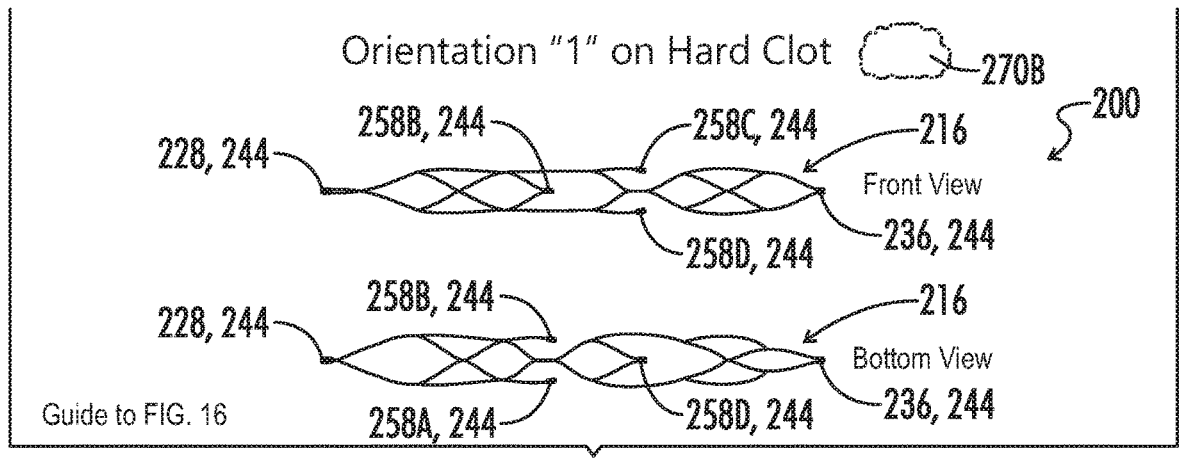
FIGS. 16A-H illustrate stepwise use of the distal body of FIG. 11 in retrieving a hard clot; the distal body is in Orientation 1.
Figure 16B:
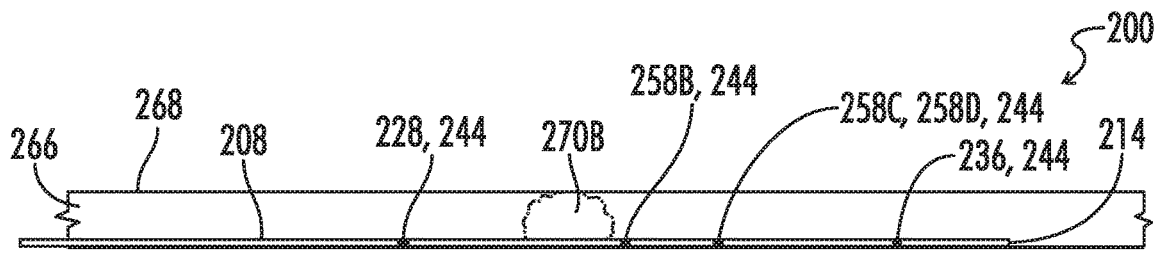
Figure 16C:
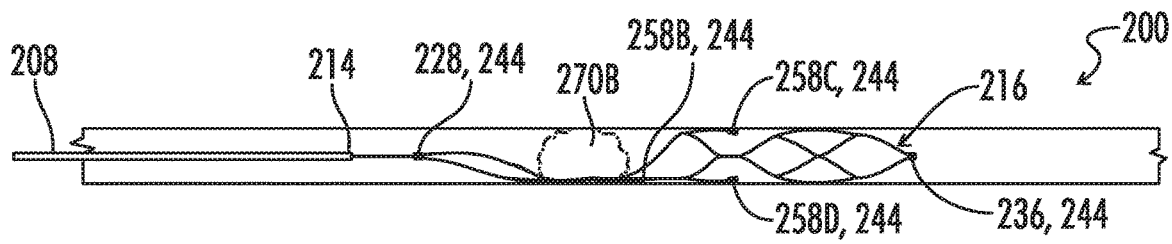
Figure 16D:
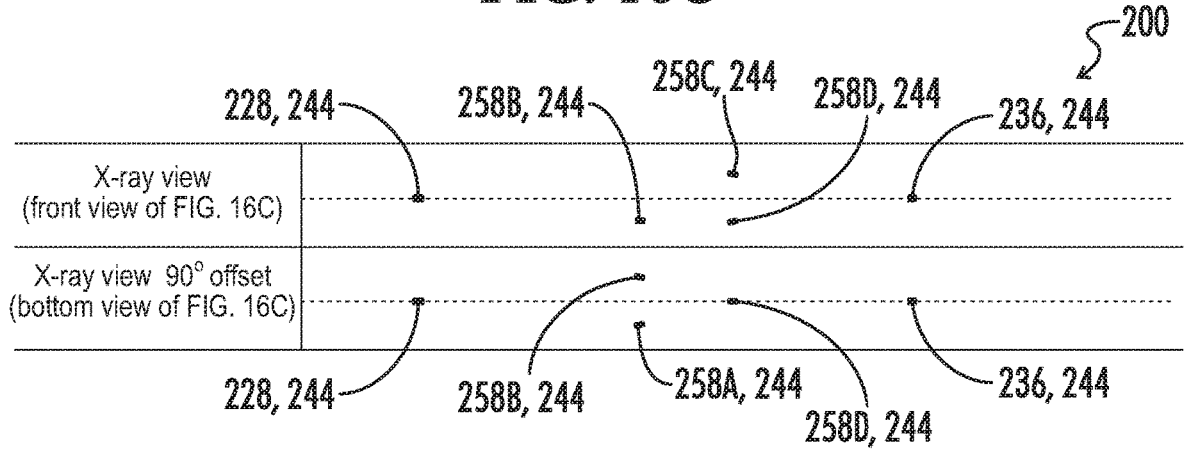
Figure 16E:
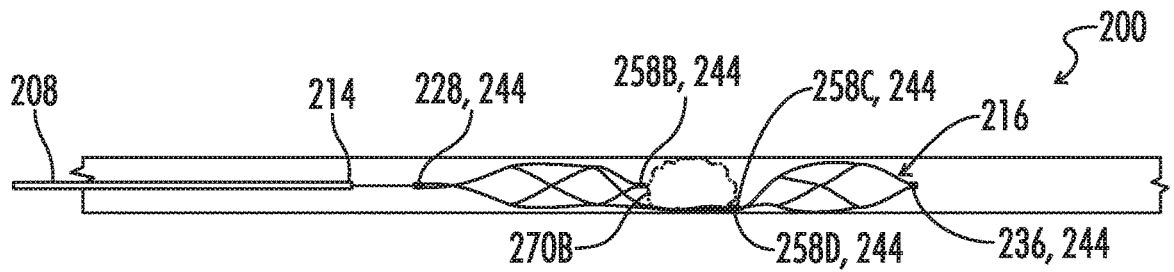
Figure 16F:
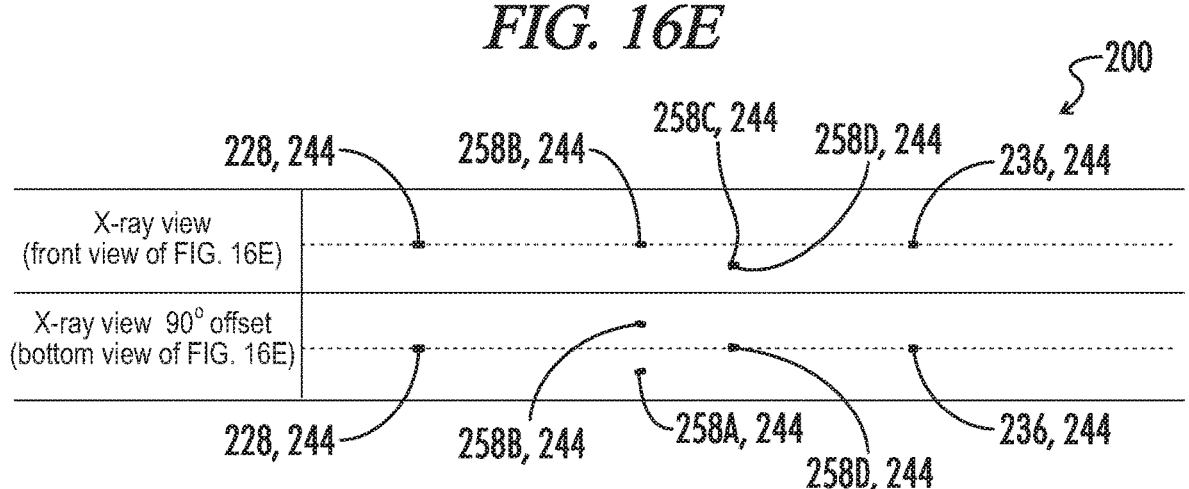
Figure 16G:
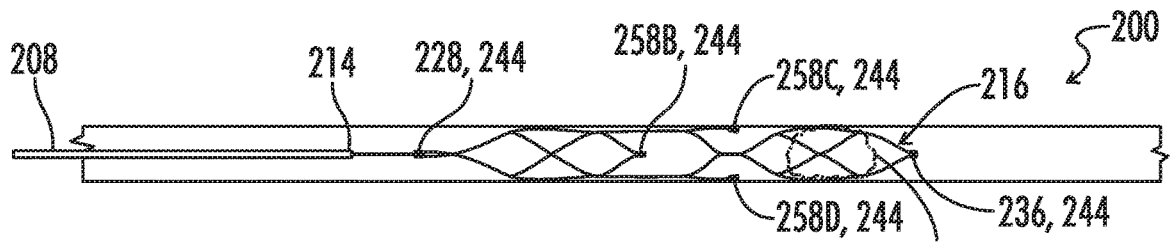
Figure 16H:
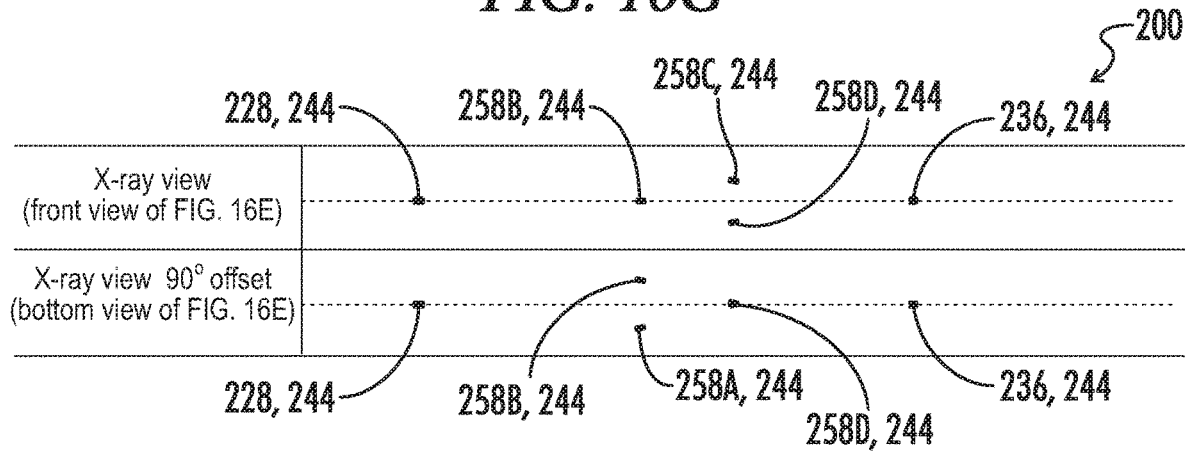

FIGS. 16A-H illustrate stepwise use of the distal body 216 in retrieving a hard clot 270B in a human intracranial artery 266. (In FIGS. 16A-H, the distal body 216 is in Orientation 1). First, as always, the surgeon determines the location of the clot 270B in the vessel 266 using, for example, a contrast dye injected proximal and distal to the clot 270B. Next, the delivery catheter 208, which is enveloping the distal body 216, is positioned in the blood vessel 266 so that the two proximal, unattached distal-pointing crowns 258A and 258B are immediately distal to the clot 270B. See FIG. 16B. The distal body 216 is then deployed from the delivery catheter 208 by moving the catheter 208 proximally. The hard clot 270B, which is located above the distal body 216, collapses the distal body 216, as shown in FIG. 16C. However, at this time, the surgeon is unaware that the clot 270B has collapsed the distal body 216. Thus, without moving the distal body 216, the surgeon irradiates the x-ray markers at a first vantage point (i.e., from the front of the distal body 216; i.e., into the page). As shown in FIG. 16D, the first vantage point shows four rows of x-ray markers. The first row is, as always, a single point, representing the x-ray marker located in the proximal tube—i.e., 228, 244. The second row is a single point, which represents the x-ray marker located at the front, proximal, unattached distal-pointing crown 258B, 244; the reason that this second row of markers is a single point is that the rear x-ray marker of the second row 258A, 244 is hidden from view because it is directly behind the front x-ray marker of the second row 258B, 244. The third row has two points, which represents the two x-ray markers located at the distal, unattached distal-pointing crowns 258C, 244 and 258D, 244; the reason that this third row of markers has two points is that neither marker in the third row is hidden from view on the x-ray at this angle—rather, one marker 258C, 244 is located above the other marker 258D, 244—and as shown in FIG. 16C, the distal body 216 is not collapsed at the distal, unattached distal-pointing crowns 258C, 244 and 258D, 244. The fourth row is, as always, a single point, representing the x-ray marker located in the distal tube 236, 244. Without moving the distal body 216, the surgeon then irradiates the markers from a second vantage point 90 degrees offset from the first vantage point (i.e., from the bottom of the distal body 216). As shown, the first row is, as always, a single point, which represents the x-ray marker located in the proximal tube 228, 244. The second row has two points, which represents the two x-ray markers located at the proximal, unattached distal-pointing crowns 258A, 244 and 258B, 244; the reason that this second row of markers shows up as two points is that neither marker in the second row is hidden from view on the x-ray at this offset angle—rather, one marker 258B, 244 is located above the other marker 258A, 244—and although the distal body 216 is collapsed at the proximal, unattached distal-pointing crowns as shown in FIG. 16C, the second row of x-ray markers have not converged because the clot 270B is on top of the second row of x-ray markers. The third row is a single point, which represents the x-ray marker located at the bottom, distal, unattached distal-pointing crown 258D, 244; the reason that this third row of markers is a single point is that the top x-ray marker of the third row 258C, 244 is directly behind the bottom x-ray marker of the third row 258D, 244, and thus, hidden from view. The fourth row is, as always, a single point, which represents the x-ray marker located in the distal tube 236, 244. The surgeon, thus, concludes that neither the second row 258A, 244 and 258B, 244 nor the third row 258C, 244 and 258D, 244 of x-ray markers (i.e., the x-ray markers at both the proximal and distal unattached distal pointing-crowns) has converged. As shown in FIG. 16E, the surgeon then moves the distal body 216 proximally so that the distal, unattached distal-pointing crowns 258C, 244 and 258D, 244 are immediately distal to the clot 270B and the surgeon then irradiates the x-markers again from the first vantage point. As shown in FIG. 16F, the first row is, as always, a single point, representing the x-ray marker located in the proximal tube 228, 244. The second row is a single point, which represents the x-ray marker located at the front, proximal, unattached distal-pointing crown 258B, 244; the reason that this second row of markers is a single point is that the rear x-ray marker of the second row 258A, 244 is hidden from view because it is directly behind the front x-ray marker of the second row 258B, 244. The third row has only one point because the clot 270B, which is on top of the third row of x-ray markers 258C, 244 and 258D, 244 (i.e., the markers at the distal, unattached distal-pointing crowns), has pushed the third row of x-ray markers 258C, 244 and 258D, 244 together. The fourth row is, as always, a single point, representing the x-ray marker located in the distal tube 236, 244. Without moving the distal body 216, the surgeon then irradiates the markers from a second vantage point 90 degrees offset from the first vantage point (i.e., from the bottom of the distal body). As shown, the first row is, as always, a single point, which represents the x-ray marker located in the proximal tube 228, 244. The second row has two points, which represents the two x-ray markers located at the proximal, unattached distal-pointing crown 258A, 244 and 258B, 244; the reason that this second row of markers shows up as two points is that neither marker in the second row is hidden from view on the x-ray at this offset angle and the distal body 216 is not collapsed at the proximal, unattached distal-pointing crowns 258A, 244 and 258B, 244. The third row is a single point, which represents the x-ray marker located at the bottom, distal, unattached distal-pointing crown 258D, 244; the reason that this third row of markers is a single point is that the bottom x-ray marker of the third row 258D, 244 is directly in front of the top x-ray marker of the third row 258C, 244, and thus, the top x-ray marker of the third row 258C, 244 is hidden from view. The fourth row is, as always, a single point, which represents the x-ray marker located in the distal tube 236, 244. Knowing that the distal, unattached distal-pointing crowns 258C, 244 and 258D, 244 have converged as shown in FIG. 16F, the surgeon moves the distal body 216 proximally and the hard clot 270B falls into the distal body interior 222 in the enlarged cell/drop zone 262C immediately distal to the top, distal, unattached distal-pointing crown 258C. See FIG. 16G. To confirm that the hard clot 270B has entered the distal body interior 222, the surgeon takes x-rays from the first and second vantage points. The results are shown in FIG. 16H. As compared to 16F, the front x-ray view of FIG. 16H shows that the distal, unattached distal-pointing crowns 258C, 244 and 258D, 244 are not converged, and, thus, the surgeon concludes that the hard clot 270B has entered the distal body interior 222. The surgeon then removes the distal body 216 and the hard clot 270B, captured by the distal body 216, by moving the distal body 216 proximally out of the vessel 266.

Figure 17A:
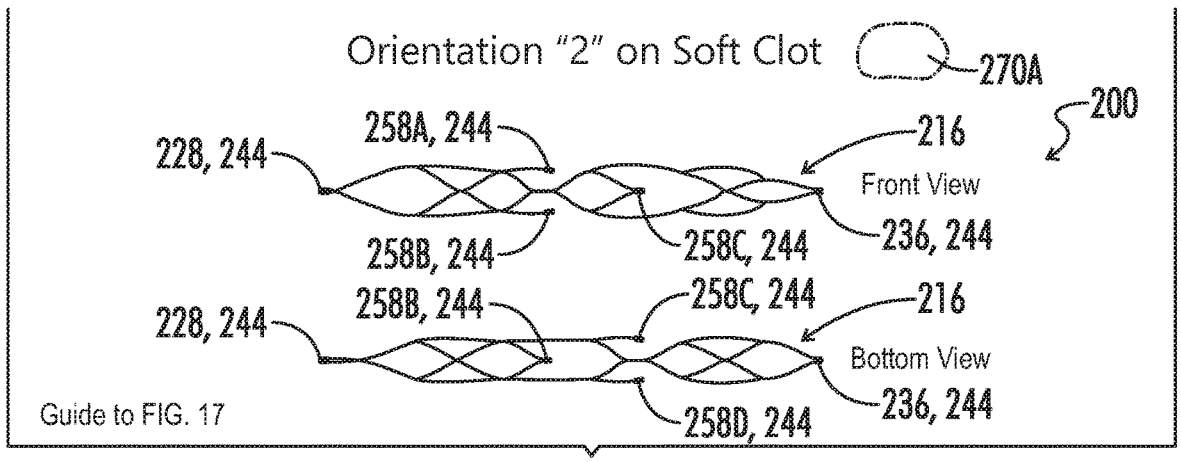
FIGS. 17A-G illustrate stepwise use of the distal body of FIG. 11 in retrieving a soft clot; the distal body is in Orientation 2.
Figure 17B:
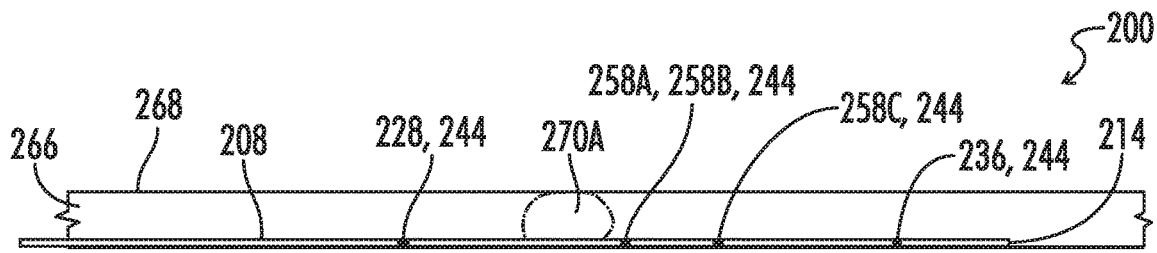
Figure 17C:
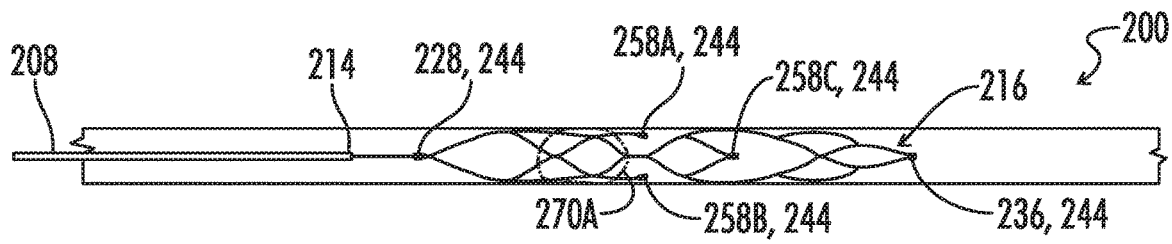
Figure 17D:
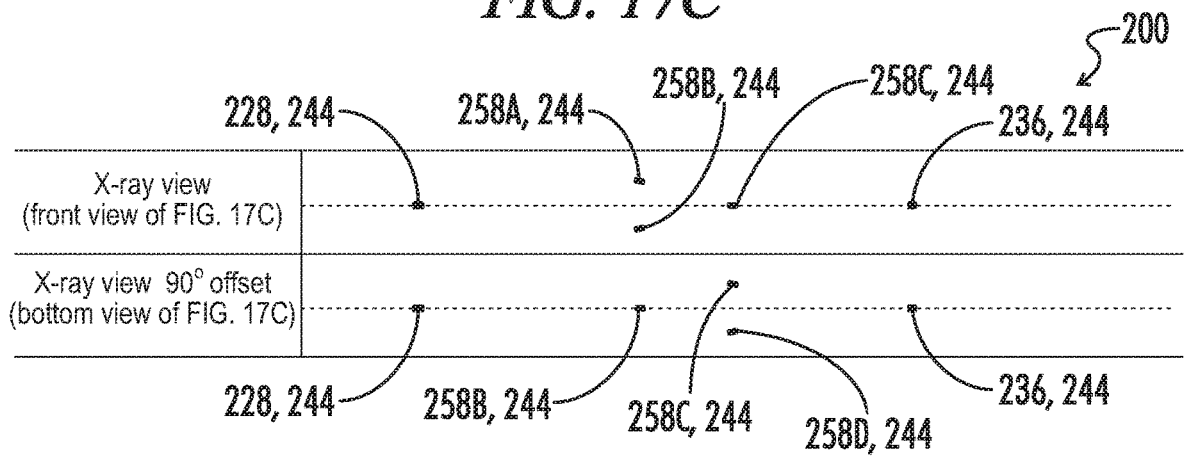
Figure 17E:
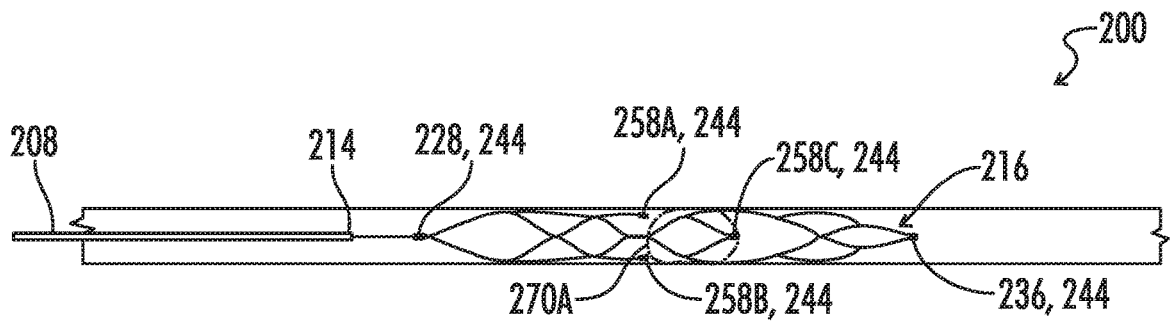
Figure 17F:
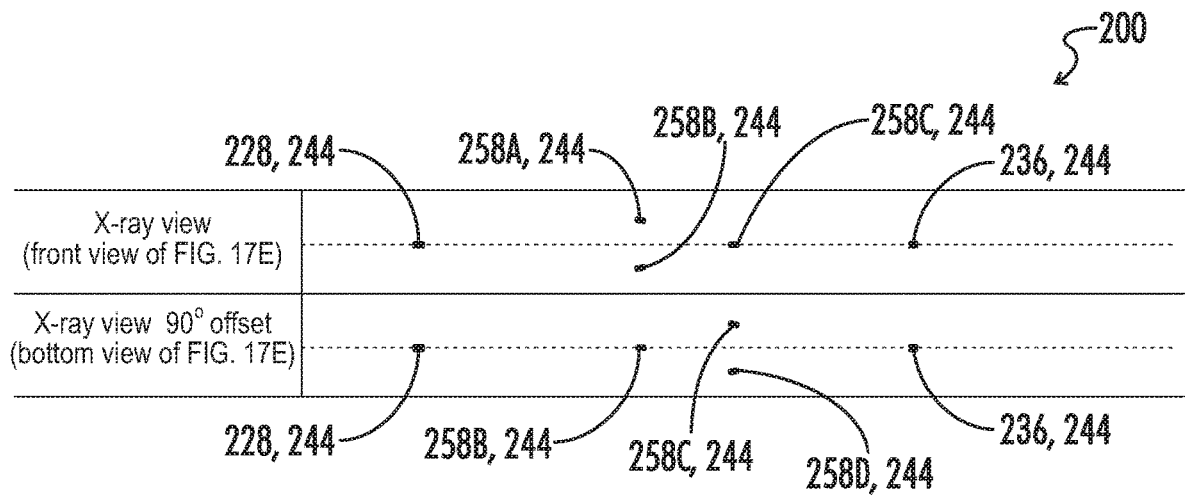
Figure 17G:
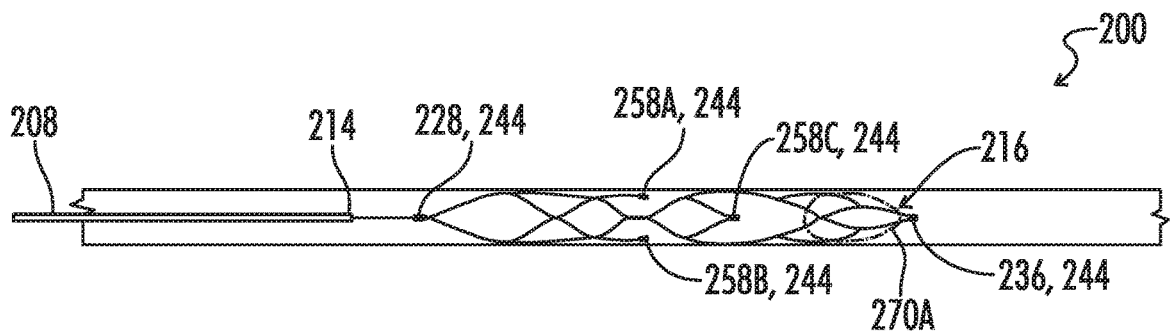

FIGS. 17A-G illustrate stepwise use of the distal body 216 in retrieving a soft clot 270A in a human intracranial artery 266. (In FIGS. 17A-G, the distal body 216 is in Orientation 2). First, as always, the surgeon determines the location of the clot 270A in the vessel 266 using, for example, a contrast dye injected proximal and distal to the clot 270A. Next, the delivery catheter 208, which is enveloping the distal body 216, is positioned in the blood vessel 266 so that the two proximal, unattached distal-pointing crowns 258A and 258B are immediately distal to the clot 270A. See FIG. 17B. The distal body 216 is then deployed from the catheter 208 by moving the catheter 208 proximally. The soft clot 270A, which is unable to collapse the distal body 216, then enters the distal body interior 222. See FIG. 17C. However, at this time, the surgeon is unaware that the clot 270A has entered into the distal body interior 222. Thus, without moving the distal body 216, the surgeon irradiates the x-ray markers at a first vantage point (i.e., from the front of the distal body; into the page). As shown in FIG. 17D, the first vantage point shows four rows of x-ray markers. The first row is, as always, a single point, representing the x-ray marker located in the proximal tube 228, 244. The second row has two points, which represents the two x-ray markers located at the proximal, unattached distal-pointing crowns 258A, 244 and 258B, 244; the reason that this second row of markers is two points is that neither marker in the second row is hidden from view on the x-ray at this angle—rather, one marker 258A, 244 is located above the other marker 258B, 244— and as shown in FIG. 17C, the distal body 216 is not collapsed at the proximal, unattached distal-pointing crowns 258A, 244 and 258B, 244. The third row has a single point, which represents the x-ray marker located at the front (in Orientation 2), distal, unattached distal-pointing crown 258C, 244; the reason that this third row of markers is a single point is that the rear (in Orientation 2) x-ray marker 258D, 244 of the third row is hidden from view because it is directly behind the front x-ray marker 258C, 244 of the third row. The fourth row is, as always, a single point, representing the x-ray marker located in the distal tube 236, 244. Without moving the distal body, the surgeon then irradiates the markers from a second vantage point 90 degrees offset from the first vantage point (i.e., from the bottom of the distal body, as shown in this view). As shown, the first row is, as always, a single point, which represents the x-ray marker located in the proximal tube 228, 244. The second row is a single point, which represents the x-ray marker located at the bottom (in Orientation 2), proximal, unattached distal-pointing crown 258B, 244; the reason that this second row of markers is a single point is that the top (in Orientation 2) x-ray marker of the second row 258A, 244 is directly behind the bottom x-ray marker of the second row 258B, 244, and thus, hidden from view. The third row has two points, which represents the two x-ray markers located at the distal, unattached distal-pointing crowns 258C, 244 and 258D, 244; the reason that this third row of markers shows up as two points is that neither marker in the third row is hidden from view on the x-ray at this offset angle and the distal body 216 is not collapsed at the distal, unattached distal-pointing crowns 258C, 244 and 258D, 244. The fourth row is, as always, a single point, which represents the x-ray marker located in the distal tube 236, 244. The surgeon, thus, concludes that neither the second row 258A, 244 and 258B, 244 nor the third row of x-ray markers 258C, 244 and 258D, 244 (i.e., the x-ray markers at both the proximal and distal unattached distal pointing-crowns) has converged. As shown in FIG. 17E, the surgeon then moves the distal body 216 proximally relative to the clot 270A so that the distal, unattached distal-pointing crowns 258C, 244 and 258D, 244 are immediately distal to the clot 270A and then the surgeon irradiates the x-markers again from the first vantage point and the second vantage point. As shown in FIG. 17F, the results are the same as FIG. 17D. With the results from FIGS. 17D and 17F, the surgeon concludes that neither the second row 258A, 244 and 258B, 244 nor the third row of x-ray markers 258C, 244 and 258D, 244 (i.e., the x-ray markers at both the proximal and distal unattached distal pointing-crowns) were converged at either the original position of the distal body 216 (FIGS. 17C and 17D) or the position after moving the distal body 216 proximally (FIGS. 17E and 17F), and, thus, the distal body 216 was expanded in the vessel 266 in both positions. Thus, the surgeon concludes that the clot 270A is a soft clot 270A that has entered into the distal body interior 222 and the surgeon removes the distal body 216 and the soft clot 270A, captured by the distal body 216, by moving the distal body 216 proximally out of the vessel 266, as shown in FIG. 17G.

Figure 18A:
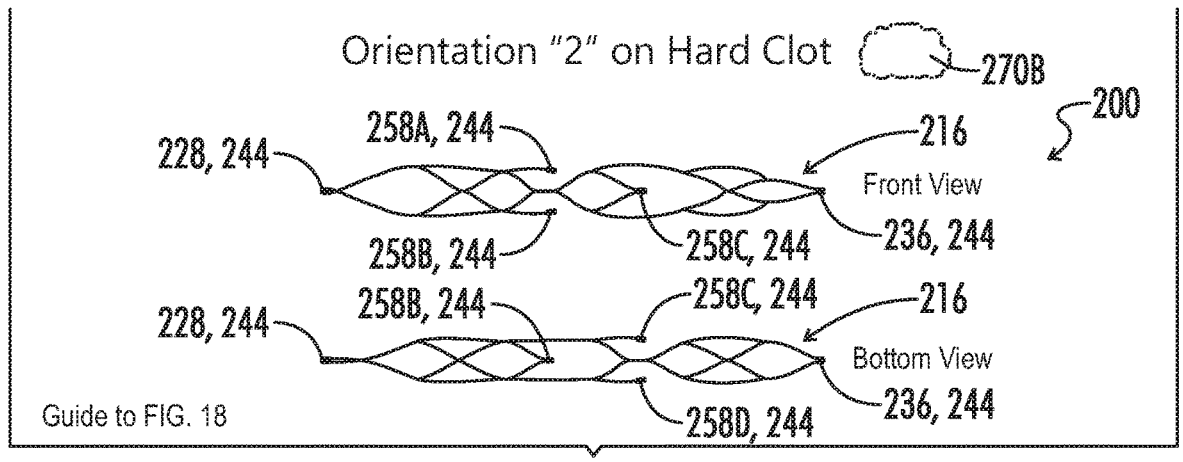
FIGS. 18A-G illustrate stepwise use of the distal body of FIG. 11 in retrieving a hard clot; the distal body is in Orientation 2.
Figure 18B:
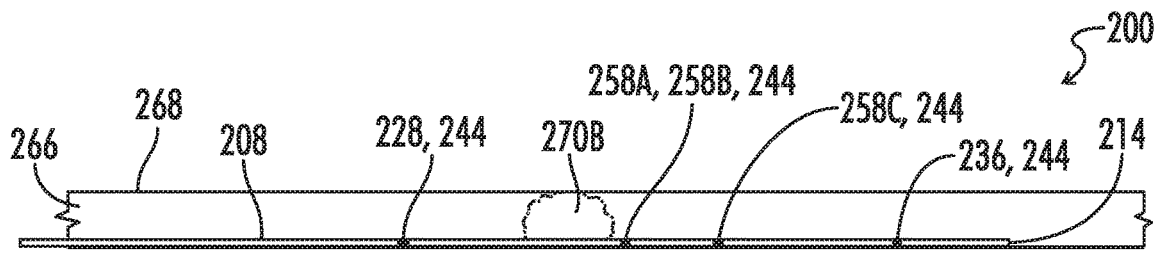
Figure 18C:
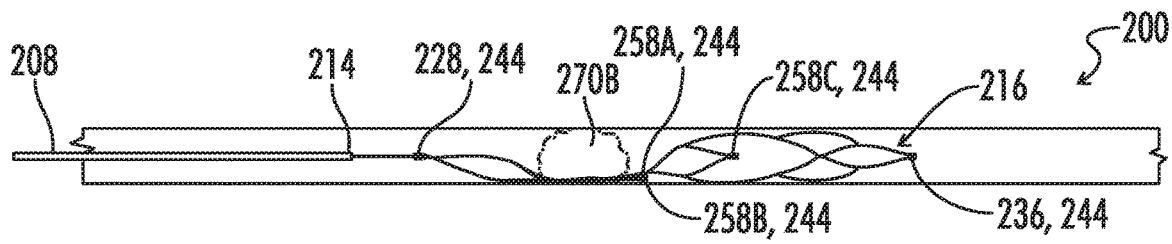
Figure 18D:
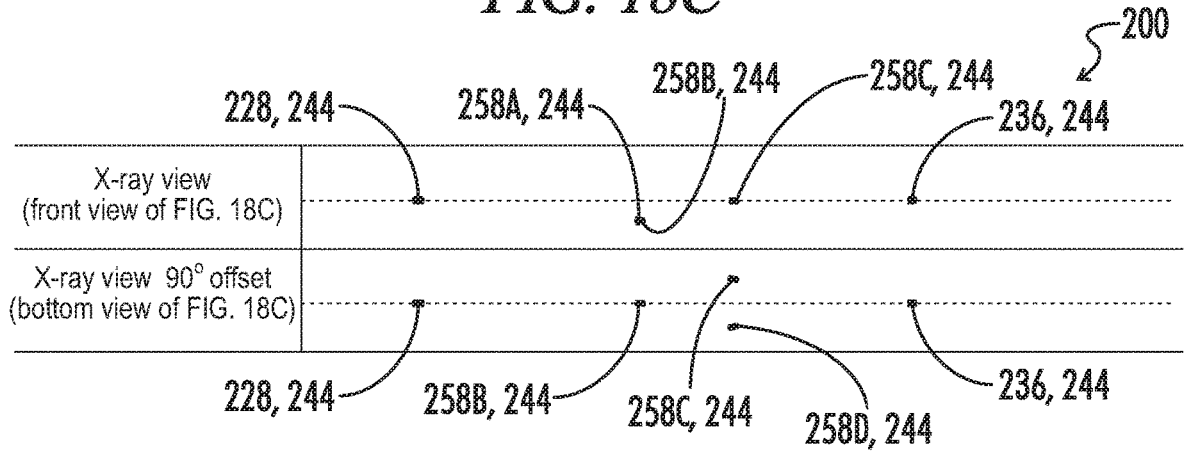
Figure 18E:
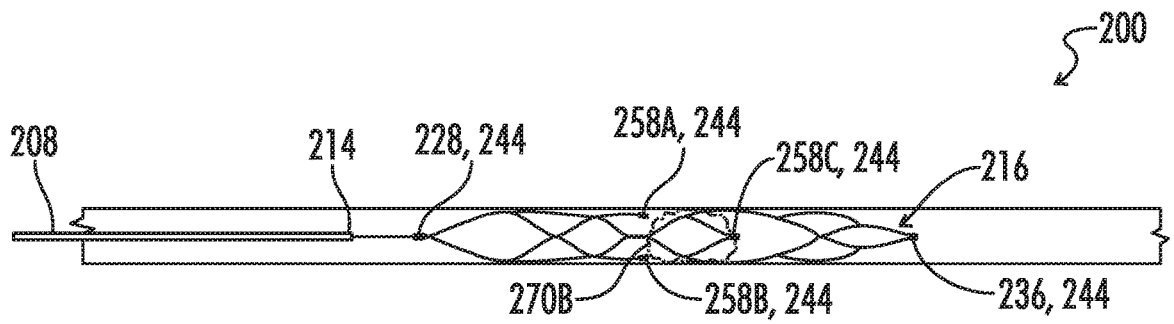
Figure 18F:
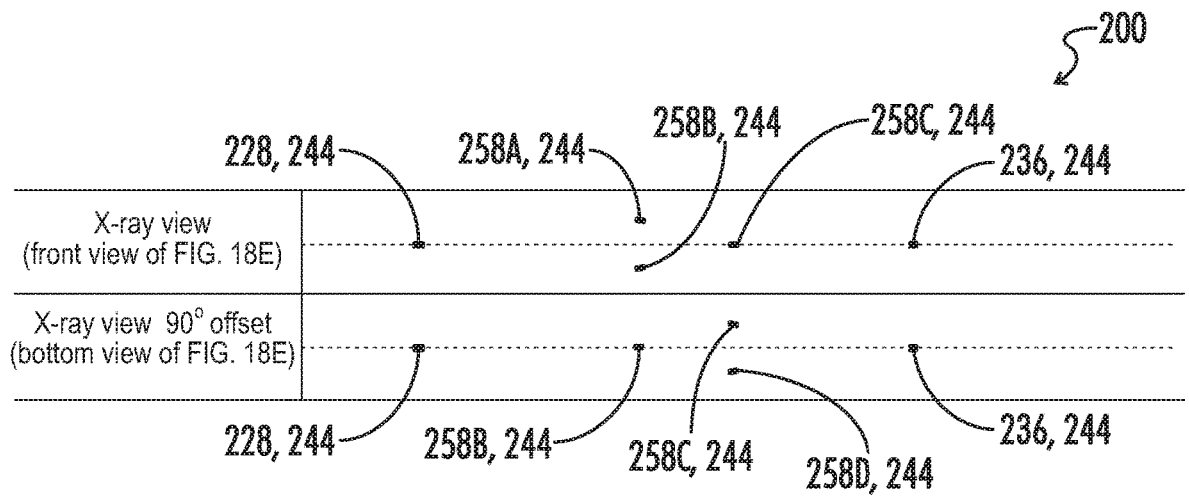
Figure 18G:
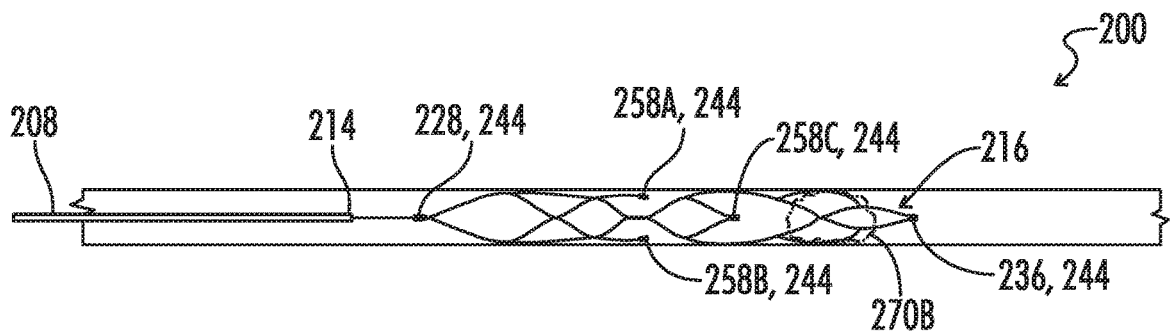

FIGS. 18A-G illustrate stepwise use of the distal body 216 in retrieving a hard clot 270B in a human intracranial artery 266. (In FIGS. 18A-G, the distal body 216 is in Orientation 2). (As described below, the primary differences between FIGS. 18A-G and FIGS. 16A-G is that the clot 270B enters the distal body interior 222 in an enlarged cell/drop zone 262A immediately distal to one of the proximal, unattached distal-pointing crowns 258A in FIGS. 18A-G, as compared to FIGS. 16A-G where the clot 270B enters the distal body interior 222 in an enlarged cell/drop zone 262C immediately distal to one of the distal, unattached distal-pointing crowns 258C). First, as always, the surgeon determines the location of the clot 270B in the vessel 266 using, for example, a contrast dye injected proximal and distal to the clot 270B. Next, the delivery catheter 208, which is enveloping the distal body 216, is positioned in the blood vessel 266 so that the two proximal, unattached distal-pointing crowns 258A and 258B are immediately distal to the clot 270B. See FIG. 18B. The distal body 216 is then deployed from the catheter 208 by moving the catheter 208 proximally. The hard clot 270B, which is located above the distal body 216, collapses the distal body 216, as shown in FIG. 18C. However, at this time, the surgeon is unaware that the clot 270B has collapsed the distal body 216. Thus, without moving the distal body 216, the surgeon irradiates the x-ray markers at a first vantage point (i.e., from the front of the distal body in Orientation 2; into the page). As shown in FIG. 18D, the first vantage point shows four rows of x-ray markers. The first row is, as always, a single point, representing the x-ray marker located in the proximal tube 228, 244. The second row has only one point because the clot 270B, which is on top of the second row of x-ray markers 258A, 244 and 258B, 244 (i.e., the markers at the proximal, unattached distal-pointing crowns), has pushed them together. The third row has only one point, which represents the x-ray marker located at the front (in Orientation 2), proximal, unattached distal-pointing crown 258C, 244; the reason that this third row of markers is a single point is that the rear (in this view) x-ray marker of the third row 258D, 244 is hidden from view because it is directly behind the front x-ray marker of the third row 258C, 244. The fourth row is, as always, a single point, representing the x-ray marker located in the distal tube 236, 244. Without moving the distal body, the surgeon then irradiates the markers from a second vantage point 90 degrees offset from the first vantage point (i.e., from the bottom of the distal body 216). As shown, the first row is, as always, a single point, which represents the x-ray marker located in the proximal tube 228, 244. The second row has a single point because the top (in Orientation 2) x-ray marker of the second row 258A, 244 is located behind the bottom (in Orientation 2) x-ray marker 258B, 244 and thus, the top x-ray marker of the second row 258A, 244 is hidden from view. The third row has two points, which represents the x-ray markers located at the distal, unattached distal-pointing crowns 258C, 244 and 258D, 244; in this x-ray view neither of the x-ray markers of the third row is hidden from view. The fourth row is, as always, a single point, which represents the x-ray marker located in the distal tube 236, 244. The surgeon, thus, concludes that the second row of x-ray markers 258A, 244 and 258B, 244 (i.e., the x-ray markers at the proximal, unattached distal pointing-crowns) has converged. As shown in FIG. 18E, the surgeon then moves the distal body 216 proximally so that the distal, unattached distal-pointing crowns 258C, 244 and 258D, 244 are immediately distal to the clot 270B. Unbeknownst to the surgeon, the clot 270B enters the distal body interior 222 immediately distal to the top (in Orientation 2), proximal unattached distal-pointing crown 258A and the distal body 216 is no longer collapsed. The surgeon then irradiates the x-markers again from the first vantage point. As shown in FIG. 18F, the first row is, as always, a single point, representing the x-ray marker located in the proximal tube 228, 244. The second row has two x-ray markers because the distal body 216 is not collapsed and neither the top (in Orientation 2) 258A, 244 nor the bottom 258B, 244 (in Orientation 2) x-ray marker of the second row (i.e., the marker at the proximal, unattached distal-pointing crowns) is hidden from view. The third row has only one point because the rear (in Orientation 2), distal unattached distal-pointing crown 258D, 244 is hidden behind the front (in Orientation 2), distal, unattached distal pointing-crown 258C, 244. The fourth row is, as always, a single point, representing the x-ray marker located in the distal tube 236, 244. Without moving the distal body 216, the surgeon then irradiates the markers from a second vantage point 90 degrees offset from the first vantage point (i.e., from the bottom of the distal body 216). As shown, the first row is, as always, a single point, which represents the x-ray marker located in the proximal tube 228, 244. The second row has a single point because the x-ray marker at the top (in Orientation 2), proximal, unattached distal-pointing crown 258A, 244 is hidden behind the bottom (in Orientation 2), proximal, unattached-distal pointing crown 258B, 244. The third row has two points because neither the front nor the rear x-ray markers at the distal, unattached, distal-pointing crowns 258C, 244 and 258D, 244 is hidden from view. The fourth row is, as always, a single point, which represents the x-ray marker located in the distal tube 236, 244. Based on the information from FIGS. 18D and 18F, the surgeon concludes that the clot 270B has entered into the distal body interior 222. The surgeon then removes the distal body 216 and the hard clot 270B, captured by the distal body 216, by moving the distal body 216 proximally out of the vessel 266, as shown in FIG. 18G. Upon comparing FIGS. 16A-G and FIGS. 18A-G it will be appreciated that the orientation of the enlarged cells/drop zone 262A-D relative to the orientation of a hard clot 270B determine which enlarged cell/drop zone 262A, 262B, 262C, or 262D, the hard clot 270 enters the distal body interior 222 through. For example, in FIG. 16C, the hard clot 270B is located above the distal body 216, and thus, the hard clot 270B must enter through the enlarged cell/drop zone located at the top of the distal body, which in the orientation of the distal body shown in FIGS. 16A-G, is the enlarged cell/drop zone 262C immediately distal to the top, distal, unattached, distal-pointing crown 258C. In FIG. 18C, the hard clot 270B is again located above the distal body and, thus, the hard clot 270B must enter through the enlarged cell/drop zone located at the top of the distal body. However, in FIG. 18C, the enlarged cell/drop zone located at the top of the distal body 216, in the orientation of the distal body 216 shown in FIGS. 18A-G, is the enlarged cell/drop zone 262A immediately distal to the top, proximal, unattached, distal-pointing crown 258A.

Figure 19A:
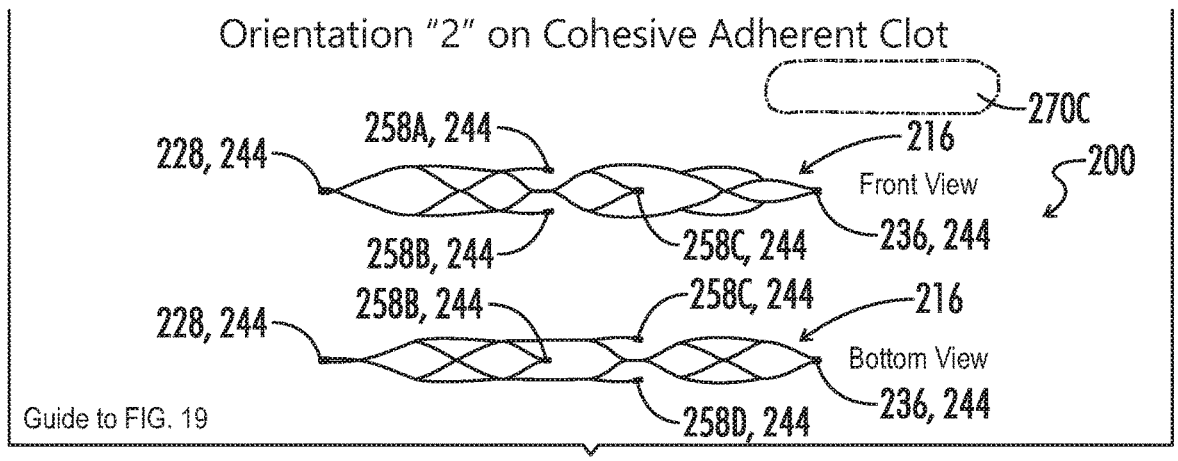
FIGS. 19A-N illustrate stepwise use of the distal body of FIG. 11 in retrieving a deformable, cohesive adherent clot; the distal body is in Orientation 2.
Figure 19B:
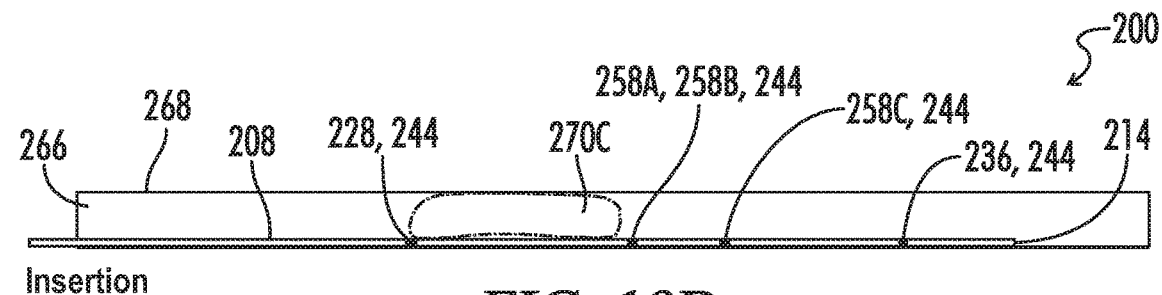
Figure 19C:
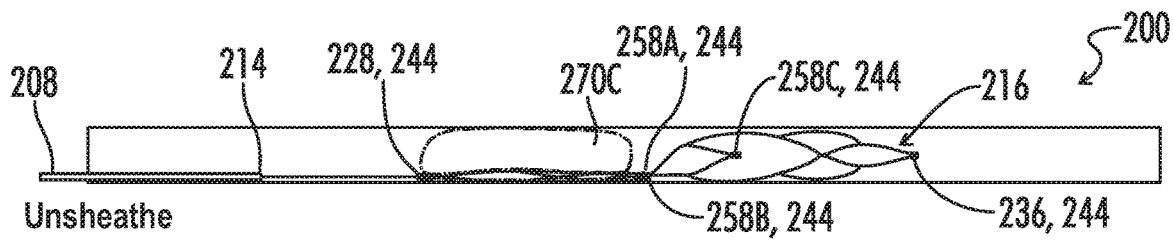
Figure 19D:
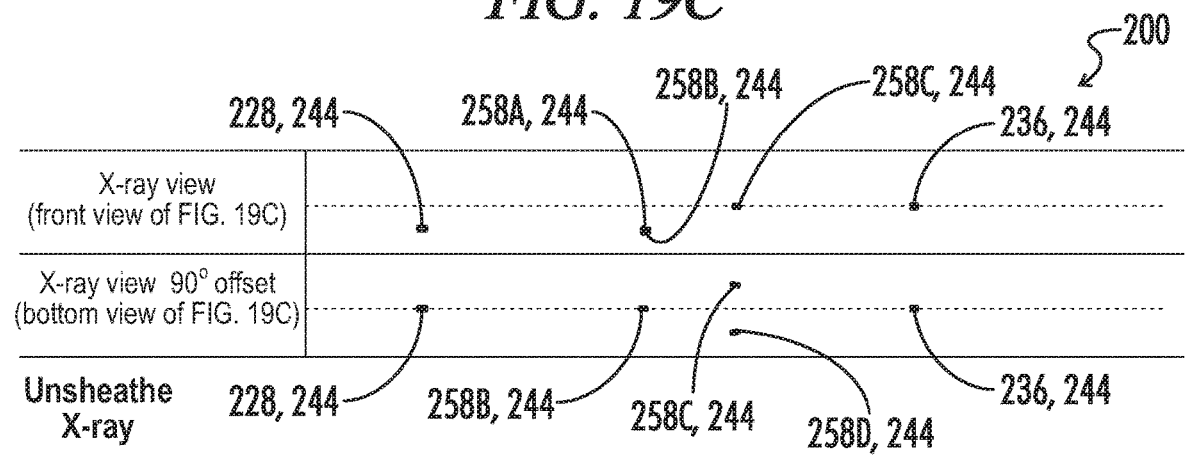
Figure 19E:
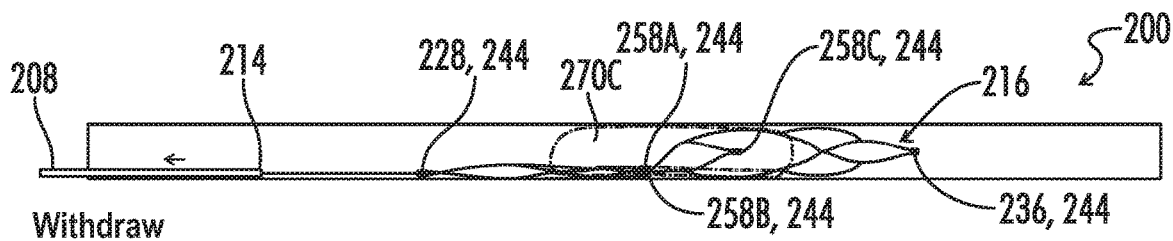
Figure 19F:
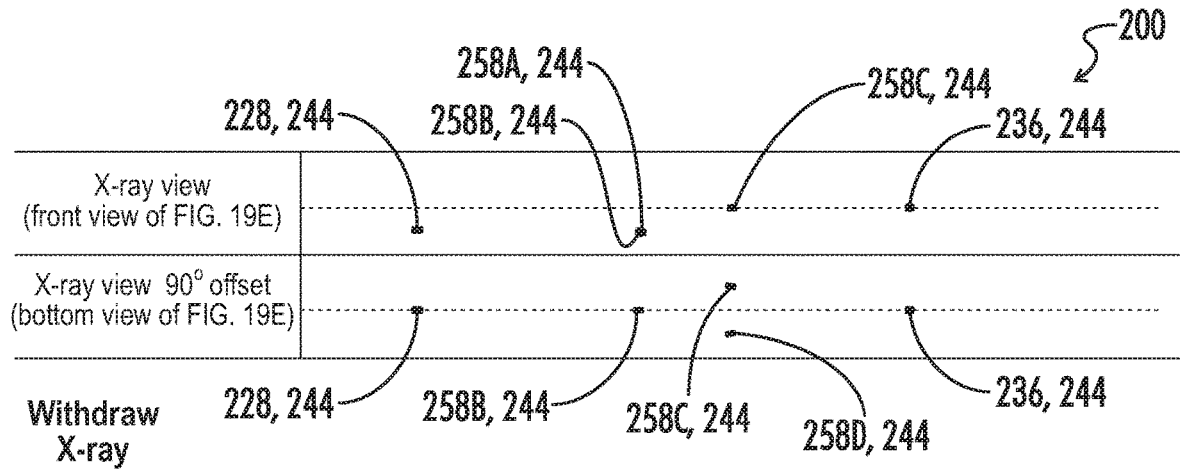
Figure 19G:
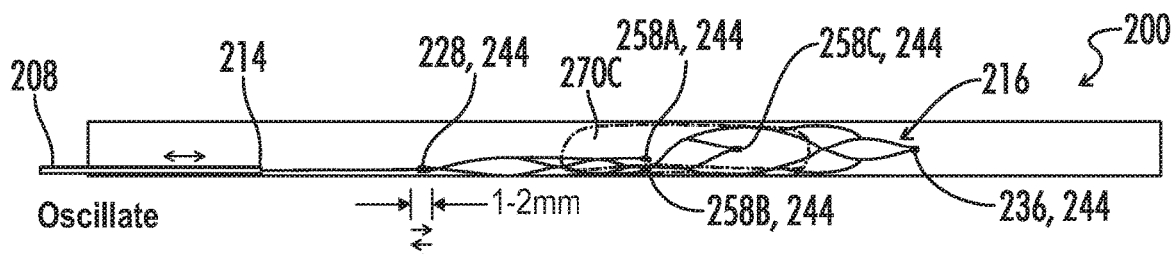
Figure 19H:
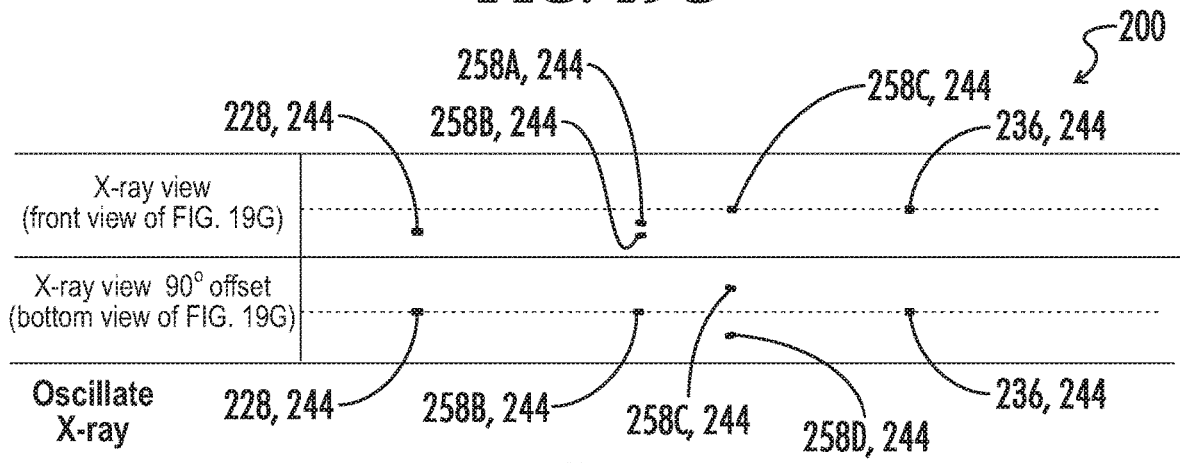
Figure 19I:
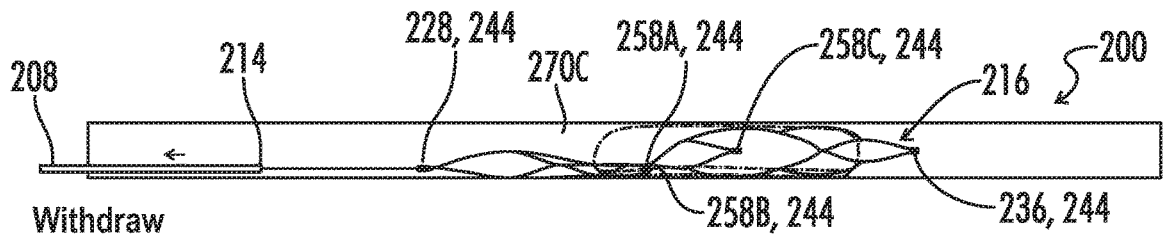
Figure 19J:
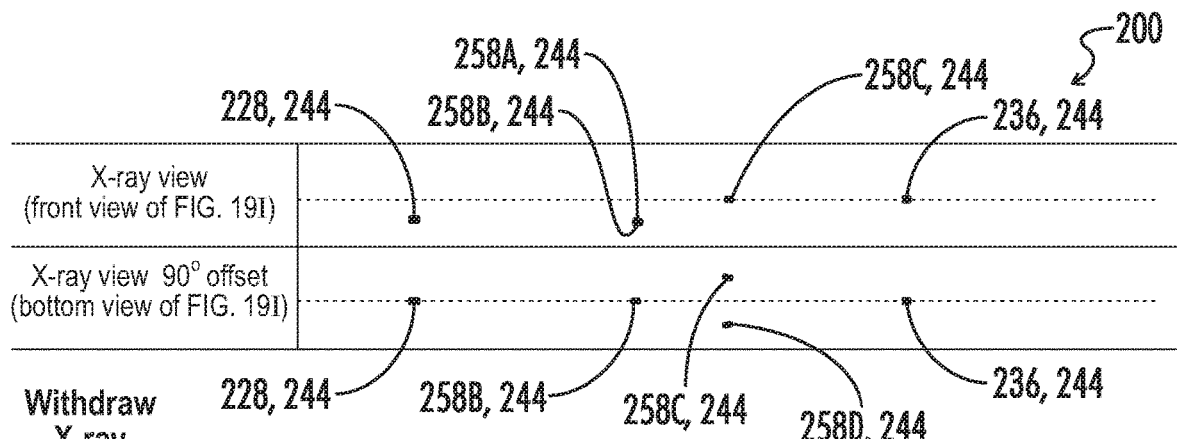
Figure 19K:
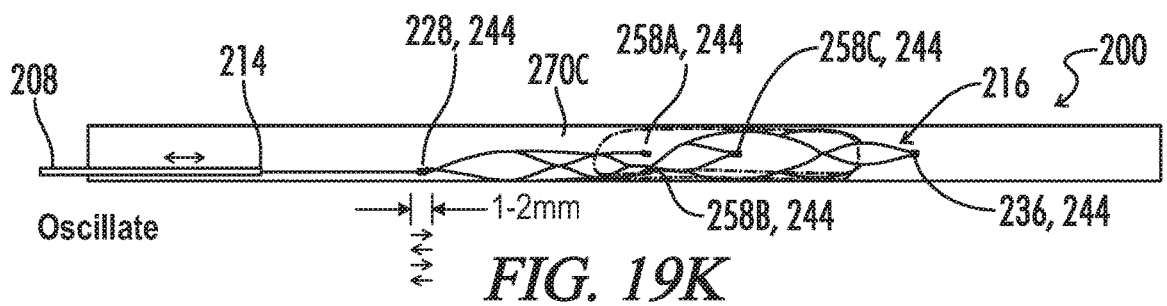
Figure 19L:
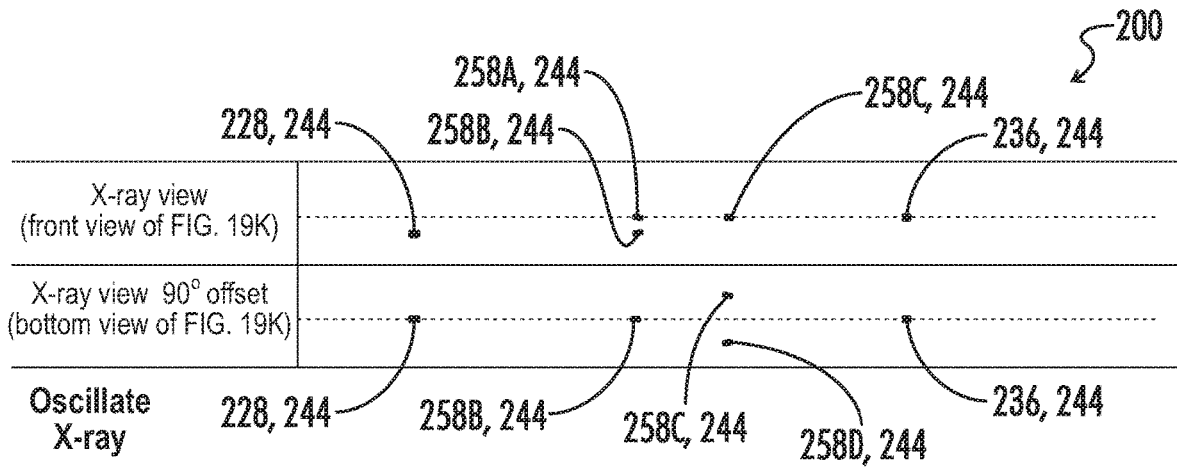
Figure 19M:
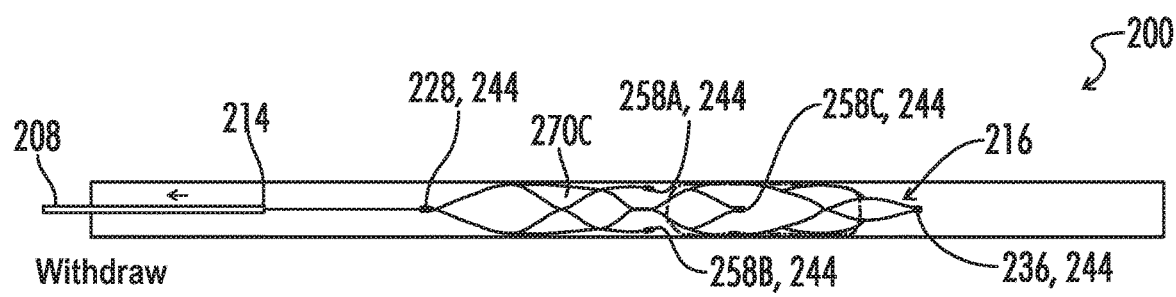
Figure 19N:
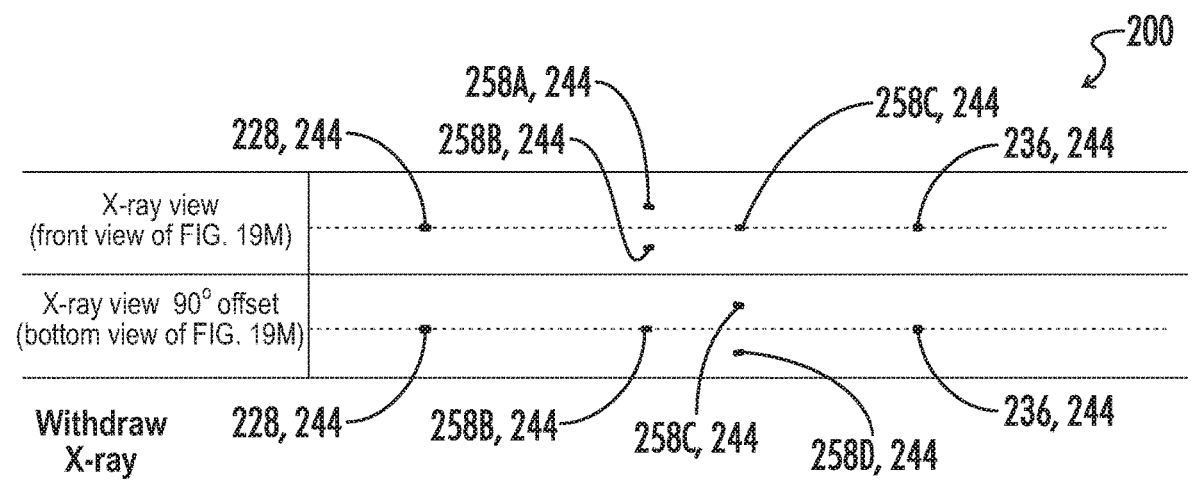

FIGS. 19A-N illustrate stepwise use of the distal body 216 in retrieving a deformable cohesive, adherent clot 270C— i.e., a clot that is difficult to break up and is tightly adhered to the vessel wall 268—in a human intracranial artery 266. (In FIGS. 19A-N, the distal body 216 is in Orientation 2). First, as always, the surgeon determines the location of the clot 270C in the vessel 266 using, for example, a contrast dye injected proximal and distal to the clot 270C. Next, the delivery catheter 208, which is enveloping the distal body 216, is positioned in the blood vessel 266 so that the two proximal, unattached distal-pointing crowns 258A and 258B are immediately distal to the clot 270C. See FIG. 19B. The distal body 216 is then deployed from the catheter 208 by moving the catheter 208 proximally. The deformable, cohesive adherent clot 270C, which is located above the distal body 216, collapses the distal body 216, as shown in FIG. 19C. However, at this time, the surgeon is unaware that the clot 270C has collapsed the distal body 216. Thus, without moving the distal body 216, the surgeon irradiates the x-ray markers at a first vantage point (i.e., from the front of the distal body; i.e., into the page). As shown in FIG. 19D, the first vantage point shows four rows of x-ray markers. The first row is, as always, a single point, representing the x-ray marker located in the proximal tube 228, 244. The second row has a single point, corresponding to the top (in Orientation 2) and bottom (in Orientation 2), proximal, unattached distal-pointing crowns 258A, 244 and 258B, 244, which have converged because the clot 270C is collapsing the distal body 216. The third row has a single point, which represents the x-ray marker located at the front (in Orientation 2), distal, unattached distal-pointing crown 258C, 244; the x-ray marker located at the rear, distal, unattached distal-pointing crown 258D, 244 is hidden from view. The fourth row is, as always, a single point, representing the x-ray marker located in the distal tube 236, 244. Without moving the distal body 216, the surgeon then irradiates the markers from a second vantage point 90 degrees offset from the first vantage point (i.e., from the bottom of the distal body). As shown, the first row is, as always, a single point, which represents the x-ray marker located in the proximal tube 228, 244. The second row has a single point, which corresponds to the bottom (in Orientation 2), proximal, unattached distal-pointing crown 258B, 244; the top (in Orientation 2), proximal, unattached distal-pointing crown 258A, 244 is located behind the bottom, proximal, unattached distal-pointing crown 258B, 244 and hidden from view. The third row has two points, which correspond to the front (in Orientation 2) 258C, 244 and rear 258D, 244 (in Orientation 2), distal, unattached distal-pointing crowns, neither of which is blocked in this view. The fourth row is, as always, a single point, which represents the x-ray marker located in the distal tube 236, 244. As shown in FIG. 19E, the surgeon then moves the distal body 216 proximally (i.e., slightly withdraws the distal body 216). The surgeon then irradiates the x-markers again from the first and second vantage points. As shown in FIG. 19F, the results are exactly the same as in FIG. 19D. Based on the observation that the proximal, unattached distal-pointing crowns 258A, 244 and 258B, 244 have converged at both the original position (FIGS. 19C and 19D in which the proximal, unattached distal-pointing crowns 258A, 244 and 258B, 244 are immediately distal to the clot 270C) and the second position (FIGS. 19E and 19F), the surgeon concludes that the clot 270C is a deformable cohesive, adherent clot 270C. The surgeon then oscillates the distal body 216 proximally and distally a small distance (e.g., about 1 mm to about 2 mm) in the vessel 266, and the clot 270C begins to enter the distal body 216, as shown in FIG. 19G. The surgeon then irradiates the x-markers again from the first and second vantage points. As shown in FIG. 19H, the results are exactly the same as in FIG. 19D and FIG. 19F except that the second row of markers 258A, 244 and 258B, 244 (at the proximal, unattached distal-pointing crowns) are beginning to move apart. The surgeon then moves the distal body 216 proximally again, as shown in FIG. 19I. The surgeon then irradiates the x-markers again from the first and second vantage points. As shown in FIG. 19J, the results are exactly the same as in FIGS. 19D and 19F, as the clot 270C has caused the second row of markers 258A, 244 and 258B, 244 to re-converge. The surgeon then oscillates the distal body 216 proximally and distally a small distance (e.g., about 1 mm to about 2 mm) in the vessel 266, and the clot 270C begins to further enter the distal body interior 222, as shown in FIG. 19K. The surgeon then irradiates the x-markers again from the first and second vantage points. As shown in FIG. 19L, the results are the same as in FIG. 19H. The surgeon then moves the distal body 216 again proximally, and, instead of collapsing the second row of markers 258A, 244 and 258B, 244, the clot 270C fully enters the distal body interior 222, as shown in FIG. 19M. The surgeon then irradiates the x-markers again from the first and second vantage points. As shown in FIG. 19N, the results show that the second row of markers 258A, 244 and 258B, 244 (at the proximal, unattached distal-pointing crowns) have moved apart. Satisfied that the x-ray markers in the second row 258A, 244 and 258B, 244 (at the proximal, unattached distal-pointing crowns) are sufficiently far apart and that the x-ray markers in the third row (at the distal, unattached distal-pointing crowns) 258C, 244 and 258D, 244 have stayed far apart, the surgeon concludes that the deformable cohesive, adherent clot 270C has been sufficiently captured by the distal body 216 and the surgeon then removes the distal body 216 and the clot 270C, captured by the distal body 216, by moving the distal body 216 proximally out of the vessel 266.

Several observations can be made from FIGS. 15-19, as indicated above. For example, the x-ray markers at the proximal and distal, unattached distal-pointing crowns 258A-D, 244 provide the surgeon feedback concerning the interaction between the distal body 216 and the clot 270 in the blood vessel 266. In addition, the guiding principle of a soft clot 270A is that the soft clot 270A does not collapse the distal body 216, and thus, x-ray markers at the proximal and distal, unattached distal-pointing crowns 258A-D, 244 always appear as two points except when a marker is hidden behind another marker (due to the view). When it comes to a hard clot 270B, the hard clot 270B is generally able to enter the distal body interior 222 without needing to oscillate the distal body 216 proximally and distally (unlike a deformable cohesive, adherent clot 270C). However, to capture the hard clot 270B, the hard clot 270B must be oriented properly relative to the enlarged cell/drop zones 262A, 262B, 262C, or 262D. (This is the reason that the distal body 216 has four enlarged cells/drop zones: one enlarged cells/drop zone at 0 degrees 262B, one enlarged cells/drop zone at 90 degrees 262C, one enlarged cells/drop zone at 180 degrees 262A and one enlarged cells/drop zone at 270 degrees 262D). As a guiding principle, an enlarged cell/drop zone 262A, 262B, 262C, or 262D is properly oriented to the clot 270B when the x-ray markers at the proximal, unattached distal-pointing crowns 258A, 244 and 258B, 244 or the distal, unattached distal pointing crowns 258C, 244 and 258D, 244 are together at both a first x-ray view and a second x-ray view 90 degrees relative to the first x-ray view, and the hard clot 270B can enter the enlarged cell/drop zone 262A, 262B, 262C, or 262D by moving the distal body 216 proximally. See FIGS. 16F and 18D. Finally, the guiding principal of retrieval of deformable cohesive, adherent clots 270C is that oscillation of the distal body 216 causes the deformable cohesive, adherent clots 270C to gradually enter the distal basket interior 222 over time.

Figure 20A:
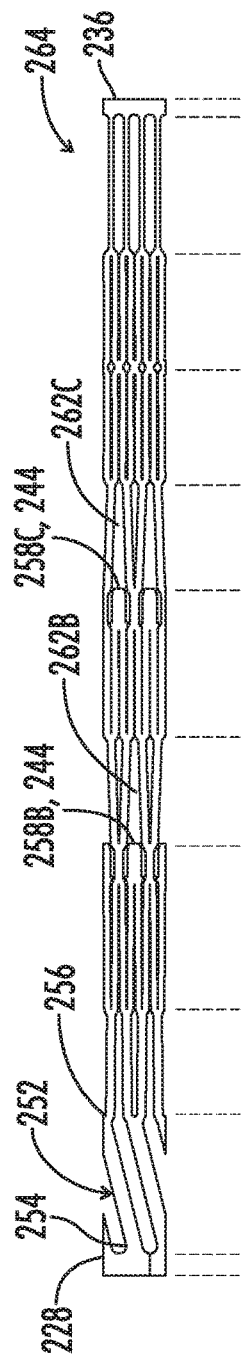
FIG. 20A illustrates a view of a native memory metal tube used to manufacture a distal body of yet another embodiment of the present invention; the native tube has been rolled out flat, the lines in the tube indicate where the tube has been cut by a laser, and the distal body of FIGS. 20A-20C is slightly shorter than the distal body of FIGS. 11-19 and is meant for use in tortuous blood vessels.
Figure 20B:
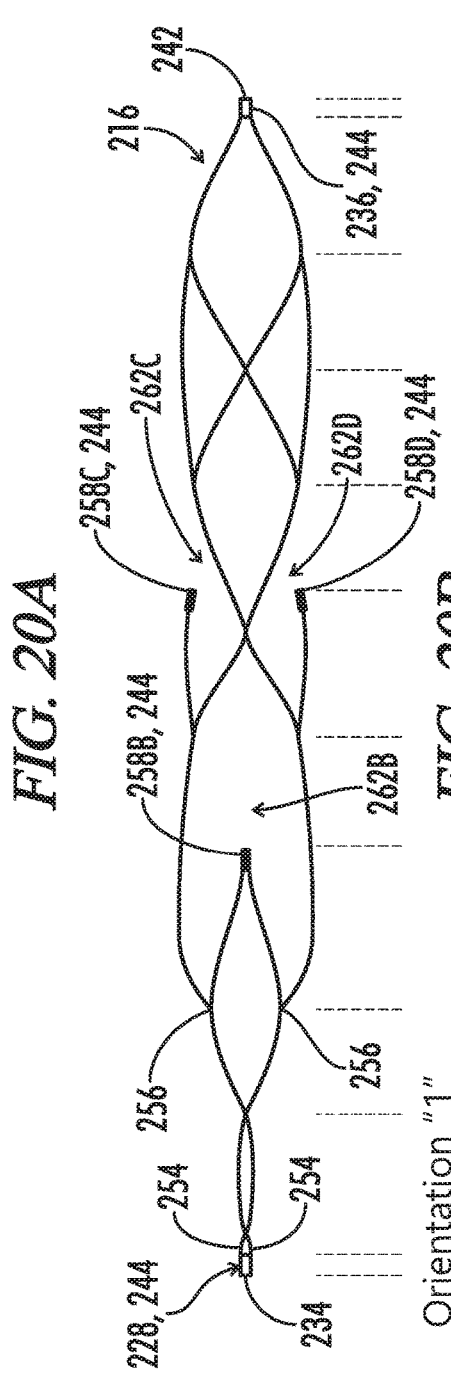
FIG. 20B illustrates a first, perspective view of the distal body manufactured from the native tube of FIG. 20A; the distal body is in Orientation 1.
Figure 20C:
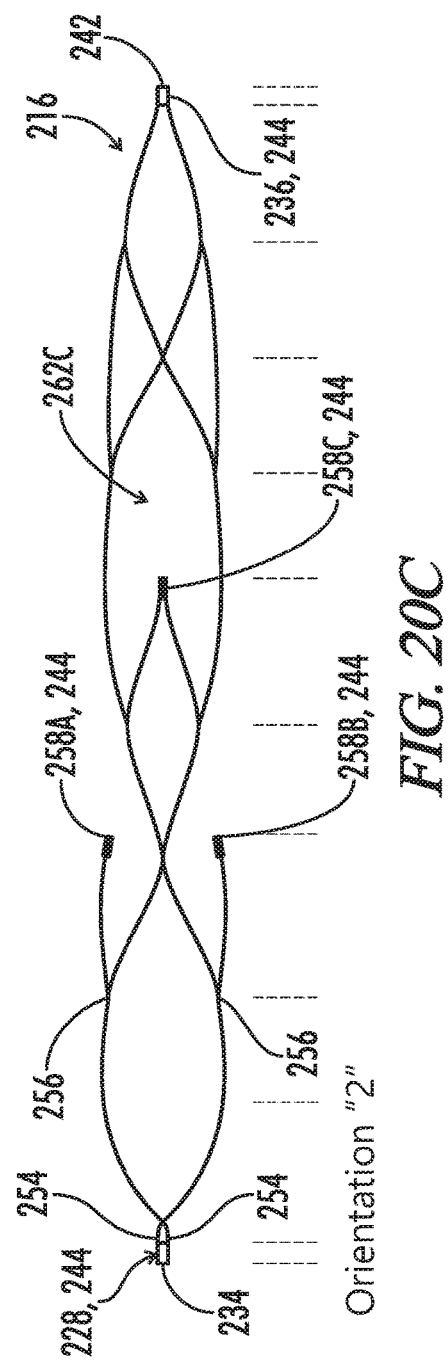
FIG. 20C illustrates a second, perspective view of the distal body manufactured from the native tube of FIG. 20A; the distal body is in Orientation 2.
Figure 21:
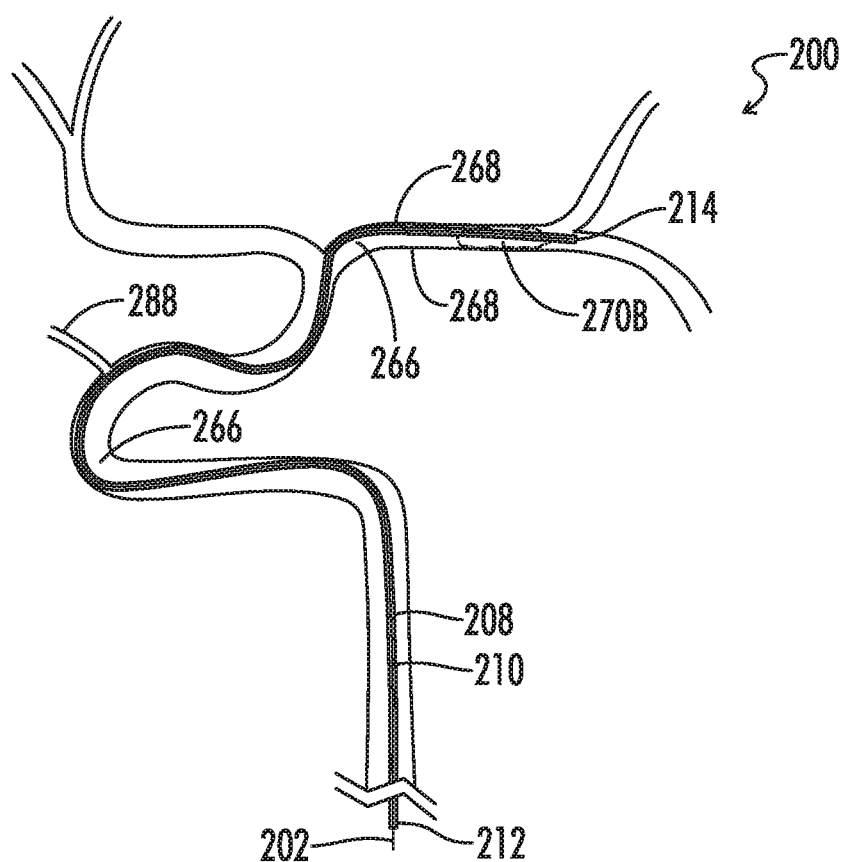
FIG. 21 shows a perspective view of a clot retrieval system that includes the distal body of FIGS. 20B-C being delivered in a blood vessel using a delivery catheter.
Figure 22:
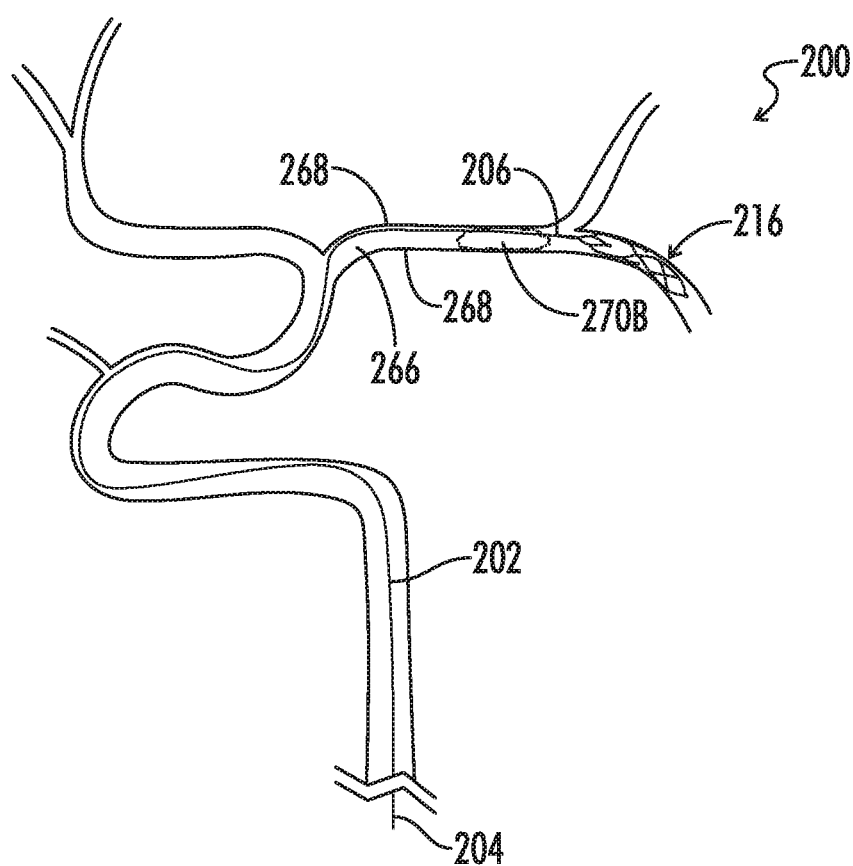
FIG. 22 shows a perspective view of the distal body of FIG. 21, after deployment of the distal body and retraction of the delivery catheter, in a blood vessel.
Figure 23:
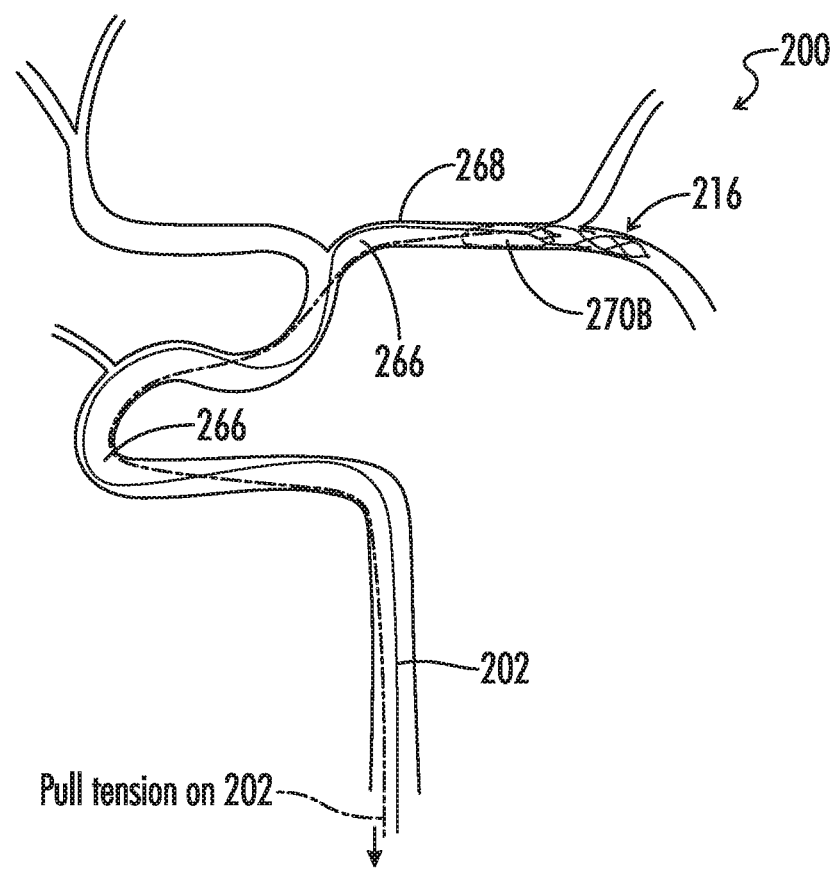
FIG. 23 shows a perspective view of the distal body of FIG. 21; as compared to FIG. 22, the distal body has been moved proximally and tension has been exerted on the pull wire.
Figure 24:
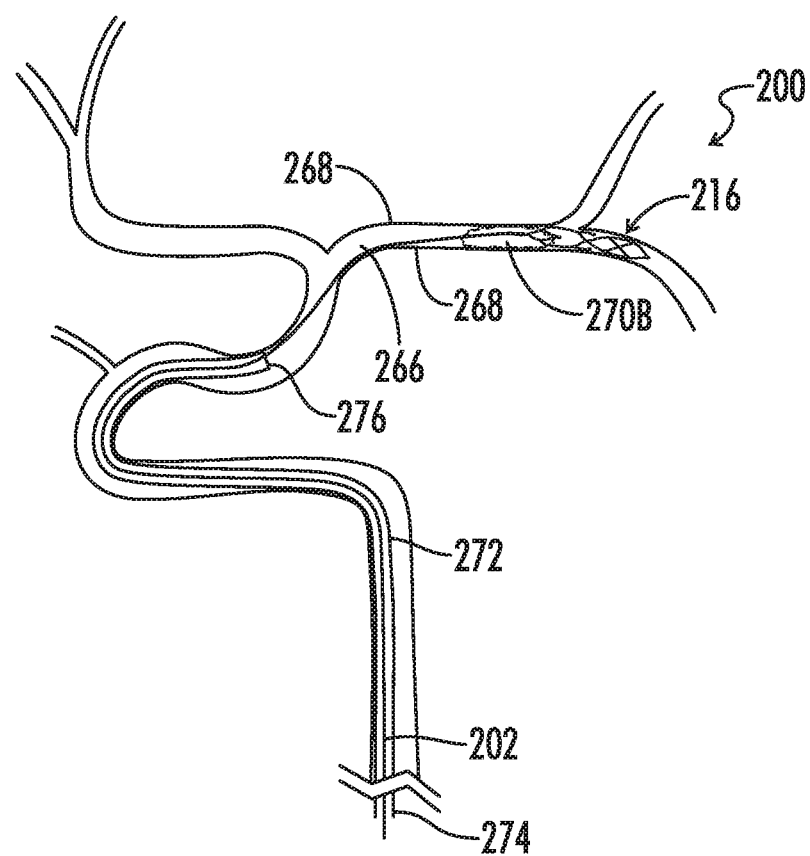
FIG. 24 shows a perspective view of a suction catheter that is being delivered over the pull wire of the system of FIG. 21.
Figure 25:
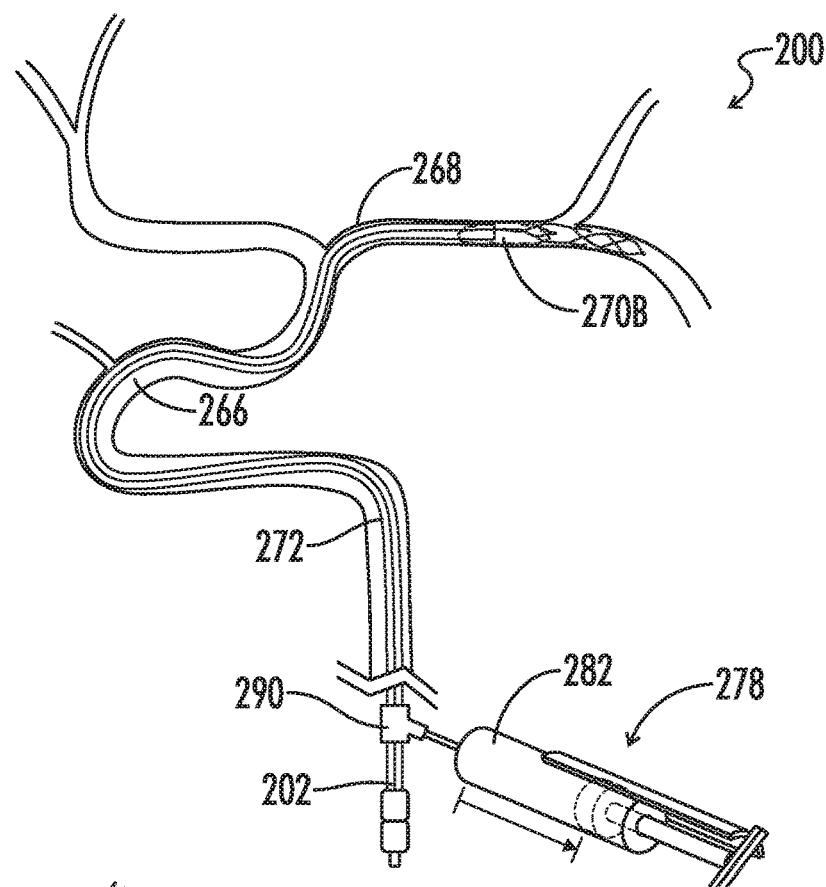
FIG. 25 shows a perspective view of the distal end of the suction catheter of FIG. 24 being pushed into a clot; a syringe is sucking the clot to the suction catheter because the user has pulled back on the lever of the syringe.
Figure 26:
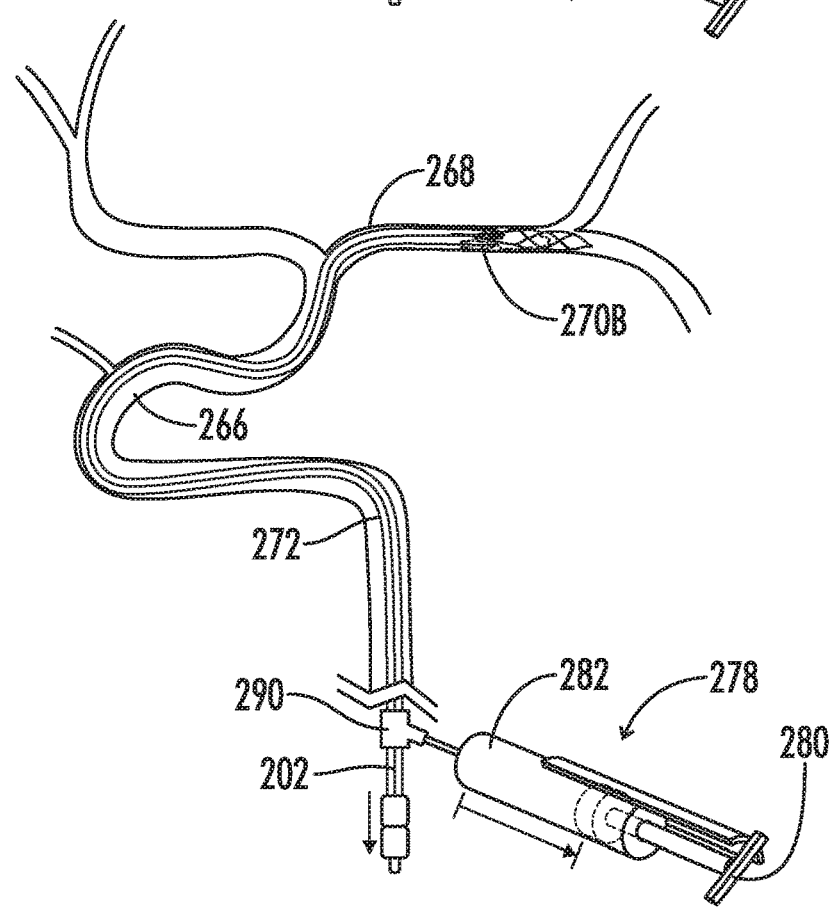
FIG. 26 shows a perspective view of the distal end of the suction catheter of FIG. 24 being pushed into a clot.
Figure 27:
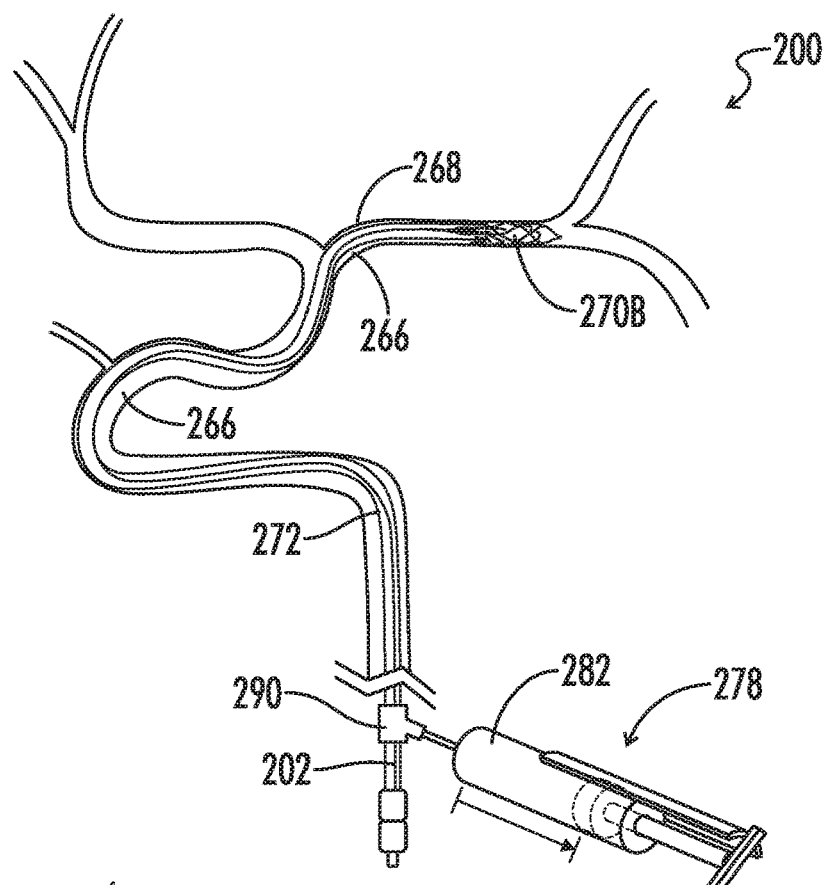
FIG. 27 shows a perspective view of the system of FIG. 24.
Figure 28:
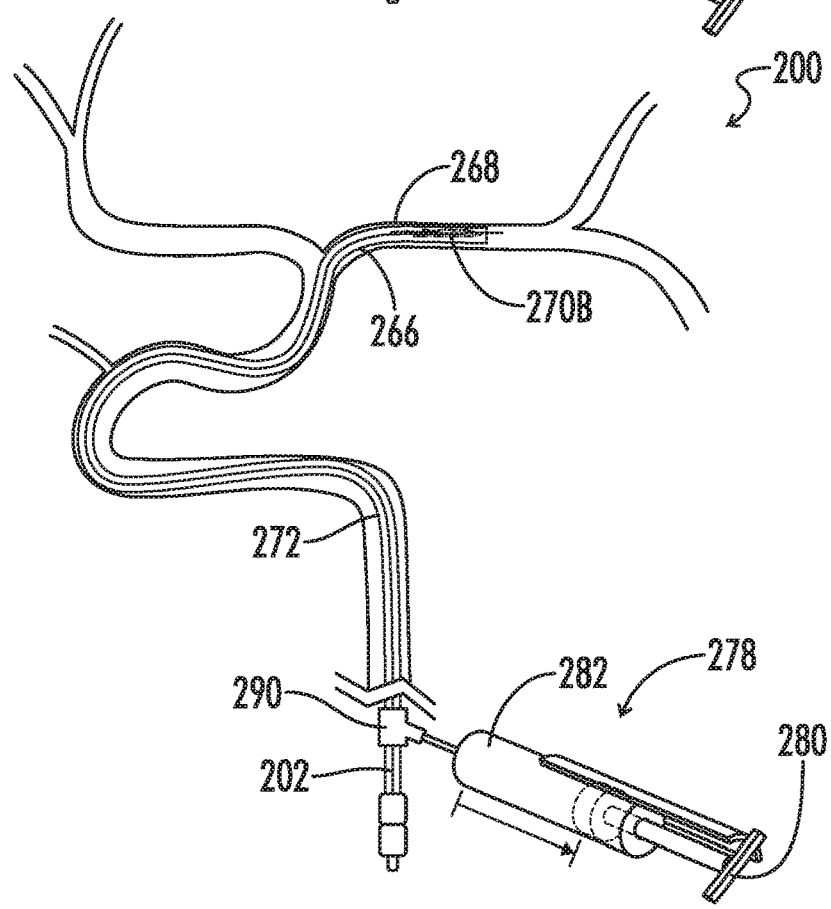
FIG. 28 shows a perspective view of the system of FIG. 24.
Figure 29:
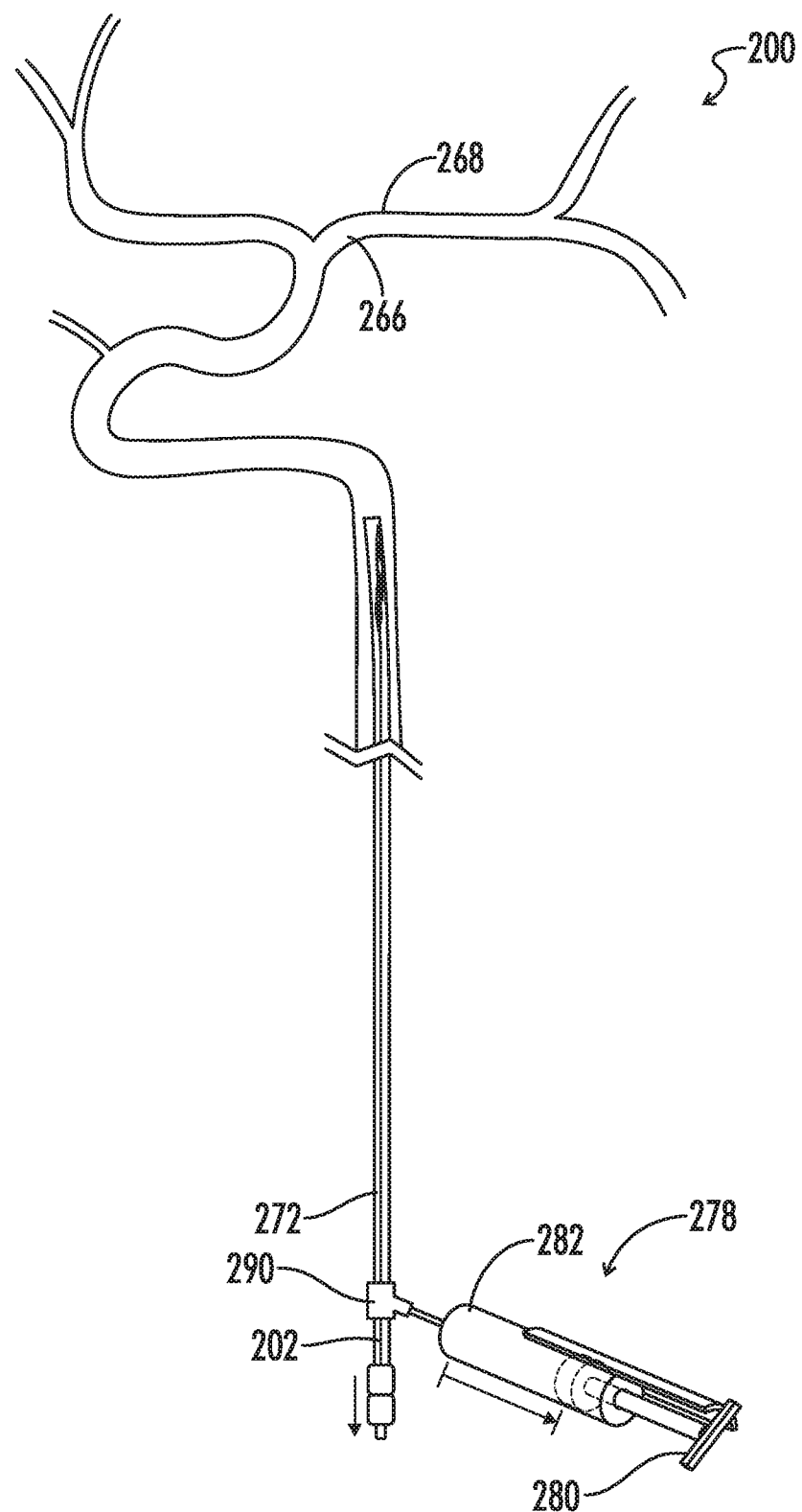
FIG. 29 shows a perspective view of the system of FIG. 24; the system, and captured clot, is being removed proximally from the vessel.

FIGS. 20A, 20B and 20C show a distal body 216 that is similar to the distal body 216 of FIGS. 14A, 14B and 14C except that the distal body 216 of FIGS. 20A, 20B and 20C is slightly shorter and its unattached, distal-pointing crowns 258A, 258B, 258C, and 258D are closer to the proximal tube 228. The shortened distal body 216 of FIGS. 20A, 20B and 20C is particularly adapted for tortuous blood vessels 266. FIG. 21-29 show stepwise deployment of the distal body 216 of FIGS. 20A, 20B and 20C in use with a manual (i.e., hand-operated), volume-dependent (i.e. volume locked) suction catheter 272 that is locked at between about 10 to about 60 cubic centimeters (cc). Optionally, the suction catheter 272 has an outer diameter of between about 0.05 inches and about 0.09 inches and its outer diameter is substantially larger than the outer diameter of the delivery catheter 208. The clot 270 is located in the vessel 266 through the use of, for example, contrast dye injected proximal and distal to the clot 270. As shown in FIG. 21, a delivery catheter 208 containing the distal body 216 of FIGS. 20A, 20B and 20C is positioned in the tortuous vessel 266 distal to the clot 270. The delivery catheter 208 is withdrawn, deploying the distal body 216. See FIG. 22. The distal body 216 is moved proximally relative to the clot 270 and tension is exerted on pull wire 202. See FIG. 23. While maintaining tension on the pull wire 202, a suction catheter 272 having a proximal end 274 and a distal end 276 is delivered over the pull wire 202 that is attached to the distal body 216. See FIG. 24. (The reason for exerting tension on the pull wire 202 is that the pull wire 202 serves as the guide/track for the movement of the suction catheter 272 and without tension, the suction catheter 272 and pull wire 202 could end up in the ophthalmic artery 288). The distal end 276 of the suction catheter 272 is positioned against the clot 270. A syringe 278 is attached to the suction catheter 272 using a rotating hemostatic valve 290, which allows the surgeon to aspirate while a pull wire 202 is in the system. The surgeon aspirates the syringe 278 by pulling back on the lever 280 to a mark on the base 282 corresponding to between about 10 and about 60 cubic centimeters of fluid. The surgeon then locks the lever 280 (and attached plunger) into place, leaving the suction catheter 272 under suction. The surgeon captures the clot 270 in the distal body 216 using the techniques described in FIGS. 15-19. The distal body 216 and clot 270 become captured by the suction catheter 272. See FIGS. 27 and 28. The surgeon then removes the suction catheter 272 and the distal body 216 and the clot 270, captured by the suction catheter 272, by moving the suction catheter 272 proximally out of the vessel 266. See FIG. 29. It is believed that the suction catheter 272 would be helpful in the event that a small portion of the clot 270 breaks off when retrieving the clot 270 using the distal body 216.

To examine effectiveness of the systems 200, the systems 200 of FIGS. 11-20, without the use of a suction catheter 272, were used to retrieve soft and hard clots 270A and 270B induced in a pig weighing between 30 to 50 kg. The weight of the pig was chosen so that the size of its vessels 266 would be approximate to the size of a human vessel. The pig was anesthetized. Several hard clots 270B were prepared by mixing pig blood and barium and incubating the mixture for 2 hours. Several soft clots 270A were prepared by mixing pig blood, thrombin and barium and incubating the mixture for 1 hour. The clots 270A and 270B, each of which had a width of 4 to 6 mm and a length of 10 to 40 mm, were then inserted into a vessel 266 having a diameter of 2 to 4 mm. (Only one clot 270A and 270B was located in the vessel 266 at a time). Angiograms were then performed to confirm occlusion. After waiting ten minutes after confirming occlusion, the distal bodies 216 of FIGS. 11-20 were then delivered distal to the clots 270A and 270B as described above and were used to retrieve the clots 270A and 270B as described in FIGS. 11-19. In each case, the distal bodies 216 were successful in retrieving the clots 270A and 270B. As shown, the distal body height in the relaxed state tapers/decreases as the proximal strips 252 approach the proximal hub/junction/tube 228 and also tapers/decreases as the basket strips 291 located at the distal end 220 of the basket 246 converge at the distal hub/junction/tube 236.

Figure 32:
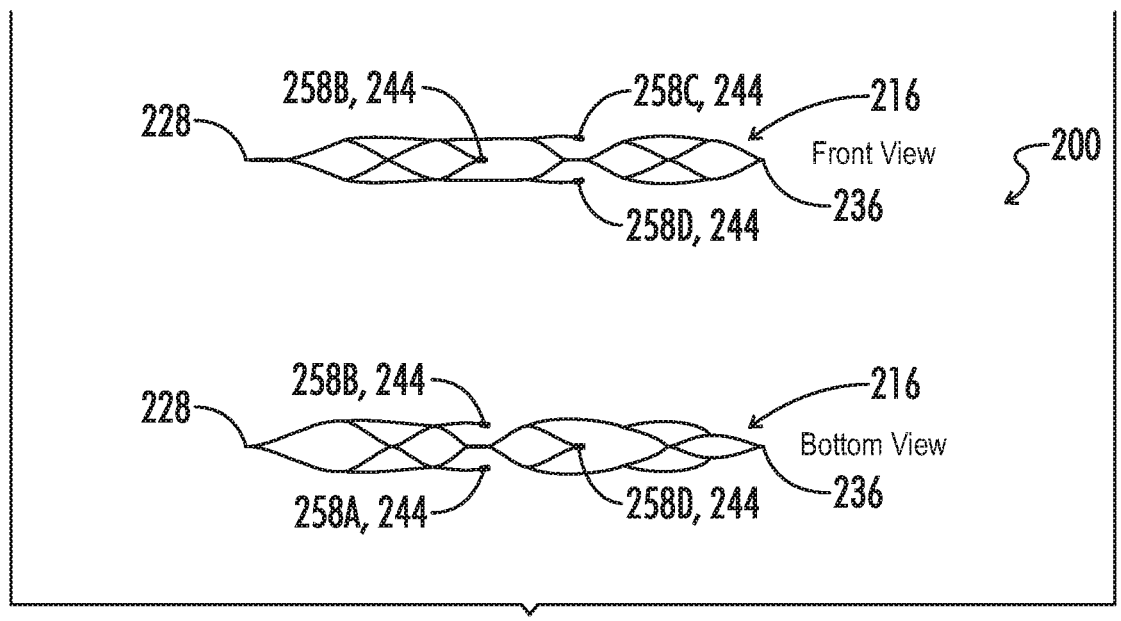
FIG. 32 illustrates an alternate embodiment of a distal body; in the distal body of FIG. 32, the proximal strips converge and are soldered or welded at the proximal hub/junction and the basket strips located at the distal end of the basket converge and are soldered or welded at the distal hub/junction.

The Alternate Embodiment of FIG. 32

FIG. 32 shows a distal body 216 in which the proximal strips proximal ends 254 converge and are soldered or welded at the proximal hub/junction 228 and the basket strips 291 located at the distal end 220 of the basket 246 converge and are soldered or welded at the distal hub/junction 236. To create such an embodiment, the distal body 216 may be prepared from a single tube, as described above, and the proximal and distal tubes may be clipped and the proximal ends 254 of the proximal strips 252 soldered or welded together (and optionally to the pull wire 202) and the basket strips 291 located at the distal end 220 of the basket 246 may also be welded or soldered or welded together. Optionally, the proximal and distal hubs/junctions 228 and 236 may include x-ray markers 244 as described above.

The Embodiments of FIGS. 33A-49

During the development of the medical devices shown in FIGS. 11-20, it became apparent that it would be desirable to make devices from a single tube of memory metal (e.g., nitinol) that had a larger outer diameter than the inner diameter of the catheter. More particularly, it was desirable to create the baskets from a single tube having an outer diameter of 0.025 inches but deploy the baskets from a catheter having an inner diameter of 0.021 inches. This was not possible if the uncut proximal and distal ends of the tube were left intact in the device (as shown in FIG. 2 for example). Thus, a new method was developed to attain this objective, as shown in FIGS. 33-49. One method to achieve this was to create scoring lines (referred to below as perforations 814, 816, 835 and 838) so that uncut excess material of first tube wall 803 would tend to tear cleanly and consistently along the scoring lines 814, 816, 835 and 838, as described below.

Figure 33A:
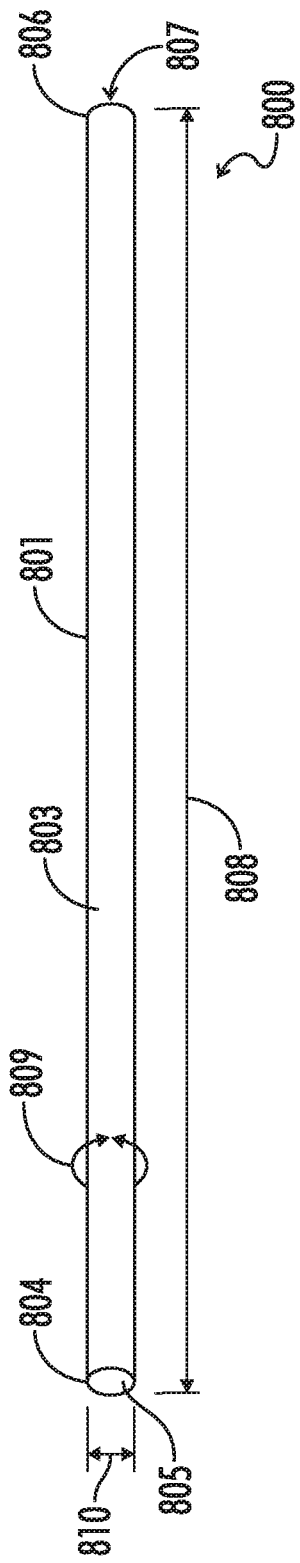
FIG. 33A illustrates a side, elevation view of a memory metal tube.
Figure 33B:
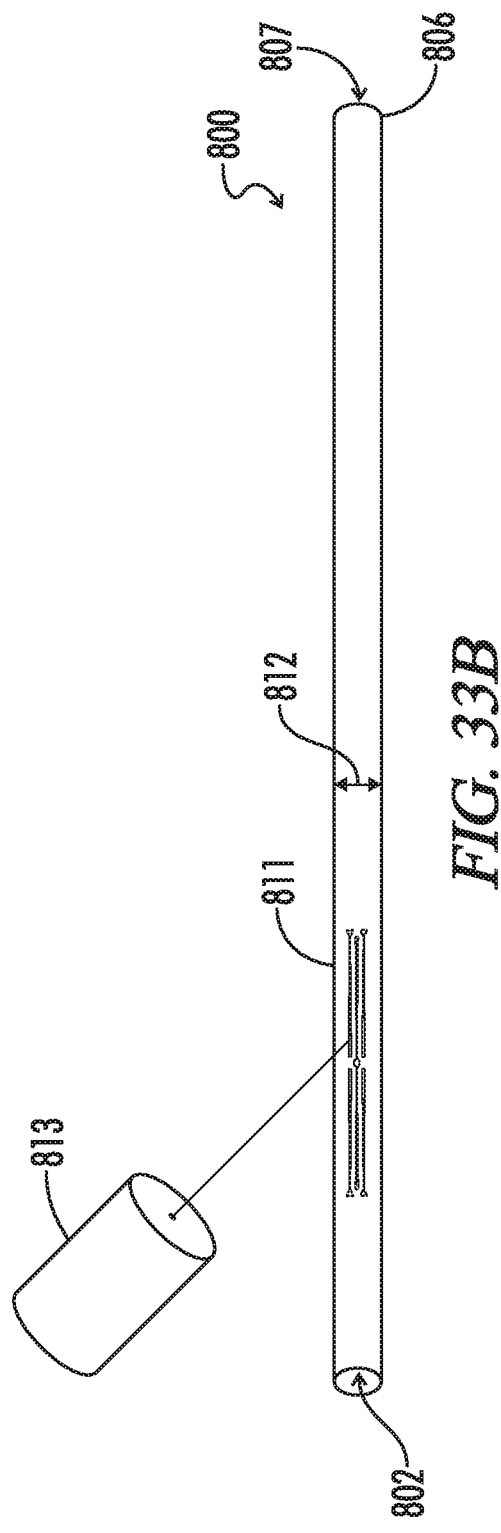
FIG. 33B illustrates a side, elevation view of the memory metal tube of FIG. 33A being cut by a laser.
Figure 34:
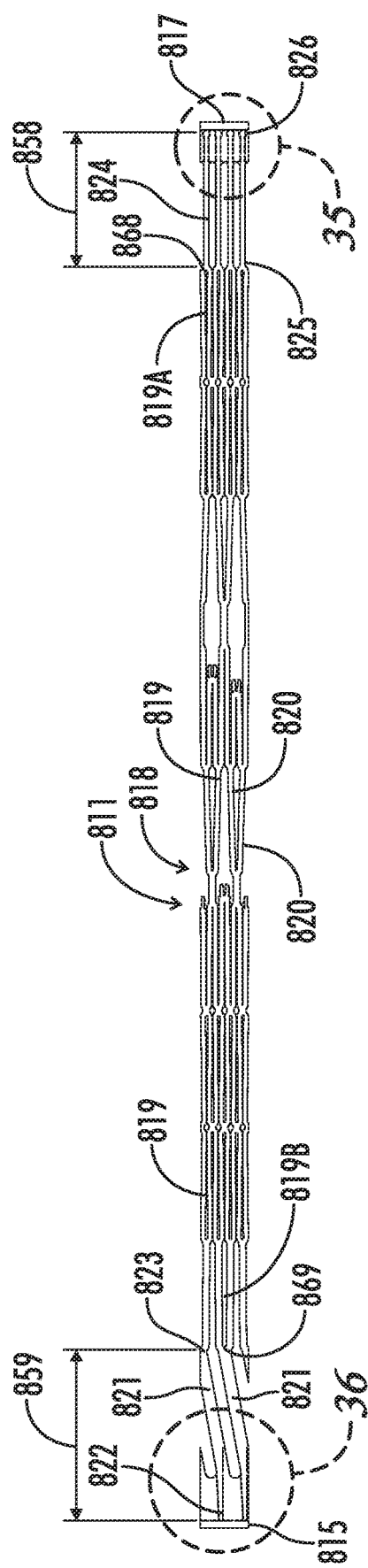
FIG. 34 illustrates a side, elevation view of the memory metal tube of FIG. 33B after being cut by a laser.
Figure 35:
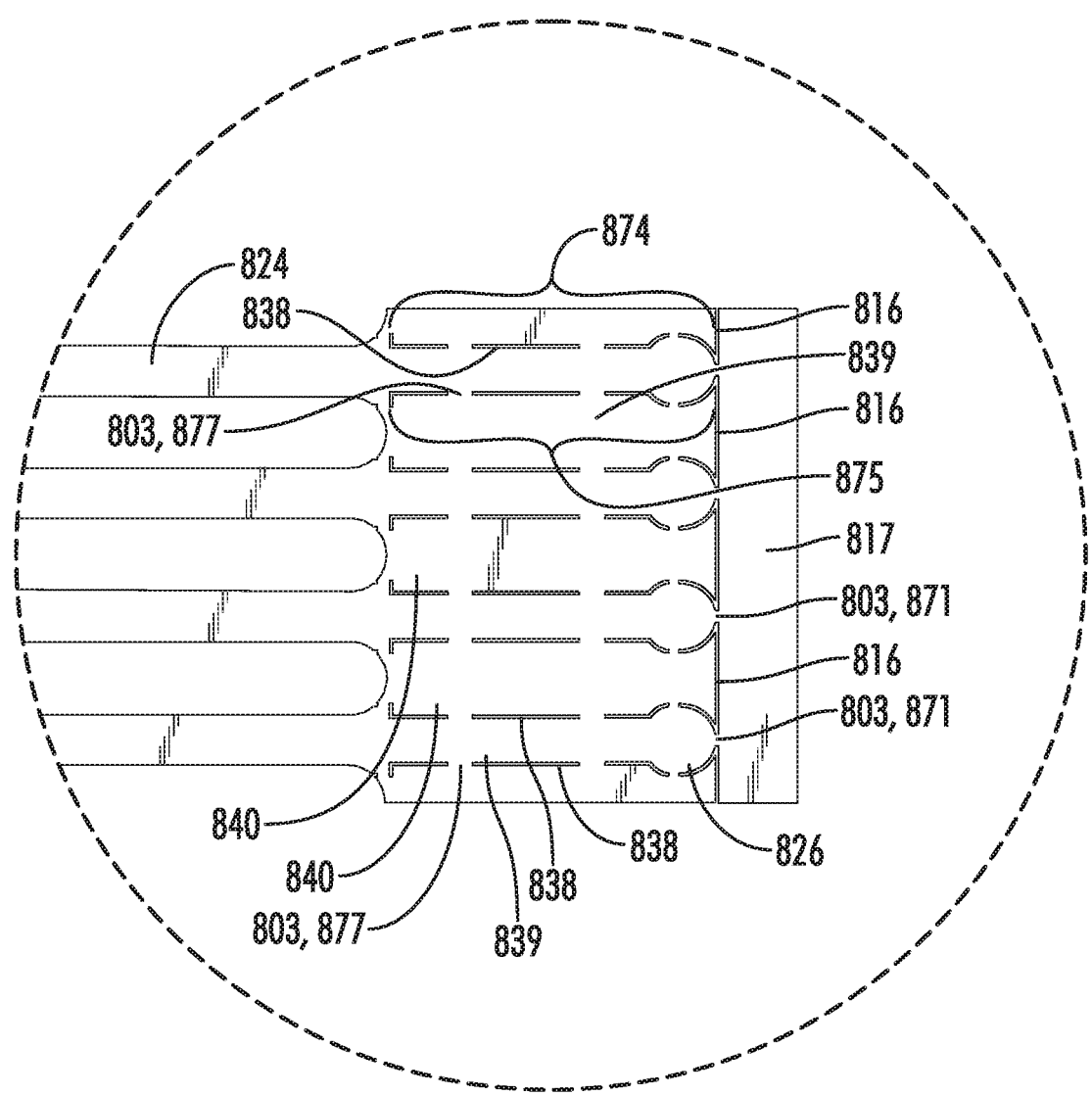
FIG. 35 illustrates a side, elevation view of the circled area labelled 35 in FIG. 34 (namely, the distal portion of the cut memory metal tube of FIG. 34—the distal portion includes the distal ends of the distal memory metal strips, the distal end tabs and the distal longitudinal tabs)
Figure 36:
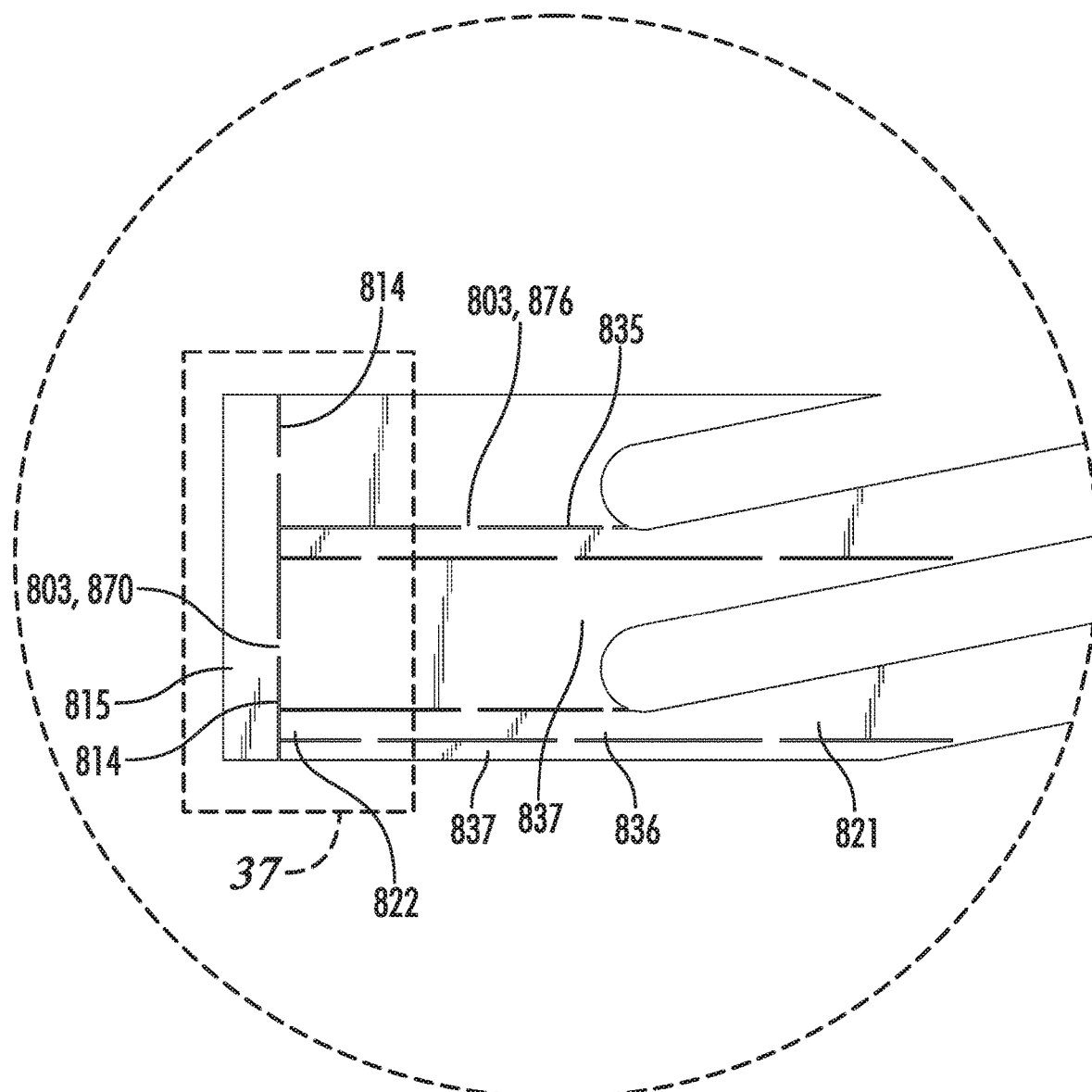
FIG. 36 illustrates a side, elevation view of the circled area labelled 36 in FIG. 34 (namely, the proximal portion of the cut memory metal tube of FIG. 34—the proximal portion includes the proximal ends of the proximal memory metal strips, the proximal end tabs and the proximal distal longitudinal tabs)
Figure 37:
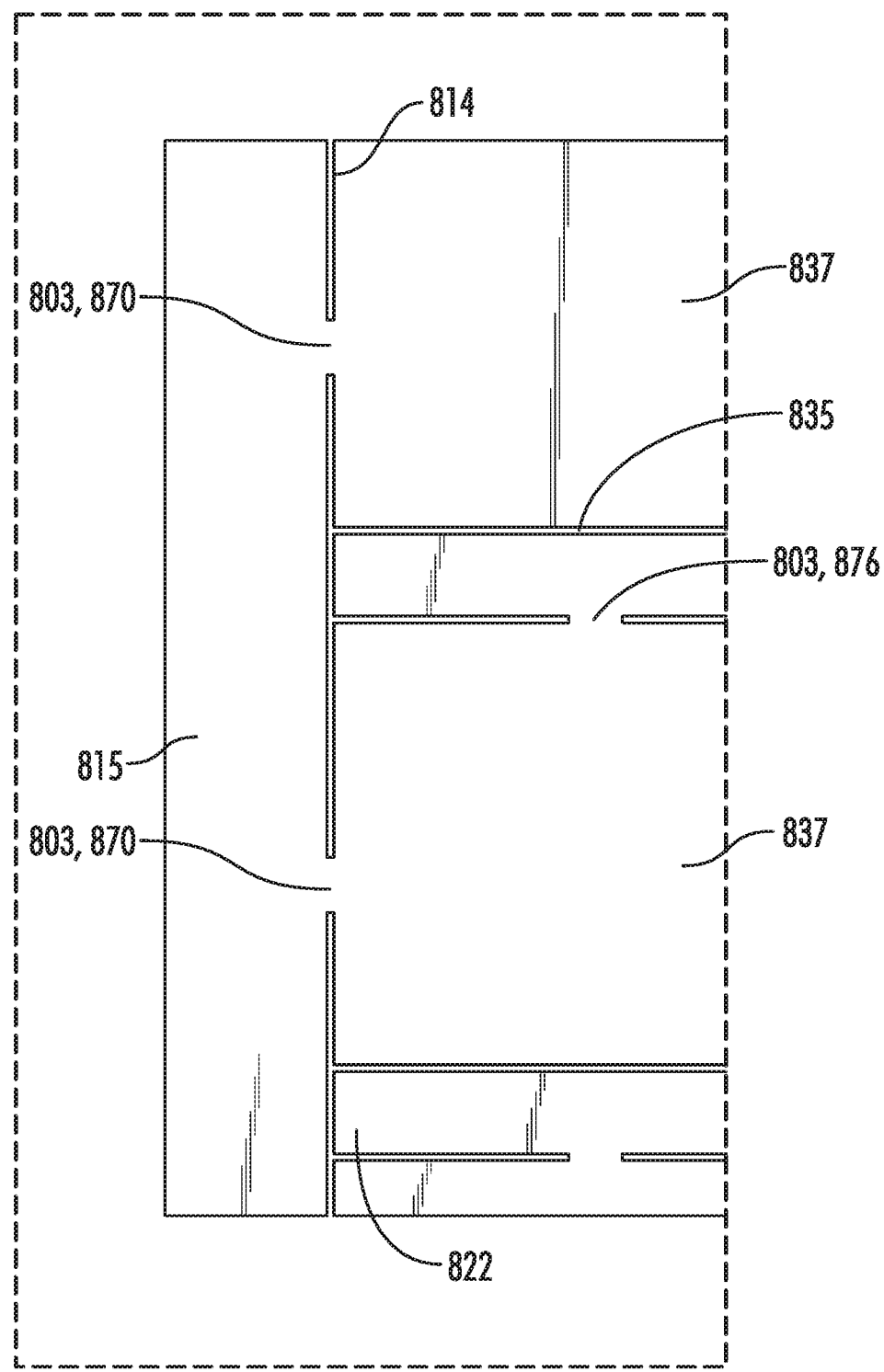
FIG. 37 illustrates a side, elevation view of the circled area labelled 37 in FIG. 36 (namely, a close-up of the proximal portion of the cut memory metal tube of FIG. 36)
Figure 38:
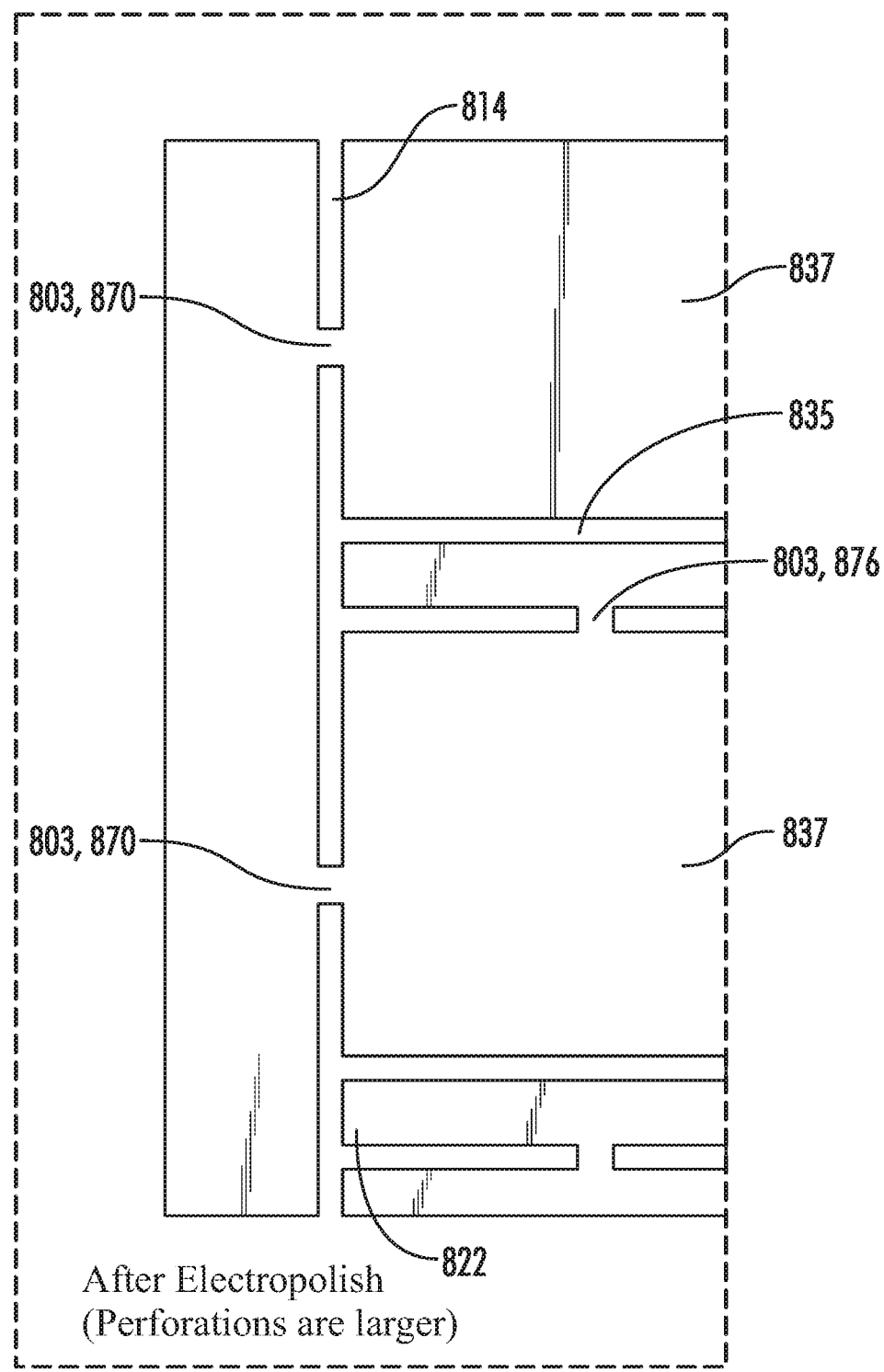
FIG. 38 illustrates a side, elevation view of the close-up of the proximal portion of the cut memory metal tube of FIG. 37 after electropolishing.
Figure 39:
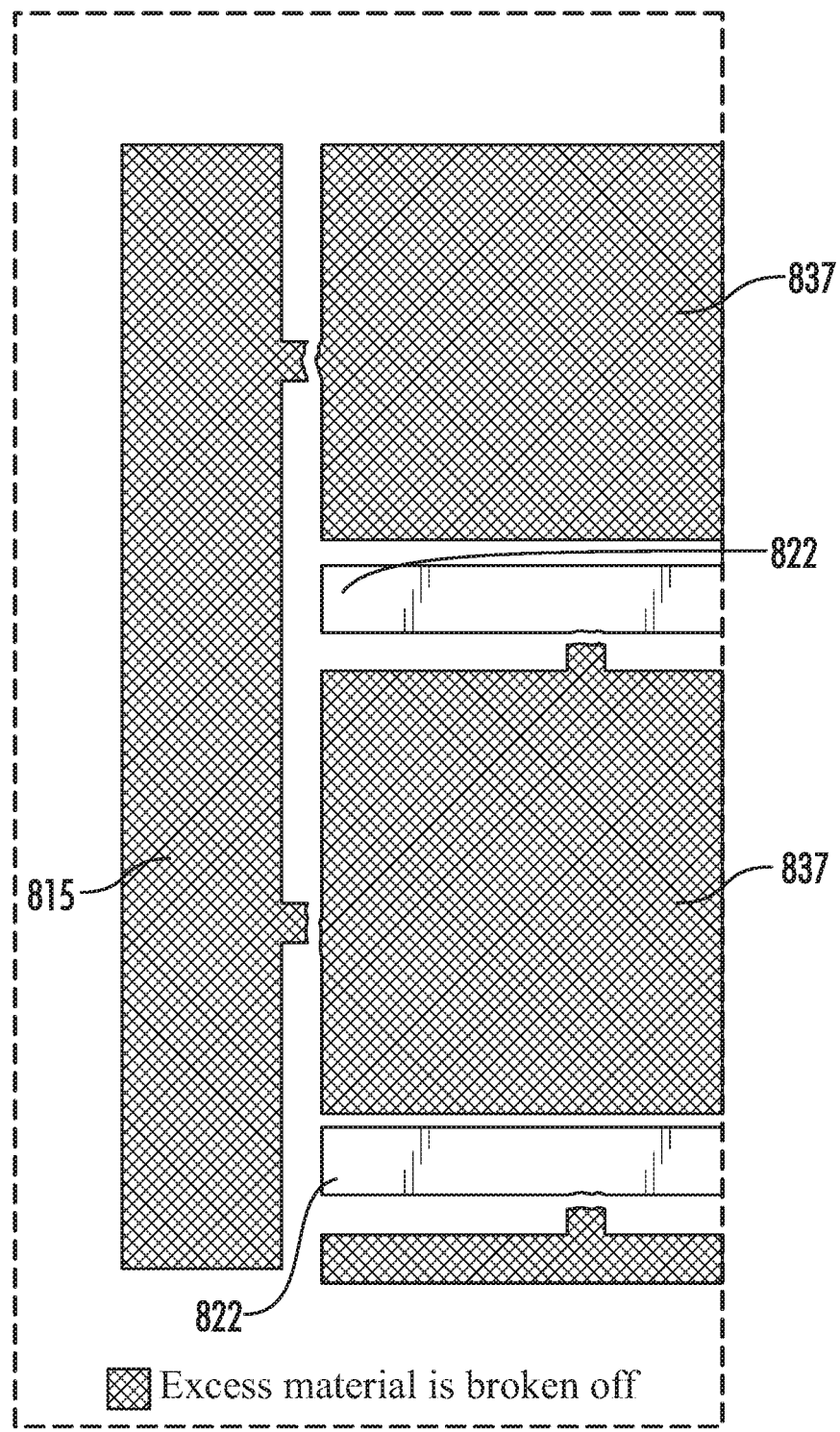
FIG. 39 illustrates a side, elevation view of the close-up of the proximal portion of the cut memory metal tube of FIG. 37 after electropolishing and tearing along the perforations.
Figure 40:
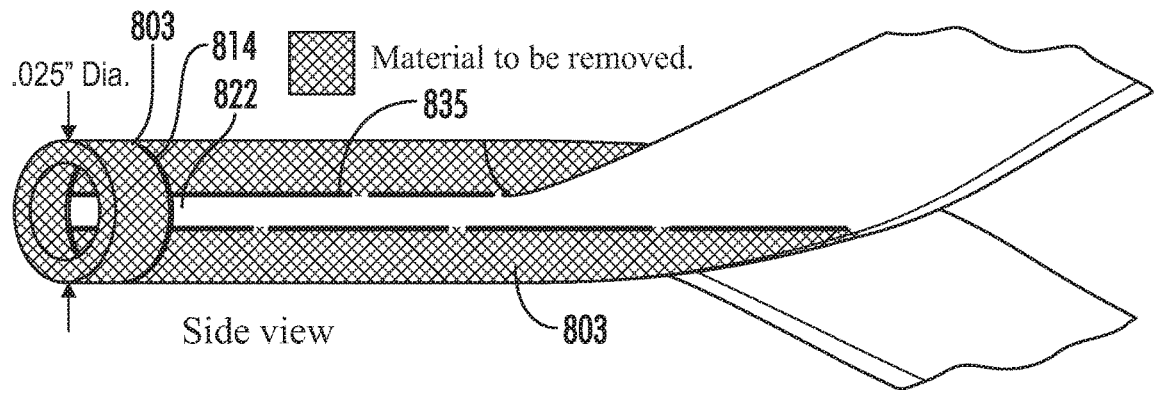
FIG. 40 illustrates a side, elevation view of the close-up of the proximal portion of the cut memory metal tube of FIG. 36.
Figure 41:
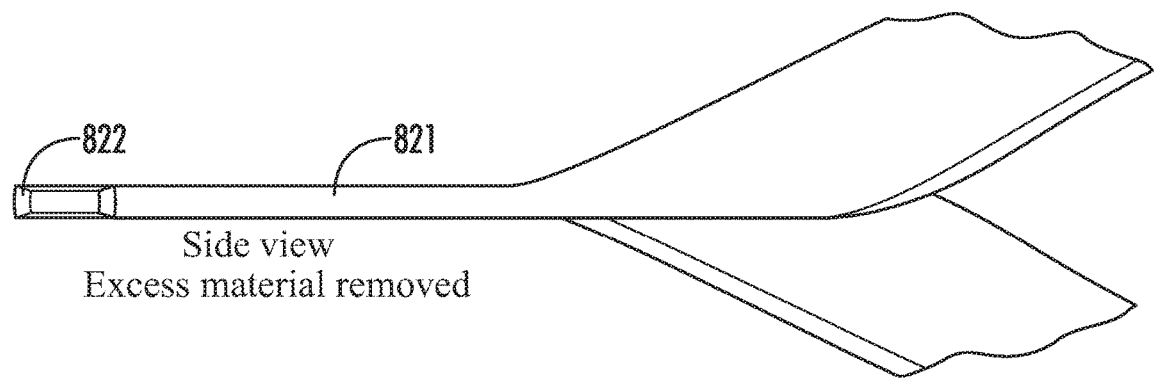
FIG. 41 illustrates a side, elevation view of the proximal portion of the cut memory metal tube of FIG. 40 after electropolishing and after tearing along the perforations to remove the proximal end tab and the proximal longitudinal tabs from the proximal segments of the proximal memory metal strips.
Figure 42:
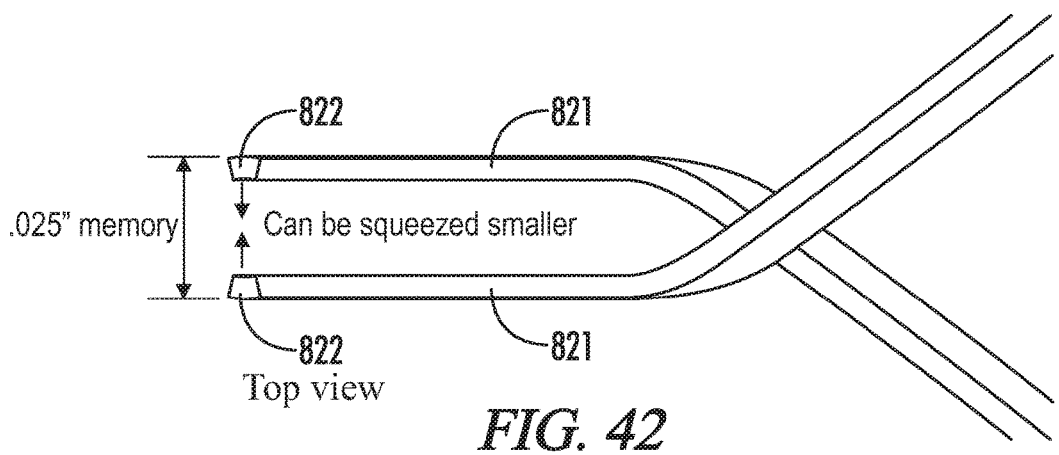
FIG. 42 illustrates another side elevation view of the proximal portion of the cut memory metal tube of FIG. 40 after electropolishing and after tearing along the perforations to remove the proximal end tab and the proximal longitudinal tabs from the proximal segments of the proximal memory metal strips; as compared to FIG. 41, the proximal end of the cut memory metal tube has been rotated 90 degrees in FIG. 42.

More particularly, as shown in FIGS. 33-49, the present disclosure provides: a method of manufacturing a medical device 827 comprising:

a) providing a first tube 800 comprised of a memory metal, the first tube 800 having a first tube exterior 801, a first tube hollow interior 802, a first tube wall 803 separating the first tube exterior 801 from the first tube hollow interior 802, a first tube proximal end 804 comprising a first tube proximal aperture 805 leading to the first tube hollow interior 802, a first tube distal end 806 comprising a first tube distal aperture 807 leading to the first tube hollow interior 802, a first tube length 808 extending from the first tube proximal end 804 to the first tube distal end 806, a first tube perimeter 809 (more particularly a circumference if first tube 800 is generally cylindrical) generally perpendicular to the first tube length 808, a first tube width 810 (more particularly an outer diameter if first tube 800 is generally cylindrical) generally perpendicular to the first tube length 808, and a middle portion 811 between the first tube proximal end 804 and the first tube distal end 806, the middle portion 811 having a middle portion width 812 (more particularly an outer diameter if first tube 800 is generally cylindrical) generally parallel to the first tube width/diameter 810 (see FIG. 33A) (preferably the first tube width 810 is uniform along the first tube length 808 in step a) as shown in FIG. 33A);

b) using a cutting instrument 813 (e.g. a laser) to cut portions of the wall 803 of the first tube 800 (see FIG. 33B) and form i) a plurality of non-contiguous proximal perimeter perforations 814 located adjacent to the first tube proximal end 804 and spaced about the perimeter/circumference 809 of the first tube 800 and each proximal perimeter perforation 814 is separated by a proximal perimeter gap 870 (representing uncut portions of the wall 803), the plurality of non-contiguous proximal perimeter perforations 814 and proximal perimeter gap 870 define a proximal end tab 815 located at the proximal end 804 of the first tube 800 (see FIGS. 34, 36, 37 and 40); ii) a plurality of non-contiguous distal perimeter perforations 816 located adjacent to the first tube distal end 806 and spaced about the perimeter/circumference 809 of the first tube 800 and each distal perimeter perforation 816 is separated by a distal perimeter gap 871 (representing uncut portions of the wall 803), the plurality of non-contiguous distal perimeter perforations 816 and the distal perimeter gaps 871 defining a distal end tab 817 located at the distal end 806 of the first tube 800 (see FIGS. 34 and 35); iii) a matrix 818 in the middle portion 811 comprising a plurality of middle portion memory metal strips 820 forming a plurality of cells 819 (see FIG. 34); iv) a plurality of proximal memory metal strips 821 connecting the middle portion 811 to the proximal end tab 815, each proximal memory metal strip 821 having a proximal memory metal strip proximal end 822 connected to the proximal end tab 815, a proximal memory metal strip distal end 823 connected to a cell 819 of the middle portion 811 and a proximal memory metal strip length 859 extending from the proximal memory metal strip proximal end 822 to the proximal memory metal strip distal end 823 (see FIGS. 34, 36, 37 and 40); and v) a plurality of distal memory metal strips 824 connecting the middle portion 811 to the distal end tab 817, each distal memory metal strip 824 having a distal memory metal strip distal end 826 connected to the distal end tab 817, a distal memory metal strip proximal end 825 connected to a cell 819 of the middle portion 811, and a distal memory metal strip length 858 extending from the distal memory metal strip proximal end 825 to the distal memory metal strip distal end 826, wherein the proximal end tab 815 connects the proximal ends 822 of the proximal memory metal strips 821 and the distal end tab 817 connects the distal ends 826 of the distal memory metal strips 824 (see FIGS. 34 and 35);

c) shape setting at least the middle portion 811 (e.g., the middle portion 811 and at least a portion of the proximal memory metal strips 821 and distal memory metal strips 824) to expand the width/diameter 812 of the middle portion 811 (preferably by expanding the middle portion 811 using a mandrel such as that shown in FIGS. 30 and 31 to form a basket 851);

d) after step c), polishing (e.g. electropolishing) the first tube 800, wherein said polishing expands the plurality of proximal perimeter perforations 814 about the first tube perimeter/circumference 809 and expands the plurality of the distal perimeter perforations 816 about the first tube perimeter/circumference 809 (see FIG. 38, which shows expanding the proximal perimeter perforations 814 so that adjacent proximal perimeter perforations 814 approach each other and the proximal perimeter gaps 870 becoming smaller; the distal perimeter perforations 816 expand in a similar manner);

e) tearing along the plurality of proximal perimeter perforations 814 to free the proximal ends 822 of the proximal memory metal strips 821 from the proximal end tab 815 and each other and tearing along the plurality of distal perimeter perforations 816 to free the distal ends 826 of the distal memory metal strips 824 from the distal end tab 817 and each other (see FIGS. 39 and 41, which shows removing of the proximal end tab 815; the distal end tab is 817 removed in a similar manner);

f) joining the free distal ends 826 of the distal memory metal strips 824 (see FIG. 45) and joining the free proximal ends 822 of the proximal memory metal strips 821 (see FIGS. 42, 43E-43G and 44) to form a medical device 827 comprised of the joined distal ends 826 of the distal memory metal strips 824, the joined proximal ends 822 of the proximal memory metal strips 821, and the shape set middle portion 811, the medical device 827 having a medical device length 828 extending at least from the joined distal ends 826 of the distal memory metal strips 824 to at least the joined proximal ends 822 of the proximal memory metal strips 821 and a medical device width 829 generally perpendicular to the medical device length 828 (the term "at least" refers to the fact that the medical device 827 may include a lead wire at the distal end as described previously); and g) inserting the medical device 827 into a catheter 830 comprising a catheter interior 831 having an interior width 832 (more particularly an inner diameter if the catheter 830 is generally cylindrical), an open catheter proximal end (not shown in FIGS. 33-49 but shown as 212 in FIG. 21) leading to the catheter interior 831, an open catheter distal end 833 leading to the catheter interior 831, the catheter 830 comprised of a biocompatible material, wherein the catheter interior width 832 (more particularly inner diameter if the catheter 830 is generally cylindrical) is less than the first tube width/outer diameter 810, wherein the medical device 827 comprises a collapsed state wherein the medical device width 829 is less than the catheter interior width/diameter 832 and an expanded state wherein the medical device width 829 is greater than the catheter interior width/diameter 832, and further wherein the catheter 830 is configured to envelope the medical device 827 when the medical device 827 is in the collapsed state (see FIG. 81).

Optionally, the first tube 800 is generally cylindrical in shape and comprises a first tube diameter 810 and a first tube circumference 809 and the proximal perimeter perforations 816 are arranged in a generally straight line about the circumference 809 of the first tube 800 (see FIGS. 34, 36, 37, 40 and 46) and the distal perimeter perforations 816 are arranged in a generally straight line about the circumference 809 of the first tube 800 (see FIGS. 34-35).

Figure 46:
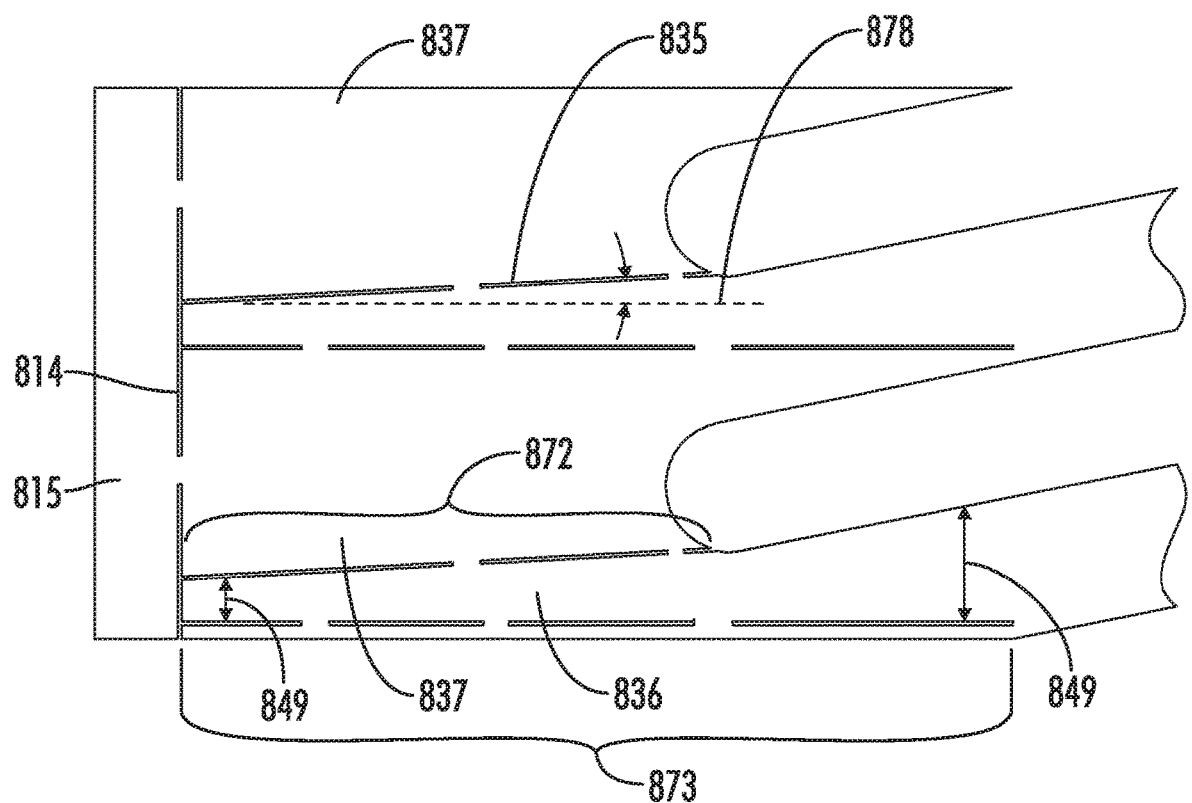
FIG. 46 illustrates a side elevation view of the proximal portion of the cut memory metal tube and is similar to FIG. 36; the line is merely drawn in to show how each proximal memory metal strips tapers adjacent to the proximal end of the respective proximal memory metal strips (and the line is not present in the device).
Figure 47:
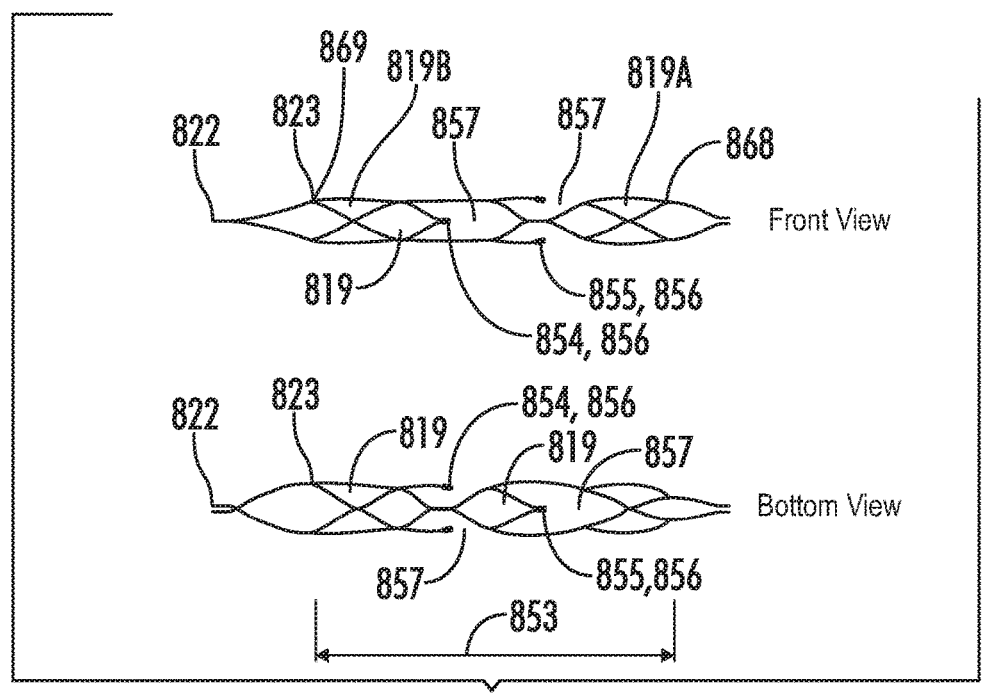
FIG. 47 illustrate side views of a middle portion cut from the memory metal tube of FIG. 33B and expanded using the mandrel of FIG. 31.
Figure 48:
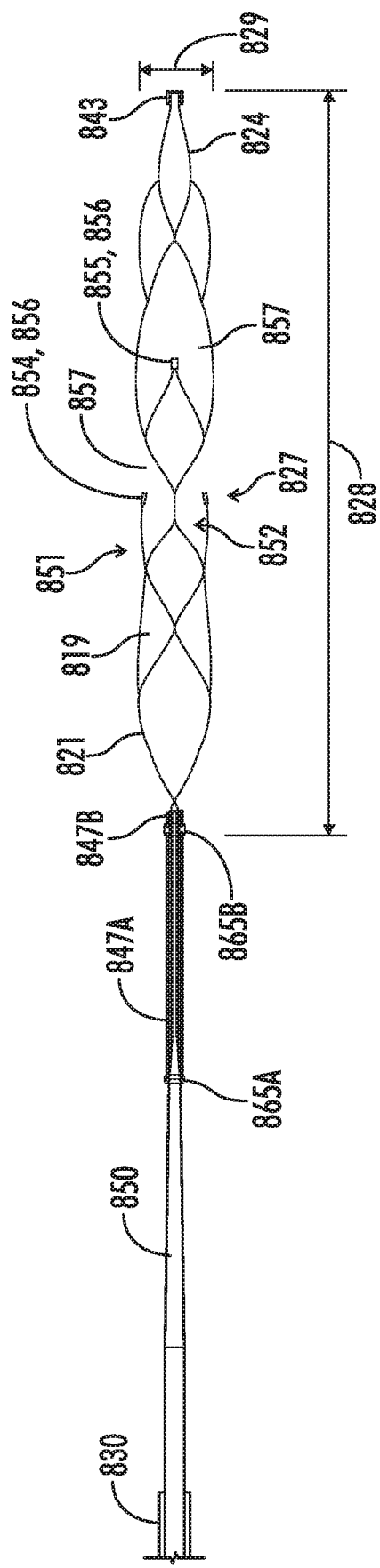
FIG. 48 illustrates a medical device that includes the catheter of FIG. 44, the pull wire of FIG. 44, the coil system, which is attached to the proximal memory metal strips as shown in FIG. 44, the basket of FIG. 47 and the re-joined distal ends of the distal memory metal strips of FIG. 45.
Figure 49:
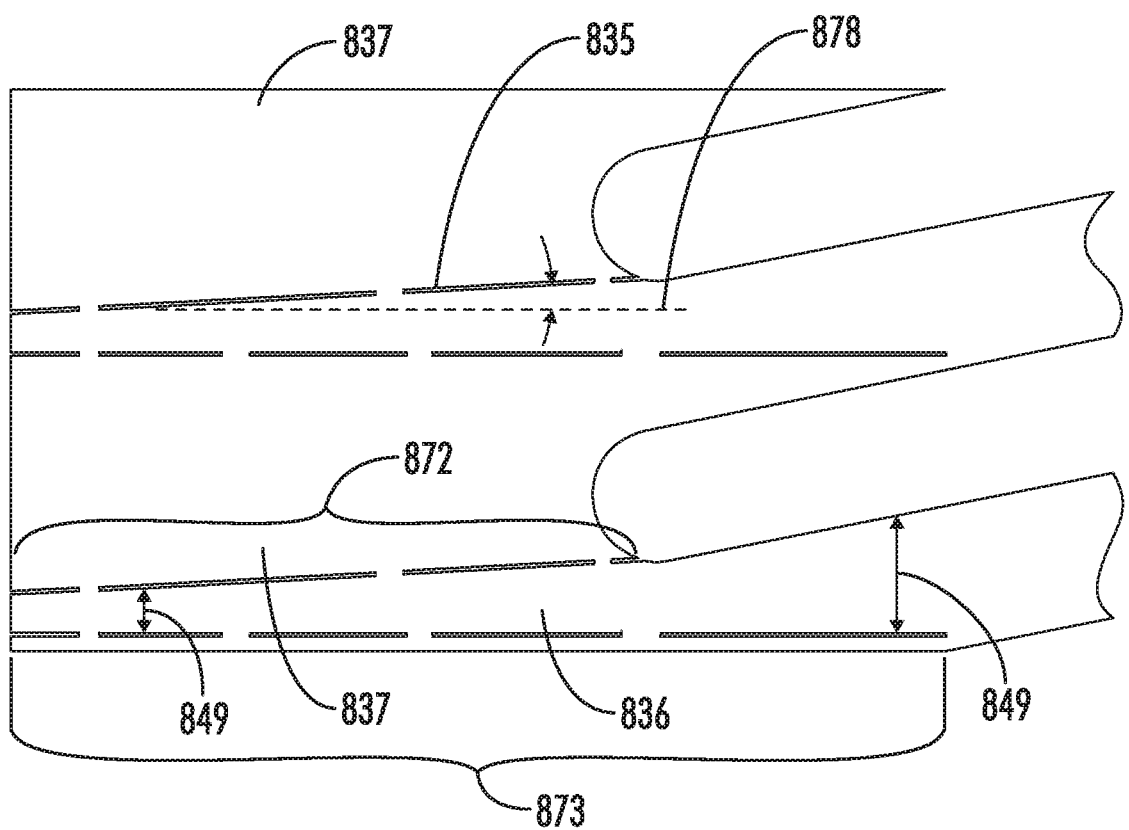
FIG. 49 illustrates a side, elevation view of proximal memory metal strips and longitudinal perforations at the proximal end of a cut memory metal tube of another embodiment of the present invention.
Figure 52:
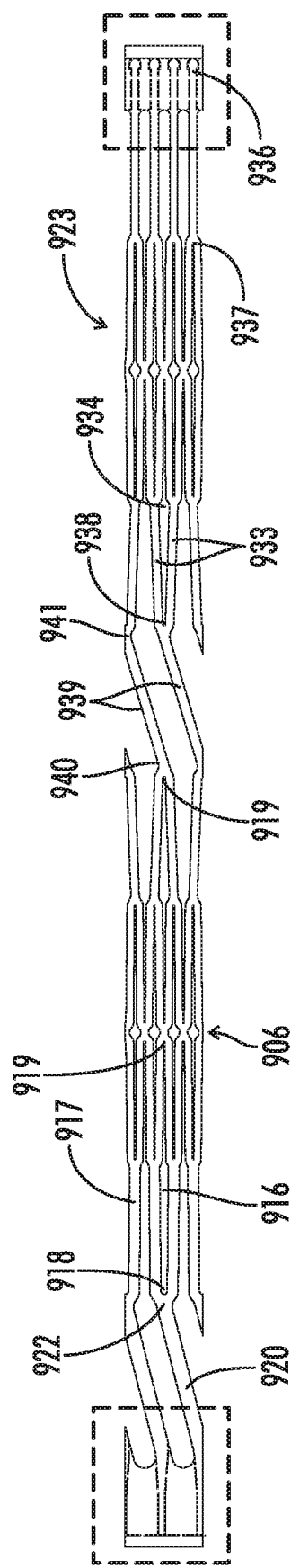
FIG. 52 illustrates a side, elevation view of a memory metal tube being cut by a laser to form a deployable dual basket system of another embodiment of the present invention.
Figure 53A:
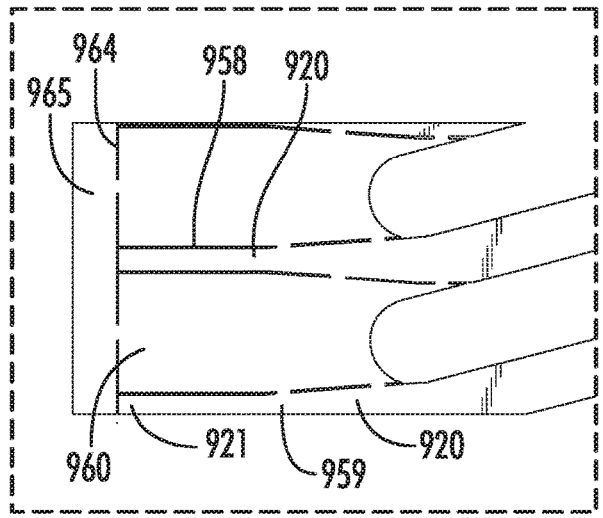
FIG. 53A illustrates a side elevation view of the proximal end of the memory metal tube of FIG. 49.
Figure 53B:
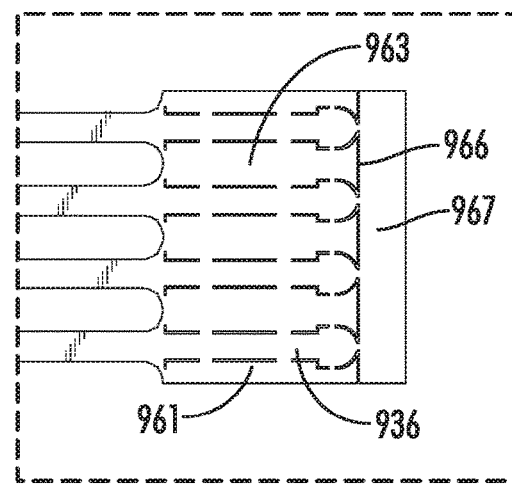
FIG. 53B illustrates a side elevation view of the distal end of the memory metal tube of FIG. 52.
Figure 53C:
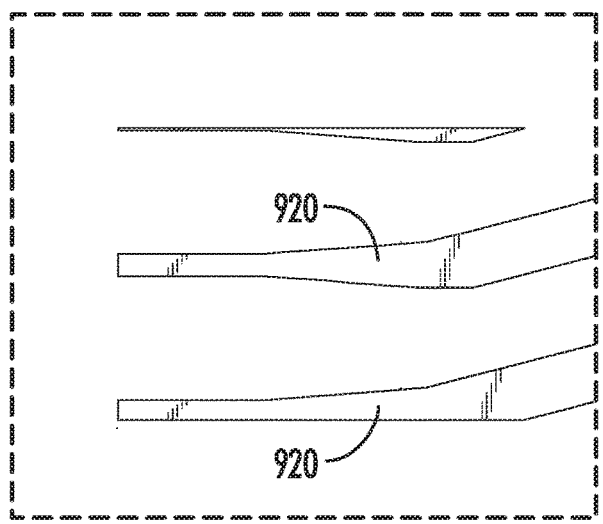
FIG. 53C illustrates a side elevation view of the proximal tether memory metal strips prepared from the tube of FIG. 53A after removing the proximal longitudinal tabs and the proximal perimeter tabs.
Figure 53D:
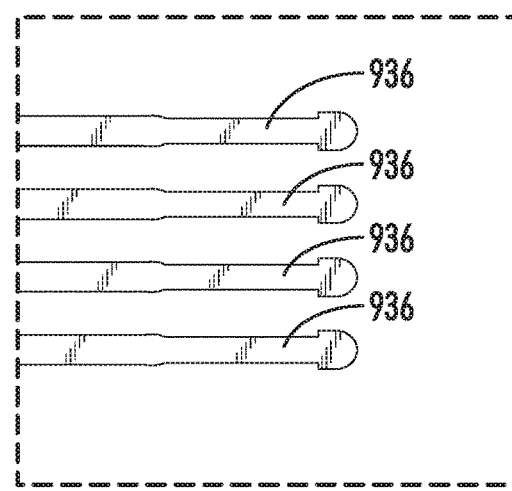
FIG. 53D illustrates a side elevation view of the distal basket memory metal strips prepared from the tube of FIG. 53A after removing the distal longitudinal tabs and the distal perimeter tabs.

Optionally step b) further comprises using the cutting instrument 813 to cut additional portions of the wall 803 of the first tube 800 and form a plurality of non-contiguous proximal longitudinal perforations 835 located in a proximal segment 836 of each proximal memory metal strip 821 adjacent to the proximal end 822 of the respective proximal memory metal strip 821 and extending generally along the first tube length 808 (see FIGS. 34, 36, 37, 46 and 49). Each adjacent non-contiguous proximal longitudinal perforation 835 is separated by a proximal longitudinal gap 876 (representing uncut portions of the wall 803). The proximal longitudinal perforations 835 and the proximal longitudinal gaps 876 form a first longitudinal side 872 and a second longitudinal side 873 of each proximal segment 836. It will be understood that the non-contiguous proximal longitudinal perforations 835 extend generally along the first tube length 808 but are not necessarily parallel to the first tube length 808 as shown in FIGS. 46 and 49 as indicated by reference line 878; the reference line 878 is not a component of the system but is merely drawn in the illustration to show the angle. A proximal longitudinal tab 837 is located between and connects adjacent proximal segments 836 of proximal memory metal strips 821 and is formed of uncut portions of the wall 803.

Optionally step b) further comprises using the cutting instrument 813 to cut additional portions of the wall 803 of the first tube 800 and form a plurality of non-contiguous distal longitudinal perforations 838 located in a distal segment 839 of each distal memory metal strip 824 adjacent to the distal end 826 of the respective distal memory metal strip 824 and extending generally along the first tube length 808 (see FIGS. 34 and 35). Each adjacent non-contiguous distal longitudinal perforation 838 is separated by a distal longitudinal gap 877 (representing uncut portions of the wall 803). The distal longitudinal perforations 838 and the distal longitudinal gaps 877 form a first longitudinal side 874 and a second longitudinal side 875 of each distal segment 839. It will be understood that the non-contiguous distal longitudinal perforations 838 extend generally along the first tube length 808 but are not necessarily parallel to the first tube length 808 as best seen in FIG. 35. A distal longitudinal tab 840 is located between and connects adjacent distal segments 839 of distal memory metal strips 824 and is formed of uncut portions of the wall 803.

Preferably, the polishing expands the plurality of proximal longitudinal perforations 835 about the first tube length 808 (see FIG. 38) and expands the plurality of the distal longitudinal perforations 838 about the first tube length 808 (so that adjacent proximal longitudinal perforations 835 on the first longitudinal side 872 of the proximal segment 836 approach each other, so that adjacent proximal longitudinal perforations 835 on the second longitudinal side 873 of the proximal segment 836 approach each other, so that adjacent distal longitudinal perforations 838 on the first longitudinal side 874 of the distal segment 839 approach each other, and so that adjacent distal longitudinal perforations 838 on the second longitudinal side 875 of the distal segment 839 approach each other), and step e) further comprises tearing along the plurality of proximal longitudinal perforations 835 to remove the proximal longitudinal tabs 837 (see FIGS. 39 and 41) and disconnect the proximal segments 836 from each other and tearing along the plurality of distal longitudinal perforations 838 to remove the distal longitudinal tabs 840 and disconnect the distal segments 839 from each other.

Optionally, after step d), the plurality of proximal longitudinal perforations 835 become nearly continuous (see FIGS. 39 and 41), the plurality of distal longitudinal perforations 838 become nearly continuous, the plurality of proximal perimeter perforations 814 become nearly continuous (see FIGS. 39 and 41) and the plurality of distal perimeter perforations 816 become nearly continuous.

Figure 44:
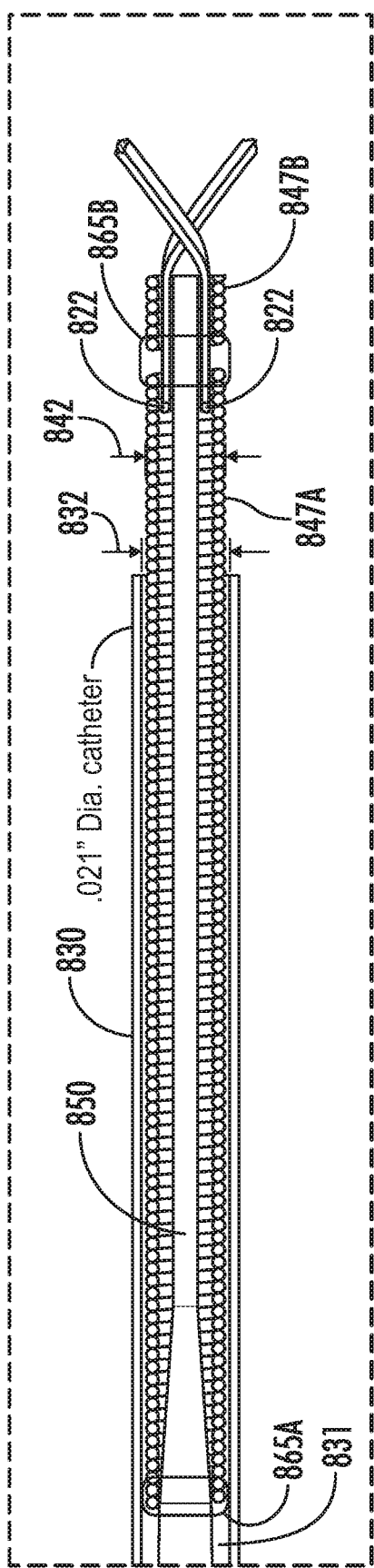
FIG. 44 illustrates a side, elevation view of the coil system of FIG. 43G being placed through a distal end of a catheter.
Figure 45:
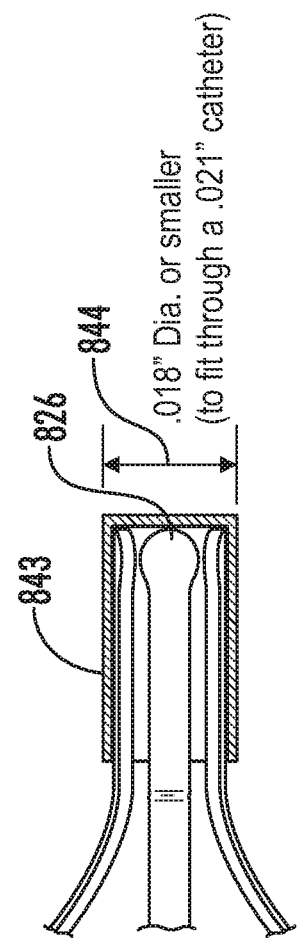
FIG. 45 illustrates a side, elevation view of a tube (referred to herein as a third tube) being used to re-join distal ends of distal memory metal strips; the distal ends of the distal memory metal strips were initially joined by a distal end tab and distal longitudinal tabs.

Optionally, the first tube 800 is generally cylindrical in shape and comprises a first tube outer diameter 810, wherein said catheter 830 is generally cylindrical in shape and comprises a catheter inner diameter 832 (interior diameter), wherein said step of joining the free proximal ends 822 of the proximal memory metal strips 821 comprises attaching the free proximal ends 822 of the proximal memory metal strips 821 to a second tube 841, the second tube 841 generally cylindrical in shape and comprising a second tube outer diameter 842, wherein said step of joining the free distal ends 826 of the distal memory metal strips 824 comprises attaching the free distal ends 826 of the distal memory metal strips 824 to a third tube 843, the third tube 843 generally cylindrical in shape and comprising a third tube outer diameter 844, and further wherein said second tube outer diameter 842 and said third tube outer diameter 844 are less than said first tube outer diameter 810 and less than said catheter inner diameter 832 (see FIGS. 44 and 45).

Figure 43A:
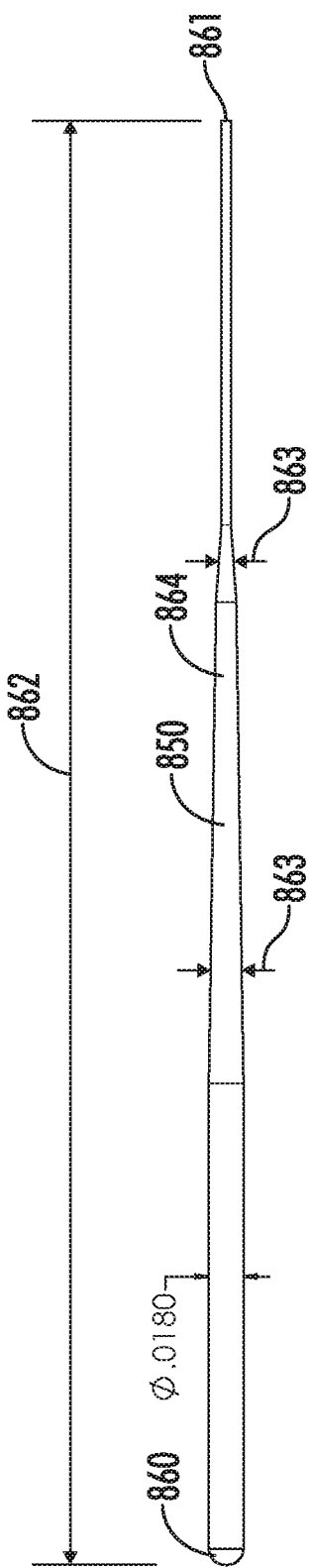
FIG. 43A illustrates a side elevation view of a pull wire.
Figure 43B:
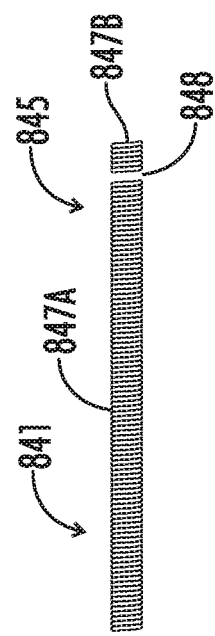
FIG. 43B illustrates a side elevation view of a coil system that includes a core and a coil wrapped around the core.
Figure 43C:
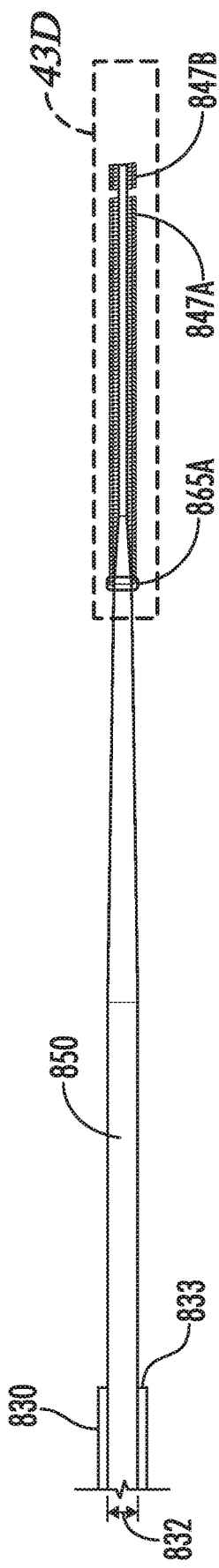
FIG. 43C illustrates a side elevation of the pull wire of FIG. 43A being soldered to the coil system of FIG. 43B.
Figure 43D:
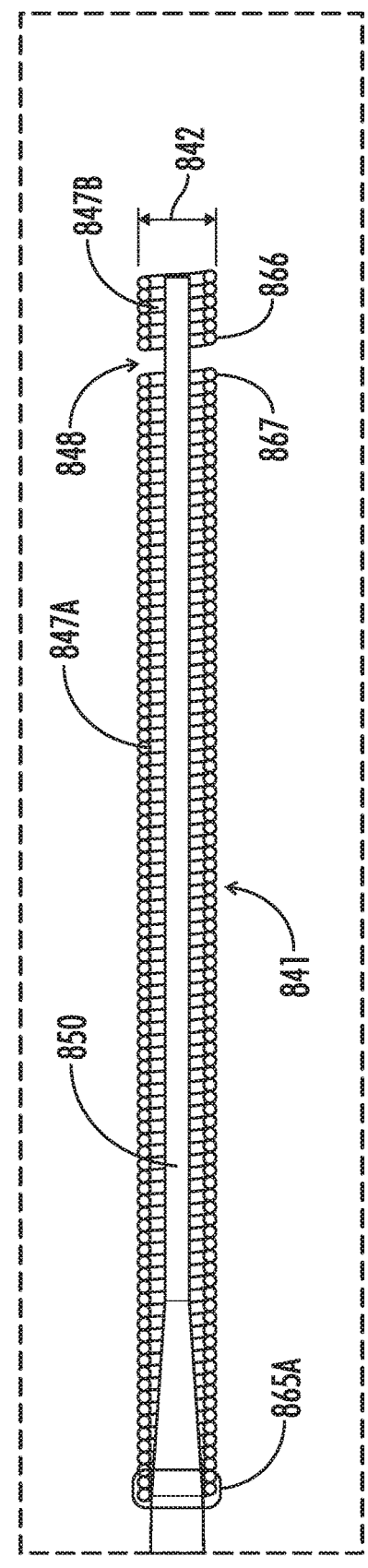
FIG. 43D illustrates a close-up, side elevation view of the area denoted by the dashed rectangle in FIG. 43C (namely, the distal end of the pull wire and the coil system of FIG. 43C).

FIGS. 43A-43G illustrate an embodiment where the second tube 841 is a coil system 845. For example, the method may include providing a pull wire 850. (See FIG. 43A). The next step may be providing a coil system 845 that includes a proximal coil 847A and a distal coil 847B separated by a longitudinal space 848 between the proximal end 866 of the distal coil 847B and the distal end 867 of the proximal coil 847A. (See FIG. 43B). The next step may involve soldering the pull wire 850 to the proximal coil 847A so that the pull wire 850 is surrounded by the proximal coil 847A. (See FIGS. 43C and 43D; soldering denoted by the numeral 865A). The next step may involve joining the proximal ends 822 of the proximal memory metal strips 821 by soldering the proximal ends 822 of the proximal memory metal strips 821 at the longitudinal space 848 between the coils 847A and 847B. (See FIGS. 43E-43G; soldering is denoted by the numeral 865B). As shown in FIG. 43F, the proximal memory metal strips 821 are located between the pull wire 850 (which forms a core of the coil system 845) and the proximal coil 847A. Optionally, the pull wire 850 comprises a pull wire proximal end 860, a pull wire distal end 861, a pull wire length 862 extending from the pull wire proximal end 860 to the pull wire distal end 861 and a pull wire width 863 generally perpendicular to the pull wire length 862 and further wherein said pull wire width 863 comprises a segment 864 in which the pull wire width 863 tapers proximally along the pull wire length 862. (See FIG. 43A).

Optionally, the proximal memory metal strips 821 comprise a width 849 generally perpendicular to the first tube length 808 and further wherein said widths 849 of said proximal memory metal strips 821 taper as the proximal memory metal strips 821 approach the proximal end tab 815 (see FIG. 46 and FIG. 49).

The middle portion 811 may be shape-set in any form. Preferably, the middle portion 811 is shape set in the form of a basket 851, as described above, that is configured to capture a foreign object in a lumen of an animal such as an intracranial thrombus. For example, optionally the middle portion memory metal strips 820 of said shape set middle portion 811 form a basket 851 comprising a basket interior 852 and a basket length 853 generally parallel to the medical device length 828. Optionally, in the expanded state, the basket 851 comprises a first pair of distal crowns 854 not attached to another cell 819 of the basket 851 and pointing generally in the distal direction, the distal crowns 854 in the first pair of distal crowns 854 located approximately the same distance along the basket length 853 and between 150 degrees and 180 degrees relative to each other, and further wherein the basket 851 further comprises a second pair of distal crowns 855 not attached to another cell 819 of the basket 851 and pointing generally in the distal direction, the second pair of distal crowns 855 located distally relative to the first pair of distal crowns 854, each of the distal crowns in the second pair of distal crowns 855 located between 60 degrees and 90 degrees relative to a distal crown in the first pair of distal crowns 854, the distal crowns in the second pair of distal crowns 855 located approximately the same distance along the basket length 853 and further wherein each of the distal crowns in the first and second pair of distal crowns 854 and 855 comprises an x-ray marker 856, the x-ray maker 856 more visible under x-ray as compared to the middle portion strips 820 when the basket 851 is located in a cranial blood vessel inside the body of a human and the x-ray is taken from outside the human's body and further wherein each distal crown in the first and second pair of distal crowns 854 and 855 forms part of a cell 819. Optionally, each distal crown in the first and second pair of distal crowns 854 and 855 forms part of an enlarged cell 857 and further wherein the surface area of the enlarged cells 857 in the relaxed state is greater than the surface area of the other cells 819 of the basket 811 and further wherein the enlarged cells 857 are configured to allow a thrombus to pass therethrough and into the basket interior 852, and further wherein the basket 811 comprises a non-uniform outward radial force along the basket length 853 due to the offset enlarged cells 857. (See FIG. 47). Optionally, in step b), each distal end 823 of each proximal memory metal strip 821 is connected to a proximal crown 869 of a proximal cell 819B of the middle portion 811, said proximal crown 869 of said proximal cell 819B located at the proximal end of the basket 811 and pointing generally in the proximal direction, and each proximal end 825 of each distal memory metal strip 824 is connected to a distal crown 868 of a distal cell 819A, each distal crown 868 pointing generally in the distal direction and located at the distal end of the basket 811 (see FIGS. 34 and 47). In other words, in the preferred embodiment the middle portion 811 preferably forms a basket 851 as described with the basket embodiment shown in FIGS. 11-20. However, other basket designs are also possible. Preferably, in the medical device 827, the middle portion width/diameter 812 in the expanded state tapers as the proximal memory metal strips 821 approach the second tube 841 and as the distal memory metal strips 824 approach the third tube 843. (See FIG. 48). (Preferably, the proximal memory metal strips 821 twist as shown in FIGS. 40-42, 44 and 47-48 and as described above with respect to FIGS. 11 and 20 for example—i.e., each distal end 823 of the respective proximal memory metal strip 821 is 180 degrees offset from the proximal end 822 of the same respective proximal memory metal strip 821).

Optionally, in the expanded state, the medical device width 829 is less than the medical device length 828. Optionally, said catheter inner diameter 832 is at least about 0.001 inches (e.g, between 0.001 and 0.015 inches, preferably between 0.003 and 0.015 inches) less than said first tube outer diameter 810. The medical device 827 may further include a lead wire at the distal end as described previously.

After step e), the proximal end tab 815, the distal end tab 817, the proximal longitudinal tabs 837 and the distal longitudinal tabs 840 are discarded.

Optionally, after step e), the proximal memory metal strips 821 comprise a smooth periphery and the distal memory metal strips 824 comprise a smooth periphery. In other words, preferably, the proximal end tabs 815 tear cleanly along the proximal perimeter perforations 814, the distal end tabs 817 tear cleanly along the distal perimeter perforations 816, the proximal longitudinal tabs 837 tear cleanly along the proximal longitudinal perforations 835 and the distal longitudinal tabs 840 tear cleanly along the distal longitudinal perforations 838.

The steps of the method described above with reference to FIGS. 33-49 may be performed simultaneously or in any suitable order. In addition, one or more of the steps, such as step d) may be omitted. Further, step c) (expanding the middle portion 811) may be performed using methods now known or hitherto developed. Moreover, the first tube 800 may only include proximal perimeter perforations 814, proximal longitudinal perforations 835, distal perimeter perforations 816 and/or distal longitudinal perforations 838. In other words, the first tube 800 may be cut to include only perimeter perforations 814 and/or 816 or only longitudinal perforations 835 and/or 838 as shown in FIG. 49 which only includes proximal longitudinal perforations 835 that extend to the proximal end 804 of the first tube 800). Preferably, the first tube 800 is cut to include at least proximal longitudinal perforations 835 and distal longitudinal perforations 838.

The Embodiments of FIGS. 50-56

FIGS. 50-56 illustrate another catheter-delivered endovascular device. The catheter-delivered endovascular device 890 of FIGS. 50-56 may be used to retrieve a clot or other foreign object from a lumen of an animal. In addition, the catheter-delivered endovascular device 890 of FIGS. 50-56 may be used to open a constricted blood vessel 950 in the case of a subarrachnoid hemorrhage induced vasospasm or other vasospasm.

The catheter-delivered endovascular device 890 of FIGS. 50-56 includes a pull wire 891 having a proximal end, a distal end 892 and a pull wire longitudinal axis 894 extending from the proximal end to the distal end 892. The pull wire 891 may have one or more features described above with respect to the systems of FIGS. 1-49, and may be comprised of a biocompatible metallic material for example.

Optionally, the catheter-delivered endovascular device 890 further includes a deployable dual basket system 895 attached to the pull wire 891 and comprising a system perimeter/circumference 896 separating a system interior 897 from a system exterior 898, a system proximal end 899, a system distal end 900, a system height 901 having a system height center 902, a system width 903 perpendicular to the system height 901 and having a system width center 904, a system longitudinal axis 905 from the system proximal end 899 to the system distal end 900 and extending through the system height center 902 and system width center 904. The system height 901 and width 903 may vary along the system longitudinal axis 905, as seen in FIGS. 50-51, e.g., a smaller height and width at the proximal end 899, the distal end 900, and the middle of the system as seen in FIGS. 50-51. The system 895 is preferably generally in the form of a tapered cylinder with a variable diameter constituting the system height 901 and system width 903, and accordingly, the system perimeter 896 is preferably a system circumference.

Figure 56A:
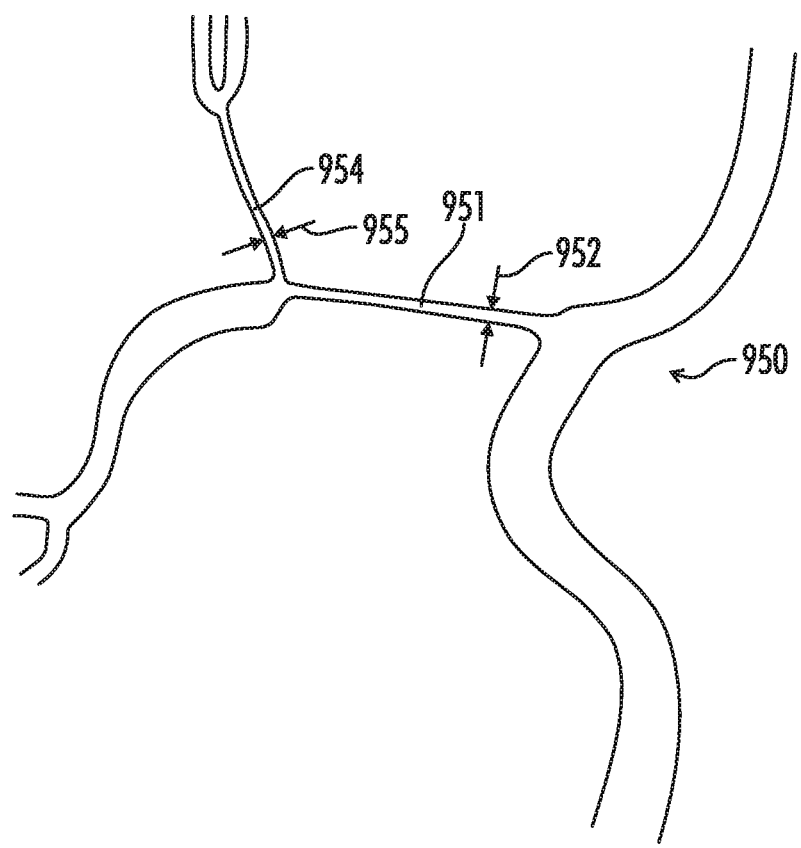
FIGS. 56A-56E illustrate deployment and use of a catheter-delivered endovascular device that includes the deployable dual basket system of FIGS. 50 and 51 to treat a human having a subarrachnoid hemorrhage induced vasospasm in a constricted blood vessel having a proximal region having a constricted height and a constricted width and a distal region having a constricted height and a constricted width.
Figure 56B:
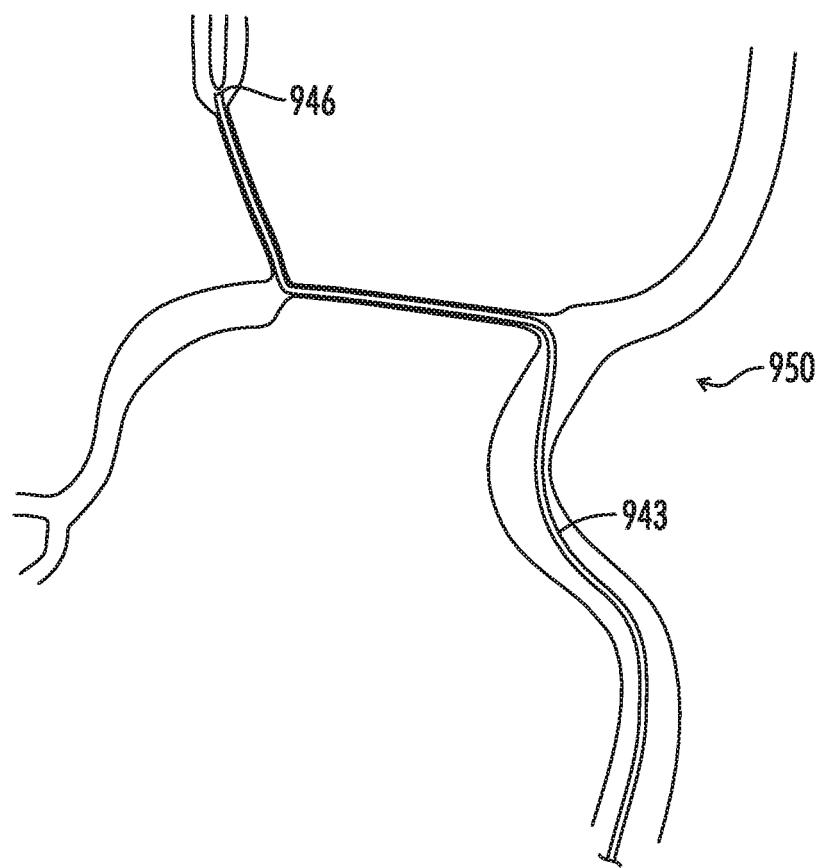
Figure 56C:
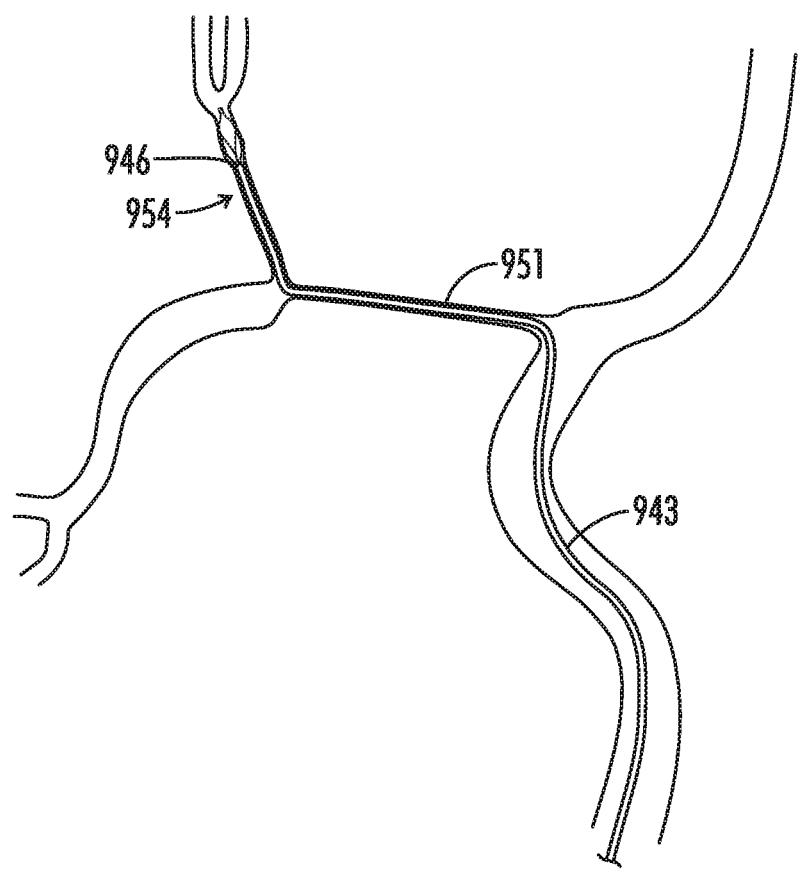
Figure 56D:
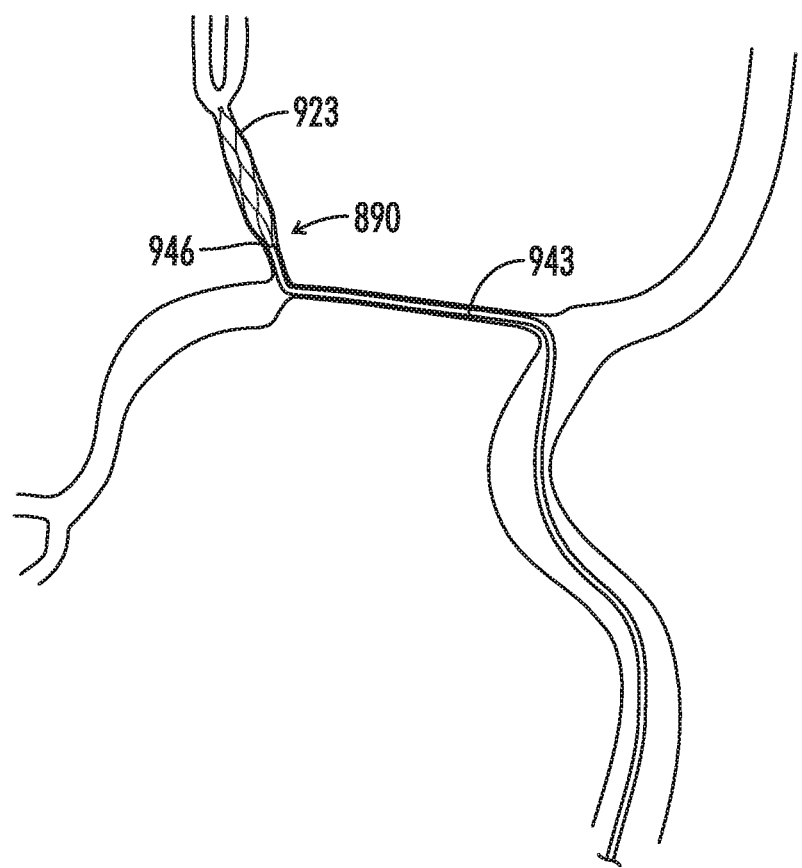
Figure 56E:
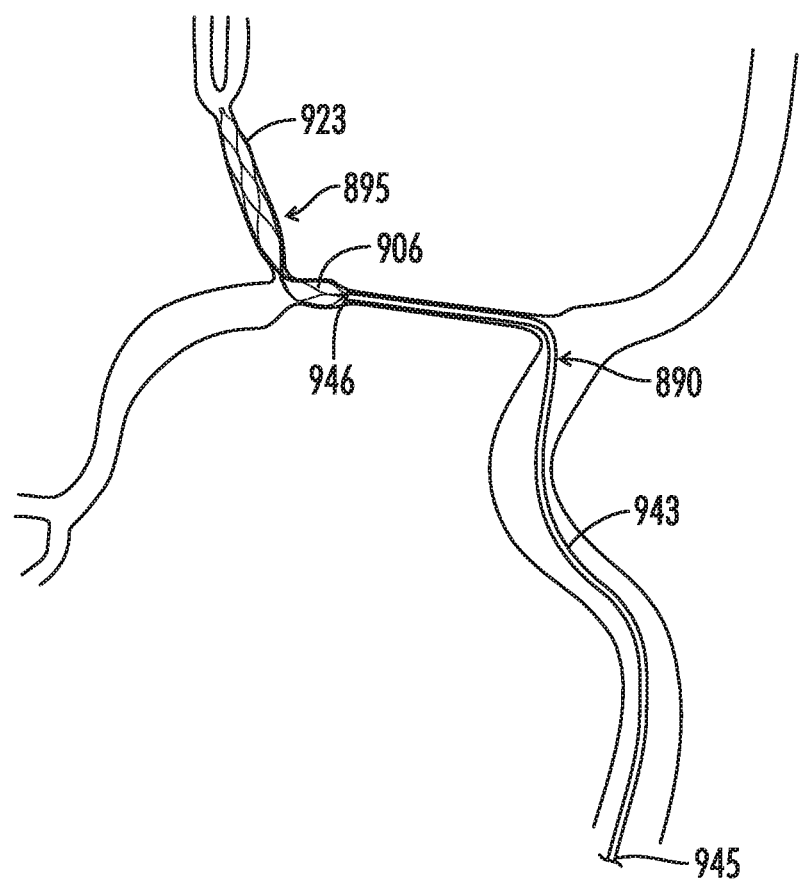
Figure 56F:
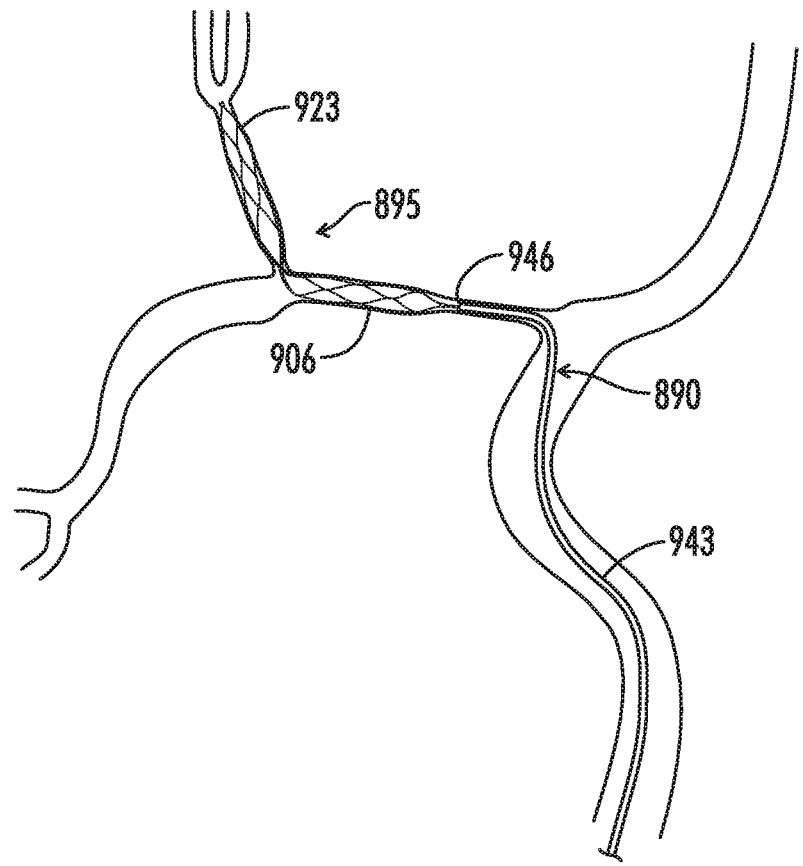
Figure 56G:
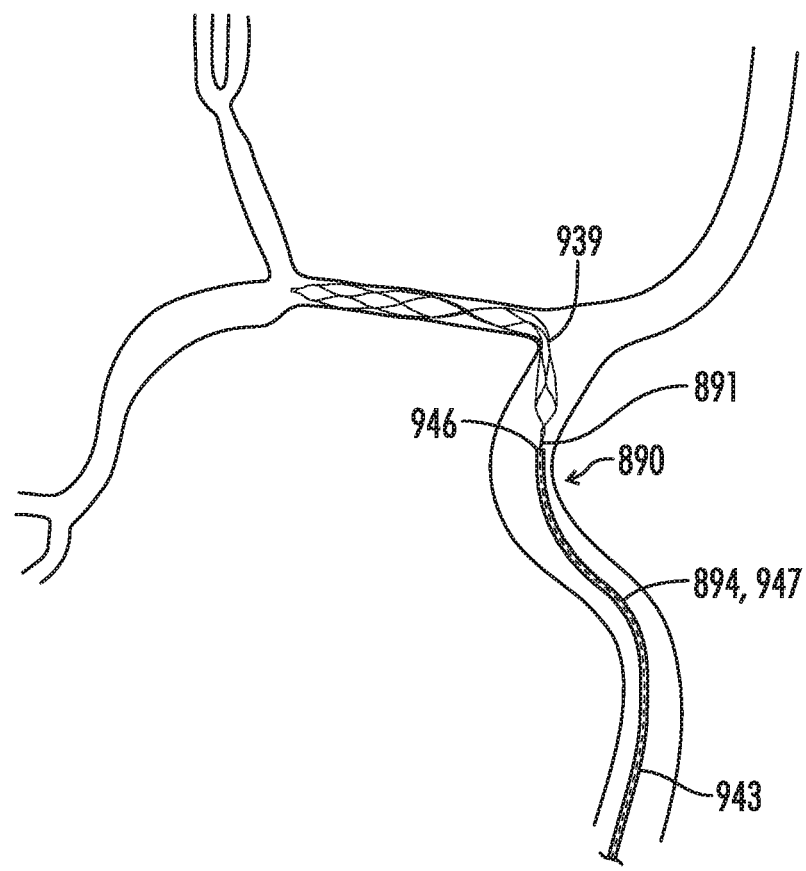
Figure 56H:
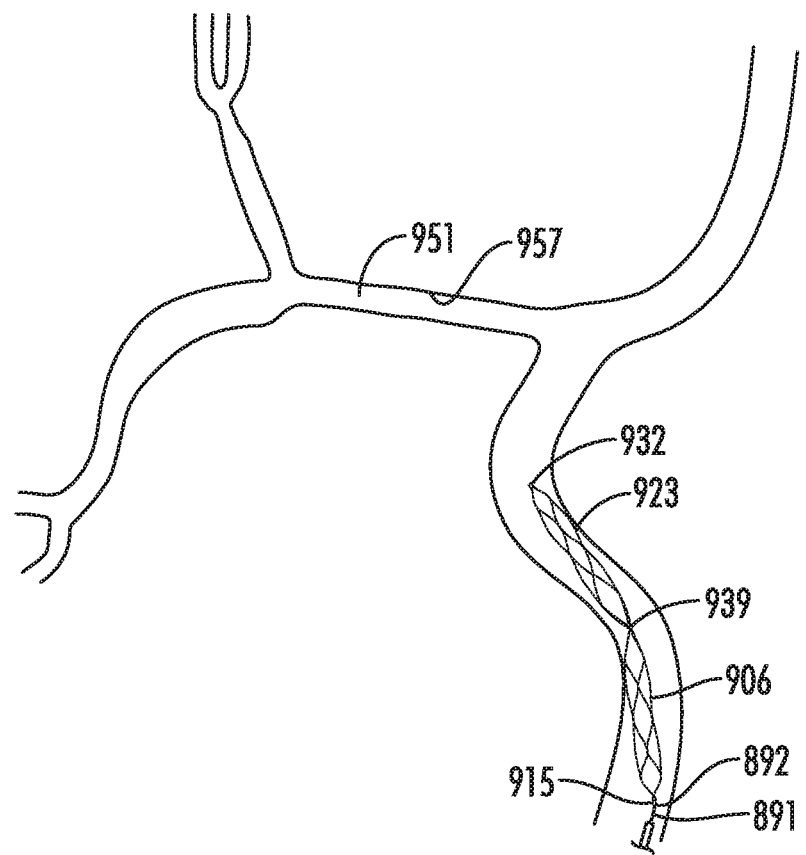

Optionally, the deployable dual basket system 895 includes a proximal basket 906 attached to the pull wire 891, the proximal basket 906 comprising a proximal basket perimeter/circumference 907 separating a proximal basket interior 908 from a proximal basket exterior 909, a proximal end 910 forming the system proximal end 899, a distal end 911, a proximal basket height 912 generally parallel to the system height 901, a proximal basket width 913 generally parallel to the system width 903 and perpendicular to the proximal basket height 912, a proximal basket longitudinal axis 914 extending from the proximal basket proximal end 910 to the distal end 911 and generally parallel to the system longitudinal axis 905 and generally perpendicular to the proximal basket height 912 and proximal basket width 913, a proximal junction 915 located at the proximal end 910 of the proximal basket 906, a plurality of proximal cells 916 distal to the proximal junction 915 and defined by a plurality of proximal basket memory metal strips 917, each proximal cell 916 comprising a proximal crown 918 located at the proximal end of the proximal cell 916 and pointing generally in the proximal direction and a distal crown 919 located at the distal end of the proximal cell 916 and pointing generally in the distal direction, a plurality of proximal tether memory metal strips 920 located between the proximal junction 915 and the proximal cells 916 and connecting the proximal cells 916 to the proximal junction 915, each proximal tether memory metal strip 920 having a proximal end 921 attached to the proximal junction 915, a distal end 922 attached to a proximal crown 918 of a proximal cell 916. Due to the fact that the proximal basket 906 is preferably formed from a memory metal tube, as with the prior embodiments, the proximal basket 906 preferably has a relaxed/expanded state (as shown in FIGS. 50, 51, 56F, 56G, and 56H) wherein the proximal basket 906 has a first height 912 and a first width 913, and a collapsed state (see FIGS. 56B, 56C and 56D, in which the proximal basket 906 is in the catheter interior 944)

wherein the proximal basket 906 has a second height and a second width, the second height less than the first height 912 and the second width less than the first width 913. (FIG. 56E shows the distal end 911 of the proximal basket 906 in the relaxed state and the proximal end 910 (which is not clearly visible) is in the collapsed state.

Optionally, the deployable dual basket system 895 further includes: a distal basket 923 distal to the proximal basket 906 and comprising a distal basket circumference 924 separating a distal basket interior 925 from a distal basket exterior 926, a proximal end 927, a distal end 928 forming the system distal end 900, a distal basket height 929 generally parallel to the system height 901, a distal basket width 930 generally parallel to the system width 903 and generally perpendicular to the distal basket height 929, a distal basket longitudinal axis 931 extending from the distal basket proximal end 927 to the distal basket distal end 928 and generally parallel to the system longitudinal axis 905, a distal junction 932 located at the distal end 928 of the distal basket 923, a plurality of distal cells 934 proximal to the distal junction 932 and defined by a plurality of distal basket memory metal strips 933, each distal cell 934 comprising a proximal crown 938 located at the proximal end of the distal cell 934 and pointing generally in the proximal direction and a distal crown 937 located at the distal end of the distal cell 934 and pointing generally in the distal direction. Due to the fact that the distal basket 923 is preferably formed from a memory metal tube, as with the prior embodiments, the distal basket 923 preferably has a relaxed/expanded state (as shown in FIGS. 50, 51, and 56E-56H) wherein the distal basket 923 has a first height 929 and a first width 930, and a collapsed state (see FIG. 56B in which the distal basket 923 is in the catheter interior 944) wherein the distal basket 923 has a second height and a second width, the second height less than the first height 929 and the second width less than the first width 930. (FIG. 56C shows the distal end 928 of the distal basket 923 in the expanded state and the proximal end 927 (which is in the catheter interior 944) is in the collapsed state).

Optionally, the deployable dual basket system 895 further includes a plurality of basket connector tether memory metal strips 939 located between the proximal basket 906 and the distal basket 923 and connecting the proximal basket 906 to the distal basket 923 and located between the proximal basket 906 and the distal basket 923. Optionally, each basket connector tether memory metal strip 939 has a proximal end 940 attached to a distal crown 919 of a cell 916 located at the distal end of the proximal basket 906 and a distal end 941 attached to a proximal crown 938 of a cell 934 located at the proximal end of the distal basket 923, and a basket connector tether memory metal strip longitudinal axis extending from the proximal end 940 of the basket connector tether memory metal strip 939 to the distal end 941 of the basket connector tether memory metal strip 939.

As previously mentioned, the catheter-delivered endovascular device 890 further includes a catheter 943 having an interior 944, a proximal end 945 leading to the interior 944 and a distal end 946 leading to the interior 944, the catheter 943 comprised of a biocompatible material and configured to envelope the deployable dual basket system 895 when the proximal basket 906 and distal basket 923 are in the collapsed state. The catheter 943 may have one or more features described above with respect to the catheters of the systems shown in FIGS. 1-49 and may be polymeric as described above.

Figure 54:
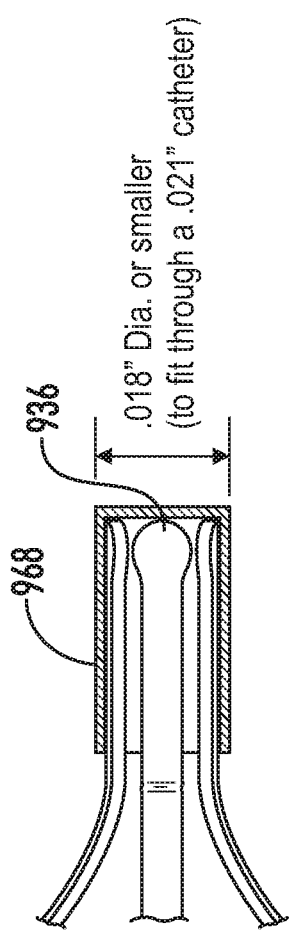
FIG. 54 illustrates use of a third tube to re-join the distal basket memory metal strips of FIG. 53D.
Figure 55:
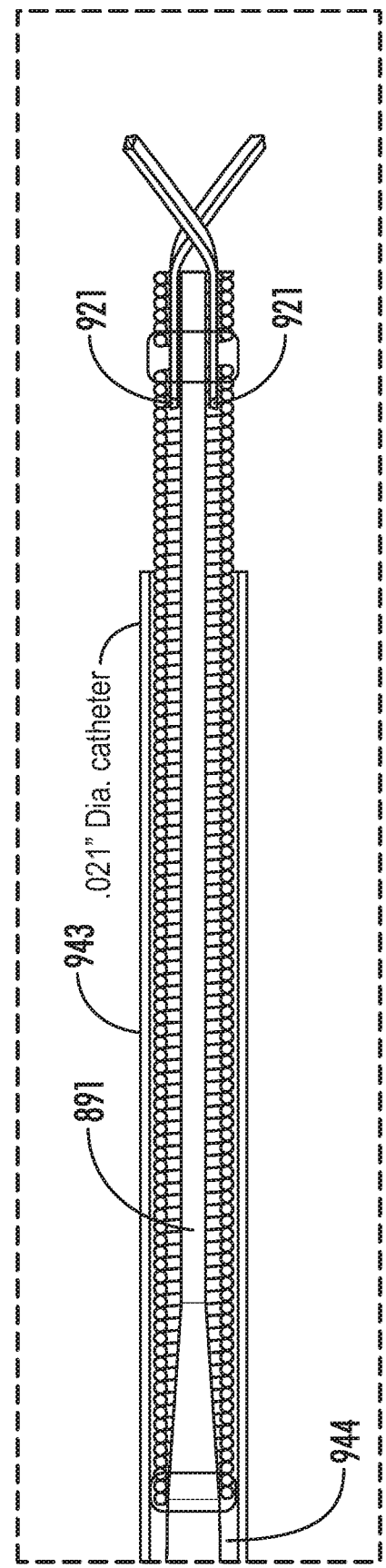
FIG. 55 illustrates use of a coil to re-join the proximal tether memory metal strips of FIG. 53C.

Optionally, in the relaxed state and the collapsed state, each basket connector tether memory metal strip 939 rotates a degree of rotation about the system circumference 896 relative to the proximal basket longitudinal axis 914, the distal basket longitudinal axis 931 and the system longitudinal axis 905. Optionally, each basket connector tether memory metal strip 939 rotates in the same direction; for example, if the deployable dual basket system 895 has two basket connector tether memory metal strips 939 both will rotate clockwise or both will rotate counterclockwise as viewed from the system proximal end 899. The reason that the basket connector tether memory metal strips 939 both preferably rotate in the same direction is that the deployable dual basket system 895 is preferably initially made from a single memory metal tube using the cut pattern for the basket connector tether memory metal strips 939 shown in FIG. 52 (the memory metal tube is shown flat in FIG. 52 for illustration purposes). As discussed below, after cutting the tube and removing the proximal end of the tube and the distal end of the tube, the proximal tether memory metal strips 920 may be re-joined as shown in FIG. 55 using coil and the distal basket memory metal strips distal ends 936 may be rejoined using third tube 968 as shown in FIG. 54. The rotating basket connector tether memory metal strips 939 preferably provide a flex point so that the deployable dual basket system 895 may navigate tortuous blood vessels 950, as shown in FIG. 56. It will be understood that the rotation is a characteristic of the connector tether memory metal strips 939 and does not refer to user manipulation of the connector tether memory metal strips 939—i.e., the connector tether memory metal strips 939 rotate without user manipulation.

Optionally, each basket connector tether memory metal strip 939 rotates a greater degree of rotation in the collapsed state as compared to the degree of rotation of the same basket connector tether memory metal strip 939 in the relaxed state if the basket connector tether memory metal strips 939 are prepared from a single memory metal tube that is expanded and shape set. The reason for this is that the collapsed state mimics the native portion and has the diameter of the tube from which the deployable dual basket system 895 is cut, whereas the relaxed state has a greater diameter, and accordingly, the basket connector tether memory metal strips 939 must travel a greater distance in the relaxed state. Thus, for example, a given basket connector tether memory metal strip 939 may rotate 180 degrees for example in the collapsed state but only 90 degrees in the relaxed state. Optionally, in the relaxed state, the basket connector tether memory metal strips 939 each rotate at least about fifteen degrees in the same direction relative to the proximal basket longitudinal axis 914 and the distal basket longitudinal axis 931. In the collapsed state, the distal end 941 of a first basket connector tether memory metal strip 939 is located between about 90 degrees and about 270 degrees relative to the proximal end 940 of the same basket connector tether memory metal strip 939, and further wherein in the collapsed state, the distal end 941 of a second basket connector tether memory metal strip 939 is located between about 90 degrees and about 270 degrees relative to the proximal end 940 of the same basket connector tether memory metal strip 939.

Due to the fact that the basket connector tether memory metal strips 939 rotate, in the relaxed state and the collapsed state, a distal crown 919 of the proximal basket 906 attached to the proximal end 940 of a basket connector tether memory metal strip 939 is offset about the system circumference 896 relative to the proximal crown 938 of the distal basket 923 attached to the distal end 941 of the same basket connector tether memory metal strip 939, and accordingly, the distal crown 919 of the proximal basket 906 will rotate a greater extent in the collapsed state as compared to the relaxed state.

Optionally, at least some of the distal basket memory metal strips 933 are located at the distal end 928 of the distal basket 923, wherein each of the distal basket memory metal strips 933 located at the distal end 928 of the distal basket 923 have a distal end 936, wherein each of the distal ends 936 of the distal basket memory metal strips 933 located at the distal end 928 of the distal basket 923 converge at the distal junction 932 and further wherein the distal basket 923, in the relaxed state, comprises a tapered region 948 in which the distal basket height 929 and width 930 decrease as the distal basket memory metal strips 933 located at the distal end 928 of the distal basket 923 approach the distal junction 932. Likewise, optionally, the proximal basket 906, in the relaxed state, comprises a tapered region 949 in which the proximal basket height 912 and width 913 decrease as the proximal tether memory metal strips 920 approach the proximal junction 915. In other words, the proximal tapered region 949 represents a low point in the proximal basket width 913 and height 912 and the distal tapered region 948 represents a low point in the distal basket width 930 and height 929, which prevents the device 890 from injuring a blood vessel 950 when used to treat vasospasm, as shown in FIGS. 56A-56H for example.

Optionally, in the relaxed state, the radial force of the deployable dual basket system 895 from the proximal ends 940 of the basket connector tether memory metal strips 939 to the distal ends 941 of the basket connector tether memory metal strips 939 is less than the radial force of the proximal basket 906, as measured from the proximal crowns 918 of the cells 916 of the proximal basket 906 attached to the plurality of proximal memory metal strips 920 to the distal crowns 919 of the cells 916 of the proximal basket 906 attached to the plurality of basket connector tether memory metal strips 939. The decreased radial force of the basket tether memory metal strips 939 is designed to allow the deployable dual basket system 895 to navigate the tortuous blood vessels 950, as previously mentioned.

Optionally, the system 895 has only two basket connector tether memory metal strips 939.

Optionally, in the relaxed state, the height 912 of the proximal basket 906 is greater than the height 929 of the distal basket 923 and further wherein the width 913 of the proximal basket 906 is greater than the width 930 of the distal basket 923. Optionally, in the relaxed state, the radial force of the distal basket 923, as measured from the proximal crowns 938 of the cells 934 of the distal basket 923 attached to the plurality of basket connector tether memory metal strips 939 to the distal-most crown 937 of the distal cells 934 of the distal basket 923, is less than the radial force of the proximal basket 906 as measured from the proximal crowns 918 of the cells 916 of the proximal basket 906 attached to the plurality of proximal memory metal strips 920 to the distal crowns 919 of the cells 916 of the proximal basket 906 attached to the plurality of basket connector tether memory metal strips 919. The decreased height 929, width 930 and radial force of the distal basket 923, as compared to the proximal basket 906, is designed to prevent vessel damage given that blood vessels 950 generally taper from the proximal end to the distal end. Optionally, in the relaxed state, the radial force of the proximal basket 906 is substantially uniform from the proximal crowns 918 of the cells 916 of the proximal basket 906 attached to the plurality of proximal memory metal strips 920 to the distal crowns 919 of the cells 916 of the proximal basket 906 attached to the plurality of basket connector tether memory metal strips 939 (i.e., substantially uniform along the length of the proximal basket 906). Similarly, optionally, in the relaxed state, the radial force of the distal basket 923 is substantially uniform from the proximal crowns 938 of the cells 934 of the distal basket 923 attached to the plurality of basket connector tether memory metal strips 939 to the distal-most crown 937 of the distal cells 934 of the distal basket 923.

Optionally, the proximal basket interior 908 and the distal basket interior 925 are generally hollow and the proximal basket cells 916 are spaced about the circumference of the proximal basket 906 and the distal basket cells 934 are spaced about the circumference 924 of the distal basket 923.

Optionally, the basket connector tether memory metal strips 939 do not traverse the system interior 897. In other words, the connector tether memory metal strips 939, the proximal basket cells 916 and the distal basket cells 934 each define a portion of the perimeter of the deployable dual basket system 895.

Optionally, each of the distal crowns 919 of the proximal basket 906 connected to the basket connector tether memory metal strips 939 are approximately the same distance from the proximal junction 915 and further wherein each of the proximal crowns 938 of the distal basket 923 connected to the basket connector tether memory metal strips 939 are approximately same distance from the distal junction 932.

Optionally, each of the proximal crowns 918 and 938 are connected to a memory metal strip extending proximally from the proximal crowns 918 and 938 and each of the distal crowns 919 and 937 are connected to a memory metal strip extending distally from the distal crowns 919 and 937 (i.e., the proximal crowns 918 and 938 and distal crowns 919 and 937 are connected to either the proximal tether memory metal strips 920, the proximal basket memory metal strips 917, the distal basket memory metal strips 933 or the basket connector tether memory metal strips 939). In other words, there are no free crowns and the proximal basket 906 and distal basket 923 have a closed cell design to prevent vessel injury.

Optionally, the proximal tether memory metal strips form 920 flex points of the deployable dual basket system 895. The proximal tether memory metal strips 920 may also rotate. For example, in the collapsed state, the distal end 922 of a first proximal tether memory metal strip 920 may be located between about 90 degrees and about 270 degrees relative to the proximal end 921 of the same proximal tether memory metal strip 920, and further wherein in the collapsed state, the distal end 922 of a second proximal tether memory metal strip 920 may be located between about 90 degrees and about 270 degrees relative to the proximal end 921 of the same proximal tether memory metal strip 920. Optionally, the first and second proximal memory metal strips 920 intersect/cross adjacent and distal to the proximal junction 915, as seen in FIGS. 50 and 51. In other words, the length/longitudinal axis of the proximal tether memory metal strips 920 (and the length/longitudinal axis of the basket connector tether memory metal strips 939) is preferably angled relative to the system longitudinal axis 905, the proximal basket longitudinal axis 914 or the distal basket longitudinal axis 931.

Optionally, the basket connector tether memory metal strips 939 form the sole attachment of the proximal basket 906 to the distal basket 923.

As mentioned, the device 890 of FIGS. 50-56 may be used to open a constricted blood vessel in the case of a subarachnoid hemorrhage induced vasospasm, as seen in FIG. 56. It will be understood that the term "blood vessel" includes more than one vessel, as four artery branches are shown in FIG. 56, namely, the M2 middle cerebral artery (MCA), the M1 middle cerebral artery (MCA), the internal carotid artery (ICA) and the A1 anterior cerebral artery (ACA).

For example, the device 890 may be used in a method of treating a human having a subarrachnoid hemorrhage induced vasospasm in a constricted blood vessel 950 having a proximal region 951 having a constricted height 952 and a constricted width and a distal region 954 having a constricted height 955 and a constricted width, the method comprising the steps of:

a) providing the deployable dual basket system 895, wherein the distal basket 923 and the proximal basket 906 are in the collapsed state and located in the catheter interior 944;

b) positioning the deployable dual basket system 895 in the blood vessel 950 so that the distal end 946 of the catheter 943 is distal to the distal region 954 of the blood vessel 950;

c) deploying the proximal basket 906 and the distal basket 923 from the distal end 946 of the catheter 943 into the distal region 954 of the blood vessel 950; and d) allowing the height 929 and width 930 of the distal basket 923 and the proximal basket 906 to increase and cause the height 955 and width of the distal region 954 of the blood vessel 950 to increase. Optionally, the method further includes e) moving the deployable dual basket system 895 proximally in the relaxed state within the blood vessel 950 and into the proximal region 951 to cause the height 952 and width of the proximal region 951 of the blood vessel 950 to increase; and f) withdrawing the deployable dual basket system 895 from the blood vessel 950 and out of the human.

As mentioned above, the term "blood vessel" may or may not include multiple blood vessels. For example, in FIG. 56, the constricted distal region 954 of the blood vessel 950 is the M2 of the middle cerebral artery and the constricted proximal region 951 of the blood vessel 950 is the M1 segment of the middle cerebral artery. Alternatively, the proximal region 951 and distal region 954 may be two discrete (albeit connected) blood vessels.

The blood vessel 950 is lined with endothelium 957 and preferably the method comprises performing steps a)-f) without damaging the endothelium 957.

The devices 895 of FIGS. 50-56 may be manufactured by any suitable method. In an exemplary embodiment, the device 895 is assembled in a method similar to FIGS. 33A-49. The method may include: a) providing a first tube comprised of a memory metal as previously described with respect to FIGS. 33A-49; b) using a cutting instrument to cut portions of the first tube wall and form a proximal matrix (i.e., the precursor to proximal basket 906) in the proximal middle portion comprising a plurality of proximal middle portion memory metal strips forming a plurality of proximal matrix cells, each proximal matrix cell having a proximal crown pointing generally in the proximal direction and a distal crown pointing generally in the distal direction and a proximal matrix cell length extending from the proximal crown to the distal crown and generally parallel to the first tube longitudinal axis; ii) a plurality of proximal tether memory metal strips 920, each proximal tether memory metal strip 920 having a proximal tether memory metal strip proximal end 921, a proximal tether memory metal strip distal end 922 connected to a proximal crown of a proximal matrix cell and a proximal memory metal strip length extending from the proximal tether memory metal strip proximal end 921 to the proximal tether memory metal strip distal end 922, the proximal tether memory metal strips 920 formed by moving the cutting instrument at an angle (e.g., between about 90 degrees and 270 degrees relative to the first tube longitudinal axis); iii) a distal matrix (i.e., the precursor to the distal basket 923) in the proximal middle portion comprising a plurality of distal middle portion memory metal strips forming a plurality of distal matrix cells, each distal matrix cell having a proximal crown pointing generally in the proximal direction and a distal crown pointing generally in the distal direction and a distal matrix cell length extending from the proximal crown to the distal crown and generally parallel to the first tube longitudinal axis; iv) a plurality of basket connector tether memory metal strips 939, each basket connector tether memory metal strip 939 having a basket connector tether memory metal strip proximal end 940 connected to a distal crown of a proximal matrix cell, a basket connector tether memory metal strip distal end 941 connected to a proximal crown of a distal matrix cell and a basket connector tether memory metal strip length extending from the basket connector tether memory metal strip proximal end 940 to the basket connector tether memory metal strip distal end 941, the basket connector tether memory metal strips 939 formed by rotating the first tube about the first tube longitudinal axis relative to the cutting instrument so that the proximal end 940 of a basket connector tether memory metal strip 939 is located between about 90 degrees and about 270 degrees relative to the distal end 941 of the same basket connector tether memory metal strip 939; and v) a plurality of proximal longitudinal perforations 958 as described previously, wherein a proximal longitudinal tab 960 is located between and connects adjacent proximal segments 959 of adjacent proximal tether memory metal strips 920 and is formed from uncut portions of the first tube wall; c) shape setting at least the proximal middle portion and the distal middle portion to expand the width of the proximal middle portion and the distal middle portion and form a proximal basket 906 comprised of the proximal matrix cells and a distal basket 923 comprised of the distal matrix cells, the proximal basket 906 and the distal basket 923 connected by the basket connector tether memory metal strips 939; d) after step c), polishing the first tube, wherein said polishing expands the plurality of proximal longitudinal perforations 958 so that the proximal longitudinal gaps become smaller and adjacent proximal longitudinal perforations 958 approach each other; e) tearing along the plurality of proximal longitudinal perforations 958 to free the proximal segments 959 of the proximal tether memory metal strips 920 from the proximal longitudinal tabs 960 and each other; f) joining the free proximal segments 959 of the proximal tether memory metal strips 920 (e.g., using a coil as shown in FIG. 55) to form a medical device comprised of the joined proximal segments 959 of the proximal tether memory metal strips 920, the proximal basket 906, the basket connector tether memory metal strips 939, and the distal basket 923, the medical device having a medical device length extending at least from the distal basket 923 to at least the joined proximal segments 959 of the proximal tether memory metal strips 920 and a medical device width generally perpendicular to the medical device length; and g) inserting the medical device into a catheter 943 comprising a catheter interior 944 having an interior width, an open catheter proximal end 945 leading to the catheter interior 944, an open catheter distal end 946 leading to the catheter interior 944, the catheter 943 comprised of a biocompatible material, wherein the medical device comprises a collapsed state wherein the medical device width is less than the catheter interior width and a relaxed state wherein the medical device width is greater than the catheter interior width, wherein the catheter 943 is configured to envelope the medical device when the medical device is in the collapsed state, and further wherein the catheter interior width is less than the first tube outer width.

Optionally, the process further includes forming distal longitudinal perforations 961, distal longitudinal tabs 963 and rejoining the distal basket memory metal strip distal ends 936 using a third tube 968 as described previously and shown in FIG. 54. In addition, the process may include forming proximal perimeter perforations 964, proximal end tab 965, distal perimeter perforations 966 and distal end tab 967. It will be appreciated that the manufacturing process has been described and illustrated in abbreviated form due to the similarities to FIGS. 33A-49. As with FIGS. 33A-49, the process of FIGS. 52-55 allows one to form the proximal and distal baskets 906 and 923 from a tube having a first tube diameter, and then removing the proximal and distal ends of the first tube (and attaching coil and third tube 968, which have a smaller diameter than the first tube diameter) in order to allow the deployable dual basket system 895 to fit inside a catheter having a diameter less than the first tube diameter.

Optionally, the cells 916 of the proximal basket 906 are substantially equal in size to each other and to the cells 934 of the distal basket 923 in the relaxed state—e.g., the surface area of the cells 916 and 934 may vary by no more than 5%.

The deployable dual basket system 895 of FIGS. 50-56 may have a length of, for example, between about 10 mm (millimeters) and 60 mm, more preferably between about 30 mm and about 60 mm.

The system of FIGS. 50-56 may include a lead wire extending from the distal junction 932, as described above with respect to the systems of FIGS. 1-49.

The Embodiments of FIGS. 57-72

FIGS. 57-72 illustrate another embodiment of the present invention in which the distal body 1018 includes a proximal portion 1042 that has cells 1044 and a distal portion 1048 that has mesh openings 1056. The proximal portion 1042 may be similar to the baskets shown in FIGS. 11-56 above. With respect to the distal portion 1048, the mesh openings 1056 may be small openings that serve to impede blood flow, as well as to capture any small emboli captured by the basket 1040 from escaping through the basket 1040.

Figure 60:
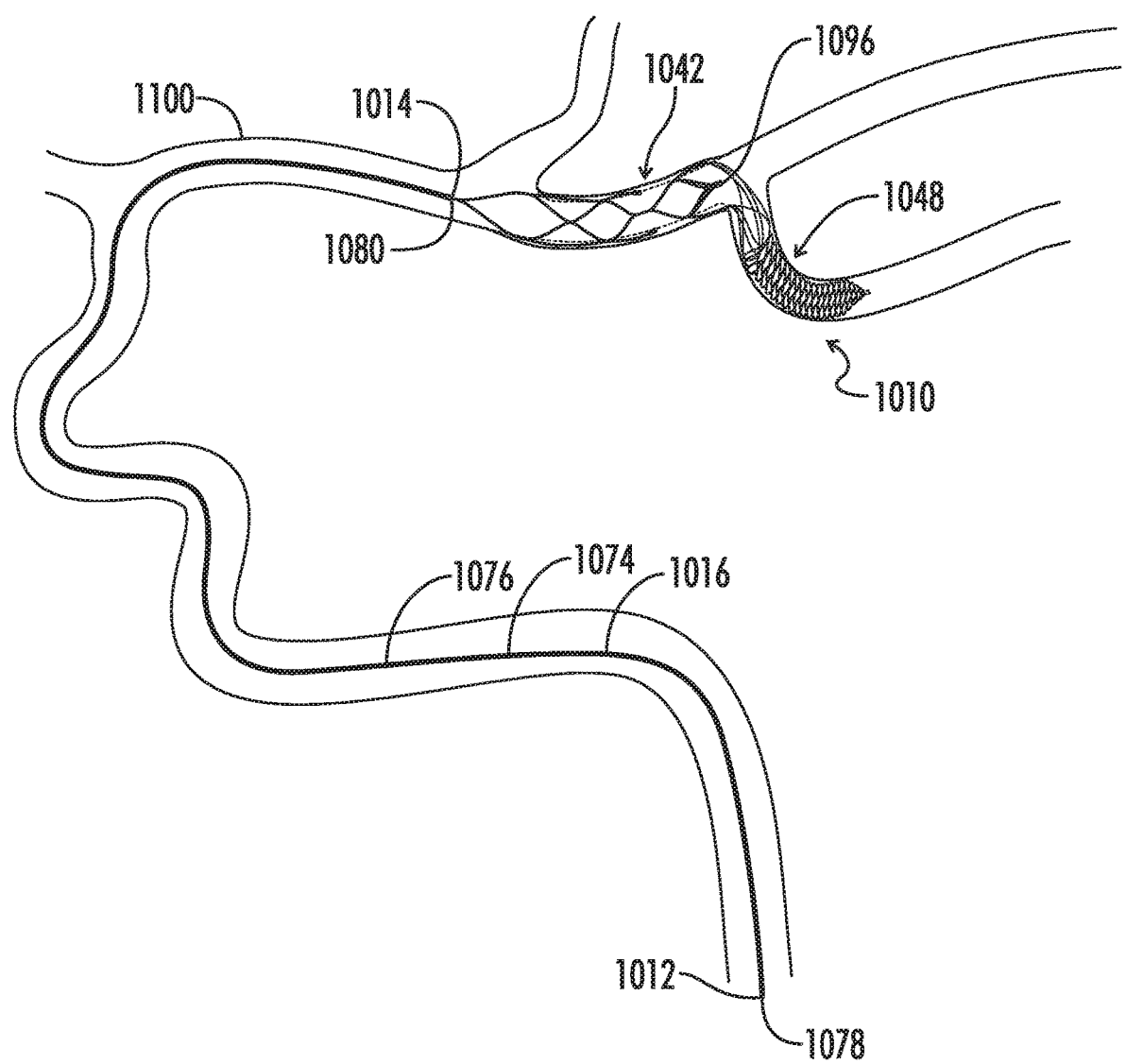
FIG. 60 illustrates use of the deployable basket system of FIG. 57 in a blood vessel.
Figure 61:
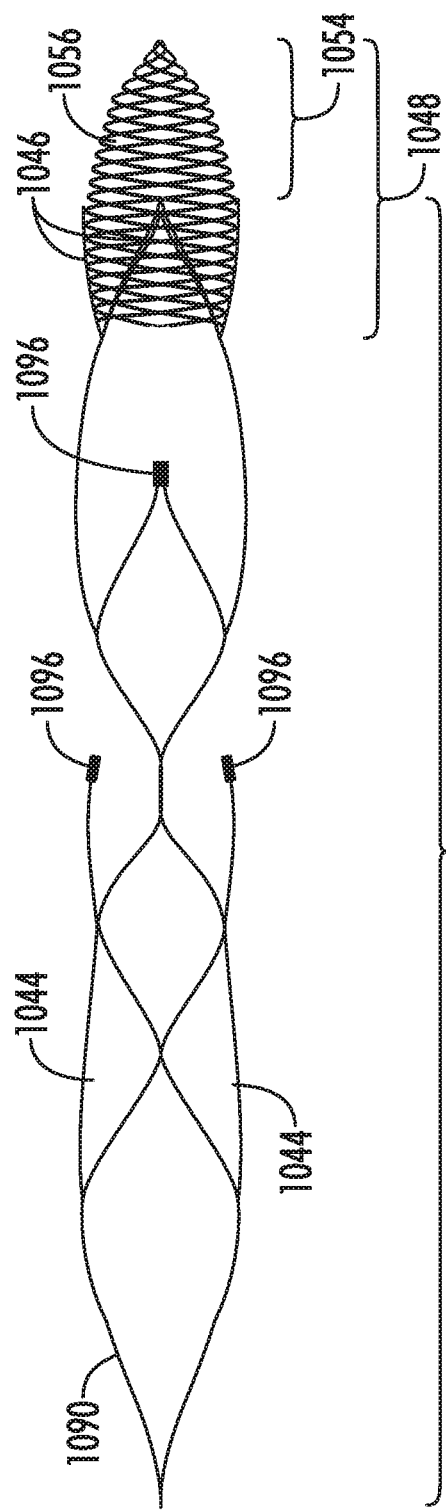
FIG. 61 illustrates a side elevation view of a deployable basket system of another embodiment of the present invention.
Figure 62:
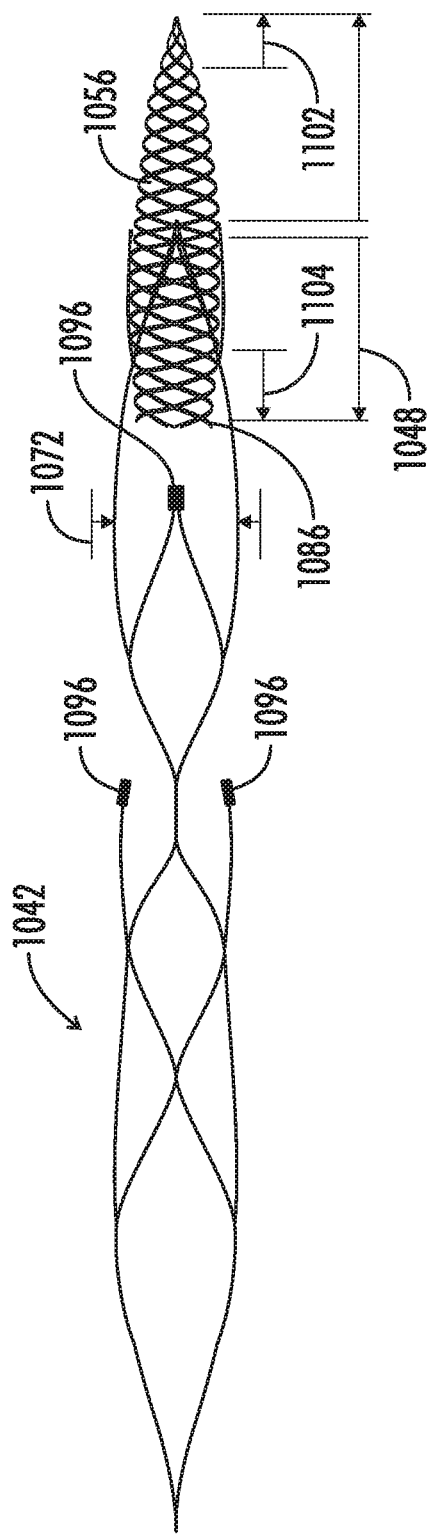
FIG. 62 illustrates a side elevation view of the deployable basket system of FIG. 61.
Figure 65:
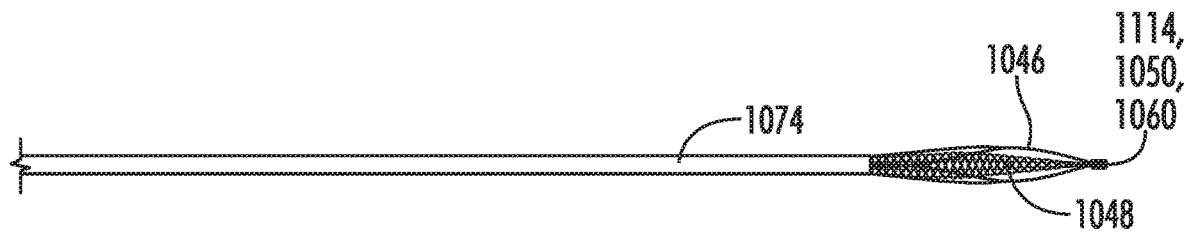
FIG. 65 illustrates a side elevation view of a deployable basket system of another embodiment of the present invention.
Figure 66:
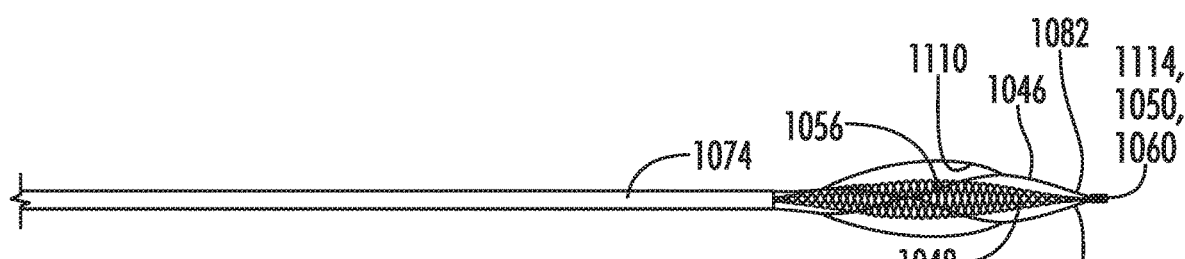
FIG. 66 illustrates a side elevation view of the deployable basket system of FIG. 65 at a second step of deployment from the catheter.

Five iterations of the design are shown in FIGS. 57-72. FIGS. 57-60 show an embodiment where the proximal end 1086 of a woven linear strand 1058 of a distal portion 1048 is attached to the distal end 1082 of a basket memory metal strip 1046 of the proximal portion 1042. In such case, the distal portion 1048 may elongate as shown by comparing FIG. 58 (relaxed state) and FIG. 59 (partially collapsed state) when the distal body 1018 moves to the collapsed state. FIG. 60 shows how the distal portion 1048 of some embodiments of the present invention is able to navigate tortuous blood vessel's 1100 due to the increased flexibility and decreased radial force of the distal portion 1048 as compared to the proximal portion 1042 in some embodiments of the present invention. The distal ends 1082 of the basket memory metal strips 1046 may be attached to the proximal ends 1086 of the woven linear strands 1058 by welding, soldering or a crimp for example FIGS. 61-62 show a second embodiment in which the distal portion 1048 is attached to the interior of the proximal portion 1042 (e.g., by welding, soldering or the like) at multiple connection points 1050 and the distal portion 1048 and the proximal portion 1042 partially overlap. As shown by comparing FIG. 61 (relaxed state) and FIG. 62 (partially collapsed state), the distal portion 1048 elongates distal and proximal to the connection points 1050 in moving from the relaxed state to the collapsed state. Meanwhile, the segment at the connection points 1050 preferably does not elongate as shown in FIG. 62. FIGS. 63-64 show an embodiment in which the distal portion 1048 is fully located in the proximal portion interior 1052. In FIGS. 63-64, the sole connection point 1050 of the proximal portion 1042 and the distal portion 1048 is the distal body distal junction 1060, which may be in the form of a distal tube, including a coil, as previously described. More particularly, the distal ends 1082 of the basket memory metal strips 1046 located at the distal end 1064 of the basket 1040 and the distal ends 1108 of the woven linear strands 1058 meet at the distal body distal junction 1060. FIGS. 65-68 show a fourth embodiment. Similar to FIGS. 63-64, the design shown in FIGS. 65-68 includes the distal portion 1048 fully located within the proximal portion interior 1052 and the sole connection point 1050 of the proximal portion 1042 and the distal portion 1048 is the distal body distal junction 1060, which may be in the form of a distal tube. Again, more particularly, the distal ends 1082 of the basket memory metal strips 1046 located at the distal end 1064 of the basket 1040 and the distal ends 1108 of the woven linear strands 1058 meet at the distal body distal junction 1060. In FIGS. 65-68, the proximal ends 1086 of the woven linear strands 1058 converge at and are attached to a free-floating distal portion proximal junction 1106 that forms the proximal end 1112 of the distal portion 1048. By contrast, in FIGS. 63-64, the proximal ends 1086 of the woven linear strands do not converge and instead are preferably located adjacent to an interior surface 1110 of one or more of the basket memory metal strips 1046. A fifth iteration is shown in FIGS. 69-72. In FIGS. 69-72, the distal portion 1048 is fully located within the proximal portion interior 1052 and the distal ends 1108 of the woven linear strands 1058 meet at the distal body distal junction 1060. However, in FIGS. 69-72, the distal portion 1048 is attached to the distal body proximal junction 1038 by a tether, which among other things, is believed to assist in re-sheathing the distal body 1018 into the catheter 1074 (i.e., repositioning the distal body 1018 into the catheter 1074 after the clot has been retrieved) as well as to keep the distal portion 1048 centered and away from the vessel wall when the distal body 1018 moves around a curved vessel 1100. The tether is preferably located in the center of the height 1070 and width 1072 of the distal body 1018 in the relaxed state and preferably is parallel to the distal body longitudinal axis 1036. The tether may also slightly stretch the distal portion 1048 during the re-sheathing process. The tether may be a suture or other thin material 1116 that has a proximal end attached to the distal body proximal junction 1038 and a distal end attached to the distal portion proximal junction 1106, as shown in FIG. 69. Alternatively, the tether may be a segment of the pull wire 1016, as shown in FIGS. 70-72, in which case the tether may be comprised of stainless steel or nitinol for example. If the tether is conductive, a positive or negative charge (a current) may be propagated along the tether to the distal portion 1048 in order to interact with a blood clot captured in the distal body 1018. (For example, depending on the charge propagated, the charge may assist in clotting or in attraction to a charged blood clot). If the tether is comprised of suture material, it may be proline or nylon and nonabsorbable for example and may be size 4-0 to size 1-0. If the tether is a segment of the pull wire 1016, it may have an outer diameter of 0.002 inches to about 0.010 inches for example. FIG. 70 illustrates a particular embodiment in which a segment of the tether is in the form of a helical coil/coil spring 1200. The helical coil 1200 has a coil length generally parallel to the distal body length 1034, the helical coil 1200 has an expanded/elongated state in which the helical coil 1200 has a first length and a relaxed state in which the helical coil 1200 has a second length, the first length greater than the second length. In other words, the helical coil 1200 may stretch as illustrated by the arrows in FIG. 70 if tension is exerted on the tether in an effort to avoid damage to the tether. The helical coil 1200 is preferably adjacent to the distal portion proximal junction 1106. In FIG. 70, the helical coil 1200 is a radiopaque stretch coil soldered at the proximal end to the pull wire 1016 and epoxied at the distal end to the distal portion proximal junction 1106. The point of solder is denoted by numeral 1202.

Figure 67:
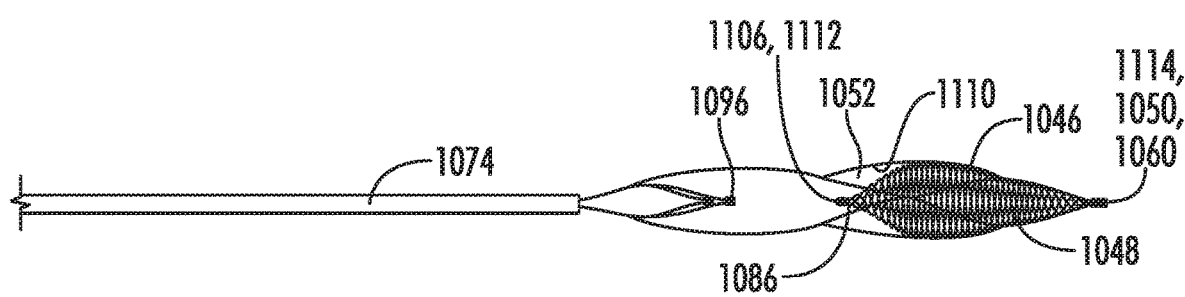
FIG. 67 illustrates a side elevation view of the deployable basket system of FIG. 65 at a third step of deployment from the catheter.

It will be understood that the dimensions provided are merely exemplary. It will also be appreciated that distal portion 1048 has a reduced height and width as compared to the proximal portion 1042 in the relaxed state in the illustrations of FIGS. 69 and 71. It will be appreciated that FIGS. 69-71 show the proximal end of the distal portion 1048 as being closed, as the proximal ends 1086 of the woven linear strands 1058 converge at and are attached to the distal portion proximal junction 1106. The convergence, which is also shown in FIGS. 67-68, is thought to prevent the distal portion woven linear strands 1058 from unraveling.

Figure 68:
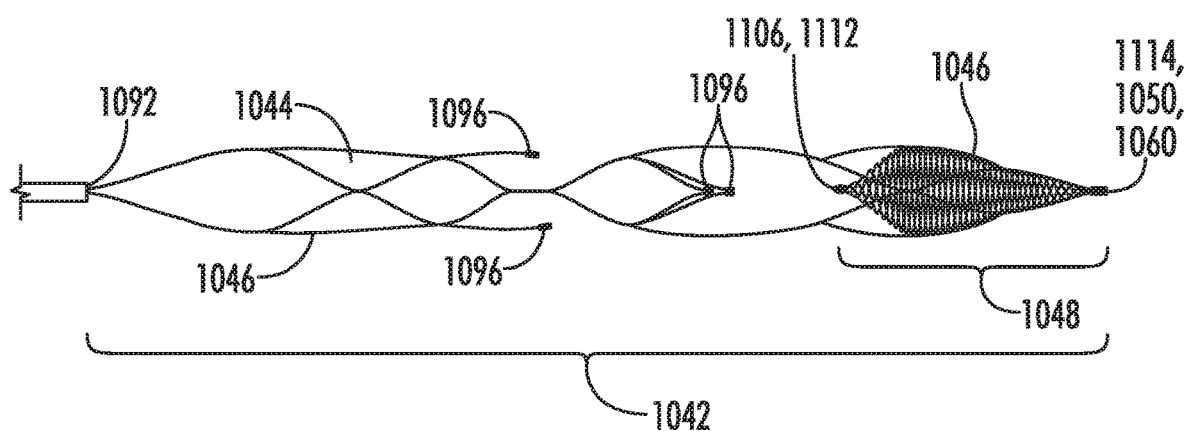
FIG. 68 illustrates a side elevation view of the deployable basket system of FIG. 65 almost fully deployed from the catheter.
Figure 69:
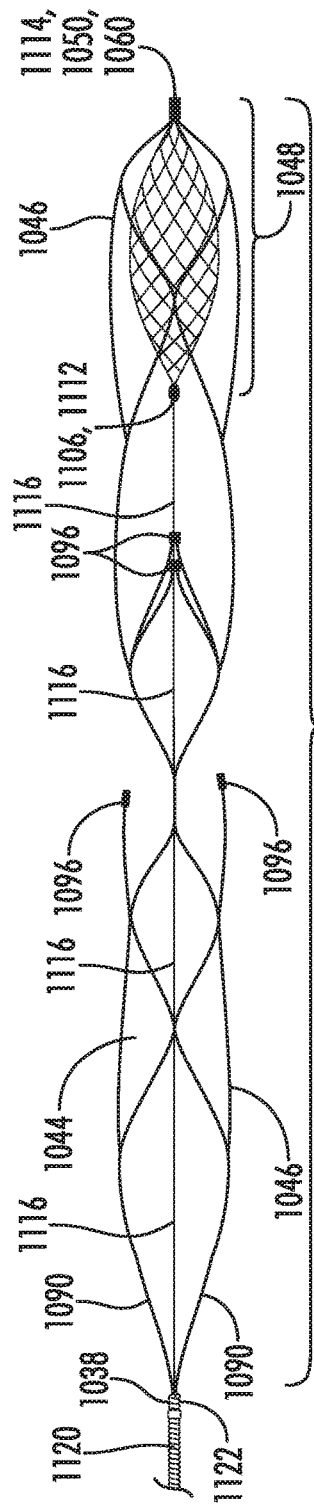
FIG. 69 illustrates a side elevation view of a deployable basket system of another embodiment of the present invention.
Figure 70:
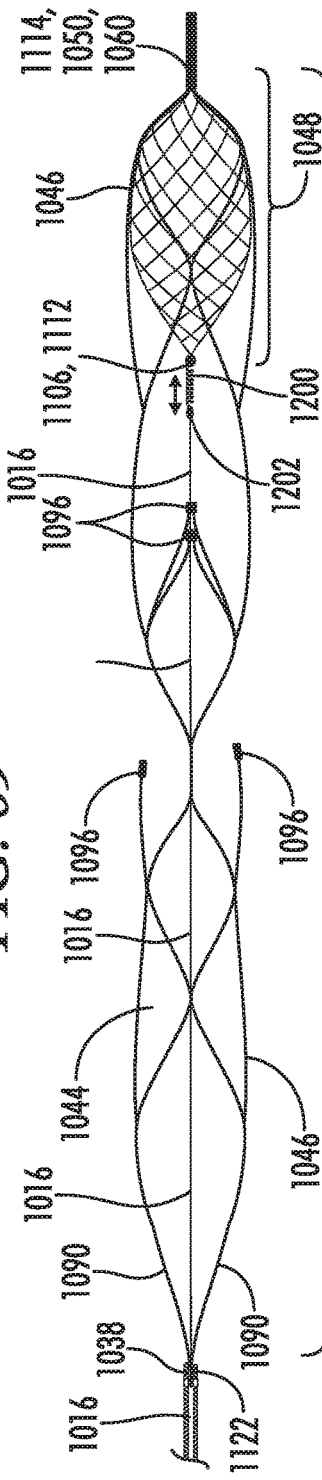
FIG. 70 illustrates a side elevation view of a deployable basket system of another embodiment of the present invention.
Figure 71A:
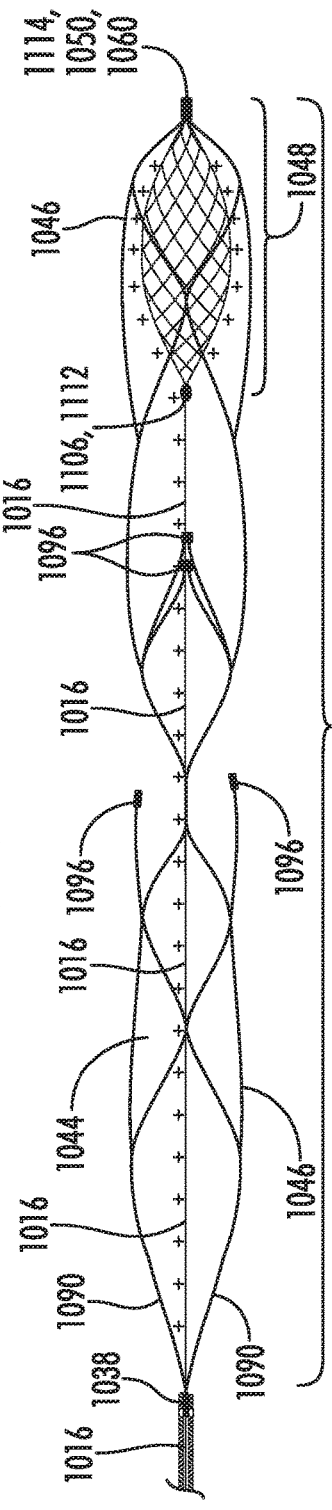
FIG. 71A illustrates a side elevation view of a deployable basket system of another embodiment of the present invention with a positive charge propagated along the pull wire to the inner body.
Figure 71B:
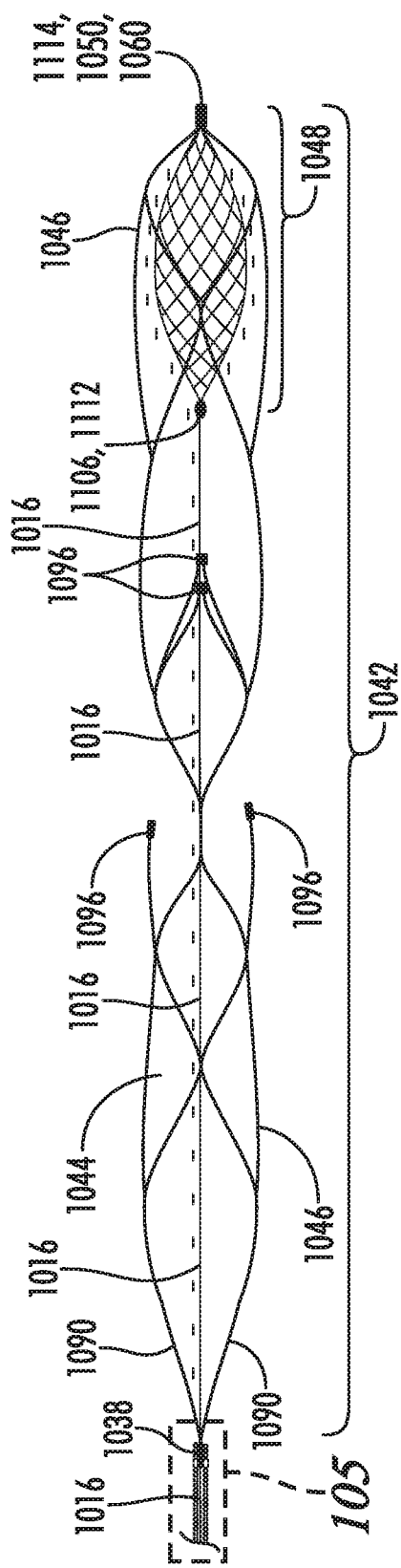
FIG. 71B illustrates a side elevation view of the deployable basket system of FIG. 71A with a negative charge propagated along the pull wire to the inner body.
Figure 72:
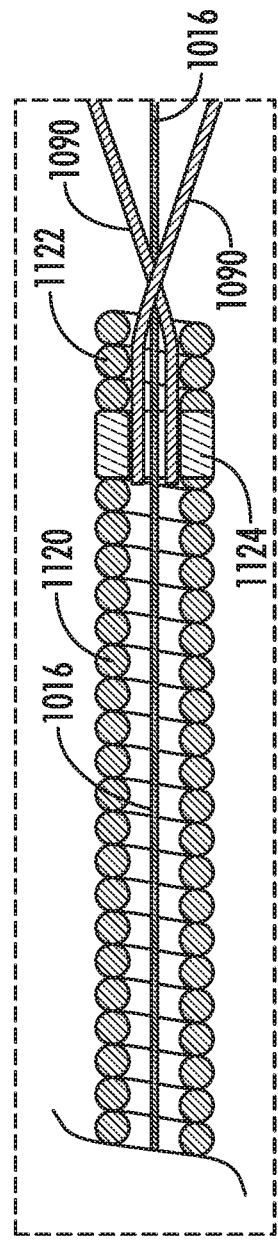
FIG. 72 illustrates a close-up cross-sectional view of the area denoted by the rectangular box labelled 105 in FIG. 71B.

Given that, in FIGS. 63-72, the distal portion 1048 is fully located within the proximal portion interior 1052, the distal portion 1048 is also referred to herein as the "distal body inner body" and the proximal portion 1042 is also referred to herein as the "distal body outer body" to more accurately reflect the fact that the woven linear strands 1058 are located within the basket memory metal strips 1046 of the proximal portion interior 1052. Optionally, as demonstrated in FIGS. 63 and 68, at least some the woven linear strands 1058 contact the interior surface 1110 of at least some of the basket memory metal strips 1046 in the relaxed state. For example, a segment of all the woven linear strands 1058 may contact the interior surface 1110 of at least some of the basket memory metal strip 1046 in the relaxed state, as shown in FIGS. 63 and 68.

In some of the embodiment of FIGS. 57-72, the proximal ends 1086 of the woven linear strands 1058 may be free; however, it is believed that they will not damage the vessel 1100 because they are located in the proximal portion/distal body outer body interior 1052.

As shown in FIGS. 57-72 the distal portion/distal body inner body 1048 is located adjacent (i.e., at or near the distal end 1064 of the distal basket 1040). In some embodiments, i.e., FIGS. 57-62, at least a segment 1054 of the distal portion/distal body inner body 1048 is located distal to the proximal portion 1042.

More particularly, as shown in FIGS. 57-72, the present disclosure further provides a system 1010 for removing objects from an interior lumen 1100 of an animal. The system 1010 may include a pull wire 1016 having a proximal end 1012 and a distal end 1014, as previously described.

The system 1010 may further include a distal body 1018 attached to the pull wire 1016, the distal body 1018 comprising a distal body perimeter 1020 separating a distal body interior 1022 from a distal body exterior 1024, a proximal end 1026 having a proximal end center 1028, a distal end 1030 having distal end center 1032, a distal body length 1034 extending from the proximal end 1026 to the distal end 1030, a longitudinal axis 1036 extending through the proximal end center 1028 and the distal end center 1032 and parallel to the distal body length 1034, and a proximal junction 1038 forming the proximal end of the distal body 1026.

The distal body 1018 may further include a proximal portion/distal body outer body 1042 comprising a basket 1040 comprised of a plurality of cells 1044 spaced about the distal body perimeter (e.g., circumference) 1020 and formed by a plurality of basket memory metal strips 1046 and a distal portion/distal body inner body 1048 connected to the proximal portion/distal body outer body 1042 at one or more connection points 1050, the proximal portion/distal body outer body 1042 comprising a proximal portion/distal body outer body interior 1052. The distal portion/distal body inner body 1048 is preferably located at the distal end 1064 of the basket 1040 and may or may not have at least a segment 1054 distal to the proximal portion 1042. The distal portion/distal body inner body 1048 may be comprised of a plurality of distal braided mesh openings 1056 formed by a plurality of woven linear strands 1058. The system may further include a distal body distal junction 1060 comprising a proximal end 1062. The proximal end 1062 of the distal body distal junction 1060 may form a distal end 1064 of the basket 1040. The distal portion/distal body inner body 1048 may have a perimeter 1066 and each woven linear strand 1058 may rotate about the distal portion/distal body inner body perimeter 1066 relative to the distal body longitudinal axis 1036 a plurality of times in a helical fashion. The helical rotation is best seen in FIGS. 58-68. In some embodiments, at least some of the distal braided mesh openings 1056 are distal to the cells 1044 as shown in FIGS. 57-62. The basket 1040 may comprise a basket interior 1068. The distal body 1018 may have a relaxed state wherein the distal body 1018 has a first height 1070 and a first width 1072, and a collapsed state wherein the distal body 1018 has a second height 1070 and a second width 1072, the second height less than the first height, the second width less than the first width.

The system may further include a catheter 1074, as previously described, having an interior 1076, a proximal end 1078 leading to the interior 1076 and a distal end 1080 leading to the interior 1076, the catheter 1074 comprised of a biocompatible material and configured to envelope the distal body 1018 when the distal body 1018 is in the collapsed state. Optionally, in the relaxed state, the median surface area of the cells 1044 is larger than the median surface area of the distal braided mesh openings 1056. In other words, the average surface area of the cells 1044 is preferably greater (preferably substantially greater) than the average surface area of the distal mesh openings 1056 in the relaxed state, as shown in FIGS. 57-58, 61, 63 and 68. Optionally, in the relaxed state, the median radial force of the distal portion/distal body inner body 1048 is substantially less than the median radial force of the proximal portion/distal body outer body 1042 (e.g., 25% or less of the radial force of the proximal portion/distal body outer body 1042), it being understood that the radial force of the proximal portion/distal body outer body 1042 may vary along its length due to the free distal crowns 1096, which may create enlarged cells 1098 as previously described.

Optionally, the radial force of the proximal portion/distal body outer body 1042 through its connection to the distal portion/distal body inner body 1048 at the connection point(s) 1050 is configured to cause the distal portion/distal body inner body 1048 to move to the relaxed state when the proximal portion/distal body outer body 1042 moves from the collapsed state to the relaxed state. The aforementioned phenomena is not present in FIGS. 63-68, where the sole connection point 150 of the distal portion/distal body inner body 1048 and the proximal portion/distal body outer body 1042 is the distal body distal junction 1060.

Optionally, the proximal portion/distal body outer body 1042 and the distal portion/distal body inner body 1048 each have a length generally parallel to the distal body length 1034, the proximal portion/distal body outer body 1042 and distal portion/distal body inner body 1048 lengths configured to elongate upon moving from the relaxed state to the collapsed state. Optionally, upon moving from the relaxed state to the collapsed state, the length of the distal portion/distal body inner body 1048 is configured to elongate a greater percentage as compared to the elongation of the proximal portion/distal body outer body 1042 as shown by comparing FIG. 66 with FIG. 68, by comparing FIG. 59 with FIG. 58, by comparing FIG. 62 with FIG. 61, and by comparing FIG. 64 with FIG. 63. Optionally, the woven linear strands 1058 rotate about the distal body distal portion/inner body perimeter 1066 relative to the distal body longitudinal axis 1036 a fewer number of times per unit of distance/length in the collapsed state as compared to the relaxed state, similar to what is seen when stretching a phone cord.

Optionally, in the relaxed state, the proximal portion/distal body outer body 1042, but not the distal portion/distal body inner body 1048, is configured to alter the shape of a curved intracranial artery, allowing the distal portion/distal body inner body 1048 to be used in tortuous vessels 1110 as shown in FIG. 60. Optionally, in the relaxed state, the distal portion/distal body inner body 1048 is more flexible than the proximal portion/distal body outer body 1042, again allowing the distal portion/distal body inner body 1048 to be used in tortuous vessels 1110 as shown in FIG. 60. Optionally, the woven linear strands 1058 are comprised of a biocompatible material such as suture, a metallic material, Dacron, Teflon or vascular graft material. The woven linear strands 1058 may be comprised of a memory metal. In some embodiments, the woven linear strands 1058 are braided filaments that have the same diameter. In some embodiments, the woven linear strands 1058 are comprised of a material similar to the PIPELINE embolization device (ev3, Plymouth, Minn.), which is a flow diverter and is said to be comprised of a 75% cobalt chromium 25% platinum tungsten bimetallic design, or the SPIDER FX embolic protection device (also made by ev3). Similar devices are made by other companies.

Optionally, the distal portion/distal body inner body 1048 in the relaxed state comprises a tapered region in which the distal body height 1070 and width 1072 decrease as the woven linear strands 1058 approach the distal body distal junction 1060 as shown in FIGS. 63 and 68-71. Optionally, in the relaxed state, the basket interior 1068 is substantially hollow.

Figure 57:
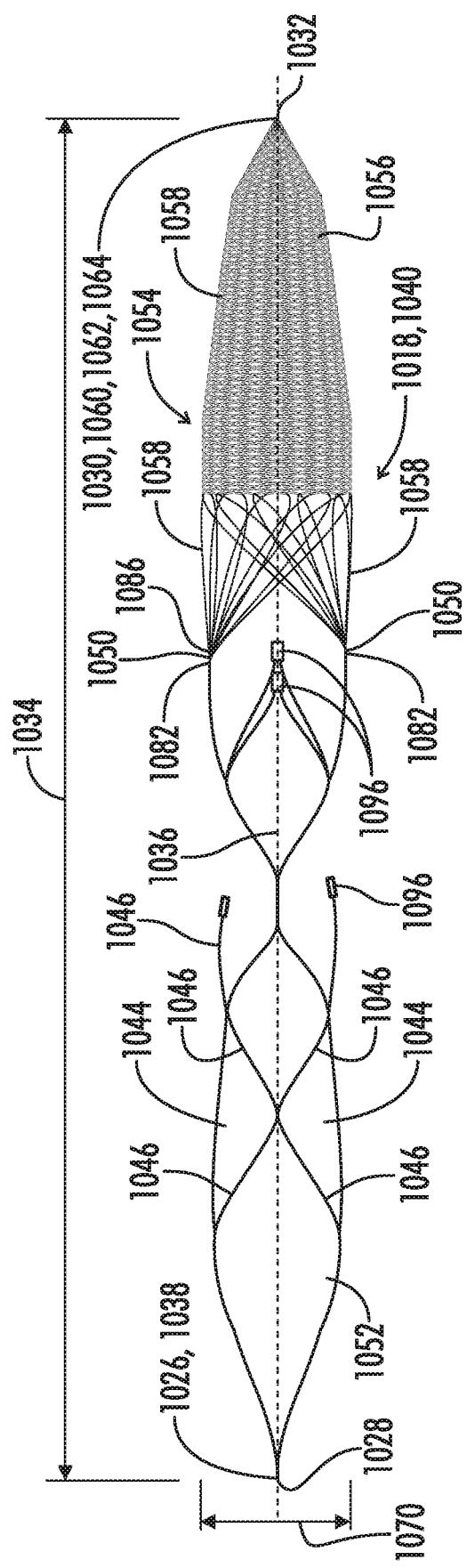
FIG. 57 illustrates a side elevation view of a deployable basket system of another embodiment of the present invention that includes a basket with a proximal portion comprising proximal cells and a distal portion comprising braided mesh openings.
Figure 58:
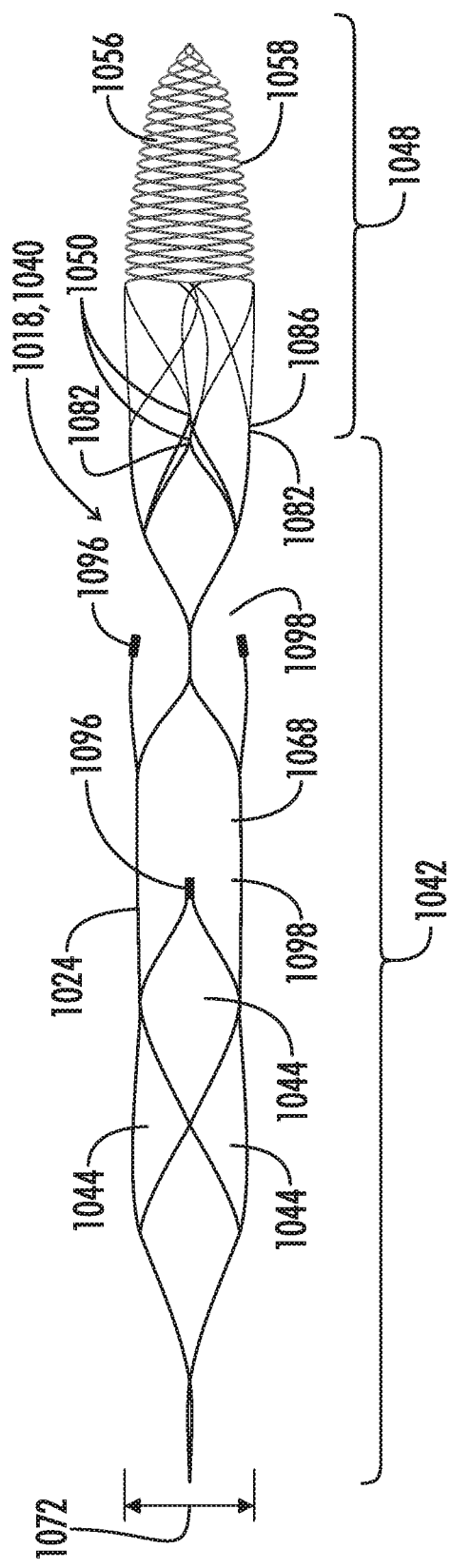
FIG. 58 illustrates another side elevation view of a deployable basket system of another embodiment of the present invention in the relaxed state; as compared to FIG. 57, the distal portion is located further distally in FIG. 58.
Figure 59:
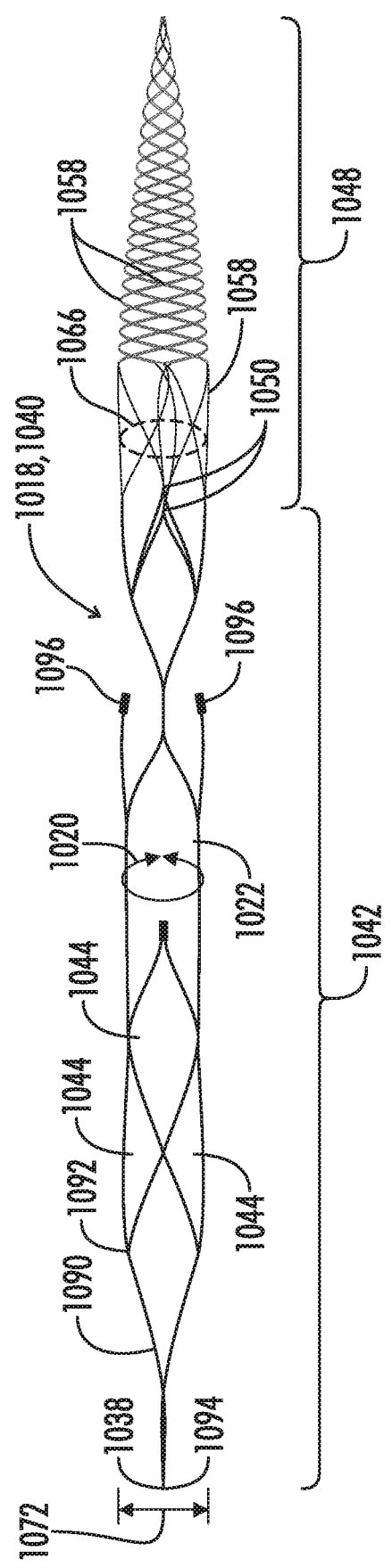
FIG. 59 illustrates a side elevation view of the deployable basket system of FIG. 58.

Optionally, the proximal portion 1042 comprises a distal end comprising between two and four basket memory metal strip distal ends 1082 and further wherein each woven linear strand 1058 comprises a proximal end 1086 attached to a basket memory metal strip distal end 1082, as shown in FIGS. 57-59. Optionally, the distal portion/distal body inner body 1048 comprises at least two woven linear strands 1058 attached to each basket memory metal strip distal end 1082. Optionally, in the relaxed state, the basket memory metal strips 1046 of the proximal portion/distal body outer body 1042 comprises an interior surface 1110 facing the distal body interior 1022 and the distal portion/distal body inner body 1048 comprises an outer/exterior surface facing and connected to the basket memory metal strips interior surface 1046, and further wherein at least a segment of the distal portion/distal body inner body 1048 is interior to the proximal portion/distal body outer body 1042, as shown in FIGS. 61 and 62. Optionally, each woven linear strand 1058 comprises a free proximal end 1086 and further wherein all free proximal ends 1086 of the woven linear strands 1058 are located in the proximal portion/distal body outer body interior 1052, as shown in FIGS. 61-68. Optionally, the distal portion/distal body inner body 1048 is configured to elongate proximally and distally relative to the proximal portion/distal body outer body 1048 and the plurality of connection points 1050 upon moving from the relaxed state to the collapsed state, as shown in FIG. 62.

Optionally, the distal portion/distal body inner body 1048 is attached to the proximal portion/distal body outer body 1042 by at least two connection points 1050, and further wherein said at least two connection points 1050 are located a slightly different distance from the proximal junction 1038 in the relaxed state. Optionally, said at least two connection points 1050 are located a slightly different distance from the proximal junction 1038 in the collapsed state. In other words, the connection points 1050 may be staggered slightly in the relaxed and collapsed states to aid collapsing of the distal body 1018.

Optionally, a plurality of woven linear strand proximal ends 1088 are connected to each basket memory metal strip distal end 1082.

Optionally, in the relaxed state, the distal portion/distal body inner body 1048 impedes blood flow to a greater extent than the proximal portion/distal body outer body 1042 when the proximal portion/distal body outer body 1042 and the distal portion/distal body inner body 1048 are placed in a blood vessel 1100.

Optionally, the distal portion/distal body inner body 1048 is configured to reduce blood flow by at least 25% (preferably at least 50%) when the distal portion/distal body inner body 1048 is placed in a blood vessel 1100, which may obviate the need for a suction catheter.

Optionally, the distal portion/distal body inner body 1048 is radiopaque.

Optionally, the proximal portion/distal body outer body 1042 of the distal body 1018 further comprises a plurality of proximal strips 1090, each proximal strip 1090 having a distal end 1092 attached to a cell 1044 (more particularly a proximal crown of a cell 1044) and a proximal end 1094, the proximal ends 1094 of the proximal strips 1090 converging at the proximal junction 1038. Preferably, in the relaxed state, the length of the distal portion/distal body inner body 1048 is no more than 33% of the length of the proximal portion/distal body outer body 1042 (e.g., the length of the distal portion/distal body inner body 1048 may be about 2% to about 33% of the length of the proximal portion/distal body outer body 1042).

Optionally, in the relaxed state, as previously described, the proximal portion/distal body outer body may include offset free distal crowns 1096 with x-ray markers and offset enlarged cells 1098. More particularly, the proximal portion/distal body outer body 1042 may comprise a first pair of distal crowns 1096 not attached to another cell of the basket 1040 and pointing generally in the distal direction, the distal crowns 1096 in the first pair of distal crowns 1096 located approximately the same distance from the proximal junction 1038 and between 150 degrees and 180 degrees relative to each other, and further wherein the basket 1040 further comprises a second pair of distal crowns 1096 not attached to another cell of the basket 1040 and pointing generally in the distal direction, the second pair of distal crowns 1096 located distally relative to the first pair of distal crowns 1096, each of the distal crowns 1096 in the second pair of distal crowns 1096 located between 60 degrees and 90 degrees relative to a distal crown 1096 in the first pair of distal crowns 1096, the distal crowns 1096 in the second pair of distal crowns 1096 located approximately the same distance from the distal body proximal junction 1038, each of the distal crowns 1096 forming a portion of a cell 1044. Optionally, each distal crown 1096 in the first and second pair of distal crowns 1096 forms part of a different enlarged cell/drop zone 1098, each enlarged cell/drop one 1098 having a center and the centers of the enlarged cells 1098 of the first pair of distal crowns 1096 located approximately 180 degrees relative to each other (e.g., between 150 and 180 degrees) and approximately 90 degrees (e.g., between 60 and 90 degrees) relative to the centers of the enlarged cells/drop zones 1098 of the second pair of distal crowns 1096. Optionally, the surface area of the enlarged cells/drop zones 1098 in the relaxed state is greater than the surface area of the other cells 1044 of the basket 1040. Optionally, the enlarged cells/drop zones 1098 are configured to allow a thrombus to pass therethrough and into the basket interior 1068. The distal crowns 1096 may include x-ray markers as previously described.

The proximal portion/distal body outer body 1042 differs from the distal portion/distal body inner body 1048 in several physical characteristics. For example, the proximal portion/distal body outer body 1042 is preferably prepared by using a laser to cut a single memory metal tube similar to the embodiments of FIGS. 11-20, for example (e.g., as shown in FIGS. 1A, 1B 33A and 33B); whereas the distal portion/distal body inner body 1048 is preferably prepared from woven linear strands 1058. In addition, the woven linear strands 1058 preferably slide relative to each other, whereas the basket memory metal strips 1046 of the proximal portion/distal body outer body 1042 meet at fixed nodes (crowns). In addition, the woven linear strands 1058 may be cylindrical in shape, whereas the basket memory metal strips 1046 may be trapezoidal in shape, and the width/diameter of the woven linear strands 1058 may be substantially smaller (e.g., five times or ten times smaller) than the maximum width of the basket memory metal strips 1046. FIG. 72 illustrates coupling of the proximal strip proximal ends 1094 using a coil comprising a proximal coil 1120 and a distal coil 1122 separated by a gap 1124, similar to FIGS. 43A-G, 44 and 55. FIG. 72 also illustrates rotation of the proximal strips 1090.

The system 1010 may be used method of removing a blood clot from a blood vessel 1100 of an animal, the method comprising the steps of: a) providing the system 1010; b) positioning the system 1010 in the blood vessel 1100; c) deploying the distal body 1018 from the distal end 1080 of the catheter 1074; d) allowing the height 1070 and width 1072 of the distal body 1018 to increase; e) moving the blood clot into the basket interior 1068; and f) moving the distal body 1018 (and captured blood clot) proximally out of the blood vessel 1100.

Optionally, the method further includes applying contrast dye proximally and distally to the blood clot.

The embodiments of FIGS. 57-72 may include a lead wire 286 as described previously. The lead wire 286 may extend from the distal end 1030 of the distal body 1018 and the distal body distal junction 1060 as shown in FIG. 73A. Alternatively, the distal body distal junction 1060 may be elongated, as shown in FIG. 70, which depicts the distal body distal junction 1060 as an elongated coil to prevent damage to the vessel.

The Embodiments of FIGS. 73-80

FIGS. 73-80 illustrate how an active agent 1128 can be used with the embodiments of FIG. 57-72. The active agent 1128 may be a pharmaceutical or biologic that is configured to dissolve in the blood vessel 1100 and has therapeutic efficacy in the case of an ischemic stroke. For example, the active agent 1128 may be a reolytic (clot dissolving agent) such as tissue plasminogen activator (TPA), abciximab or urokinase for example. The active agent 1128 may also be an reo-adhesive agent to allow the woven linear strands 1058 to swell when contracting blood to further reduce porosity of the distal body inner body 1048. The active agent 1128 may also be a neuroprotective agent such as minocycline. The term active agent 1128 includes those now known and later developed.

Figure 73:
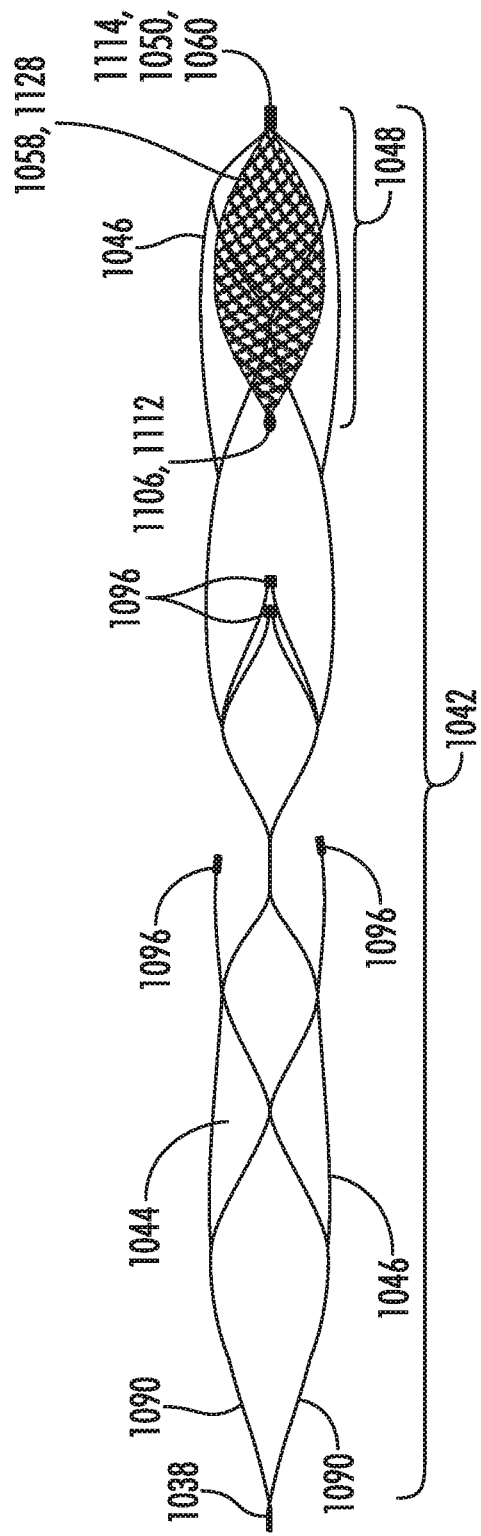
FIG. 73 illustrates a side elevation view of a deployable basket system of another embodiment of the present invention in which an active agent is coating the woven linear strands of the distal body inner body.
Figure 73A:
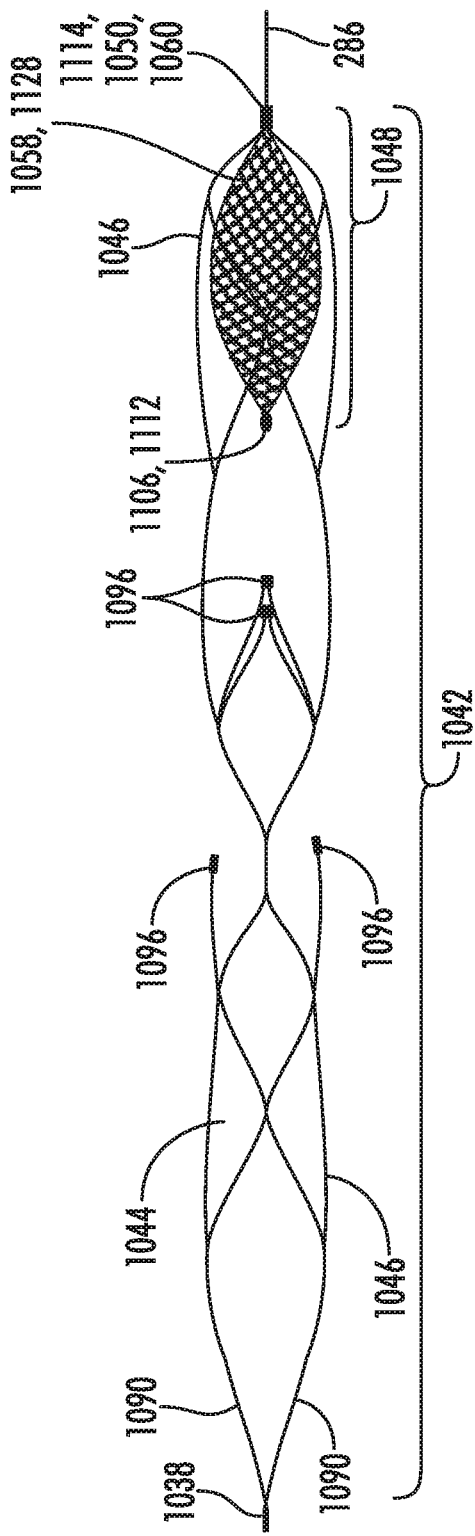
FIG. 73A illustrates a side elevation view of a deployable basket system of another embodiment of the present invention in which an active agent is coating the woven linear strands of the distal body inner body.

More particularly, FIG. 73 illustrates active agent 1128 that coats the woven linear strands 1058. In further detail, the distal body inner body 1048 has an increased surface area due to the number of woven linear strands 1058. For example, in an exemplary embodiment, the distal body inner body 1048 is comprised of between thirty six and sixty woven linear strands 1058. This increased surface area allows for a high concentration of active agent 1128 per unit length. The location of the active agent 1128 at the distal body inner body 1048 may have several advantages including but not limited to 1) run off of active agent 1128 at the distal end 1030 of the distal body 1018 into stroke territory where ischemia exists; 2) to prevent formation of new clot on woven linear strands 1058 during deployment and retrieval; 3) to increase adherence/stickiness of the distal body inner body 1048 to trap/adhere to the clot 1126; and 4) so that the active agent 1128 is located in the distal capture portion of the distal body 1018. Though not shown, the distal body 1018 of FIG. 73 may include a tether as previously described.

Figure 74:
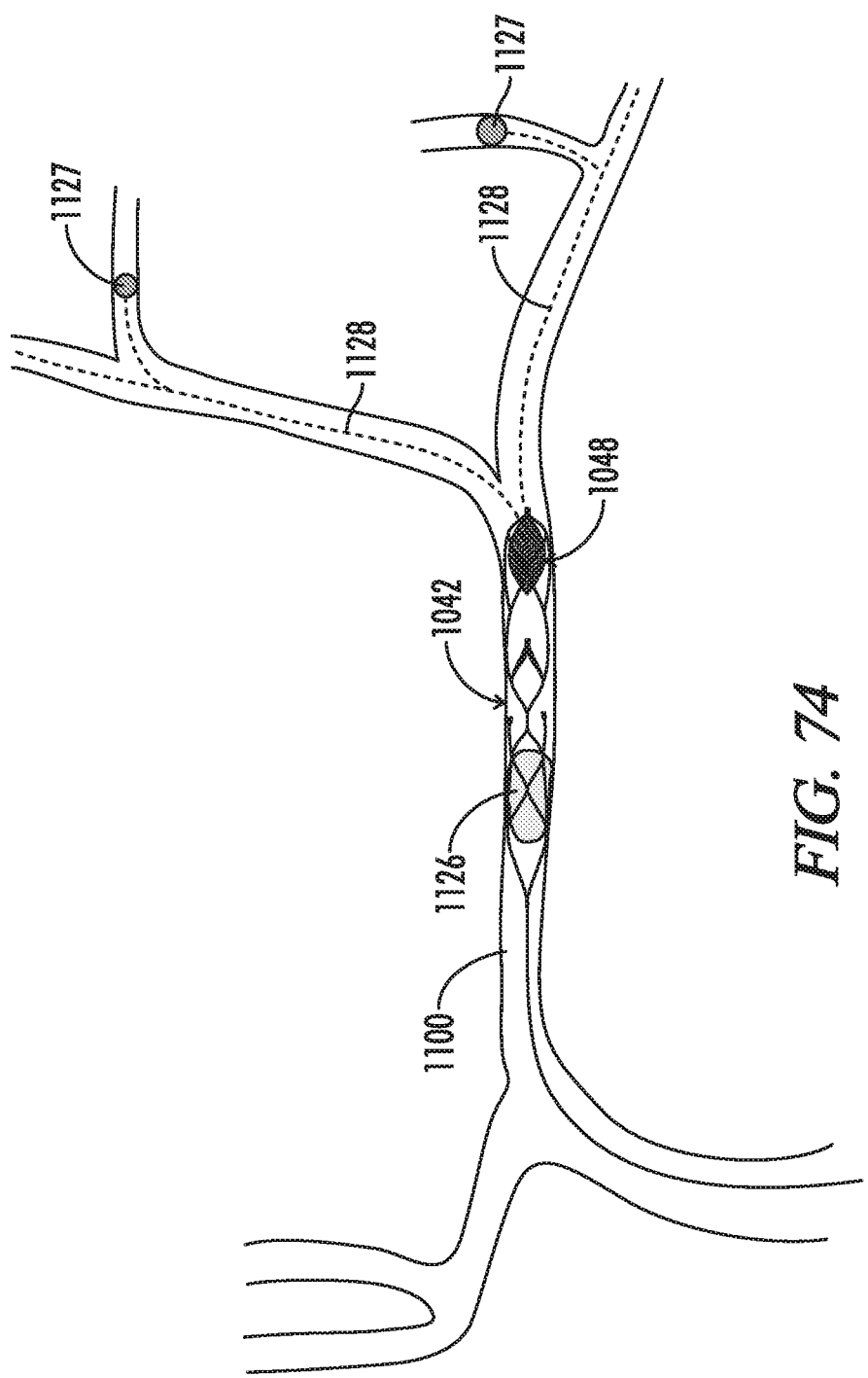
FIG. 74 illustrates a side elevation view of the deployable basket system of FIG. 73 in use in a blood vessel delivering the active agent to dissolve distal emboli.

FIG. 74 illustrates use of the system of FIG. 73 in a blood vessel 1100. As shown in FIG. 74, the main blood clot 1126 causing the ischemia is captured by the distal body outer body 1042. The active agent 1128, which may be a reolytic agent, may be used to dissolve the secondary clot/distal emboli 1127.

Figure 75:
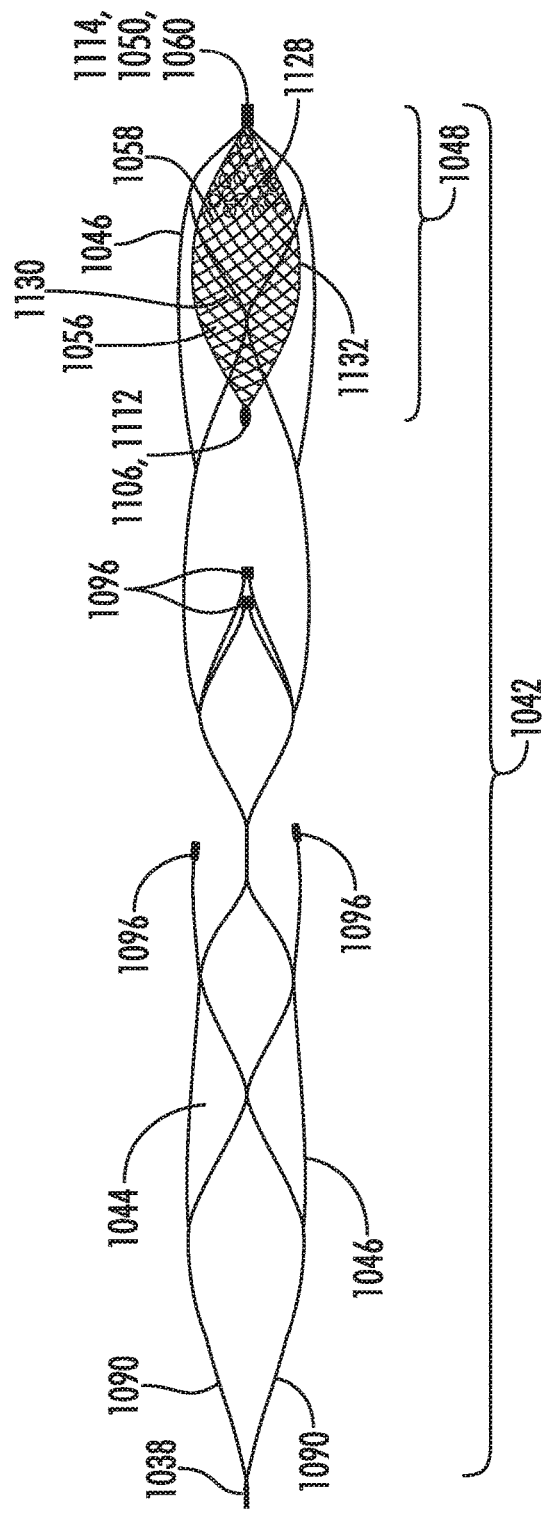
FIG. 75 illustrates a side elevation view of a deployable basket system of another embodiment of the present invention in which an active agent is located in the interior of the distal body inner body.

FIG. 75 illustrates active agent 1128 that are located in the distal body inner body interior 1130. More particularly, the active agent 1128 may in the form of particles that are trapped in the distal body inner body interior 1130 by the woven linear strands 1058. Each distal braided mesh opening 1056 may have a width of less than 100 microns and the D90 particle size diameter/width of the active agent 1128 (prior to dissolving) may be larger than 200 microns for example so the particles are trapped in the distal body inner body interior 1130. The particles may then slowly dissolve in the presence of blood flow through the distal portion of the distal body 1018 over a period of minutes before dissolving to a size that allows the dissolved particles to flow to the blood vessels 1110 within the stroke territory where they completely dissolve. As the distal body inner body 1048 is preferably tapered at its proximal end 1112 and distal end 1114 (e.g., in the shape of an American football), the distal braided mesh openings 1056 may be exponentially smaller at the distal body inner body proximal end 1112 and distal body inner body distal end 1114 than the distal braided mesh openings 1056 along the middle portion of the distal body inner body 1132. FIG. 75 shows the particles of active agent 1128 congregating at the distal body inner body distal end 1114 where the width of the distal braided mesh openings 1056 is significantly less than 100 microns. Though not shown, the distal body 1018 of FIG. 75 may include a tether as previously described.

Figure 76:
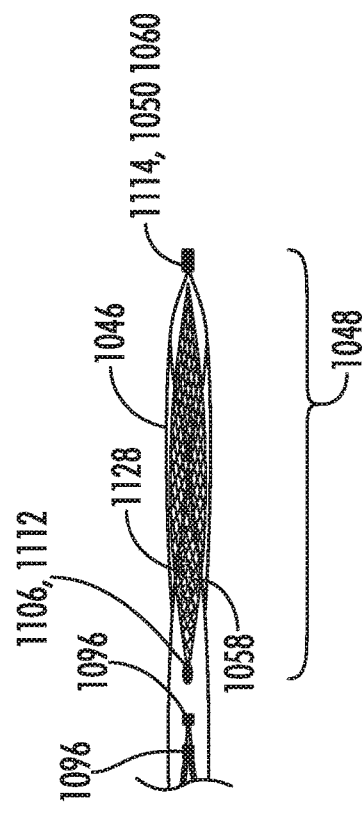
FIG. 76 illustrates a side elevation view of the deployable basket system of FIG. 75 with the distal body in the collapsed state.

FIG. 76 shows the distal body 1018 in the collapsed state with drug particles distributed evenly in nearly a single file line.

Figure 77:
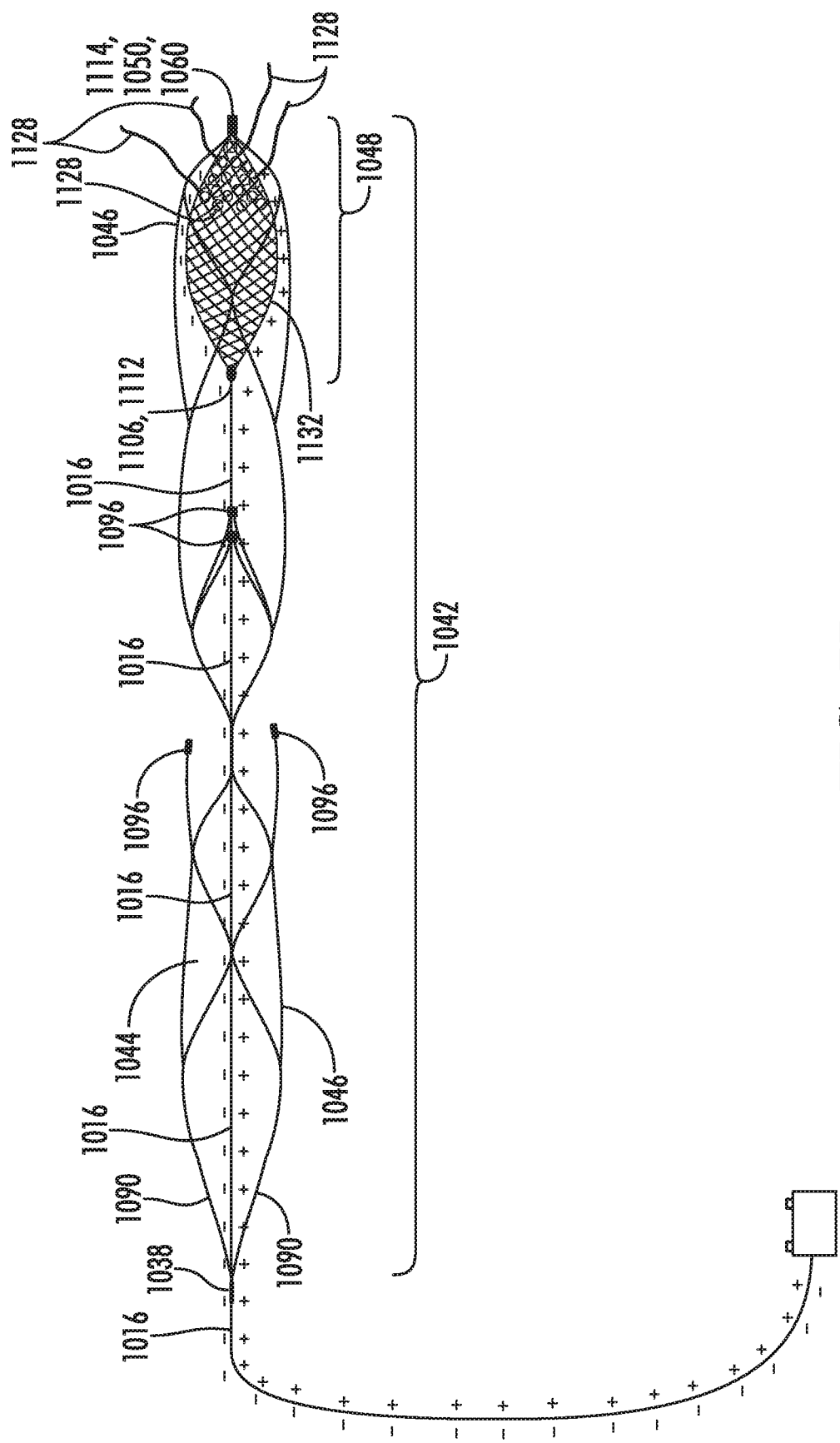
FIG. 77 illustrates a side elevation view of the deployable basket system of another embodiment of the present invention with a negative and positive charge being used to deliver the active agent into the blood vessel.

FIG. 77 illustrates electrolysis to release the active agent 1128 from the distal body inner body interior 1130. (A similar method may be used to release the active agent coating of FIG. 73). For example, a positive or negative charge may be propagated along the pull wire 1016 to cause elution of the active agent 1128 due to the presence of the positive or negative charge. The system may take advantage of the "floating"/middle portion of the distal body inner body 1132 allowing build up of selective charge without grounding on the wall of the blood vessel 1100.

Figure 78:
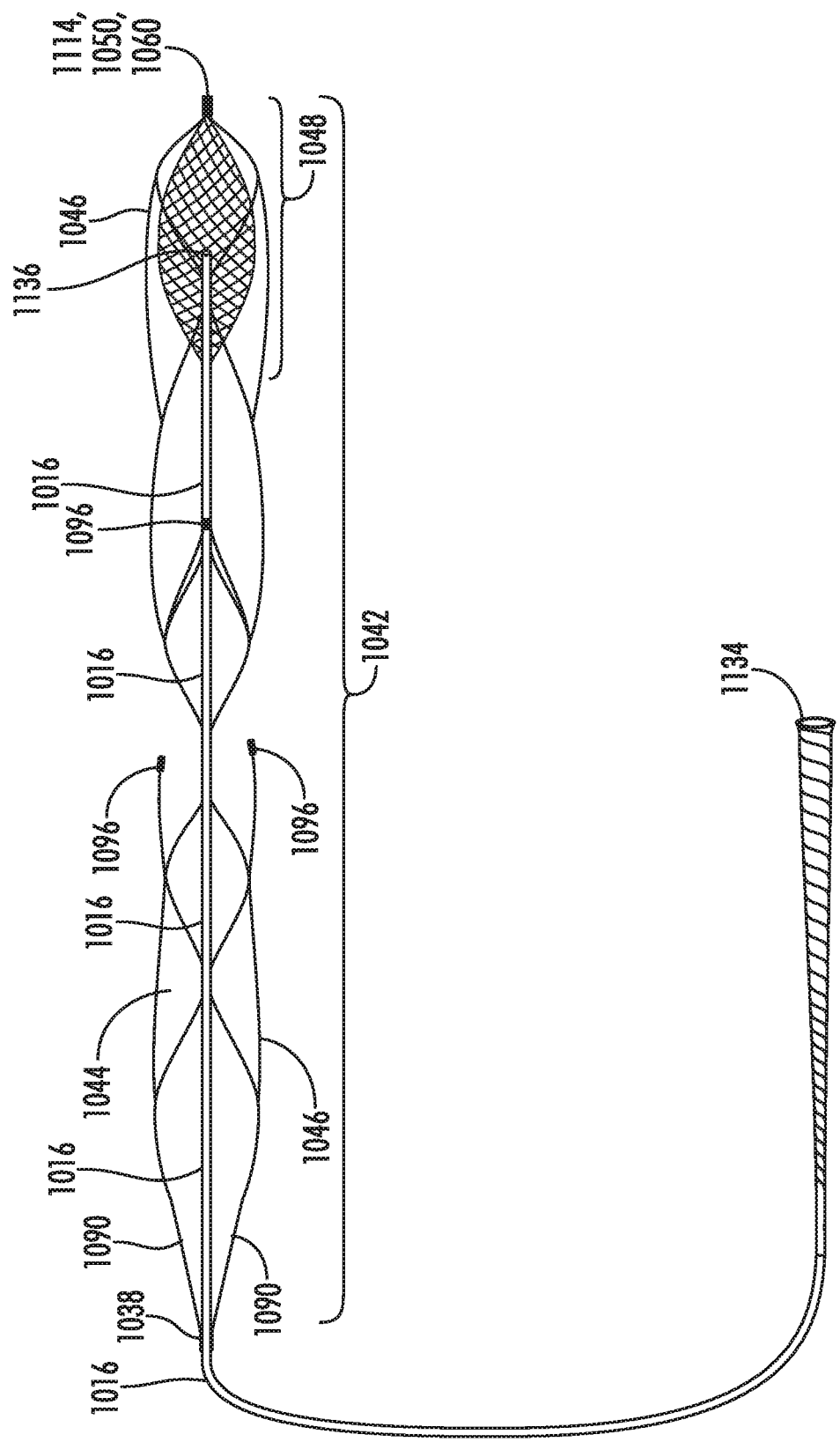
FIG. 78 illustrates a side elevation view of a deployable basket system of another embodiment of the present invention with an active agent delivery catheter.
Figure 79:
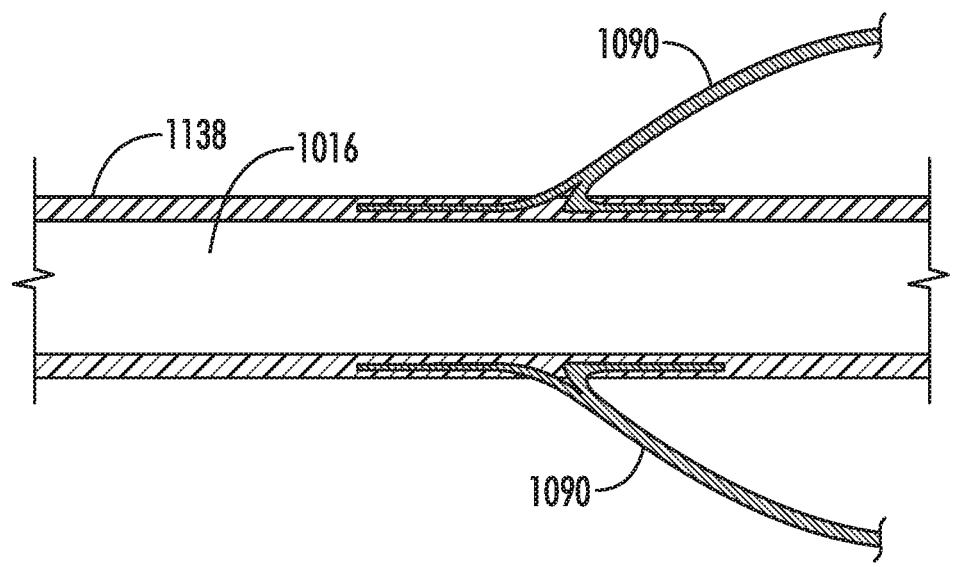
FIG. 79 illustrates a cross-sectional view of proximal strips attached to an active agent delivery catheter.
Figure 80:
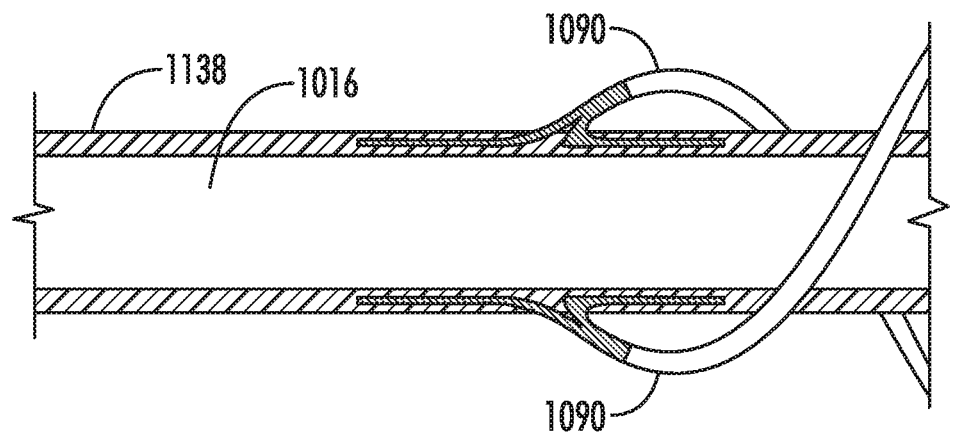
FIG. 80 illustrates a cross-sectional view of proximal strips attached to an active agent delivery catheter.

FIG. 78 illustrates an embodiment where the pull wire 1016 is in the form of a catheter that may be used to deliver the active agent 1128. For sake of labelling and differentiating from the previous catheter 1074, the pull wire 1016 that is in the form of a catheter and used to deliver the active agent 1128 is labelled with the numeral 1016 and is called the active agent delivery catheter. The active agent delivery catheter 1016 may have an open proximal end 1134 for receiving the active agent 1128 and an open distal end 1136 for delivering the active agent 1128. The active agent delivery catheter 1016 may be attached to the distal body 1018 at at least the distal body proximal junction 1038 and may be a braided design and proximally stiff with a distal progression of flexibility matching a typical core-coil delivery wire. The catheter distal end 1136 may be positioned at the distal body proximal junction 1038 (not shown), in the basket interior 1068 proximal to the distal body inner body 1048 (not shown), within the distal body inner body interior 1130 (the embodiment shown in FIG. 78), or at the distal body distal junction 1060 (not shown), depending on where the user desires to deliver the active agent 1128. The proximal strips 1090 may be mounted within the wall 1138 of the active agent delivery catheter 1016, as shown in FIGS. 79-80, so as not to interfere with the delivery of the active agent 1128. The active agent delivery catheter 1016 may be wider at the proximal end 1134 as shown in FIG. 78 and reinforced with nitinol or other support material for pushability. The active agent delivery catheter 1016 may be no wider than 0.027 inches so that the active agent delivery catheter 1016 may be delivered through a standard microcatheter 1074. If desired the active agent delivery catheter 1016 may be perforated to allow delivery of the active agent 1128 along the distal body length 1034.

The embodiments of FIGS. 73-80 may include a lead wire 286, as shown in FIG. 73A, or an elongated distal body distal junction 1060, as described previously.

PART LIST FOR FIGS. 57-80

| Description | Number |
|---|---|
| System | 1010 |
| pull wire proximal end | 1012 |
| pull wire distal end | 1014 |
| pull wire | 1016 |
| Pull wire wall | 1017 |
| distal body | 1018 |
| distal body perimeter | 1020 |
| distal body interior | 1022 |
| distal body exterior | 1024 |
| proximal end | 1026 |
| proximal end center | 1028 |
| distal end | 1030 |
| distal end center | 1032 |
| distal body length | 1034 |
| longitudinal axis | 1036 |
| proximal junction | 1038 |
| basket | 1040 |
| proximal portion/distal body outer body | 1042 |
| cells | 1044 |
| basket memory metal strips | 1046 |
| distal portion/distal body inner body | 1048 |
| connection points | 1050 |
| proximal portion/distal body outer body interior | 1052 |
| distal segment | 1054 |
| distal braided mesh openings | 1056 |
| woven linear strands | 1058 |
| distal junction | 1060 |
| distal junction proximal end | 1062 |
| basket distal end | 1064 |
| distal portion perimeter | 1066 |
| basket interior | 1068 |
| distal body height | 1070 |
| distal body width | 1072 |
| catheter | 1074 |
| catheter interior | 1076 |
| catheter proximal end | 1078 |
| catheter distal end | 1080 |
| basket memory metal strips distal end | 1082 |
| proximal end of strand | 1086 |
| proximal strip | 1090 |
| proximal strip distal end | 1092 |
| proximal strip proximal end | 1094 |
| distal crowns | 1096 |
| enlarged cells | 1098 |
| vessel/lumen | 1100 |
| distal elongation | 1102 |
| proximal elongation | 1104 |
| distal portion/distal body inner body proximal junction | 1106 |
| distal end of strand | 1108 |
| basket memory metal strip interior surface | 1110 |
| distal portion/distal body inner body proximal end | 1112 |
| distal portion/distal body inner body distal end | 1114 |
| Suture tether | 1116 |
| Proximal coil | 1120 |
| Distal coil | 1122 |
| Gap | 1124 |
| Main Clot | 1126 |
| Secondary clot/distal emboli | 1127 |
| Active agent | 1128 |
| distal portion/distal body inner body interior | 1130 |
| distal portion/distal body inner body middle portion | 1132 |
| Active agent delivery catheter open proximal end | 1134 |
| Active agent delivery catheter open distal end | 1136 |
| Active agent delivery catheter wall | 1138 |
| Helical coil | 1200 |
| Solder location | 1202 |

Having now described the invention in accordance with the requirements of the patent statutes, those skilled in the art will understand how to make changes and modifications to the disclosed embodiments to meet their specific requirements or conditions. Changes and modifications may be made without departing from the scope and spirit of the invention, as defined and limited solely by the following claims. In particular, although the system has been exemplified for use in retrieving blood clots, the system may be used to retrieve other objects from animal lumens. In addition, the steps of any method described herein may be performed in any suitable order and steps may be performed simultaneously if needed.

Terms of degree such as "substantially", "about" and "approximately" as used herein mean a reasonable amount of deviation of the modified term such that the end result is not significantly changed. For example, these terms can be construed as including a deviation of at least ±5% of the modified term if this deviation would not negate the meaning of the word it modifies.

What is claimed is:

1. A system for removing objects from an interior lumen of an animal, the system comprising:
a pull wire having a proximal end and a distal end;
a distal body attached to the pull wire and comprising a distal body proximal end comprising a distal body proximal junction, a distal body distal end comprising a distal body distal junction, a distal body length extending from the distal body proximal end to the distal body distal end, a distal body longitudinal axis extending from the distal body proximal junction to the distal body distal junction, and a distal body height and width perpendicular to the distal body length, the distal body comprising:
a distal body outer body extending from the distal body proximal end to the distal body distal end, the distal body outer body comprising the distal body proximal junction and the distal body distal junction, the distal body outer body comprising a distal body outer body perimeter separating a distal body outer body interior from a distal body outer body exterior, the distal body outer body comprising a basket comprised of a plurality of cells spaced about the distal body outer body perimeter and formed by a plurality of basket memory metal strips, wherein at least some of the basket memory metal strips are located at a distal end of the basket, wherein each of the basket memory metal strips located at the distal end of the basket have a distal end, and wherein each of the distal ends of the basket memory metal strips located at the distal end of the basket converge at, and are attached to, the distal body distal junction;
a distal body inner body comprised of a plurality of braided mesh openings formed by a plurality of woven linear strands, the distal body inner body having a distal body inner body perimeter, each woven linear strand rotating about the distal body inner body perimeter relative to the distal body longitudinal axis a plurality of times in a helical fashion, the distal body inner body comprising a distal body inner body proximal end and a distal body inner body distal end,
wherein the distal body has a relaxed state wherein the distal body has a first height and a first width, and a collapsed state wherein the distal body has a second height and a second width, the second height less than the first height, the second width less than the first width,
wherein the system further comprises a catheter having an interior, a proximal end leading to the interior and a distal end leading to the interior, the catheter comprised of a biocompatible material and configured to envelop the distal body when the distal body is in the collapsed state,
wherein the woven linear strands comprise a proximal end and a distal end,
wherein, in the relaxed state, the median surface area of the cells is larger than the median surface area of the braided mesh openings,
wherein, the distal body inner body and the distal body outer body each have a length generally parallel to the distal body length, the distal body inner body and distal body outer body lengths configured to elongate upon moving from the relaxed state to the collapsed state,
wherein, in the collapsed state and in the relaxed state, the distal body inner body is located in the distal body outer body interior,
wherein the woven linear strands rotate about the distal body inner body perimeter relative to the distal body longitudinal axis a fewer number of times per unit of length in the collapsed state as compared to the relaxed state,
wherein the proximal ends of at least some of the woven linear strands converge at and are attached to a distal body inner body proximal junction, and
further wherein the distal body inner body proximal junction forms the proximal end of the distal body inner body, and
further wherein the system further comprises a tether connecting the distal body proximal junction to the distal body inner body proximal junction.

2. The system of claim 1 wherein the tether comprises a segment in the form of a helical coil, the helical coil having a coil length generally parallel to the distal body length, the helical coil having an expanded state in which the helical coil has a first length and a relaxed state in which the helical coil has a second length, the first length greater than the second length.

3. The system of claim 2, wherein the helical coil is adjacent to the distal body inner body proximal junction.

4. The system of claim 2, wherein the helical coil is configured to move to the expanded state when tension is exerted on the tether.

5. The system of claim 1 wherein the tether is a segment of the pull wire.

6. The system of claim 1 wherein the tether is comprised of a conductive material.

7. The system of claim 1 wherein the tether is comprised of a synthetic polymer.

8. The system of claim 1 wherein the tether comprises a proximal end attached to the distal body proximal junction and a distal end attached to the distal body inner body proximal junction.

9. The system of claim 1, wherein the tether is located approximately in the center of the distal body height and the distal body width when the distal body is in the relaxed state and the tether is generally parallel to the distal body longitudinal axis when the distal body is in the relaxed state.

10. The system of claim 1 wherein, the basket memory metal strips are located on the distal body outer body perimeter and comprise an interior surface facing the distal body outer body interior and an exterior surface opposite the interior surface, and further wherein in the relaxed state, at least some of the woven linear strands contact the interior surface of at least some of the basket memory metal strips.

11. The system of claim 1 wherein the distal body inner body proximal junction is located approximately in the center of the distal body height and the distal body width in the relaxed state.

12. The system of claim 1 wherein the distal body inner body comprises a distal body inner body height and a distal body inner body width and wherein the distal body inner body in the relaxed state comprises a distal body inner body proximal tapered region in which the distal body inner body height and the distal body inner body width decrease as the proximal ends of the woven linear strands approach the distal body inner body proximal junction.

13. The system of claim 1 wherein, in the relaxed state, the basket does not have any free crowns that point generally in the proximal direction.

14. The system of claim 1 wherein the distal body outer body further comprises a plurality of proximal strips, each proximal strip having a distal end attached to a proximal crown of a cell and a proximal end, the proximal ends of the proximal strips converging at the distal body proximal junction.

15. The system of claim 1, wherein the proximal ends of each of the woven linear strands converge at and are attached to the distal body inner body proximal junction and further wherein the distal ends of each of the woven linear strands converge at and are attached to the distal body distal junction.

16. The system of claim 1, wherein in the relaxed state, the distal body inner body is more flexible than the distal body outer body and wherein, in the relaxed state, the median radial force of the distal body inner body is substantially less than the median radial force of the distal body outer body.

17. The system of claim 1, wherein the distal body inner body comprises a distal body inner body height and a distal body inner body width, wherein the distal body inner body in the relaxed state comprises a distal body inner body distal tapered region in which the distal body inner body height and the distal body inner body width decrease as the woven linear strand distal ends approach the distal body inner body distal end, wherein the distal body outer body comprises a distal body outer body height and a distal body outer body width, and further wherein the distal body outer body comprises a tapered region in which the distal body outer body height and the distal body outer body width decrease as the distal ends of the basket memory metal strips located at the distal end of the basket approach the distal body distal junction.

18. The system of claim 1, wherein, in the relaxed state, the distal body inner body impedes blood flow to a greater extent than the distal body outer body when the distal body outer body and the distal body inner body are placed in a blood vessel.

19. The system of claim 1, wherein, prior to removal of an obstruction, the distal body inner body is configured to automatically reduce blood flow when the distal body inner body is placed in a blood vessel.

20. The system of claim 1, wherein, in the relaxed state, the distal body outer body comprises a first pair of distal crowns not attached to another cell of the basket and pointing generally in the distal direction, the distal crowns in the first pair of distal crowns located approximately the same distance from the distal body proximal junction and located between 150 degrees and 180 degrees relative to each other, and further wherein the basket further comprises a second pair of distal crowns not attached to another cell of the basket and pointing generally in the distal direction, the second pair of distal crowns located distally relative to the first pair of distal crowns, each of the distal crowns in the second pair of distal crowns located between 60 degrees and 90 degrees relative to a distal crown in the first pair of distal crowns, the distal crowns in the second pair of distal crowns located approximately the same distance from the distal body proximal junction, each of the distal crowns forming a portion of a cell, wherein each distal crown in the first and second pair of distal crowns forms part of a different enlarged cell, each enlarged cell having a center, wherein the centers of the enlarged cells of the first pair of distal crowns are between 150 degrees and 180 degrees relative to each other and between 60 degrees and 90 degrees relative to the centers of the enlarged cells of the second pair of distal crowns, wherein the enlarged cells are configured to allow a thrombus to pass therethrough and into the basket interior.

21. The system of claim 20 wherein, in the relaxed state, the distal body inner body proximal junction is located distally relative to the first and second pair of distal crowns.

22. The system of claim 1 wherein the distal body inner body is radiopaque.

23. The system of claim 1, wherein, in the relaxed state, the distal body inner body length is no more than about 33% of the distal body outer body length.

24. The system of claim 1 wherein the system further comprises a lead wire extending distally from the distal body distal junction.

25. The system of claim 1 wherein the distal body inner body proximal end is substantially closed.

26. The system of claim 1 wherein, in the relaxed state, the distal body outer body does not have any free crowns that point generally in the proximal direction.

27. A method of removing a blood clot from a blood vessel of an animal, the method comprising the steps of:
a) providing the system of claim 1;
b) positioning the system in the blood vessel;
c) deploying the distal body from the distal end of the catheter;
d) allowing the height and width of the distal body to increase;
e) moving the blood clot into the interior of the distal body outer body; and
f) moving the distal body proximally out of the blood vessel.

28. The method of claim 27 wherein the method further comprises propagating an electrical charge from the pull wire, through the tether, and to the distal body inner body.

29. The system of claim 1 wherein the distal body inner body distal end is connected to the distal body distal junction.

30. The system of claim 1 wherein, in the relaxed state, the distal body inner body is hollow.

31. The system of claim 1 wherein the distal body inner body distal junction is located distal to at least some of the plurality of cells.

32. The system of claim 1 wherein a first set of the woven linear strands rotate clockwise about the distal body inner body perimeter relative to the distal body longitudinal axis and a second set of the woven linear strands rotate counterclockwise about the distal body inner body perimeter relative to the distal body longitudinal axis.

33. The system of claim 1, wherein in the relaxed state, the surface area of the distal braided mesh openings varies along the length of the distal body inner body.

34. The system of claim 33, wherein, in the relaxed state, the distal braided mesh openings having the smallest surface area are located at the distal body inner body proximal end and the distal body inner body distal end.

35. A system for removing objects from an interior lumen of an animal, the system comprising:
a pull wire having a proximal end and a distal end;
a distal body attached to the pull wire and comprising a distal body proximal end comprising a distal body proximal junction, a distal body distal end comprising a distal body distal junction, a distal body length extending from the distal body proximal end to the distal body distal end, a distal body longitudinal axis extending from the distal body proximal junction to the distal body distal junction, and a distal body height and width perpendicular to the distal body length, the distal body comprising:

a distal body outer body extending from the distal body proximal end to the distal body distal end, the distal body outer body comprising the distal body proximal junction and the distal body distal junction, the distal body outer body comprising a distal body outer body perimeter separating a distal body outer body interior from a distal body outer body exterior, the distal body outer body comprising a basket comprised of a plurality of cells spaced about the distal body outer body perimeter and formed by a plurality of basket memory metal strips, wherein at least some of the basket memory metal strips are located at a distal end of the basket, wherein each of the basket memory metal strips located at the distal end of the basket have a distal end, and wherein each of the distal ends of the basket memory metal strips located at the distal end of the basket converge at, and are attached to, the distal body distal junction;

a distal body inner body comprised of a plurality of braided mesh openings formed by a plurality of woven linear strands, the distal body inner body having a distal body inner body perimeter, each woven linear strand rotating about the distal body inner body perimeter relative to the distal body longitudinal axis a plurality of times in a helical fashion, the distal body inner body comprising a distal body inner body proximal end comprising a distal body inner body distal junction, the distal body inner body distal junction located distal to at least some of the plurality of cells, the distal body inner body further comprising a distal body inner body distal end, wherein the distal body has a relaxed state wherein the distal body has a first height and a first width, and a collapsed state wherein the distal body has a second height and a second width, the second height less than the first height, the second width less than the first width, wherein the system further comprises a catheter having an interior, a proximal end leading to the interior and a distal end leading to the interior, the catheter comprised of a biocompatible material and configured to envelop the distal body when the distal body is in the collapsed state, wherein the woven linear strands comprise a proximal end and a distal end, wherein, in the relaxed state, the median surface area of the cells is larger than the median surface area of the braided mesh openings, wherein, the distal body inner body and the distal body outer body each have a length generally parallel to the distal body length, the distal body inner body and distal body outer body lengths configured to elongate upon moving from the relaxed state to the collapsed state, wherein, in the collapsed state and in the relaxed state, the distal body inner body is located in the distal body outer body interior, wherein the woven linear strands rotate about the distal body inner body perimeter relative to the distal body longitudinal axis a fewer number of times per unit of length in the collapsed state as compared to the relaxed state, wherein the proximal ends of at least some of the woven linear strands converge at and are attached to the distal body inner body proximal junction, and wherein the distal body inner body proximal junction forms the proximal end of the distal body inner body, wherein the system further comprises a tether connecting the distal body proximal junction to the distal body inner body proximal junction, wherein, the basket memory metal strips are located on the distal body outer body perimeter and comprise an interior surface facing the distal body outer body interior and an exterior surface opposite the interior surface, and further wherein in the relaxed state, at least some of the woven linear strands contact the interior surface of at least some of the basket memory metal strips, and further wherein, in the relaxed state, the distal body inner body length is no more than about 33% of the distal body outer body length.

36. The system of claim 35 further wherein the distal body inner body distal end is connected to the distal body distal junction.

* * * * *